United States Patent [19]

Pedersen et al.

[11] Patent Number: 5,639,641
[45] Date of Patent: Jun. 17, 1997

[54] RESURFACING OF RODENT ANTIBODIES

[75] Inventors: Jan T. Pedersen; Stephen M. J. Searle; Anthony R. Rees, all of Bath, United Kingdom; Michael A. Roguska, Ashland; Braydon C. Guild, Concord, both of Mass.

[73] Assignee: Immunogen Inc., Cambridge, Mass.

[21] Appl. No.: 942,245

[22] Filed: Sep. 9, 1992

[51] Int. Cl.$^6$ .......................... C12N 15/00; C07K 16/00; A61K 39/395
[52] U.S. Cl. .................. 435/69.6; 435/172.1; 530/387.3; 530/387.7; 530/388.3
[58] Field of Search .......................... 530/387.3, 387.7, 530/388.8; 435/69.6, 172.1

[56] References Cited

U.S. PATENT DOCUMENTS

| | | | |
|---|---|---|---|
| 4,816,397 | 3/1989 | Boss et al. | 435/252.3 |
| 4,816,567 | 3/1989 | Cabilly et al. | 530/387.1 |
| 5,225,539 | 7/1993 | Winter | 530/387.1 |

FOREIGN PATENT DOCUMENTS

| | | |
|---|---|---|
| 239400A2 | 3/1987 | European Pat. Off. . |
| 327378A1 | 2/1989 | European Pat. Off. . |
| 438310A1 | 1/1991 | European Pat. Off. . |
| 438312A2 | 1/1991 | European Pat. Off. . |
| 0519596 | 12/1992 | European Pat. Off. . |
| 0578515A2 | 5/1993 | European Pat. Off. . |
| WO9007861 | 7/1990 | WIPO . |
| WO9109967 | 7/1991 | WIPO . |

OTHER PUBLICATIONS

Gorman et al., "Reshaping a Therapeutic CD4 Antibody", Proc. Natl. Acad. Sci., U.S.A., vol. 88, (1991) pp. 4181–4185.
Padlan, "A Possible Procedure for Reducing the Immunogenicity of Antibody Variable Domains While Preserving Their Ligand–Binding Properties", Molecular Immunology, vol. 28, No. 4/5, (1991) pp. 489–498.
Bobrzecka et al., "The Method of Controlled Rearrangement of Protein Disulphides and Its Use for Synthesis of Chimeric Immunoglobulin G", Immunology Letters, vol. 2, (1980) pp. 151–155.
Konieczny et al., "The Combination of IgM Subunits and Proteolytic IgG Fragments by Controlled Formation of Interchain Disulphides", Haematologia, vol. 14, No. (1), (1981) pp. 95–99.
Morrison et al., "Chimeric Human Antibody Molecules: Mouse Antigen–Binding Domains with Human Constant Region Domains", Proc. Natl. Acad. Sci., U.S.A., vol. 81, (1984) pp. 6851–6855.

LoBuglio et al., "Mouse/Human Chimeric Monoclonal Antibody in Man: Kinetics and Immune Response", Proc. Natl. Acad. Sci., U.S.A., vol. 86, (1989) pp. 4220–4224.

Martin et al., "Molecular Modeling of Antibody Combining Sites", Methods In Enzymology, vol. 203, (1991) pp. 121–153.

Martin et al., "Modeling Antibody Hypervariable Loops: A Combined Algorithm", Proc. Natl. Acad. Sci., U.S.A., vol. 86, (1989) pp. 9268–9272.

Morrison, "In Vitro Antibodies: Strategies for Production and Application", Annu. Rev. Immunol., vol. 10, (1992) pp. 239–265.

Waldmann, "Monoclonal Antibodies in Diagnosis and Therapy", Science, vol. 252, (1991) pp. 1657–1662 pp. 121–153.

Eduardo A. Padlan, *A Possible Procedure for Reducing the Immunogenicity of Antibody Variable Domains While Preserving Their Ligand–Binding Properties*, Molecular Immunology, vol. 28, pp. 489–498, 1991.

Stanfield et al. TibTelh vol. 12 1994 p. 275.

*Primary Examiner*—Lila Feisee
*Assistant Examiner*—Julie E. Reeves
*Attorney, Agent, or Firm*—Sughrue, Mion, Zinn, Macpeak & Seas

[57] ABSTRACT

The invention relates to a method for providing, via resurfacing, humanized rodent antibodies that have improved therapeutic efficacy due to the presentation of a human surface in the variable region. In the method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Ångstroms of any atom of any residue of the complementarity determining regions of the rodent antibody; and (5) the humanized rodent antibody having binding specificity is produced.

16 Claims, 15 Drawing Sheets

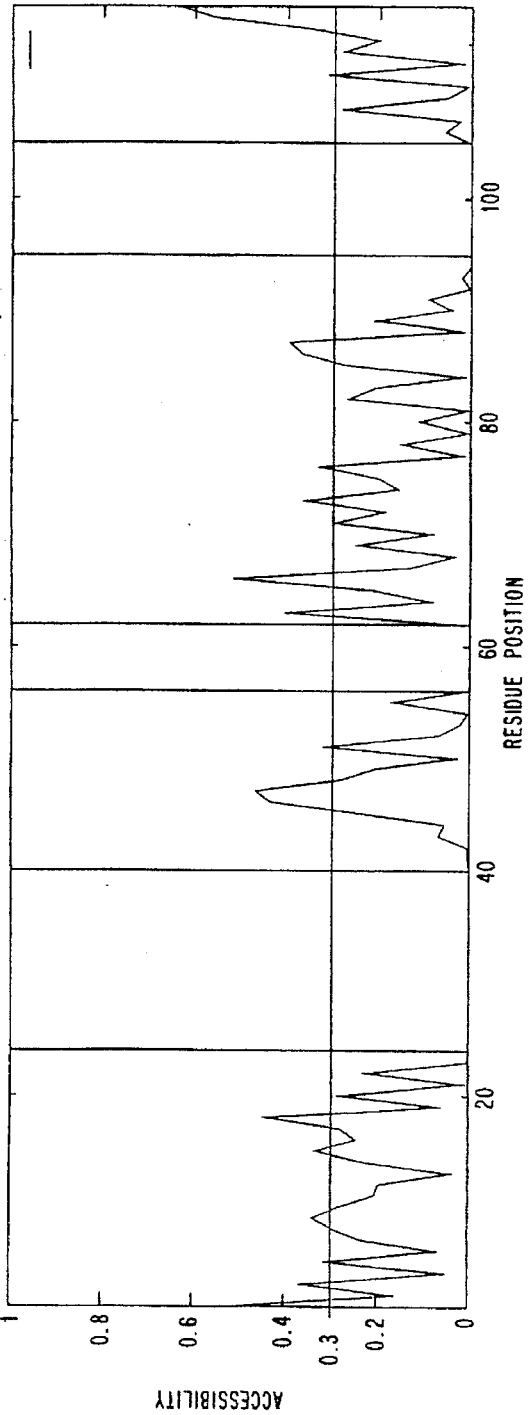

FIG. 4A

Light Chain Sequences

```
                                    10         20         30         40         50         60         70
                                    ----+----+----+----+----+----+----+----+----+----+----+----+----+----+
1 N901L                            :DVLMTQTPLSLPVSLPVSLGDQASISC RSSQIIHSDGNTY-LE WFLQKPGQSPKLLIY KVSNRFS GVPDRFSG
2 KOL                              :QSVLTQPPSASG-TPGQRVTISC SGTSSNIGS---STVN WYQQLPGMAPKLLIY RDAMRPS GVPDRFSG
3 N901L/KOL                        :QVLMTQTPSSLPVTLGQQASISC RSSQIIHSDGNTY-LE WFLQKPGQSPKLLIY KVSNRFS GVPDRFSG
4 KV2F$HUMAN                       :DVVMTQSPLSLPVTLGQPASISC RSSQSLVYSDGNTY-LN WFQQRPGQSPRRLIY KVSNRDS GVPDRFSG
  [most identical seq]
5 N901L/KV2F                       :DVLMTQSPLSLPVTLGQPASISC RSSQIIHSDGNTY-LE WFQQRPGQSPRLLIY KVSNRFS GVPDRFSG
  [CDR grafted]
6 KV4B$HUMAN                       :DIVMTQSPDSLAVSLGERATINC KSSQSVLYSSNNKNYLA WYQQKPGQPPKLLIY WASTRES GVPDRFSG
  [most identical surf]
7 N901L/KV4B                       :DVLMTQTPDSLPVSLGDRASISC RSSQIIHSDGNTY-LE WFLQKPGQSPKLLIY KVSNRFS GVPDRFSG
  [Resurfaced]
                                                                  [     L1     ]                    [ L2 ]

80         90         100        110
                                    ----+----+----+----+----+----+----+
1 N901L                            :SGSGTDFTLMISRVEAEDLGVYYC FQGSH--VPHT FGGGTKLEI-             (SEQ ID NO: 25)
2 KOL                              :SKSGASASLAIGGLQSEDETDYYC AAWDVSLNAYV FGTGTKVTVL            ( 44)
3 N901L/KOL                        :SGSGTSFTLAISRVEAEDEGVYYC FQGSH--VPHT FGGGTKLEI-            (104)
4 KV2F$HUMAN                       :SGSGTDFTLKISRVEAEDVGVYYC MQGTH--WSWT FGGGTKVEIK          ( 87)
  [most identical seq]
5 N901L/KV2F                       :SGSGTDFTLKISRVEAEDVGVYYC FQGSH--VPHT FGGGTKVEI-            (101)
  [CDR grafted]
6 KV4B$HUMAN                       :SGSGTDFTLTISSLQAEDVAVYYC QQYDT---IPT FGGGTKVEIK          ( 71)
  [most identical surf]
7 N901L/KV4B                       :SGSGTDFTLMISRVEAEDLGVYYC FQGSH--VPHT FGGGTKLEI-            (109)
  [Resurfaced]
                                                                  [ L3 ]
```

(SEQ ID NO: 25)
(SEQ ID NO: 26)
(SEQ ID NO: 27)
(SEQ ID NO: 28)
(SEQ ID NO: 29)
(SEQ ID NO: 30)
(SEQ ID NO: 31)

FIG. 4B

Heavy Chain Sequences

```
                        120        130        140        150        160        170        180
                        --+---------+---------+---------+---------+---------+---------+-------
1 N901H                 :DVQLVESGGGLVQPGGSRKLSCAASGFTFS SFGMH-- WVRQAPEKGLEWVA YISSGSF--TIY HADTVKG
2 KOL                   :EVQLVQSGGGVVQPGRSLRLSCSSSGFIFS SYAMY-- WVRQAPGKGLEWVA IIWDDGS--DQH YADSVKG
3 N901H/KOL              :EVQLVESGGGVVQPGRSLRLSCAASGFIFS SFGMH-- WVRQAPGKGLEWVA YISSDGF--TIY HADSVKG
4 G36005                :QVQLVESGGGVVQPGRSLRLSCAASGFTFS SYAMH-- WVRQAPGKGLEWVA VISYDGS--NKY YADSVKG
  [most identical seq]
5 N901H/G36005          :QVQLVESGGGVVQPGRSLRLSCAASGFTFS SFGMH-- WVRQAPGKGLEWVA YISSGSF--TIY YADSVKG
  [CDR grafted]
6 PL0123                :EVQLVESGGGLVQPGGSLRLSCAASGFTFS SYWMS-- WVRQAPGKGLEWVA NIKQDGS--EKY YVDSVKG
  [most identical surf]
7 N901H/PL0123          :EVQLVESGGGLVQPGGSLRLSCAASGFTFS SFGMH-- WVRQAPGKGLEWVA YISSGSF--TIY HADSVKG
  [Resurfaced]                                        [  H1  ]                  [   H2    ]

190        200        210        220        230        240
                        --+---------+---------+---------+---------+---------+------
1 N901H                 :RFTISRDNPKNTLFLQMTSLRSEDTAMYYCAR MRKGYAM--------DY WGQGTTVTVS  (SEQ ID NO: 32)
2 KOL                   :RFTISRDNSKNTLFLQMDSLRPEDTGVYFCAR DGGHGFCSSASCFGPDY WGQGTPVTVS ( 77) (SEQ ID NO: 33)
3 N901H/KOL             :RFTISRDDPKNTLFLQMTSLRSEDTAMYYCAR MRKGYAM--------DY WGQGTTVTVS (106) (SEQ ID NO: 34)
4 G36005                :RFTISRDNSKNTLYLQMNSLRAEDTAVYYCAR DRKDWGWALF------- WGQGTLVTVS ( 89) (SEQ ID NO: 35)
  [most identical seq]
5 N901H/G36005          :RFTISRDNSKNTLYLQMNSLRAEDTAVYYCAR MRKGYAM--------DY WGQGTLVTVS (103) (SEQ ID NO: 36)
  [CDR grafted]
6 PL0123                :RFTISRDNAKNSLYLQMNSLRAEDTAVYYCAR ----------------- ---------- ( 74) (SEQ ID NO: 37)
  [most identical surf]
7 N901H/PL0123          :RFTISRDNAKNTLFLQMTSLRAEDTAMYYCAR MRKGYAM--------DY WGQGTTVTVS (110) (SEQ ID NO: 38)
  [Resurfaced]                                   [       H3      ]
```

RESURFACING OF RODENT ANTIBODIES

FIELD OF THE INVENTION

The present invention relates to the development of prediction rules that can be used to accurately model the variable regions (V-regions) of antibodies. The development of these rules and their application in the predictive molecular restructuring of the surfaces of variable domains of non-human monoclonal antibodies enables changing of the surface, i.e., resurfacing, of these monoclonal antibody V-regions to replicate the surface characteristics found on human antibody V-regions. This method of resurfacing non-human monoclonal antibody V-regions to resemble human antibody V-regions is expected to permit the production of functional altered antibodies, which retain the binding parameters of the original non-human monoclonal antibody, with improved therapeutic efficacy in patients due to the presentation of a human surface on the V-region.

BACKGROUND OF THE INVENTION

General Background of Antibodies

Murine monoclonal antibodies are widely used as diagnostic and therapeutic agents in the treatment of human disease. Mice can be readily immunized with foreign antigens to produce a broad spectrum of high affinity antibodies. Invariably, the introduction of murine or other rodent antibodies into humans results in the production of a human anti-mouse antibody (HAMA) response due to the presentation of a foreign protein in the body. The production of HAMA in patients can result from the introduction of foreign antibody in a single dose or from extended use in therapy, for example, for the treatment of cancer. Extended use of murine antibody is generally limited to a term of days or weeks in patients before concerns of anaphylaxis arise. Moreover, once HAMA has developed in a patient, future use of murine antibodies for diagnostic or therapeutic purposes is often precluded for the same reasons.

Beyond ethical considerations, attempts to produce human monoclonal antibodies have not been highly successful for a number of reasons. The production in vitro of human monoclonals rarely results in high affinity antibodies. In vitro cultures of human lymphocytes yield a restricted range of antibody responses relative to the broad spectrum of reactive antibodies produced in vivo through direct immunization of mice. Additionally, in humans, immune tolerance prevents the successful generation of antibodies to self-antigens. All of these factors have contributed to the search for ways to modify the structures of murine monoclonal antibodies to improve their use in patients. Many investigators have attempted to alter, reshape or humanize murine monoclonal antibodies in an effort to improve the therapeutic application of these molecules in patients.

Strategies of Antibody Humanization

The earliest reports of the controlled rearrangement of antibody domains to create novel proteins was demonstrated using rabbit and human antibodies as described by Bobrzecka, K. et al. (Bobrzecka, K., Konieczny, L., Laidler, P. and Rybarska, J. (1980), Immunology Letters 2, pp. 151–155) and by Konieczny et al. (Konieczny, L., Bobrzecka, K., Laidler, P. and Rybarska, J. (1981), Haematologia 14 (I), pp. 95–99). In those reports, the protein subunits of antibodies, rabbit Fab fragments and human Fc fragments, were joined through protein disulfide bonds to form new, artificial protein molecules or chimetic antibodies.

Recombinant DNA technology was used to construct gene fusions between DNA sequences encoding mouse antibody variable light and heavy chain domains and human antibody light chain (LC) and heavy chain (HC) constant domains to permit expression of the first recombinant "near-human" antibody (chimeric antibody) product (Morrison, S. L., Johnson, M. J., Herzenberg, L. A. and Oi, V. T. (1984), Proc. Natl. Acad. Sci. U.S.A. 81, pp. 6851–6855).

The kinetics and immune response in man to chimeric antibodies has been examined (LoBuglio, A. F., Wheeler, R. H., Trang, J., Haynes, A., Rogers, K., Harvey, E. B., Sun, L., Ghrayeb, J. and Khazaeli, M. B. (1989), Proc. Natl. Acad. Sci. 86, pp. 4220–4224).

Chimeric antibodies contain a large number of non-human amino acid sequences and are immunogenic in man. The result is the production of human anti-chimera antibodies (HACA) in patients. HACA is directed against the murine V-region and can also be directed against the novel V-region/C-region (constant region) junctions present in recombinant chimeric antibodies.

To overcome some of the limitations presented by the immunogenicity of chimeric antibodies, the DNA sequences encoding the antigen binding portions or complementarity determining regions (CDR's) of murine monoclonal antibodies have been grafted by molecular means in the DNA sequences encoding the frameworks of human antibody heavy and light chains (Jones, P. T., Dear, P. H., Foote, J., Neuberger, M. S. and Winter, G. (1986), Nature 321, pp. 522–525; Riechmann, L., Clark, M., Waldmann, H. and Winter, G. (1988), Nature 332, pp. 323–327). The expressed recombinant products called reshaped or humanized antibodies are comprised of the framework of a human antibody light or heavy chain and the antigen recognition portions, CDR's, of a murine monoclonal antibody. Several patent applications have been filed in this area including, for example, European Patent Application, Publication No. 0239400; European Patent Application, Publication Nos. 0438310A1 and 0438310A2; International Patent Publication No. WO 91/09967; and International Patent Publication No. WO 90/07861.

However, it is questionable whether European Patent Application (EP), Publication No. 0239400 is truly enabling. It is not assured in this patent that the best fit is made to assure proper presentation of the CDR loops at the antibody combining site.

EP Publication Nos. 0438310A1 and 0438310A2 go a step beyond EP Publication No. 0239400 by protecting the importance of uniquely selected human frameworks for the human light chain (LC) and heavy chain (HC) V-regions. These V-region frameworks should show a high degree of sequence similarity with the frameworks of the murine monoclonal antibody and present the CDR's in the appropriate configuration. However, the criteria for sequence matching are no more sophisticated than simple homology searching of the antibody protein or DNA databases.

International Patent Publication No. WO 91/09967 attempts a further variation of the method disclosed in EP Publication No. 0239400. In International Patent Publication No. WO 91/09967, homology of the donor sequences and the acceptor framework is not important, rather it discloses that a selected set of residues in the LC and HC are critically important to humanization. The ability to make changes at these positions is the basis of International Patent Publication No. WO 91/09967.

International Patent Publication No. WO 90/07861 proposes four important criteria for designing humanized antibodies. 1) Homology between human acceptor and non-human donor sequences. 2) Use donor rather than acceptor amino acids where the acceptor amino acid is unusual at that position. 3) Use donor framework amino acids at positions adjacent to the CDR. 4) Use donor amino acids at framework positions where the sidechain atom is within 3 Angstroms of the CDR in a 3-D model. The first antibody humanized by this method retained less than ⅓ the affinity of the original monoclonal antibody.

None of the above methods for designing a humanized antibody is predictable due to the questions that surround CDR framework interactions. By replacement of murine framework with human framework, there is no guarantee of identical conformations for CDR's because i) the $V_L$-$V_H$ interaction is not identical in all V-regions and ii) accurate prediction of the CDR-framework interactions are key to faithful reproduction of the antigen binding contacts.

The above methods do not offer a general solution to solving the issues surrounding antibody humanization, rather the methods as outlined in each reference above involve a substantial amount of trial and error searching to obtain the desired affinity in the final humanized product. More importantly, there is no guarantee that corrective changes in framework amino acids will leave the reshaped V-regions resembling the surface character of a truly human antibody. Therefore, it can be argued that antibodies humanized by the above methods may be immunogenic in man.

Antigenicity of Antibodies

The antigenicity/immunogenicity of an antibody, including recombinant reshaped antibody products, introduced into humans can be viewed as a surface phenomenon. In general one can view the immune system as scanning the surface of a protein introduced to the body. If the $F_V$ portion of a humanized antibody 'opens-up' in the circulation then internal residues can be presented to the immune system. On the other hand, if the $F_V$ portion is stable and tightly packed then only the surface residues presented by the V-regions and the interface between the $V_L$ and $V_H$ regions will be 'scanned'.

Surface Reshaping or Resurfacing of Antibodies

The notion of surface presentation of proteins to the immune system raises the prospect of redesigning murine monoclonal antibodies to resemble human antibodies by humanizing only those amino acids that are accessible at the surface of the V-regions of the recombinant $F_V$. The resurfacing of murine monoclonal antibodies to reduce their immunogenicity could be beneficial in maintaining the avidity of the original monoclonal antibody in the reshaped version, because the natural framework-CDR interactions are retained. The value of maintaining the integrity of the framework-CDR interactions has been illustrated as summarized below.

In a recent research report, two different reshaped versions of the rat monoclonal antibody, Campath-9 (anti-human CD4), were generated (Gorman, S. D., Clark, M. R., Routledge, E. G., Cobbold, S. P. and Waldmann, H. (1991), Proc. Natl. Acad. Sci. U.S.A. 88, pp. 4181–4185). In one version, $pV_H NEW/C_{G1}$, the acceptor $V_H$ framework was from the human NEW-based heavy chain, which has 47% identical residues to the Campath-9 $V_H$. While in the second version, $pV_H KOL/C_{G1}$, the acceptor $V_H$ framework was from the human KOL antibody, which has 72% identical residues to Campath-9 $V_H$. Each reshaped antibody contained the identical $V_L$ domain from the human REI antibody sequence. However, the recombinant product of $pV_H KOL/C_{G1}$ had an avidity for CD4 that was substantially greater than the product of $pV_H NEW/C_{G1}$. The authors proposed a reshaping strategy where human sequences, that are highly homologous to the rodent antibody of interest, are transferred, by in vitro mutagenesis, into the rodent V-region to create a "bestfit" reshaped antibody. This strategy uses the term "bestfit" to describe the modeling process, however, there is no quantitative formula employed to assess "bestfit", and so in effect, the process is subjective. Additionally, there is no resurfacing concept presented in that paper.

The concept of reducing rodent-derived antibody immunogenicity through the replacement of exposed residues in the antibody framework regions which differ from those of human origin is discussed in a recent paper (Padlan, E. A. (1991), Molecular Immunology 28, pp. 489–498). In that paper, the variable domains of two antibody structures, KOL (human) and J539 (mouse), are examined. The crystal structures of the Fab fragments of these two antibodies have been elucidated to high resolution. The solvent accessibility of the exposed framework residues in the variable domains of these two antibodies were compared to a sequence database of human and murine antibody V-region subgroups. On the basis of his findings, Padlan proposed to reduce the antigenicity of allogeneic variable domains [murine V-regions], through replacement of the exposed residues in the framework regions with residues usually found in human antibodies. In murine sequences with the highest similarity to a given human sequence, the number of changes necessary to "humanize" a murine V-region surface would range from 6–15 amino acid changes per V-region. This reference suggests how to convert one antibody surface into another but no general method is developed. Application of the procedure is provided by two examples, a worst-case and a best-case.

Worst Case:

Among the representative murine kappa $V_L$ sequences examined for which its autologous $V_H$ has been sequenced, $S107V_L$ has the most residues that need to be replaced to humanize it. $S107V_L$ is most similar to the members of the human subgroup VKIV and JK2. The exposed or partially exposed residues that need to be replaced are those at positions 9, 10, 14, 15, 16, 17, 18, 22, 41, 63, 80, 85, 85, 100 and 106. Murine V-region $S107V_H$ is most similar in its framework to the members of the human subgroup VHIII and JH6. The exposed or partially exposed residues in $S107V_H$ that need to be replaced are those at positions 3, 40, 68, 73, 75, 76, 82b and 89. A total of 23 residues need to be replaced to humanize the variable domains of S107.

Best Case:

Among the murine $V_H$ sequences examined for which the autologous $V_L$ has also been sequenced, $MOPC21V_H$ has the least number of residues that need to be replaced to humanize it. $MOPC21V_H$ is most similar in its framework to the members of the human subgroup HIII and JH6. The exposed or partially exposed residues that need to be replaced are those at positions 1, 42, 74, 82a, 84, 89 and 108. $MOPC21V_L$ is most similar in its framework to human subgroup VKIV and JK4. The exposed or partially exposed residues that need to be replaced are those at positions 1, 9, 12, 15, 22, 41, 63, 68, 83 and 85. A total of 17 amino acids need to be replaced to humanize the variable domains of MOPC21.

Of the light chains in the Best- and Worst-Case examples cited above, $S107V_L$ required changes at 15 positions and $MOPC21V_L$ required changes at 10 positions. Only seven of the changes are common to both of these light chain sequences (see underlined residues). Moreover, of the heavy chain residues that need to be replaced to humanize the respective V-regions, $S107V_H$ required changes at 8 positions and $MOPC21V_H$ required changes at 7 positions. In this instance, only one position is common to both of these heavy chain sequences (see residues in boldface).

An analysis of S107 V-regions alone would not have led to the prediction of which residues to change in MOPC21. The reason for this is that the surface residues in Padlan's analysis are only determined by reference to the crystal structure analysis of one antibody. In addition, the basis for defining the surface exposure of an amino acid at a particular position on that crystal structure is a continuous gradient of change, e.g., the fractional solvent accessibility values (Padlan, E. A. (1990), Molecular Immunology 28, pp. 489–498) were computed, where: 0 to 0.2=completely buried, 0.2 to 0.4=mostly buried, 0.4 to 0.6=partly buried/partly exposed, 0.6 to 0.8=mostly exposed, and 0.8 or above=completely exposed. By limiting the analysis of exposed surface residues to a single crystal structure and by superimposing a broad range of solvent accessibility ratios on exposed residues, such a modeling strategy could be expected to have a wide margin of error in its calculations. This model fails to take into account the great majority of structural information available in the database for other antibody crystal structures.

SUMMARY OF THE INVENTION

Accordingly, it is an object of this invention to provide humanized rodent antibodies or fragments thereof, and in particular, humanized rodent monoclonal antibodies that have impinged therapeutic efficacy in patients due to the presentation of a human surface on the V-region. This and other objects have been attained by providing a method for determining how to humanize a rodent antibody or fragment thereof by resurfacing the method comprising:

(a) determining the conformational structure of the variable region of the rodent antibody or fragment thereof by constructing a three-dimensional model of the rodent antibody variable region;

(b) generating sequence alignments from relative accessibility distributions from x-ray crystallographic structures of a sufficient number of rodent and human antibody variable region heavy and light chains to give a set of heavy and light chain framework positions wherein the alignment positions are identical in 98% of the sufficient number of rodent antibody heavy and light chains;

(c) defining for the rodent antibody or fragment thereof to be humanized a set of heavy and light chain surface exposed amino acid residues using the set of framework positions generated in step (b);

(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;

(e) substituting, in the amino acid sequence of the rodent antibody or fragment thereof to be humanized the set of heavy and light chain surface exposed amino acid residues defined in step (c) with the set of heavy and light chain surface exposed amino acid residues identified in step (d);

(f) constructing a three-dimensional model of the variable region of the rodent antibody or fragment thereof resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the rodent antibody or fragment thereof to be humanized; and (h) changing any residues identified in step (g) from the human to the original rodent amino acid residue to thereby define a rodent antibody humanizing set of surface exposed amino acid residues; with the proviso that step (a) need not be conducted first, but must be conducted prior to step (g).

Also provided is a method for producing a humanized rodent antibody or fragment thereof from a rodent antibody or fragment thereof, the method comprising:

(I) carrying out the above-described method for determining how to humanize a rodent antibody or fragment thereof by resurfacing; and (II) modifying the rodent antibody or fragment thereof by replacing the set of rodent antibody surface exposed amino acid residues with the rodent antibody humanizing set of surface exposed amino acid residues defined in step (h) of the above-described method.

In a preferred embodiment, the rodent antibody or fragment thereof is a murine antibody, and most preferably murine antibody N901.

BRIEF DESCRIPTION OF THE FIGURES

FIG. 3A graphically shows the relative accessibility for the heavy chain and FIG. 3B graphically shows the relative accessibility for the light chain.

FIGS. 4A SEQ ID NOS: 25-31 and 4B SEQ ID NOS: 32-38 show alignments of sequences generated using the three methods of humanization. Sequences are: 1) Original rodent N901. 2+3) KOL (Marquart, M. Deisenhofer, J. and Huber, R. (1980), J. Mol. Biol. 141, pp. 369-391) and reshaped N901 using KOL surface. 4+5) Most homologous sequences, L(KV2F) (Klobeck, H., Meindl, A., Combriato, G., Solomon, A. and Zachau, H. (1985), Nucleic Acids Res. pp. 6499-6513) and H(G36005) (Schroeder, H. and Wang, J. (1990), Proc. Natl. Acad. Sci. U.S.A. 87), and reshaped N901 using these sequences. 6+7) Most homologous with respect to surface residues, L(KV4B) (Klobeck, H., Bronkamp, G., Combriato, G., Mocikat, R., Pohelnz, H. and Zachau, H. (1985), Nucleic Acids Res. 3, pp. 6515-6529) and H(PLO123) (Bird, J., Galili, N., Link, M., Sites, D. and Sklar, J. (1988), J. Exp. Med. 168, pp. 229-245), and reshaped N901 using these sequences. The numbering is the same as used in the antibody modelling program ABM (trademark for commercial software, Oxford Molecular Ltd., Oxford, U.K.), which is based on structural conservation and not sequence homology as used by Padlan et al. (Kabat, E. A., Wu, T. T., Reid-Miller, M., Perry, H. M. and Gottesman, K. S. (1987), Sequences of Proteins of Immunological Interest. U.S. Department of Health and Human Services, Fourth Edition). The sequence changes which have to be introduced in order to resurface N901 with a given sequence are marked with bars, back-mutations as determined from $F_V$ models are marked with stars. The sequence homology of given sequences to N901 are shown in brackets after each sequence.

FIG. 9A: D1.3, FIG. 9B: 36-71, FIG. 9C: Gloop-2, FIG. 9D: 3D6.

DETAILED DESCRIPTION OF THE INVENTION

Figure 1:
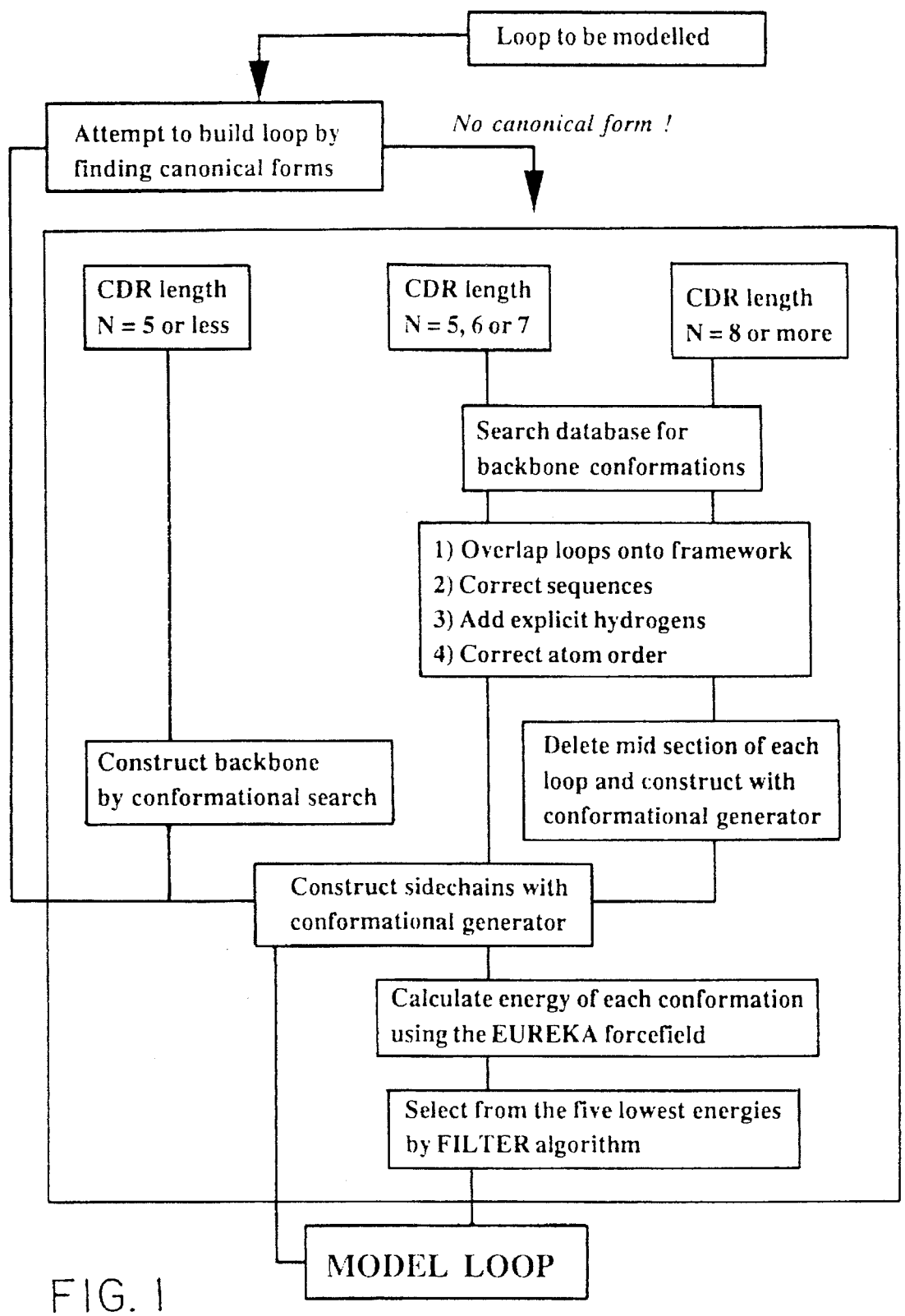
FIG. 1 shows an algorithm that can be used for constructing a three-dimensional model of the rodent antibody variable region.

The existence of specific, yet different, surface patches in murine and human antibodies may be the origin of the inherited immunogenicity of murine antibodies in humans. Statistical analysis of a database of unique human and murine antibody $F_V$ fragments has revealed that certain combinations of residues in exposed surface positions are specific for human and murine sequences. The combinations are not the same in human and murine $F_V$ domains. However, it is possible to define families of surface residues for the two species of antibodies. These families reveal a novel method for the "humanization" or reshaping of murine antibodies. Humanization is the modification of the solvent accessible surface of a non-human antibody or fragment thereof to resemble the surface of a chosen human antibody or fragment thereof such that the modified non-human antibody or fragment thereof exhibits lower immunogenicity when administered to humans. Such a process applies in the present application to antibody variable regions but could equally well apply to any other antibody fragment. The method is considered to be generally applicable to humanization of rodent antibodies.

According to the present invention, a statistical analysis is presented which is based on accessibility calculated for a range of antibody crystal structures. When this information is applied to an antibody sequence database, it is possible to discriminate between human and murine antibodies at the sequence level purely on the basis of their surface residue profiles.

Rational Resurfacing Approach

There are several key features of the resurfacing approach of the present invention.

1) This method uses as a starting point, construction of a three-dimensional model of a rodent variable region by known methods;

2) A large number (e.g., twelve) of antibody $F_V$ or Fab fragment x-ray crystallographic structures are analyzed to produce an unambiguous set of surface exposed amino acid residues that will be positionally identical (about 98%) for a majority of antibodies. The set is produced by identifying all those residues whose solvent accessibility is above a given cut-off (typically 30%), calculated using a modification of the method of Kabsch and Sander (Kabsch, W. and Sander, C. (1983), Biopolymers 22, pp. 2257-2637) in which explicit atomic radii are used for each atom type to predict sidechain positions as is described below in more detail;

3) Using a complete human antibody database, the best set of human heavy and light chain surface exposed amino acid residues is selected on the basis of their closest identity to the set of surface amino acid residues of the murine antibody;

4) In order to retain the conformational structure of the CDRs of the rodent antibody, replacement of any human surface exposed amino acid with the original rodent surface exposed amino acid residue is carried out whenever a surface residue in either the rodent or resurfaced antibody is calculated from the three-dimensional model to be within 5 Angstroms of a CDR residue.

Figure 2:
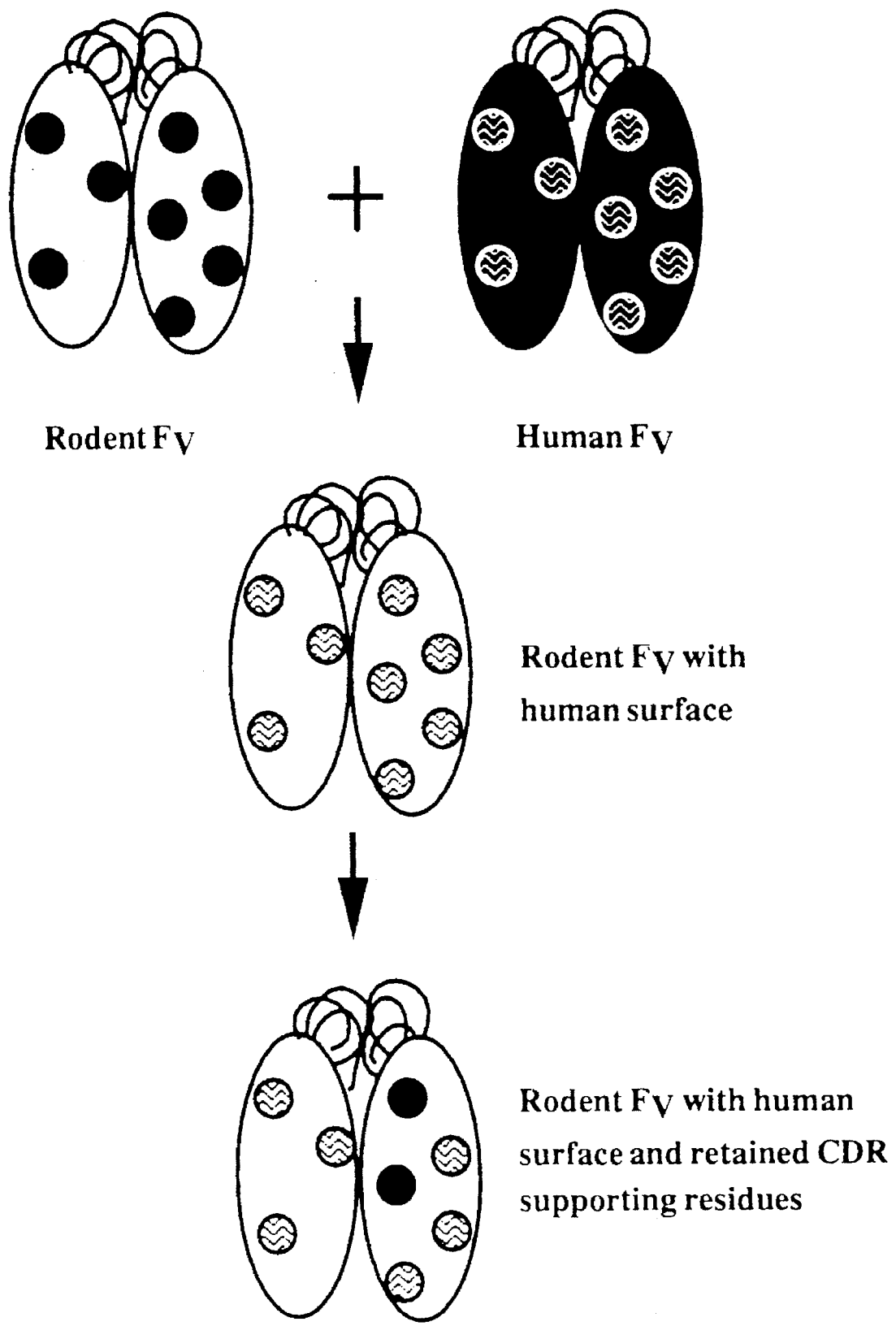
FIG. 2 is a diagram showing the approach to determine how to humanize a rodent antibody or fragment thereof according to the present invention.

The general resurfacing approach of the present invention is illustrated in FIG. 2. The approach can be divided into two stages. In the first, the rodent framework (white) is retained and only the surface residues changed from rodent (dark grey circles) to the closest human pattern (light grey circles). This should remove the antigenicity of the rodent antibody. In the second stage, surface residues within 5 Angstroms of the CDRs are replaced with the rodent equivalents in an attempt to retain antigen binding and CDR conformation.

The method of the present invention is applicable to whole antibodies as well as antibody fragments. Suitable antibody fragments that can be used can readily be determined by the skilled artisan. Examples of some suitable fragments include a single chain antibody (SCA), an antibody $F_v$ fragment, Fab fragment, $F(ab')_2$ fragment, Fab' fragment, or other portion of an antibody comprising the binding site thereof.

According to the present invention, an important step in the method for determining how to modify a rodent antibody or fragment thereof by resurfacing is to determine the conformational structure of the variable region of the rodent antibody or fragment thereof to be humanized by constructing a three-dimensional model of the rodent antibody variable region. This can be done by known methods such as those described, for example, in Martin et al. (Martin, A. C. R., Cheetham, J. C. and Rees, A. R. (1989), Proc. Natl. Acad. Sci. U.S.A. 86, pp. 9268–9272; Methods in Enzymology (1991), 203, pp. 121–152) and as described in detail in Example 2.

Martin et al. describe an algorithm which is depicted in FIG. 1. The algorithm applies to murine and human antibodies equally well. The present inventors therefore expect that, based on sequence similarity between antibodies of different species (Kabat, E. A. Segments of Proteins of Immunological Interest, National Institutes of Health, U.S.A. 1991), the algorithm will work equally well for rat and other rodent antibodies.

Briefly, the algorithm depicted in FIG. 1 can be summarized as follows. The framework region of an antibody to be modelled is selected on the basis of sequence homology and constructed by a least squares fit onto the six conserved strands of the variable region β-barrel. Light and heavy chain complementarity determining regions are constructed using a combination of canonical structures (Chothia, C. and Lesk, A. M. (1987), J. Molec. Bio. 196, pp. 901–917), database searching and conformational searching. Detailed descriptions of these methods are described in Example 2 herein and in the above two references (Martin et al. 1989 and 1991).

According to the present invention, another three-dimensional model is also constructed. The other three-dimensional model is of the rodent antibody variable region having human antibody surface amino acid residues substituted therein at particular rodent antibody surface residue positions.

This other three-dimensional model is constructed by carrying out the series of steps described next.

The first of the steps is to generate sequence alignments from relative accessibility distributions from x-ray crystallographic structures of a sufficient number of rodent antibody variable region heavy and light chains to give a set of framework positions of surface exposed amino acid residues the positions of which are 98% identical in a majority of the variable regions.

As used herein, the term "framework" means the antibody variable region from which the complementarity determining regions have been excluded.

"Complementarity determining regions" means those amino acid sequences corresponding to the following numbering system as defined by Kabat, E. A. (In Sequences of Immunological Interest, N.I.H., U.S.A., 1991).

| Light Chain | L1 | residues | 24–34 |
| Light Chain | L2 | residues | 50–56 |
| Light Chain | L3 | residues | 89–97 |
| Heavy Chain | H1 | residues | 31–358 |
| Heavy Chain | H2 | residues | 50–58 |
| Heavy Chain | H3 | residues | 95–102 |

A sufficient number of rodent antibody fragments that need to be analyzed in order to produce the set of framework positions of surface exposed amino acid residues can readily be determined by the skilled artisan through routine experimentation using a database of antibody sequences. Thus, this step can be conducted using suitable databases now in existence or later compiled.

The x-ray crystallographic structures are used to determine relative accessibility distributions of surface exposed amino acid residues. The relative accessibility distributions identify all those residues whose solvent accessibility is above a given cut-off (typically 30%), calculated using a modification of the method of Kabsch and Sander (Kabsch, W. and Sander C. (1983), Biopolymers 22, pp. 2257–2637) in which explicit atomic radii are used for each atom type.

The relative accessibility distributions determined from the x-ray crystallographic structures can then be used to generate sequence alignments which give a set of framework positions of surface exposed amino acid residues the positions of which are 98% identical in a majority of the variable regions.

Figure 3B:
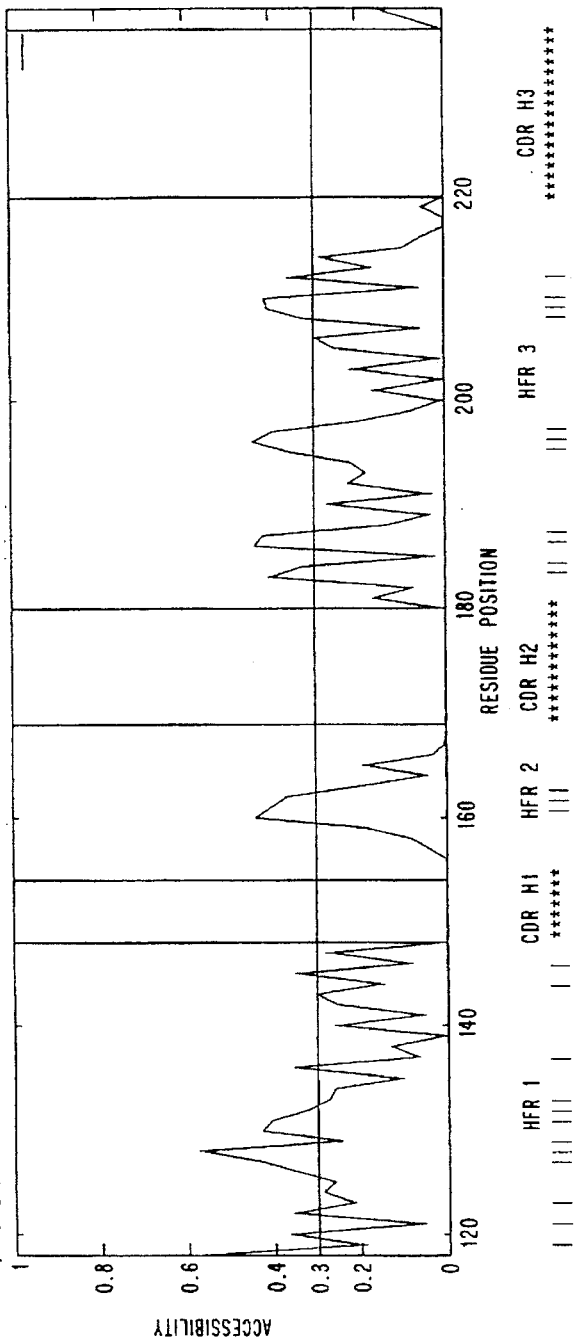
FIGS. 3A SEQ ID NOS: 1–12 and 3B SEQ ID NOS: 13–24 are plots of relative accessibility of amino acid residues for twelve antibody $F_V$ structures, mapped onto the sequence alignment of these structures. Structures Glb2 (Jeffrey, P. D., Doctor of Philosophy Thesis, University of Oxford, United Kingdom, 1991), D1.3 (Amit, A. G., Mariuzza, R. A., Phillips, S. E. V. and Poljak, R. J. (1986), Science 233, pp. 747–753), 3D6 (Grunow, R., Jahn, S., Porstman, T., Kiessig, T., Steinkeller, H., Steindl, F., Mattanovich, D., Gurtler, L., Deinhardt, F., Katinger, H. and von R., B. (1988), J. Immunol. Meth. 106, pp. 257–265) and 36–71 (5fab) (Rose, D. R., Strong, R. K., Margolis, M. N., Gefter, M. L. and Petsko, G. A. (1990), Proc. Natl. Acad. Sci. U.S.A. 87, pp. 338–342) are not yet present in the Brookhaven database. The other structures used were: 2hfl (Sheriff, S., Silverton, E. W., Padlan, E. A., Cohen, G. H., Smith-Gill, S. J., Finzel, B. C. and Davies, D. R. (1987), Proc. Natl. Acad. Sci. U.S.A. 84, pp. 8075–8079), 3hfm (Padlan, E., Silverton, E., Sheriff, S., Cohen, G., Smith-Gill, S. and Davies, D. (1989), Proc. Natl. Acad. Sci. U.S.A. 86, pp. 5938–5942), 2fbj (Mainhart, C. R., Potter, M. and Feldmann, R. J. (1984), Mol. Immunol. 21, pp. 469–478), 3fab (Saul, F. A., Amzel, L. M. and Poljak, R. J. (1978), J. Biol. Chem. 253, pp. 585–597), 4fab (Herron, J., He, X., Mason, M., Voss, E. and Edmunson, A. (1989), Proteins: Struct., Funct., Genet. 5, pp. 271–280), 2mcp (Segal, D., Padlan, E., Cohen, G., Rudikoff, S., Potter, M. and Davies, D. (1974), Proc. Natl. Acad. Sci. U.S.A. 71, pp. 4298), 2fb4 (Marquart, M. Deisenhofer, J. and Huber, R. (1980), J. Mol. Biol. 141, pp. 369–391), and 1f19 (Lascombe, M. Alzari, P., Boulot, G., Salujian, P., Tougard, P., Berek, C., Haba, S., Rosen, E., Nisonof, A. and Poljak, R. (1989), Proc. Natl. Acad. Sci. U.S.A. 86, p. 607). These structures are designated by their Brookhaven entry code. The sequence numbering used here is described in FIGS. 4A and 4B.

The set of framework positions of surface exposed amino acid residues for the variable regions of murine antibodies is shown in Table 1, set forth in Example 1, and was produced using the sequence alignments and accessibility distributions shown in FIGS. 3A and 3B.

Once a set of framework positions of surface exposed amino acid residues for the variable regions of the rodent antibodies have been generated, the surface exposed residues of the heavy and light chain pair of the rodent antibody, or fragment thereof, to be humanized can be identified using an alignment procedure such as that described in Example 1 and shown in FIGS. 3A and 3B. This defines a set of surface exposed amino acid residues of a heavy and light chain pair of a rodent antibody or antibody fragment to be humanized.

Next, a complete human antibody sequence database is used to identify a set of surface exposed amino acid residues from a human antibody variable region that have the closest positional identity to the set of surface exposed amino acid residues of the variable region of the rodent antibody that is to be humanized. The set of surface exposed amino acid residues from the human antibodies can be separately identified for a heavy chain and for a light chain that are not naturally paired and/or a set can be identified from a natural human heavy and light chain pair, that is, a pair originating from a single B cell or hybridoma clone. Preferably, the set is one from a natural human heavy and light chain pair.

A humanized rodent antibody that gives the appearance of a human antibody is then predicted by substituting the set of surface exposed amino acid residues from the rodent antibody or fragment thereof to be humanized with the set of surface exposed amino acid residues from the human antibody.

A three-dimensional model can then be constructed from the resulting, fully substituted variable region of the rodent antibody or fragment thereof. The three-dimensional model is constructed using the same known methods mentioned above for constructing a 3-D model of the original rodent antibody or fragment thereof.

While the antigenicity of this fully "resurfaced" or humanized antibody should be removed, an additional factor to be addressed is the binding affinity or the binding strength of the resurfaced antibody. Changes in the framework of the variable domain introduced through resurfacing can influence the conformation of the CDR loops and therefore antigen binding of the antibody. According to the present invention, this problem is removed by the next step which is to identify, by means of a comparison of both of the above-described three-dimensional models of the rodent antibody variable region, any residues from the set of surface exposed amino acid residues of the variable region heavy and light chain pair of the rodent or human antibody identified that are within 5 Angstroms of any atom of any residue of the rodent antibody or antibody fragment complementarity determining regions (CDRs).

Any residue(s) so identified is then changed back from the human to the original rodent amino acid residue(s).

The results of this method can then be applied to a particular rodent antibody by well known methods. Briefly, genes for the humanized variable heavy and light chain regions are constructed using standard recombinant DNA methods (Sambrook, J., Fritsch, E. F. and Maniatis, T. (1989), Molecular Cloning, Second Edition). For example, a PCR method can be used (Daugherty et al. (1991), Nucleic Acids Research 19, pp. 2471–2476).

Variable heavy chain or variable light chain gene constructs are subcloned into appropriate expression vectors. Suitable expression vectors contain either a human gamma or human kappa constant region gene, a suitable promoter, a sequence coding for a human immunoglobulin leader peptide (for example: met-gly-trp-ser-cys-ile-ile-leu-phe-leu-val-ala-thr-ala-thr (SEQ ID NO:39), Olandi et al. (1989), PNAS 86, pp. 3833–3837), and a drug selectable marker.

Heavy and light chain expression plasmids can be co-transfected, for example, by electroporation into suitable cells, for example, SP2/0 cells, and selected with an appropriate drug, G418, for example. Screening for intact antibody can be accomplished by ELISA assay. 96-well plates are coated with, for example, goat anti-human kappa chain antibody, and light chains are detected with, for example, goat anti-human antibody conjugated to alkaline phosphatase.

As another approach, light chain constructs are transfected, for example, by electroporation into suitable cells, for example, SP2/0 cells and selected, for example, in hygromycin. Screening for light chain expression can be accomplished by ELISA assay. 96-well plates are coated with, for example, goat anti-human kappa chain antibody, and light chains are detected with, for example, goat anti-human antibody conjugated to alkaline phosphatase.

A light chain producing line is then used as a host to electroporate in the heavy chain construct. The heavy chain plasmid is co-transfected with a plasmid containing the gene coding for another drug marker, for example, neomycin resistance and selected in the presence of the drug G418. Screening for intact antibody is accomplished by ELISA assay. 96-well plates are coated with, for example, goat anti-human Fc and detected with, for example, goat anti-human light chain conjugated to alkaline phosphatase.

EXAMPLE 1 AND COMPARATIVE EXAMPLES

The superiority of the presently claimed method for determining how to modify a rodent antibody or fragment thereof by resurfacing in order to produce a humanized rodent antibody will now be described by reference to the following example and comparative examples which are illustrative and are not meant to limit the present invention.

A) Analysis for Murine Antibodies

In order to determine the positions which are usually accessible on the surface of the $F_V$ domain of murine antibodies, the accessibility was calculated for twelve Fab x-ray crystallographic structures obtained from the Brookhaven database (Bernstein, F., Koetzle, T., Williams, G., Meyer, E., Brice, M., Rodgers, J., Kennard, O., Shimanouchi, T. and Tasumi, M. (1977), J. Mol. Biol. 112, pp. 535–542). The relative accessibility was calculated using the program MC (Pedersen, J. (1991)), which implements a modified version of the DSSP (Kabsch, W. and Sander, C. (1983), Biopolymers 22, pp. 2257–2637) accessibility calculation routine in which explicit atomic radii are specified for every atom. A residue was defined as being surface accessible when the relative accessibility was greater than 30%. The alignment positions of these residues were conserved in all twelve structures (98% identity). Surface accessible framework positions constitute 40% of the $F_V$ surface area. The remaining surface accessible residues are in the CDRs and in the interdomain C-terminal region. FIGS. 3A and 3B show a sequence alignment of the twelve crystal structures, the average relative accessibility, and the 30% accessibility cutoff. FIG. 3A shows the alignments and relative accessibility for the twelve murine antibody light chains and FIG. 3B shows the alignments and relative accessibility for the murine antibody heavy chains.

The surface accessible framework positions were mapped onto a database of unique human and mouse $F_V$ sequences (see lists at the end of this Example). The frequency of particular residues in each of these positions is shown in Table 1. Only residue frequencies higher than 5% are listed.

TABLE 1

Distribution of accessible residues in human $V_H$ and $V_L$ chain sequences. All of the positions appear to be conserved, which leads to the hyphothesis that immunogenecity arises from a specific combination of these surface residues. The sequence numbering is explained in FIGS. 3A and 3B.

| Position | Human | Mouse |
|---|---|---|
| Light chain | | |
| 1 | D 51 E 34 A 5 S 5 | D 76 Q 9 E 6 |
| 3 | V 38 Q 24 S 24 Y 6 | V 63 Q 22 L 5 |
| 5 | T 61 L 37 | T 87 |
| 9 | 9 26 S 26 G 17 A 14 L 7 | S 36 A 29 L 17 P 5 |
| 15 | P 62 V 25 L 12 | L 47 P 30 V 8 A 7 |
| 18 | R 57 S 18 T 13 P 6 | R 38 K 22 S 13 Q 12 T 9 |
| 46 | P 94 | P 82 S 9 |
| 47 | G 89 | G 71 D 18 |
| 51 | K 43 R 31 | K 70 Q 13 R 8 T 5 |
| 63 | G 91 | G 98 |
| 66 | D 43 S 25 A 9 | D 38 A 26 S 26 |
| 73 | S 96 | S 90 I 5 |
| 86 | P 44 A 27 S 17 T 8 | A 50 P 11 T 8 E 7 Q 6 |
| 87 | E 71 D 11 G 7 | E 91 D 6 |
| 111 | K 74 R 12 N 6 | K 93 |
| 115 | K 54 L 40 | K 87 L 5 |
| 116 | R 60 G 33 S 5 | R 89 G 9 |
| 117 | Q 50 T 37 E 6 P 6 | A 74 Q 14 P 5 R 5 |
| Heavy chain | | |
| 118 | E 47 Q 46 | E 59 Q 29 D 10 |
| 120 | Q 83 T 7 | Q 68 K 26 |
| 122 | V 59 L 15 Q 13 | Q 57 V 27 L 5 K 5 |
| 126 | G 54 A 23 P 18 | G 36 9 30 A 29 |
| 127 | G 53 E 22 A 14 D 7 | E 45 G 43 S 6 |
| 128 | L 61 V 31 F 7 | L 96 |
| 130 | K 46 Q 41 E 5 | K 52 Q 27 R 17 |
| 131 | P 95 | P 91 A 5 |
| 132 | G 74 S 16 T 7 | G 82 S 17 |

TABLE 1-continued

Distribution of accessible residues in human $V_H$ and $V_L$ chain sequences. All of the positions appear to be conserved, which leads to the hyphothesis that immunogenecity arises from a specific combination of these surface residues. The sequence numbering is explained in FIGS. 3A and 3B.

| Position | Human | Mouse |
|---|---|---|
| 136 | R 53 K 23 S 17 T 7 | K 66 S 17 R 13 |
| 143 | G 96 | G 98 |
| 145 | T 46 S 32 N 9 I 7 | T 63 S 19 N 7 A 5 D 5 |
| 160 | P 84 S 10 | P 89 H 7 |
| 161 | G 93 | G 71 E 24 |
| 162 | K 76 Q 10 R 8 | K 50 Q 30 N 10 H 5 |
| 183 | D 26 P 25 A 17 Q 10 T 7 | E 31 P 22 D 17 A 12 Q 11 |
| 184 | S 70 K 9 P 8 | K 42 S 37 T 6 |
| 186 | K 53 Q 22 R 7 N 5 | K 83 Q 7 |
| 187 | G 66 S 21 T 5 | G 62 S 18 D 10 |
| 195 | T 30 D 26 N 19 K 7 | T 36 K 30 N 26 D 6 |
| 196 | S 91 | S 76 A 16 |
| 197 | K 65 I 8 T 8 R 5 | S 46 K 34 Q 11 |
| 208 | R 46 T 18 K 17 D 6 | T 55 R 26 K 8 |
| 209 | A 50 P 21 S 13 T 8 | S 67 A 14 T 11 |
| 210 | E 46 A 18 D 13 S 9 Z 8 V 5 | E 88 D 7 |
| 212 | T 91 | T 53 S 43 |
| 222 | G 17 D 11 P 10 Y 9 V N 8 | D 67 A 18 |

None of the entire combinations of surface residues in the human sequences are found in the murine sequences and vice versa (see lists at the end of this Example). However, the residues in individual positions appear to be conserved (see Table 1). There are few residues which differ significantly between the species; these are at positions 54 and 91 of the L chain and 168 and 216 of the H chain. Of these positions only position 216 is a non conservative (V to Y) mutation. Differences between human and murine antigenicities are therefore believed to arise from the combinations of residues in these positions.

In order to determine whether the mouse sequences are more distantly related to human $F_V$ sequences than to other mouse $F_V$ sequences, the homology was calculated using a Dayhoff mutation matrix (Dayhoff, M., Barker, W. and Hunt, L. (1983), Meth. Enz. 91, pp. 524-545). The homology was calculated between all the sequences in a pool of both human and mouse sequence patches made up of the surface accessible residues. The data was then represented as a density map (not shown) in which the sequences are plotted against each other. The density map can be used to discriminate "murine surfaces" from "human surfaces".

B) Reshaping of Antibody N901

In order to test the resurfacing approach suggested by the above analysis, three humanization experiments were set up. 1) Traditional loop grafting (Verhoeyen, M. E., Saunders, J. A., Broderick, E. L., Eida, S. J. and Badley, R. A. (1991), Disease markers 9, pp. 3-4) onto a human $F_V$ framework of known structure (KOL). 2) Resurfacing approach using most similar chain. 3) Resurfacing approach using human sequences with most similar surface residues.

The antibody used was the murine anti-N901 antibody (Griffin et al. (1983), J. Imm. 130, pp. 2947-2951). The anti-N901 antibody (also referred to herein as the "N901 antibody") is available commercially from Coulter Corporation under the name NKH-1.

The alignment of the light chain sequences and heavy chain sequences in FIGS. 4A and 4B, respectively, show the original N901 antibody and the sequences used in each of the three approaches outlined here.

FIGS. 4A and 4B show alignments of sequences generated using the three methods of humanization. Sequences are: 1) Original rodent N901. 2+3) KOL (Marquart, M. Deisenhofer, J. and Huber, R. (1980), J. Mol. Biol. 141, pp. 369-391) and reshaped N901 using KOL surface. 4+5) Most homologous sequences, L(KV2F) (Klobeck, H., Meindl, A., Combriato, G., Solomon, A. and Zachau, H. (1985), Nucleic Acids Res., pp. 6499-6513) and H(G36005) (Schroeder, H. and Wang, J. (1990), Proc. Natl. Acad. Sci. U.S.A. 87) and reshaped N901 using these sequences. 6+7) Most homologous with respect to surface residues, L(KV4B) (Klobeck, H., Bronkamp, G., Combriato, G., Mocikat, R., Pohelnz, H. and Zachau, H. (1985), Nucleic Acids Res. 3, pp. 6515-6529) and H(PLO123) (Bird, J., Galili, N., Link, M., Sites, D. and Sklar, J. (1988), J. Exp. Med. 168, pp. 229-245), and reshaped N901 using these sequences. The numbering is the same as used in the antibody modelling program ABM (ABM is a trademark for commercial software, Oxford Molecular Ltd., Oxford, U.K.), which is based on structural conservation and not sequence homology as used by Padlan et al. (Kabat, E. A., Wu, T. T., Reid-Miller, M., Perry, H. M. and Gottesman, K. S. (1987), Sequences of Proteins of Immunological Interest. U.S. Department of Health and Human Services, Fourth Edition). The sequence changes which have to be introduced in order to reshape N901 with a given sequence are marked with bars, and back-mutations as determined from $F_V$ models are marked with stars. The sequence homology of a given sequence to N901 is shown in brackets after each sequence.

(1) Classical Humanization

In classical humanization the rationale is to graft the rodent CDR's onto a framework of known structure, such that CDR-framework interactions can be accurately monitored by homology modelling. The model of the humanized antibody is compared to that of the original rodent antibody, and possible CDR interacting framework residues are back mutated (marked with '*' in alignment) in order to retain the three-dimensional shape of the CDR's. In this example the antibody KOL was used, giving a low homology score of only 77 and 46 in the heavy and light chains respectively.

(2) Most Similar Chain Resurfacing

A database of nonredundant human antibody sequences was compiled from available protein and nucleotide sequences. A total of 164 H and 129 L chains were sampled.

Each of the rodent chains, L and H, were then matched and the most similar human sequence found independently (G36005/KV2F) (Schroeder, H. and Wang, J. (1990), Proc. Natl. Acad. Sci. U.S.A. 87); Klobeck, H., Meindl, A., Combriato, G., Solomon, A. and Zachau, H. (1985), Nucleic Acids Res., pp. 6499-6513). Surface residues, as outlined in Table 1, were then changed in the rodent sequences to match those of the human sequences. Subsequently a model was built of the resurfaced antibody and compared to the model of the original rodent antibody and back mutation of any CDR interacting residues was performed.

(3) Most Similar Surface Replacement According to the Present Invention

This method is identical to the above method, except that the similarity is calculated only over the surface residues outlined in Table 1 above.

The same procedure of surface mutation and subsequent back mutation was performed as in the previous methods. In this case the chosen sequences were PLO123/KV4B (Bird, J., Galili, N., Link, M., Sites, D. and Sklar, J. (1988), J. Exp. Med. 168, pp. 229-245); Klobeck, H., Bronkamp, G., Combriato, G., Mocikat, R., Pohelnz, M. and Zachau, H. (1985), Nucleic Acids Res. 3, pp. 6515-6529).

The following lists show the surface residue patterns in mouse and human light and heavy chain antibody variable regions. The sequences are ordered on similarity to one another. There are no pattern matches between mouse and human sequences although there are matches within a species.

| | MOUSE LIGHT CHAIN SURFACE PATCHES | | |
|---|---|---|---|
| 1 KV5E$MOUSE | :KTSLRPGKGSSDYEKK* | (SEQ ID NO: 40) |
| 2 PL0101 | :KTSLRPGKGSSEYEKK* | (SEQ ID NO: 41) |
| 3 N$1F19L | :QTSLRPDKGSSDHEKK* | (SEQ ID NO: 42) |
| 4 KV5U$MOUSE | :QTSLRPDKGSSDQEKK* | (SEQ ID NO: 43) |
| 5 MUSIGLDD | :QSSLRPDKGSSDQEKK* | (SEQ ID NO: 44) |
| 6 PL0220 | :QTSLRPDKGSSDPEKK* | (SEQ ID NO: 45) |
| 7 KV5J$MOUSE | :QTSLRPDKGSSDPZKK* | (SEQ ID NO: 46) |
| 8 MUSIGKABB | :QTSLRPDKGSSDPEKT* | (SEQ ID NO: 47) |
| 9 MUSIGKCLG | :QTSLRADKGSSDQEKK* | (SEQ ID NO: 48) |
| 10 MUSIGGVJ2 | :QTSLRPDKGKSDSEKK* | (SEQ ID NO: 49) |
| 11 MUSIGKCRN | :QTSLRPARGSSDQEKK* | (SEQ ID NO: 50) |
| 12 MUSIGKCLF | :QTSLKPGRGSSDPEKK* | (SEQ ID NO: 51) |
| 13 MUSIGKACM | :QTSLRPGRGSSDTEKK* | (SEQ ID NO: 52) |
| 14 MUSIGKABE | :QISLRPGKGSSDSEKK* | (SEQ ID NO: 53) |
| 15 KV5P$MOUSE | :QTSLRPGKGDSDEDKK* | (SEQ ID NO: 54) |
| 16 MUSIGKCMK | :ETALRPGKGASDADKK* | (SEQ ID NO: 55) |
| 17 KV3D$MOUSE | :VTALRPGKGASDEDKK* | (SEQ ID NO: 56) |
| 18 MUSIGKAAW | :VTALRPGKGASDEEKK* | (SEQ ID NO: 57) |
| 19 KV3G$MOUSE | :VTALRPGKGASBABKK* | (SEQ ID NO: 58) |
| 20 KV3E$MOUSE | :VTALRPGKGASDEDDE* | (SEQ ID NO: 59) |
| 21 MUSIGKAAZ | :QTSLRPDKGSSDQETT* | (SEQ ID NO: 60) |
| 22 MUSIGKCNE | :QNSLTPGKGSSSPEKK* | (SEQ ID NO: 61) |
| 23 MUSIGKBA | :VTKVRPGKGDSDSDKK* | (SEQ ID NO: 62) |
| 24 KV5A$MOUSE | :VTKVRPGKGDSDAEKK* | (SEQ ID NO: 63) |
| 25 MUSIGKV | :VTRVRPGKGDSDAEKK* | (SEQ ID NO: 64) |
| 26 MUSIGKCNM | :LTKVRPGKGDSDSEKK* | (SEQ ID NO: 65) |
| 27 MUSIGKCL1 | :VTKVRPGKGDSDSEQK* | (SEQ ID NO: 66) |
| 28 KV5B$MOUSE | :VTKVRPEKGDSDAEKK* | (SEQ ID NO: 67) |
| 29 MUSIGKCSA | :VTKVRPEKGDSDSEKK* | (SEQ ID NO: 68) |
| 30 MUSIGKCSR | :VTKVSPGKGDSDAEKK* | (SEQ ID NO: 69) |
| 31 MUSIGKCST | :VTKVRSGKGESDAEKK* | (SEQ ID NO: 70) |
| 32 MUSIGKAB | :VTSVKPGKGDSDAEKK* | (SEQ ID NO: 71) |
| 33 PL0014 | :VSSVKPGKGDSDAEKK* | (SEQ ID NO: 72) |
| 34 MUSIGKACU | :VTSAKPGKGDSDAEKK* | (SEQ ID NO: 73) |
| 35 PS0023 | :VSSAKPGKGDSDAEKK* | (SEQ ID NO: 74) |
| 36 N$2MCPL | :VTSARPGKGDSDAEKK* | (SEQ ID NO: 75) |
| 37 MUSIGKADV | :VSPAKPGKGDSDAEKK* | (SEQ ID NO: 76) |
| 38 MUSIGKCPF | :VTKARPGKGDSDVEKN* | (SEQ ID NO: 77) |
| 39 MUSIGLDE | :VTLIPPGKGDSDAEKK* | (SEQ ID NO: 78) |
| 40 MUSIGKCNZ | :VTLLQPGKGDSDAEKK* | (SEQ ID NO: 79) |
| 41 B27887 | :VTLLQPGKGDSDADKK* | (SEQ ID NO: 80) |
| 42 H28840 | :VTLLQPGKGDSDAERK* | (SEQ ID NO: 81) |
| 43 KV2G$MOUSE | :VTLLQAGKGDSDAEKK* | (SEQ ID NO: 82) |
| 44 C27887 | :VTLLQPGEGDSDAEKK* | (SEQ ID NO: 83) |
| 45 JL0029 | :LTLLQPGNGDSDAEKK* | (SEQ ID NO: 84) |
| 46 MUSIGKAEH | :VTLLQPGKGDSDAEKI* | (SEQ ID NO: 85) |
| 47 PS0074 | :VTLFQPGQGDSDPEKK* | (SEQ ID NO: 86) |
| 48 MUSIGKCNY | :VTLPQPGKGDSDAEKK* | (SEQ ID NO: 87) |
| 49 MUSIGKCNX | :VTLPQPGKGDWDAEKK* | (SEQ ID NO: 88) |
| 50 KV2D$MOUSE | :VTFLSPGQGDSDAEKK* | (SEQ ID NO: 89) |
| 51 MUSIGKADW | :ESSARPGKGDSDAEKK* | (SEQ ID NO: 90) |
| 52 KV2A$MOUSE | :VTLSSPGQGDSDAEKK* | (SEQ ID NO: 91) |
| 53 KV1A$MOUSE | :VTTAKPEKGDSDVEKK* | (SEQ ID NO: 92) |
| 54 F30534 | :VTTPKPDKGDSDVEKK* | (SEQ ID NO: 93) |
| 55 MUSIGKCLO | :VTAPRPGKGASSAEKK* | (SEQ ID NO: 94) |
| 56 G27887 | :VTAPKPGKGTSSAEKK* | (SEQ ID NO: 95) |
| 57 MUSIGVKV3 | :VTTPKPGKGASSAEKK* | (SEQ ID NO: 96) |
| 58 MUSIGKCNA | :VSAPKPGKGASSAEKK* | (SEQ ID NO: 97) |
| 59 S03410 | :VTAPRSGKGASSAEKK* | (SEQ ID NO: 98) |
| 60 B32456 | :VTAPKSGKGASSAEKK* | (SEQ ID NO: 99) |
| 61 PL0013 | :VTAPKPDKGVSSAEKK* | (SEQ ID NO: 100) |
| 62 MUSIGLAET | :VTAPKSEKGVSSAEKK* | (SEQ ID NO: 101) |
| 63 MUSIGVKV1 | :FTAPKPGKGASSAEKK* | (SEQ ID NO: 102) |
| 64 KV6K$MOUSE | :LTAPKPGRGVSSAEKK* | (SEQ ID NO: 103) |
| 65 G30560 | :VTAPKSGKGASSAEKR* | (SEQ ID NO: 104) |
| 66 MUSIGKBO | :VSAPKPGKEGSSAEKK* | (SEQ ID NO: 105) |
| 67 MUSIGKCNB | :VTAPKPRKGASSAEKK* | (SEQ ID NO: 106) |
| 68 H33730 | :VTFLSPGQGNSDAELP* | (SEQ ID NO: 107) |
| 69 MUSIGKCPC | :VTFLSPGQGNSDEDLP* | (SEQ ID NO: 108) |
| 70 KV2C$MOUSE | :VTLSSPQRGDSDAEKK* | (SEQ ID NO: 109) |
| 71 MUSIGLAV | :VTAPKSSKGGSSAEKK* | (SEQ ID NO: 110) |
| 72 MUSIGKCNH | :QTSPTPGKGSSDPEKK* | (SEQ ID NO: 111) |
| 73 KV5R$MOUSE | :QISLIPGKGSYDDEKK* | (SEQ ID NO: 112) |
| 74 KV6E$MOUSE | :VTALKSGKGASSAEKK* | (SEQ ID NO: 113) |
| 75 MUSIGKCNI | :VTALKSDKGASSGEKK* | (SEQ ID NO: 114) |

-continued

| | | |
|---|---|---|
| 76 MUSIGLDA | :VTPPSPGQGDSAAEKK* | (SEQ ID NO: 115) |
| 77 C26317 | :VTPPSPGQGDSAREKK* | (SEQ ID NO: 116) |
| 78 PS0073 | :VTVRKPGKGDSSDEKK* | (SEQ ID NO: 117) |
| 79 A23986 | :QTSVRLGQGSSDPEKK* | (SEQ ID NO: 118) |
| 80 MUSIGKABW | :KTSLRPWKGSSDSDKK* | (SEQ ID NO: 119) |
| 81 KV5D$MOUSE | :QTDVTQGQGSSQPEKK* | (SEQ ID NO: 120) |
| 82 MUSIGE6L | :QTAVSQGQGSSQSEKK* | (SEQ ID NO: 121) |
| 83 MUSIGKCOE | :LTAPRTNRGSSDSEKK* | (SEQ ID NO: 122) |
| 84 MUSIGKCKN | :VTAPSSHRGSSDTEKK* | (SEQ ID NO: 123) |
| 85 MUSIGLVD | :LLSLSPLKGDSDPEKV* | (SEQ ID NO: 124) |
| 86 S06822 | :VTAPTPDTGAIKTEKL* | (SEQ ID NO: 125) |
| 87 S06821 | :VTIPTPDTGAIKTEKL* | (SEQ ID NO: 126) |
| 88 MUSIGLAS | :AVSPTPDTGAIKTEKL* | (SEQ ID NO: 127) |
| 89 MUSIGLAR | :AVSPTPDTGAIKTEKL* | (SEQ ID NO: 128) |
| 90 LV2B$MOUSE | :AVSPTPDTGVIKTEKL* | (SEQ ID NO: 129) |
| 91 MUSIGLAN | :AVSPTPDTGAIKTEPS* | (SEQ ID NO: 130) |

HUMAN LIGHT CHAIN SURFACE PATCHES

| | | |
|---|---|---|
| 1 LV4A$HUMAN | :YLPPTPGVIRSTAMKL* | (SEQ ID NO: 131) |
| 2 LV4B$HUMAN | :YLPPTPGVIRSTAMRL* | (SEQ ID NO: 132) |
| 3 LV4E$HUMAN | :YLPPTPGLIRSTSMKL* | (SEQ ID NO: 133) |
| 4 LV4D$HUMAN | :YLPPTPGLIRSTSVKL* | (SEQ ID NO: 134) |
| 5 LV4C$HUMAN | :YLPPTPGVIRSTAEKL* | (SEQ ID NO: 135) |
| 6 LV5A$HUMAN | :YLPPTPGVIRSTAGKL* | (SEQ ID NO: 136) |
| 7 LV7A$HUMAN | :YLPATPGVVRSSAGML* | (SEQ ID NO: 137) |
| 8 LV2G$HUMAN | :SLPPSPGKVRSTAEKL* | (SEQ ID NO: 138) |
| 9 LV2I$HUMAN | :SLPPSPGKVRSTANKL* | (SEQ ID NO: 139) |
| 10 N$2RHE | :SLPPRPGKVRSSSEKL* | (SEQ ID NO: 140) |
| 11 HUMIGLAN | :SLPPRPGKVRSSSDKL* | (SEQ ID NO: 141) |
| 12 LV1A$HUMAN | :SLPPRPGRVRSSSEKL* | (SEQ ID NO: 142) |
| 13 LV1B$HUMAN | :SLPPRPGKVRSSSEQL* | (SEQ ID NO: 143) |
| 14 LV1F$HUMAN | :SLPPRPGKVRSSSEIL* | (SEQ ID NO: 144) |
| 15 LV1C$HUMAN | :SLPPKPGKIRSSTGKL* | (SEQ ID NO: 145) |
| 16 A29700 | :SLPPKPGKIRSSTGKL* | (SEQ ID NO: 146) |
| 17 HUMIGLAM4 | :SLPPKPGKIRSSTGQL* | (SEQ ID NO: 147) |
| 18 LV1D$HUMAN | :SLPPEPGKIRSSTGRL* | (SEQ ID NO: 148) |
| 19 LV2K$HUMAN | :SLAPSPGKIRSTAEKL* | (SEQ ID NO: 149) |
| 20 LV1I$HUMAN | :SLPPRPGKIRSSTGNV* | (SEQ ID NO: 150) |
| 21 LV2E$HUMAN | :SLRPSPGKVRSTAEKL* | (SEQ ID NO: 151) |
| 22 LV2D$HUMAN | :SLRPSPGKVRSTADKL* | (SEQ ID NO: 152) |
| 23 LV2C$HUMAN | :SLRPSPGKVRSTAENL* | (SEQ ID NO: 153) |
| 24 LV2J$HUMAN | :SLRPSPGKVRSAVEKL* | (SEQ ID NO: 154) |
| 25 LV1E$HUMAN | :SLPPRPGK-RSSAEKL* | (SEQ ID NO: 155) |
| 26 LV2B$HUMAN | :SLAPSPGKVRSTVERL* | (SEQ ID NO: 156) |
| 27 N$1MCWW | :SLAPSPDKIRSTPDKL* | (SEQ ID NO: 157) |
| 28 LV2H$HUMAN | :SLALSPGKVRSTAEKL* | (SEQ ID NO: 158) |
| 29 N$3MCG2 | :SLPLSAGKVRSTAEKL* | (SEQ ID NO: 159) |
| 30 LV2A$HUMAN | :SLAPSPGKVRSTAEYL* | (SEQ ID NO: 160) |
| 31 S02083 | :SLPLTPGLIRSTAEKL* | (SEQ ID NO: 161) |
| 32 HUMIGLAM2 | :SLPLTPRVIRSTAEKL* | (SEQ ID NO: 162) |
| 33 LV6C$HUMAN | :FLHPTPGTDSSSTEKL* | (SEQ ID NO: 163) |
| 34 LV6D$HUMAN | :FLLPTPGTDSSSTERL* | (SEQ ID NO: 164) |
| 35 LV6E$HUMAN | :FLHPTRVTDSSSTEKL* | (SEQ ID NO: 165) |
| 36 LV6B$HUMAN | :LLPPTPGTNSSSNDKL* | (SEQ ID NO: 166) |
| 37 HUMIGLK5G | :VLPLSPHRIRSESENL* | (SEQ ID NO: 167) |
| 38 HUMIGLVC | :SLAPSPAKFRSTAERD* | (SEQ ID NO: 168) |
| 39 HUMIGVLLS | :VTAPRPGRIRSDPEKK* | (SEQ ID NO: 169) |
| 40 HUMIGKAX | :VTAPRPGRVRSDPEKK* | (SEQ ID NO: 170) |
| 41 E30609 | :VTGPRPGRIRSDPEKK* | (SEQ ID NO: 171) |
| 42 KV3B$HUMAN | :VTGPRPGRIRSDPDKK* | (SEQ ID NO: 172) |
| 43 G30607 | :VTGPRPGRVRSDPEKK* | (SEQ ID NO: 173) |
| 44 KV3M$HUMAN | :VTGPRPGRIRSDPXKK* | (SEQ ID NO: 174) |
| 45 KV3H$HUMAN | :VTAPRPGRIRSESERK* | (SEQ ID NO: 175) |
| 46 KV3K$HUMAN | :VTGPSRGRIRSDPEKK* | (SEQ ID NO: 176) |
| 47 KV3F$HUMAN | :VTVPRPSRIRSESERK* | (SEQ ID NO: 177) |
| 48 B26555 | :VTAPGPGRIRSESERK* | (SEQ ID NO: 178) |
| 49 KV1Q$HUMAN | :QTSVRPGRVRSDPERK* | (SEQ ID NO: 179) |
| 50 KV1W$HUMAN | :QTSVRPGKVRSDPERK* | (SEQ ID NO: 180) |
| 51 KV1M$HUMAN | :QTSVRPGKVRSDPEKK* | (SEQ ID NO: 181) |
| 52 KV1R$HUMAN | :QTSVRPGKVRSEPEKK* | (SEQ ID NO: 182) |
| 53 KV1F$HUMAN | :QTSVRPGKVRSEPDKK* | (SEQ ID NO: 183) |
| 54 KV1G$HUMAN | :QTSVRPGKVRAEPEKK* | (SEQ ID NO: 184) |
| 55 KV1K$HUMAN | :QTSVRPGKVRSBPZKK* | (SEQ ID NO: 185) |
| 56 KV1D$HUMAN | :QTSVRPGKVRSDPBKK* | (SEQ ID NO: 186) |
| 57 KV1H$HUMAN | :QTSVRPGQVRSDPERK* | (SEQ ID NO: 187) |
| 58 KV1B$HUMAN | :QTSVRPGKVRSHPEKK* | (SEQ ID NO: 188) |
| 59 B27585 | :QTSVRPGNVRSDPDKK* | (SEQ ID NO: 189) |
| 60 N$1REIA | :QTSVRPGKVRSDPEKT* | (SEQ ID NO: 190) |
| 61 KV1X$HUMAN | :QTSVRPGTVRSEPEKK* | (SEQ ID NO: 191) |

| | | |
|---|---|---|
| 62 KV1L$HUMAN | :QTSVRPEKVRSEPDKK* | (SEQ ID NO: 192) |
| 63 IMGL38 | :QTSVRPGKVRSESDKK* | (SEQ ID NO: 193) |
| 64 A27585 | :QTSVRPGEVRSEPDKK* | (SEQ ID NO: 194) |
| 65 KV1N$HUMAN | :QTSVRPGBVRSBPZRK* | (SEQ ID NO: 195) |
| 66 KV1C$HUMAN | :QTSVSPGKVRSDPEKK* | (SEQ ID NO: 196) |
| 67 KV1V$HUMAN | :QTSVRPGKVNSDPEKK* | (SEQ ID NO: 197) |
| 68 KV1T$HUMAN | :QTSVRPGKVRSDPDTK* | (SEQ ID NO: 198) |
| 69 KV1U$HUMAN | :QTSVRPKKVRSDPZKK* | (SEQ ID NO: 199) |
| 70 KV1A$HUMAN | :QTSVRPKKVRFDPEKK* | (SEQ ID NO: 200) |
| 71 KV1S$HUMAN | :QTSVRSGKVRSEPETK* | (SEQ ID NO: 201) |
| 72 KV4A$HUMAN | :VTNLRPGKVRSDAEKK* | (SEQ ID NO: 202) |
| 73 KV4C$HUMAN | :VTDLRPGKVRSDAEKK* | (SEQ ID NO: 203) |
| 74 HUMIGK2A1 | :QTSVSPGNIRSESDKK* | (SEQ ID NO: 204) |
| 75 HUMIGKBA | :KTSVTPGKFRSEPEKK* | (SEQ ID NO: 205) |
| 76 HUMIGKBC | :VTILLPPGRVRSDAEKK* | (SEQ ID NO: 206) |
| 77 KV2B$HUMAN | :VTILLPPGEVRSDAEKK* | (SEQ ID NO: 207) |
| 78 KV2D$HUMAN | :VTLPPPGZVRSDAERK* | (SEQ ID NO: 208) |
| 79 KV2C$HUMAN | :VTLPPPGZVRSBAZNK* | (SEQ ID NO: 209) |
| 80 KV2E$HUMAN | :VTLPPPQQVRSDAEKK* | (SEQ ID NO: 210) |
| 81 S03876 | :VTLPPPGQVTSDAEKK* | (SEQ ID NO: 211) |
| 82 KV2A$HUMAN | :VTLPPAGQVRSDAEKR* | (SEQ ID NO: 212) |
| 83 HUMIGLAM5 | :ALSPSSGQSSSASERL* | (SEQ ID NO: 213) |

| MOUSE HEAVY CHAIN SURFACE PATCHES | | |
|---|---|---|
| 1 MUSIGHIT | :EKVGGLQPGRGTPGKASRGDSQRPES* | (SEQ ID NO: 214) |
| 2 MUSIGHIU | :EKVGGLQPGRGTPGKVSRGDSQRPES* | (SEQ ID NO: 215) |
| 3 MUSIGHIV | :EKVGGLQPGTGAPGKASRGDSQRPES* | (SEQ ID NO: 216) |
| 4 MUSIGHYM | :EKVGGLQPGRGTPGKASKGNSQRAES* | (SEQ ID NO: 217) |
| 5 PU0003 | :EKMGGLQPGRGTPGKASKGNSQRAES* | (SEQ ID NO: 218) |
| 6 MUSIGHF0 | :EKVGGLQPGRGTPGKASKGTSQRAES* | (SEQ ID NO: 219) |
| 7 A30515 | :EKVGGLQPGRGTPGKASKGTSQRAET* | (SEQ ID NO: 220) |
| 8 PL0018 | :EKVGGLKPGRGTPGKASKGTSQRAET* | (SEQ ID NO: 221) |
| 9 MUSIGHFK | :ENVGGLQPGRGTPGKASKGTSQRAET* | (SEQ ID NO: 222) |
| 10 MUSIGHFQ | :EKVGGLQSGRGTPGKASKGTSQRAET* | (SEQ ID NO: 223) |
| 11 PU0001 | :EKVGGLQSGRGTPGKASKGTSQRAES* | (SEQ ID NO: 224) |
| 12 E30540 | :EKVGGLQPGRGTPGKASKGISQRAER* | (SEQ ID NO: 225) |
| 13 HV17$MOUSE | :EKVGGLQPGRGTPGKSAKGBSZRAQS* | (SEQ ID NO: 226) |
| 14 MUSIGHLN | :EKVGGLQPGSGTPGKASKGNSQRAES* | (SEQ ID NO: 227) |
| 15 MUSIGHKG | :EKVGGLQPGSGTPGKASKGSSQRAES* | (SEQ ID NO: 228) |
| 16 PU0004 | :EKVGGLQPGRGTPRKASKGNSQRAES* | (SEQ ID NO: 229) |
| 17 MUSIGHKJ | :EKMGNLQPGSGTPGKASKGNSQRPDS* | (SEQ ID NO: 230) |
| 18 HV56$MOUSE | :EKVGGLKPGKGTPEKDSKGNARRSET* | (SEQ ID NO: 231) |
| 19 C27888 | :EKVGGLKPGKGAPEKDSKGNARRSET* | (SEQ ID NO: 232) |
| 20 MUSIGHAAF | :EKVGGLKPGKGTPERDSKGNARRSET* | (SEQ ID NO: 233) |
| 21 PH0097 | :DKVGGLKPGKGTPEKDSKGNAKRSET* | (SEQ ID NO: 234) |
| 22 E27888 | :DKVGGLKPGKGTPEKDSKGNAKRSET* | (SEQ ID NO: 235) |
| 23 MUSIGHJB | :DKVGGLKPGKGTPDKDNKGNAKKSET* | (SEQ ID NO: 236) |
| 24 MUSIGHADL | :EKVGGLTPGKGTPEKDSKGNGRRSET* | (SEQ ID NO: 237) |
| 25 A27888 | :EMVGGLKPGKGTPEKDSKGNDRRSET* | (SEQ ID NO: 238) |
| 26 H27887 | :EMVGGLKPGKGTPEKDSKGNDRRSET* | (SEQ ID NO: 239) |
| 27 B27888 | :EMVGGLKPGKGTPEKDSKGNAKRSET* | (SEQ ID NO: 240) |
| 28 B27889 | :EQVGGLKPGKGTPEKDSKGNAKKSET* | (SEQ ID NO: 241) |
| 29 D27889 | :EQVGGLKPGKGTPEKDTKGNAKKSET* | (SEQ ID NO: 242) |
| 30 HV55$MOUSE | :EQVGGLKPGKGAPEKDTKGNAKKSET* | (SEQ ID NO: 243) |
| 31 MUSIGHAGT | :EKVGGLQPGKGTPEKDSKGNAKKSET* | (SEQ ID NO: 244) |
| 32 MUSIGVH50 | :EKVGGLQPGKGTPEKDTKGNAKKSET* | (SEQ ID NO: 245) |
| 33 MUSIGHIW | :EKVGGLQPGRGTPEKDTKGNAKKSET* | (SEQ ID NO: 246) |
| 34 MUSIGHAGZ | :EKVGGLQPGKGSPEKDSKGNAKKSET* | (SEQ ID NO: 247) |
| 35 PH0098 | :DKMGGLKPGKGTPEKDSKGNAKQSET* | (SEQ ID NO: 248) |
| 36 MUSIGHIN | :EQVGGLQPGKGTPDKDSKGNAKKSET* | (SEQ ID NO: 249) |
| 37 MUSIGHAGY | :EKVGGLQPGKGTPEKDSKGNAEKSET* | (SEQ ID NO: 250) |
| 38 MUSIGHMP | :EQVGDLKPGKGTPEKDTKGNARRSET* | (SEQ ID NO: 251) |
| 39 D27888 | :ENVGDLKPGKGAPEKDSKGNARRSET* | (SEQ ID NO: 252) |
| 40 MUSIGHIP | :EQVGGLQPGKGTSDKDSKGNAKKSET* | (SEQ ID NO: 253) |
| 41 MUSIGHAGS | :EQVGGLKPGKGTPEKDSKGNAKKSGT* | (SEQ ID NO: 254) |
| 42 HV16$MOUSE | :DQVGGLQPGKGTPEKDTKGNPKRSET* | (SEQ ID NO: 255) |
| 43 B34871 | :DQVGGLQPGQGTPEKNTKGNPKRSET* | (SEQ ID NO: 256) |
| 44 PH0094 | :EKVGGLQPGKGTSEKDIKGNAKKSET* | (SEQ ID NO: 257) |
| 45 PH0096 | :DKVGGLKPGKRTPEKDNKGNAKKSET* | (SEQ ID NO: 258) |
| 46 MUSIGVH62 | :DKVGGLKLGKGTPEKDTKGNAKKSET* | (SEQ ID NO: 259) |
| 47 MUSIGHAGR | :EKVGGLQPGKGTPEKDSKGNANTSET* | (SEQ ID NO: 260) |
| 48 HV58$MOUSE | :EHVGGLKPGKGTPEKDSKGNAGRSET* | (SEQ ID NO: 261) |
| 49 H27888 | :EQVGGLQPGNGTPEKDTTGNAKRSET* | (SEQ ID NO: 262) |
| 50 HV34$MOUSE | :EKEGGLQPGKGTPEKESKGDSKRAET* | (SEQ ID NO: 263) |
| 51 HV33$MOUSE | :EKEGGLQPGKGTPEKESKGDSKRPET* | (SEQ ID NO: 264) |
| 52 MUSIGHZAB | :EKEGGLKPGKGSPEKESKGDSKRAET* | (SEQ ID NO: 265) |
| 53 N$4FABH | :EKDGGLQPGKGTPEKDSKGDSKRVEM* | (SEQ ID NO: 266) |
| 54 I27888 | :EQVGGLKPGRGTPEKDTTGDAQRSET* | (SEQ ID NO: 267) |
| 55 G27888 | :EQVGGLKPGRGTPEKDTTGNAKGSET* | (SEQ ID NO: 268) |

| | | |
|---|---|---|
| 56 HV59$MOUSE | :EKVGGSKPGKGTPEKDSKGNAKTSET* | (SEQ ID NO: 269) |
| 57 MUSIGHOE | :SDQGGLKPGKGTPEKDTKGNARRSES* | (SEQ ID NO: 270) |
| 58 N$2FVWH | :EKIGGLQPGKGDPGKPSKDNAKRSET* | (SEQ ID NO: 271) |
| 59 MUSIGHJT | :EKLGGLQPGKGDPGKPSKDNAKRSET* | (SEQ ID NO: 272) |
| 60 MUSIGHLY | :EKLGGLQPGKGDPGKPFKDNAKRSET* | (SEQ ID NO: 273) |
| 61 S06816 | :EKLGGLQPGKGDPGKLMKENAKRSET* | (SEQ ID NO: 274) |
| 62 S06817 | :ENLGGLQPGKGDPGKLXENAKRPET* | (SEQ ID NO: 275) |
| 63 MUSIGHAAI | :EKLGGLQPGNGDLGKPSKDNAKRSET* | (SEQ ID NO: 276) |
| 64 HV42$MOUSE | :EKLGPLQLGKGDPGKPSKDDAKRSET* | (SEQ ID NO: 277) |
| 65 MUSIGHAAL | :EQLGGLQPGGGTPGKPSKDNDKRSET* | (SEQ ID NO: 278) |
| 66 MUSIGHABO | :EQLGGLQPGGGTPGKASKDNDKRSET* | (SEQ ID NO: 279) |
| 67 MUSIGHEG | :EQVGGLKARKGTPEKDTTGNAKRSET* | (SEQ ID NO: 280) |
| 68 MUSIGHWN | :EMVGVLEPGKGTPEKRQEGNAKRSET* | (SEQ ID NO: 281) |
| 69 MUSIGKCLT | :EQVGGLQPKKGSPGKDSKDDSQKTET* | (SEQ ID NO: 282) |
| 70 MUSIGHZAE | :EQVGGLQPKKGSPGKDSKDDSQKTER* | (SEQ ID NO: 283) |
| 71 MUSIGHAAD | :QQVPELKPGRGTPGKEDKGTSARNDT* | (SEQ ID NO: 284) |
| 72 MUSIGHAAW | :QQVPELKPGKGTPGKDDKGTSAKNET* | (SEQ ID NO: 285) |
| 73 MUSIGHAMA | :QQVPELKPGKGTPGKDDKGTSAKNEM* | (SEQ ID NO: 286) |
| 74 MUSIGHXZ | :QQKPELKPGKGSPGQEKKSTSSTSET* | (SEQ ID NO: 287) |
| 75 A30502 | :EQQPELKPGKGTPGQEKKGKSSTSES* | (SEQ ID NO: 288) |
| 76 MUSIGHAAG | :EQQPELRPGKGTPGQEKKGKSSTSES* | (SEQ ID NO: 289) |
| 77 B30502 | :EQQPELKPGKGTPGQEKKGKSSASES* | (SEQ ID NO: 290) |
| 78 MUSIGHADG | :EQQPELKPGKGTPGKQKKGKSSTSES* | (SEQ ID NO: 291) |
| 79 MUSIGHFV | :EQQPELKPGKGTHGKQKKGKSSTSES* | (SEQ ID NO: 292) |
| 80 MUSIGHAANA | :EQQPELKPGKGSHGKQKKGKSSTSES* | (SEQ ID NO: 293) |
| 81 MUSIGHZR | :EQQPELKPGKGSHGKQKKGKSSASES* | (SEQ ID NO: 294) |
| 82 MUSIGHAI | :EQQPELKPGKGTHGKQKKGKSSTFES* | (SEQ ID NO: 295) |
| 83 MUSIGHALA | :EQQPELKPGKGTHGKQKQGKSSTFES* | (SEQ ID NO: 296) |
| 84 PL0011 | :EQQPELKPGKGTHGKEKKDKSSTSES* | (SEQ ID NO: 297) |
| 85 MUSIGKCLS | :EQQAELKPGKGSHGKQKKGKSSTSES* | (SEQ ID NO: 298) |
| 86 MUSIGHADY | :EQQPELKPGKGTHGKQKKSNSSTSES* | (SEQ ID NO: 299) |
| 87 MUSIGHWVX | :QQQAELRPGKGAPGQEKKGKSSTSES* | (SEQ ID NO: 300) |
| 88 MUSIGHADO | :QQQAELRPGKGAPGQEKKGKSSTSDS* | (SEQ ID NO: 301) |
| 89 MUSIGHVEM | :QQQAELRPGKGVPGQEKKGKSSTSDS* | (SEQ ID NO: 302) |
| 90 A24672 | :QQQPELKPGKGAPGKGKKGKSSTSES* | (SEQ ID NO: 303) |
| 91 MUSIGHJG | :QQQPELKPGKGAPGKGKKKSSTSES* | (SEQ ID NO: 304) |
| 92 JL0044 | :EQQPEAKPGKGTHGKQKKGKSSTSDS* | (SEQ ID NO: 305) |
| 93 MUSIGHBA | :QQQAELRPGKGTHGKEKKDKSSTSDS* | (SEQ ID NO: 306) |
| 94 MUSIGHAGP | :QQQAELRPGKGAPGQGKKGKSSTSES* | (SEQ ID NO: 307) |
| 95 MUSIGHVBK | :QQQAELKPGRGTPGQEKKGKSSTSES* | (SEQ ID NO: 308) |
| 96 A36194 | :EQQAELRAGKGTPGQEKKGKSSTSES* | (SEQ ID NO: 309) |
| 97 MUSIGHVBJ | :EQQAELRPGKGTPGQEKKGTSSTSES* | (SEQ ID NO: 310) |
| 98 MUSIGHADV | :QQQAELRPGKGTPGHEKKGTSSTSES* | (SEQ ID NO: 311) |
| 99 MUSIGHAAT | :QQQAELKPGKGTPGHEKKGTSSTSES* | (SEQ ID NO: 312) |
| 100 MUSIGHJL | :QQQAELRPGKGTPGHENKGTSSTSES* | (SEQ ID NO: 313) |
| 101 MUSIGHABM | :QQQAEVRPGKGTPGHEKKGTSSTSES* | (SEQ ID NO: 314) |
| 102 MUSIGHFU | :QQQAELKPGKGTPGHENKGTSSTSES* | (SEQ ID NO: 315) |
| 103 MUSIGHZZB | :QQQAELRPGKGTPGQKKGKSSASES* | (SEQ ID NO: 316) |
| 104 HV06$MOUSE | :HQQAELKPGKGTPGQQKKGKSSTSES* | (SEQ ID NO: 317) |
| 105 MUSIGHRD | :EQQVELRAGKGTPGQEKKGKSSTSES* | (SEQ ID NO: 318) |
| 106 MUSIGHVBH | :EQQAELRPGKGTPGQEKQGTSSTSES* | (SEQ ID NO: 319) |
| 107 HV01$MOUSE | :EQQAELRPGKGTPGHDNKGTSSTSES* | (SEQ ID NO: 320) |
| 108 MUSIGHADN | :QQQAEVRPGKGTPGHEKKGRSSTSES* | (SEQ ID NO: 321) |
| 109 HV05$MOUSE | :QQQAELRPGKGTPGQQKKDKSSTSES* | (SEQ ID NO: 322) |
| 110 MUSIGHAEF | :QQQAELKPGKGTPGQQKKDKSSTSES* | (SEQ ID NO: 323) |
| 111 MUSIGHAAN | :QQQAELKPGKGTPGQQKKDKSSTSDS* | (SEQ ID NO: 324) |
| 112 MUSIGHAAB | :QQQAELKPGKGSPGQQKKDKSSTSES* | (SEQ ID NO: 325) |
| 113 C30560 | :QHQAELKPGKGTPGQQKKNKSSTSES* | (SEQ ID NO: 326) |
| 114 PS0024 | :QQQAELKPGKGTPGQQNKDKSSTSES* | (SEQ ID NO: 327) |
| 115 MUSIGHRG | :EQQAELRAGKGIPGQEKKGKSSTSES* | (SEQ ID NO: 328) |
| 116 MUSIGHAAE | :QQQAELKPGKGTPGQEKKSKSSTSES* | (SEQ ID NO: 329) |
| 117 MUSIGHLX | :QQQSELKPGKGTPGQEKKSKSSTSES* | (SEQ ID NO: 330) |
| 118 HV04$MOUSE | :QQQTELKPGKGTPGQEKKSKSSTSES* | (SEQ ID NO: 331) |
| 119 MUSIGHVBG | :EQQAELRTGKGTPGQERKGKSSTSES* | (SEQ ID NO: 332) |
| 120 MUSIGHMX | :QQQAELKPGKGTPGQQKKDKSSTFES* | (SEQ ID NO: 333) |
| 121 MUSIGHAAR | :EQQAELRPGTGAPGQEKKGKSSTSES* | (SEQ ID NO: 334) |
| 122 HV15$MOUSE | :QQQPEVRPGKGTHAKQKKGKSSTSES* | (SEQ ID NO: 335) |
| 123 MUSIGHAAU | :QQQPEVRPGKDTHAKQKKGKSSTSES* | (SEQ ID NO: 336) |
| 124 MUSIGHVBO | :QQQAELKPGKGTPEQEKKGKSSTSES* | (SEQ ID NO: 337) |
| 125 A26405 | :EQQTELRAGKGTPGQEKKGRSSTSEA* | (SEQ ID NO: 338) |
| 126 HV10$MOUSE | :QQQAELKPGKGTPGREKKSKPSTSES* | (SEQ ID NO: 339) |
| 127 MUSIG3B44 | :QQQSELKPGKGTPGREKKSKPSTSES* | (SEQ ID NO: 340) |
| 128 MUSIG3B62 | :QQRAELKPGKDTPGREKKNKPSTSES* | (SEQ ID NO: 341) |
| 129 HV09$MOUSE | :QQQAELKPGKGTPGREKKSTSSTSES* | (SEQ ID NO: 342) |
| 130 MUSIGKCLP | :QQQAELKPGKGTPGQEKKSTSSTSDS* | (SEQ ID NO: 343) |
| 131 MUSIGBH | :QQQAELRPGKGTPIQQKKDKSSTSES* | (SEQ ID NO: 344) |
| 132 HV11$MOUSE | :QQQAEFKPGKGTPGREHRSKPSTSES* | (SEQ ID NO: 345) |
| 133 MUSIGHMC | :QQQAELRPGKGALGQEKKGKSSTSDS* | (SEQ ID NO: 346) |
| 134 MUSIGHAGW | :QQQPEVKPGKGAPKGKNTDKSSTSES* | (SEQ ID NO: 347) |
| 135 MUSIGHRF | :EQQAEVRAGKGSPGQEKKGKSSTSES* | (SEQ ID NO: 348) |

| | | |
|---|---|---|
| 136 MUSIGHVAD | :QQLAELKPGKGTPGHEKKGISSTSES* | (SEQ ID NO: 349) |
| 137 MUSIGHVAF | :QQQAELKPGKGKPEQEKKGTSSTSES* | (SEQ ID NO: 350) |
| 138 PL0012 | :QQQPELKPGKGRNGKENKGKSSTSES* | (SEQ ID NO: 351) |
| 139 MUSIGGVD2 | :QQQTELRPGKGRGTTGQERKGKSSTSES* | (SEQ ID NO: 352) |
| 140 S06824 | :QHQAELKPGKGTPGHENKVTSSTSES* | (SEQ ID NO: 353) |
| 141 MUSIGHRD | :EQQAELRAGKGTPGQEQKAKSSTSES* | (SEQ ID NO: 354) |
| 142 MUSIGHAAE | :QQQAELKPGKGTPGQQKTGTSSTIES* | (SEQ ID NO: 355) |
| 143 MUSIGHHS | :QQQAELKPGKGNPGQEKKSTSSASES* | (SEQ ID NO: 356) |
| 144 MUSIGHAXA | :EQQTVLRPGKGTPGQQKKGTSATNES* | (SEQ ID NO: 357) |
| 145 HV50$MOUSE | :QQLTELKPGNGTPGQEKKSKSSTSES* | (SEQ ID NO: 358) |
| 146 MUSIGHVBP | :QQQSVLRPGKGTPGQEKKGTSSTSKS* | (SEQ ID NO: 359) |
| 147 PH0100 | :LQQPVLKPGKGSHGKQKKDKSSTSES* | (SEQ ID NO: 360) |
| 148 MUSIGHAYA | :EQQPETKPGKGTLGKQKKSKSSTSES* | (SEQ ID NO: 361) |
| 149 MUSIGHCP2 | :QQQAELKPGQGTPGQEKKNKSSTPEF* | (SEQ ID NO: 362) |
| 150 MUSIGHDZ | :EQQAELRPGKGNPEQPKQGTSSTSET* | (SEQ ID NO: 363) |
| 151 MUSIGHNPI | :EQQAELRPGKGNPEQPKQGTSTTSET* | (SEQ ID NO: 364) |
| 152 S06823 | :EQQAELKPGKGNPEQPKQGTSSTSET* | (SEQ ID NO: 365) |
| 153 MUSIGHASA | :EQQAELKPGKGNPEQPKQDTSSTSET* | (SEQ ID NO: 366) |
| 154 S03484 | :EQQAELKPGKGNPEQPKQGTSSTSGT* | (SEQ ID NO: 367) |
| 155 MUSIGHVAA | :EQQAEVKPGKGNPEQPKQGTSSTSET* | (SEQ ID NO: 368) |
| 156 MUSIGHNPD | :EQQAELRPGKGNPEQPKQVTSSTSET* | (SEQ ID NO: 369) |
| 157 MUSIGHNPB | :EQQAELRPGKGNPEQPKQITSSTSET* | (SEQ ID NO: 370) |
| 158 MUSIGHEC | :EQQAELRPGRGNPEQPKQVTSSTSET* | (SEQ ID NO: 371) |
| 159 MUSIGHNPC | :EQQAELRPGRGNPEQPKHVTSSTSET* | (SEQ ID NO: 372) |
| 160 MUSIGHNPF | :EQQAELRPGKGNTEQPKQVTSSTSET* | (SEQ ID NO: 373) |
| 161 MUSIGHNPE | :EQQAELKPGKGNTEQPKLITSSTSET* | (SEQ ID NO: 374) |
| 162 A27635 | :TGQAELRPGKGAPEQGKKGKSSTSDR* | (SEQ ID NO: 375) |
| 163 MUSIGHXW | :QYQAELRPGKGTPRQQKKGKSSTSES* | (SEQ ID NO: 376) |
| 164 MUSIGHIZA | :QQQAVLRHGKGTHGQEKKGKSSTSES* | (SEQ ID NO: 377) |
| 165 MUSIGHEM | :QQQTKLGPGRGTPGQGRKGKSSTSGS* | (SEQ ID NO: 378) |
| 166 MUSIGHRH | :EQQAELRAGKGTPGQEKKGKSSVYFA* | (SEQ ID NO: 379) |
| 167 HV00$MOUSE | :EQQAELKAGKGTPGQQKQGESTRSET* | (SEQ ID NO: 380) |
| 168 N$1F9H | :QQKAELAASKGTPGQEKKGRSSTSES* | (SEQ ID NO: 381) |
| 169 MUSIGHZAD | :QQQTELRPGKGTPGQEKRGKSSNLRL* | (SEQ ID NO: 382) |
| 170 B30515 | :EKVGGLQGSSFDPGKASKGTSQRAET* | (SEQ ID NO: 383) |
| 171 MUSIGHEB | :EQQADLKLGKGNPEQPKLATPSTSET* | (SEQ ID NO: 384) |
| 172 E27889 | :EQVGGLKPGKGTPDKSDVKDNAKSET* | (SEQ ID NO: 385) |
| 173 MUSIGHAAC | :DQQPDLKPSSGSPGHPSKSTSKTTET* | (SEQ ID NO: 386) |
| 174 HV61$MOUSE | :DQQPDLKPSSGSPGNPSKSTSKTTET* | (SEQ ID NO: 387) |
| 175 MUSIGVHR2 | :DQQPDLKPSSGSPGNPSKSTSKTAET* | (SEQ ID NO: 388) |
| 176 PL0100 | :DQQPGLKPSSGSPGNPSKSTSKTTET* | (SEQ ID NO: 389) |
| 177 MUSIGHAAO | :DQQPGLKPSSGSPGNPSKNTSKTTET* | (SEQ ID NO: 390) |
| 178 MUSIGHGA6 | :DQQPGLKPSSGSPGDPSKTTSKTTET* | (SEQ ID NO: 391) |
| 179 MUSIGHJY | :DQQPGLKPSSGSPGNPSKTTSKTTET* | (SEQ ID NO: 392) |
| 180 MUSIGHGA1 | :DHQPGLKPSSGSPGNPSKNTSKTTET* | (SEQ ID NO: 393) |
| 181 MUSIGHXX | :DQQPGLKPSSGSPGNPSRSTSKTTET* | (SEQ ID NO: 394) |
| 182 HV62$MOUSE | :DQQPGLKPSAGSPGNPSKSTSKTAET* | (SEQ ID NO: 395) |
| 183 MUSIGHAAGA | :EQQPGLKPSSGSPGNPSKSTSKTSET* | (SEQ ID NO: 396) |
| 184 MUSIGHGA5 | :DQQPGLKPSSGSPGNPSKNTSKTIET* | (SEQ ID NO: 397) |
| 185 MUSIGHGA4 | :DQQPGLKPSSGSPGDPSKNTSKTPET* | (SEQ ID NO: 398) |
| 186 MUSIGHAGI | :EQQPSLKPSSGSPGNPSKSTSKTTET* | (SEQ ID NO: 399) |
| 187 PL0102 | :DQQPGLKPSSGSPGNPSKNTSETTET* | (SEQ ID NO: 400) |
| 188 HV46$MOUSE | :DQQPGLKPSSGSPGNPSKNTSETTZT* | (SEQ ID NO: 401) |
| 189 MUSIGHZT | :EQQPSLKPSSGSPGNPSKSTSKTSET* | (SEQ ID NO: 402) |
| 190 MUSIGHAGD | :EQQPSLKPSSGSPGNPSKSTSRTTET* | (SEQ ID NO: 403) |
| 191 MUSIGHAGO | :EQQPSLKPSSGSPGNPSKSTSKTAET* | (SEQ ID NO: 404) |
| 192 MUSIGAM32 | :DQQPDLKPSSGFPGNPSKSTSKTTET* | (SEQ ID NO: 405) |
| 193 MUSIGHAFX | :EQQPSLKPSSGSPGKPSKSTSKTNET* | (SEQ ID NO: 406) |
| 194 MUSIGHAGE | :EQQPSLKPSSGSPGNPSKSTFKTSET* | (SEQ ID NO: 407) |
| 195 MUSIGHAGB | :EQQPSLKPSSGSPGNPSKSTSTTSET* | (SEQ ID NO: 408) |
| 196 MUSIGHAGC | :EQQLSLKPSSGSPGNPSKSTSKTTET* | (SEQ ID NO: 409) |
| 197 MUSIGHAAM | :QQQPGLKPSFGPPGKPSQSTSKTTET* | (SEQ ID NO: 410) |
| 198 HV43$MOUSE | :QQKPGLAPSSGSPGKSTKSNSKQTDT* | (SEQ ID NO: 411) |
| 199 MUSIGMUV1 | :QQKPGLAPSSGSPGKSAKSNSKQTDT* | (SEQ ID NO: 412) |
| 200 MUSIGHAEI | :QQKPGLAPSSGSPGKSAMSNSKQTDT* | (SEQ ID NO: 413) |
| 201 MUSIGHBP | :QQKPGLAPSSGSPGKSAISNSKQTDT* | (SEQ ID NO: 414) |
| 202 MUSIGHZZA | :QQKPGLQPSSGSPGKAAISNSKQSNT* | (SEQ ID NO: 415) |
| 203 MUSIGMUV2 | :QQKPGLQPSSGSPGKAAISNSKQANT* | (SEQ ID NO: 416) |
| 204 A32456 | :QQKPVLAPSSGSPGKSAMSNSKQIDT* | (SEQ ID NO: 417) |
| 205 MUSIGHMB | :QQKPSLQPSSDSPGKAAMSNSKQADT* | (SEQ ID NO: 418) |

| HUMAN HEAVY CHAIN SURFACE PATCHES | | |
|---|---|---|
| 1 HUMIGHVS | :ERVGDLEPGRGIPGKAPKGDSKKIET* | (SEQ ID NO: 419) |
| 2 HUMIGHVR | :ERVGDLEPERGIPGKAPKGDSKKIET* | (SEQ ID NO: 420) |
| 3 H36005 | :EQVGGLKPGRGTPGKAPKGDSKKTET* | (SEQ ID NO: 421) |
| 4 PL0122 | :EQVGGLQPGKGTSGKASKGDSKKTET* | (SEQ ID NO: 422) |
| 5 HV3D$HUMAN | :EQLGGLQPGRGTPGKBSKGDSKRAET* | (SEQ ID NO: 423) |
| 6 HUMIGHAT | :EQLGGLQPGRGTPGKDSKGNSKRAET* | (SEQ ID NO: 424) |
| 7 B34964 | :EQLGGLQPGRGTPGKDSRGNSKRAET* | (SEQ ID NO: 425) |

| | | | |
|---|---|---|---|
| 8 | A34964 | :EQVGGLQPGRGTPGKDSKGNSKRAET* | (SEQ ID NO: 426) |
| 9 | PL0123 | :EQVGGLQPGRGTPGKDSKGNAKRAET* | (SEQ ID NO: 427) |
| 10 | HV3F$HUMAN | :EQVGGLQPGRGTPGKDSKGDSRRAET* | (SEQ ID NO: 428) |
| 11 | JL0048 | :EQVGGLQPGRGTPGKDSKGNSRRAET* | (SEQ ID NO: 429) |
| 12 | HV3B$HUMAN | :QQVGGLEPGRGTPGKDSKGBSKRAET* | (SEQ ID NO: 430) |
| 13 | HUMIGHBV | :EQLGDLQPGRGTPGKASKGNSKRAET* | (SEQ ID NO: 431) |
| 14 | HV3E$HUMAN | :EQVGGLQPGRGTTGKDSKGDSKRAET* | (SEQ ID NO: 432) |
| 15 | PL0116 | :QQVGGVQPGRGTPGKDSKGNSKRAET* | (SEQ ID NO: 433) |
| 16 | KV3K$HUMAN | :QQVGGVQPGRGIPGKDSKGNSKRPET* | (SEQ ID NO: 434) |
| 17 | N$2FB4H | :EQVGGVQPGRGIPGKDSKGDSKRPET* | (SEQ ID NO: 435) |
| 18 | HV3I$HUMAN | :QQVGGVQPGRGTPGKDSNGDSKRPET* | (SEQ ID NO: 436) |
| 19 | HV3J$HUMAN | :QKVGGVQPGRGTPGKDSKGNSKRTET* | (SEQ ID NO: 437) |
| 20 | HV3G$HUMAN | :QEVGGVZPGRGTPGKBSKGBSKRAET* | (SEQ ID NO: 438) |
| 21 | HV3M$HUMAN | :EQLGGLQPGRGTPGKDSNGDSKQAZT* | (SEQ ID NO: 439) |
| 22 | HV3O$HUMAN | :EQLGGLQPGRGSPGKDTNGDSKEAZT* | (SEQ ID NO: 440) |
| 23 | HV3N$HUMAN | :AQLGGLQPGRGTPGKDSNGDSKQAZS* | (SEQ ID NO: 441) |
| 24 | HV3R$HUMAN | :EQLGGLQPGRGTPGKVSQGDSKQAZT* | (SEQ ID NO: 442) |
| 25 | HV3P$HUMAN | :EQVGGLQPGRGTPGKVSQGDSKEPZT* | (SEQ ID NO: 443) |
| 26 | HUMIGHCV | :EQLGGLQPERGTPGKESKGNSMRAET* | (SEQ ID NO: 444) |
| 27 | HV3T$HUMAN | :EQVGDLQPGRGBPGKDSKGNAKRVET* | (SEQ ID NO: 445) |
| 28 | HV3U$HUMAN | :EQVGDLQPGRGNPGKDSKGNAQRPET* | (SEQ ID NO: 446) |
| 29 | PL0098 | :QQVGGVQPGRGTLGKDSKGNSKRAET* | (SEQ ID NO: 447) |
| 30 | HV3H$HUMAN | :QZVGGAZPGRGSPGKASKGBSKRAET* | (SEQ ID NO: 448) |
| 31 | HV3A$HUMAN | :QQVGGLKPGRGSPGKDSKGNAQRTZT* | (SEQ ID NO: 449) |
| 32 | HV3S$HUMAN | :DQVGGLKPGRGTPGKNSNGDSKTPZT* | (SEQ ID NO: 450) |
| 33 | HUMIGHAN | :EQLGGLQPGRGTSREDSKGNSKRAET* | (SEQ ID NO: 451) |
| 34 | HV3Q$HUMAN | :EQVGALQPGRGTPGKDSQADSKEAZT* | (SEQ ID NO: 452) |
| 35 | A36040 | :EQLGGLQPGRGTPGK----VEGSVET* | (SEQ ID NO: 453) |
| 36 | HUMIGHAN | :EQVGAFQPGRGNSGKASKGDSKRPDT* | (SEQ ID NO: 454) |
| 37 | HUMIGHAO | :EQVGAFQPGKGNSGKASKGDSKRPDT* | (SEQ ID NO: 455) |
| 38 | HUMIGHAR | :EQVGAFQPGKGNSGKASKGDSNRPDT* | (SEQ ID NO: 456) |
| 39 | HV3L$HUMAN | :QQVGGVQAGRANPGKDSRGISKRTET* | (SEQ ID NO: 457) |
| 40 | HV1A$HUMAN | :QQVAEVKPGKGTPGQQKQGESTRSET* | (SEQ ID NO: 458) |
| 41 | A32483 | :QQVAEVKPGKGTPGQQKQGTSTRSET* | (SEQ ID NO: 459) |
| 42 | HUMIGHAY | :QQVAEVKPGKGTPGQQKQGTSARSET* | (SEQ ID NO: 460) |
| 43 | HUMIGHCU | :QQVAEVKPGKGTPGQQKQGTSIRSDT* | (SEQ ID NO: 461) |
| 44 | HUMIGHBS | :QQVAEVKPGKGTPGQEKQGTSIRSDT* | (SEQ ID NO: 462) |
| 45 | HUMIGVHLS | :QQVAEVKPGKGTPGQQNQGTSTRSDT* | (SEQ ID NO: 463) |
| 46 | HUMIGHBX | :QQVGEVKPGRGTPGQQKQDTSTRSDT* | (SEQ ID NO: 464) |
| 47 | HV1C$HUMAN | :QQVAEVKPGRGTPGHPRQGASFRSDS* | (SEQ ID NO: 465) |
| 48 | H34964 | :QQVSELKPGKGTPGQQGTGTSVKAET* | (SEQ ID NO: 466) |
| 49 | HUMIGHCY | :EQVAEVKPGKGSPGKPSQGKSIKAST* | (SEQ ID NO: 467) |
| 50 | PL0119 | :EQVAEVKPGRGSPGKPSQGKSIKAST* | (SEQ ID NO: 468) |
| 51 | HV1F$HUMAN | :QQVAEVKPGRGDPGRPRQASSTISAT* | (SEQ ID NO: 469) |
| 52 | D34964 | :EQVAEVPQGKGRPGKSLQGKSLKAST* | (SEQ ID NO: 470) |
| 53 | HV1D$HUMAN | :QQMAEVKPGRGTPGKPGVVPSFFSET* | (SEQ ID NO: 471) |
| 54 | HV1E$HUMAN | :QQVAEVKPGRGTPGRYIWEPSFFNEG* | (SEQ ID NO: 472) |
| 55 | JL0047 | :QQQAGLKPSSGSPGKPSKSTSKTAAT* | (SEQ ID NO: 473) |
| 56 | HUMIGHBW | :QQQPGLKPSSGSPGKPSKSTSKTAAT* | (SEQ ID NO: 474) |
| 57 | E34964 | :QQQPGLKPSSGSPGKPSKSTSNTAAT* | (SEQ ID NO: 475) |
| 58 | HUMIGHCW | :QQQPGLKPSSGSAGKPSKSTSKTAAT* | (SEQ ID NO: 476) |
| 59 | HV2F$HUMAN | :RQQPGLKPSSGPPGKPSRGTSRSAAT* | (SEQ ID NO: 477) |
| 60 | HV2I$HUMAN | :QQQAGLKPSSGSPGRTSKSTSKTAAT* | (SEQ ID NO: 478) |
| 61 | HV2G$HUMAN | :QQEPGLRPSSGTPGRTPRSTSKTAAT* | (SEQ ID NO: 479) |
| 62 | N$3FABH | :XQEPGLRPSSGSPGRTPRSTSKTAAT* | (SEQ ID NO: 480) |
| 63 | PS0091 | :QQQPGLKPSSGSPSRVSKSTSKTPET* | (SEQ ID NO: 481) |
| 64 | HUMIGHDA | :QHQAGLKRSSGPPGKPSTSTSKTAAT* | (SEQ ID NO: 482) |
| 65 | A26555 | :ZQESGLKPTSGSPGKPSKSRSKAADA* | (SEQ ID NO: 483) |
| 66 | HV2E$HUMAN | :QTKPTLKPTTGSPGRPSKSTSKDPVT* | (SEQ ID NO: 484) |
| 67 | HV2D$HUMAN | :QTKPTLKPTTGSPGKPSRSTSRDPVS* | (SEQ ID NO: 485) |
| 68 | A36005 | :ETRPALKPTTGSPGKTSKTTSKDPVT* | (SEQ ID NO: 486) |
| 69 | HV2H$HUMAN | :QNRPALKATTGSPGKTSETTSKDPAT* | (SEQ ID NO: 487) |
| 70 | HV2A$HUMAN | :QTTPALKPKTGSPGKTSRTDSKNPVT* | (SEQ ID NO: 488) |
| 71 | HV2C$HUMAN | :QTRPALRPTTGSPGEASETTSKGPGT* | (SEQ ID NO: 489) |
| 72 | HV2B$HUMAN | :QTRPALKPTTGSPGKTSETTSRDTAY* | (SEQ ID NO: 490) |
| 73 | JL0049 | :LEGVQLWGGRGISRKYAKGNGKRDES* | (SEQ ID NO: 491) |

EXAMPLE 2

Detailed Description of Method for Constructing Three-Dimensional Model of Antibody Variable Region The references cited in the text below are listed at the end of this Example.

The first antibody Fab structure was determined in 1972. Since then, no more than about twelve Fab structures have been published, a number that represents a very small fraction of the total antibody repertoire (>$10^8$ antibodies). To understand the molecular basis of this antibody diversity will require knowledge of either a large number of x-ray structures, or the rules by which combining site topography is governed. The development of such prediction rules has now reached the point where variable regions of antibodies can be modelled to an accuracy approaching that of the medium resolution x-ray structure.

The interaction of an antibody with its cognate antigen is one of the most widely accepted paradigms of molecular recognition. To understand the antibody-antigen interaction in atomic detail requires knowledge of the three-dimensional structure of antibodies and of their antigen complexes. Traditionally such information has come from x-ray crystallographic studies (see Davies et al. for review (Davies et al., 1988)).

The modelling of antibody combining sites was first attempted by Padlan & Davies (Padlan et al., 1976) at a time when very few antibody structures were known. Nonetheless, Padlan and colleagues recognized that the key lay in high structural homology that existed within the β-sheet framework regions of different antibody variable domains. The antigen combining site is formed by the juxtaposition of six interstrand loops, or CDRs (Complementarity Determining Regions) (Kabat et al., 1987), on this framework. If the framework could be modelled by homology then it might be possible to model the CDRs in the same way. Padlan and Davies (Padlan et al., 1976) reasoned that CDR length was the important determinant of backbone conformation though the number of antibody structures was insufficient to thoroughly test this maximum overlap procedure (MOP). This notion was not picked up again until the early 1980's when Pedersen and Rees proposed a similar approach to modelling antibody combining sites based on a more extensive analysis of antibody structures (de la Pas et al., 1986).

Those essentially knowledge-based procedures are best exemplified for antibodies by the work of Chothia & Lesk (Chothia et al., 1986) who, in 1986, extended and modified the MOP procedure by introducing the concept of "key" residues. These residues allow the further subdivision of CDRs of the same length into "canonical" structures which differ in having residues at specified positions that, through packing, hydrogen bonding or the ability to assume unusual values of the torsion angels $\phi$, $\psi$ and $\omega$, determine the precise CDR conformation (Chothia et al., 1989). Similar knowledge-based methods have been proposed for predicting loop conformations in general (Thornton et al., 1988; Tramontano et al., 1989). These methods rely on the crystallographic database of protein structures. However, none of the above knowledge-based methods has been totally successful. In particular, the MOP or canonical structure approaches have succeeded in modelling only five of the six CDRs. This stems from the fact that the third CDR of the heavy chain, H3, is more variable in sequence, length and structure than any of the other CDRs.

To deal with this problem several groups have attempted to use ab initio methods to model the combining site (Bruccoleri and Karplus, 1987). The requirement with such methods is that the total allowable conformational space accessible to a particular CDR is sampled. Typical of purely geometric approaches is that of Go & Sheraga (Go and Sheraga, 1970) and more recently Palmer & Sheraga (Palmer and Sheraga, 1991), where the problem is reduced to one in which the central region of the polypeptide backbone, having characteristic bond length and bond angles, is constructed between the end points of the loop (CDR if an antibody loop) by a "chain closure" algorithm. In a modification of this algorithm, Bruccoleri & Karplus (Bruccoleri and Karplus, 1987) introduced an energy minimization procedure which greatly expanded the domain of conformational space searched during the chain closure procedure. This modification is incorporated into the conformational search program CONGEN (Bruccoleri and Karplus, 1987), which also allows the user to choose any set of standard bond length and bond angels such as the CHARMM (Brooks et al., 1983) standard geometry parameter sets. Other approaches such as minimization (Moult and James, 1986), or molecular dynamics (Fine et al., 1986) either fail to saturate conformational space or are unable to deal with the problem of long CDRs. Whichever of the ab initio methods is employed however, the problem is one of defining the selection criteria in such a way as to allow the unambiguous identification of the correct structure (in this context correct is defined by reference to an appropriate X-ray structure) within the ensemble of candidates, for every CDR. To date this has not been possible.

Recently a more holistic approach has been taken to the modelling of CDRs which combines the advantages of knowledge-based and ab initio methods in a single algorithm known as CAMAL (Combined Algorithm for Modelling Antibody Loops) (Martin et al., 1989; Martin et al., 1991). Previously this algorithm has been used to model individual CDRs in the presence of the crystal structure conformations of the other five. As is demonstrated below, CAMAL is able to predict the backbone conformations of all six CDRs of the antibody combining site to an accuracy approaching that of medium resolution x-ray structures. In addition the algorithm includes a procedure for selecting and fitting together the light and heavy chain framework regions prior to generation of CDR conformations, thus making possible the prediction of the entire variable region. Furthermore a new Monte Carlo (MC) simulated annealing method has been developed for the determination of sidechain conformations.

the Framework Region

Figure 5:
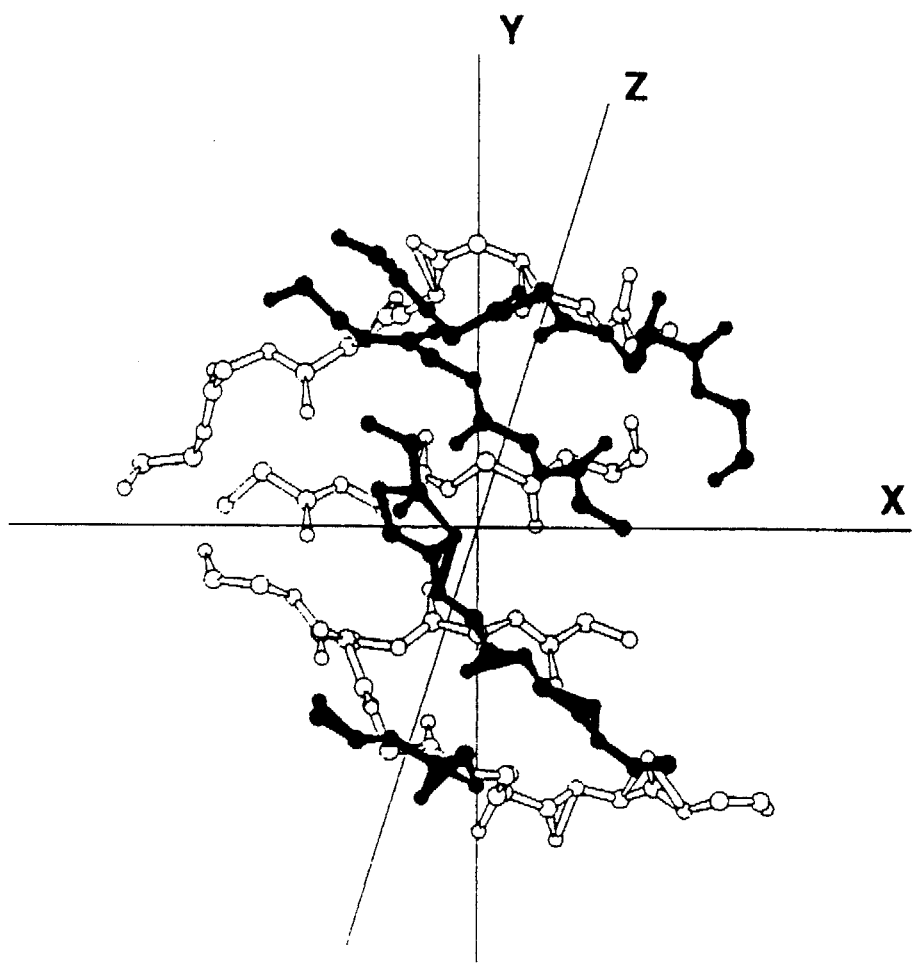
FIG. 5 is a stereo plot of mean antibody β-barrel, coordinates determined by iterative multiple fitting of eight antibody structures. Strands 7 and 8 comprise the 'take off' positions for CDR H3 and are not included in the fitting of $V_L$ and $V_H$ regions.
Figure 6:
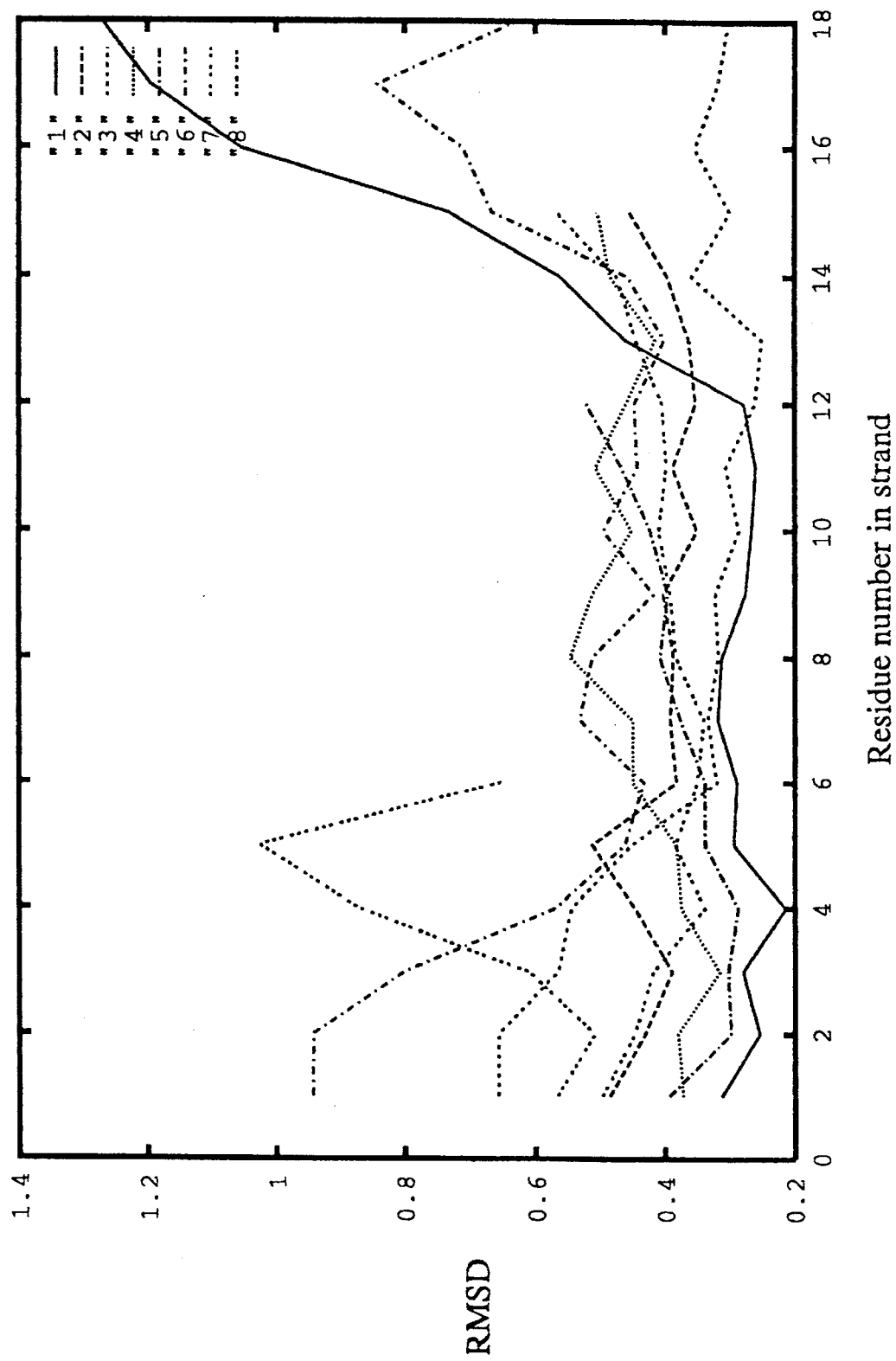
FIG. 6 is a plot of RMS deviation (RMSD) from the mean of the eight β-sheet strands comprising the framework. The RMSD was calculated from structures F19.9, 4-4-20, NEW, FBJ, KOL, HyHEL-5, HyHEL-10 and McPC603. N,Cα,C atoms are included in the plot. The residues used are shown in the alignment (Table 2). The most disordered residues are all the residues of strand HFR4, the last residue of LFR1, and the first and last residue of HFR2. The nomenclature of the strands is explained in the alignment in Table 2. LFR1-#1, LFR2-#2, LFR3-#3, LFR4-#4, HFR1-#5, HFR2-#6, HFR3-#7, HFRS4-#8.

Antibody framework regions consist of conserved β-strands that form the β-barrel structure characteristic of immunoglobulin V-type regions. In the procedure described here each V-region is built from a database of known antibody structures, using sequence homology for selection of the light (L) and heavy (H) chain V-domains. The two domains are then paired by least squares fitting on the most conserved strands of the antibody β-barrel (Table 2 and FIGS. 5 & 6). The strand orientations were determined by analyzing the barrels of known antibody crystal structures. Eight antibodies were analyzed using a multiple structure fitting program as follows. Seven structures were fitted onto one of the set selected at random and mean coordinates were calculated. All eight structures were then fitted onto these mean coordinates and new mean coordinates determined. This procedure was iterated until the mean coordinate set converged (5–10 cycles). The variance for the mean coordinates at each barrel point (N,Cα,C) was calculated. In FIG. 5 this variance is plotted against the projected positions of these points onto the conjugate axis of the barrel.

Strand 8 and all but two residues of strand 7 in both light and heavy chains were eliminated as they showed deviations greater than 3σ (standard deviation units) from the mean coordinates. These two strands comprised the takeoff points of CDR H3, and suggests that any knowledge-based prediction of CDR H3 would have to account not only for sequence and length variation in the CDR itself, but also for the position of the participating strands. The remaining mean coordinates were used as a scaffold onto which the L and H chains were fitted. Strands 7 and 8 in the final framework were obtained from the database structure used in the construction. The framework strands are marked + in the multialignment in Table 2.

The sidechains were then replaced using a . 'maximum overlap' method, in which sidechain templates were fitted on backbone atoms with the sidechain torsion angles being adjusted to match those of equivalent torsions in the parent sidechain.

The Combining Site

Figure 7:
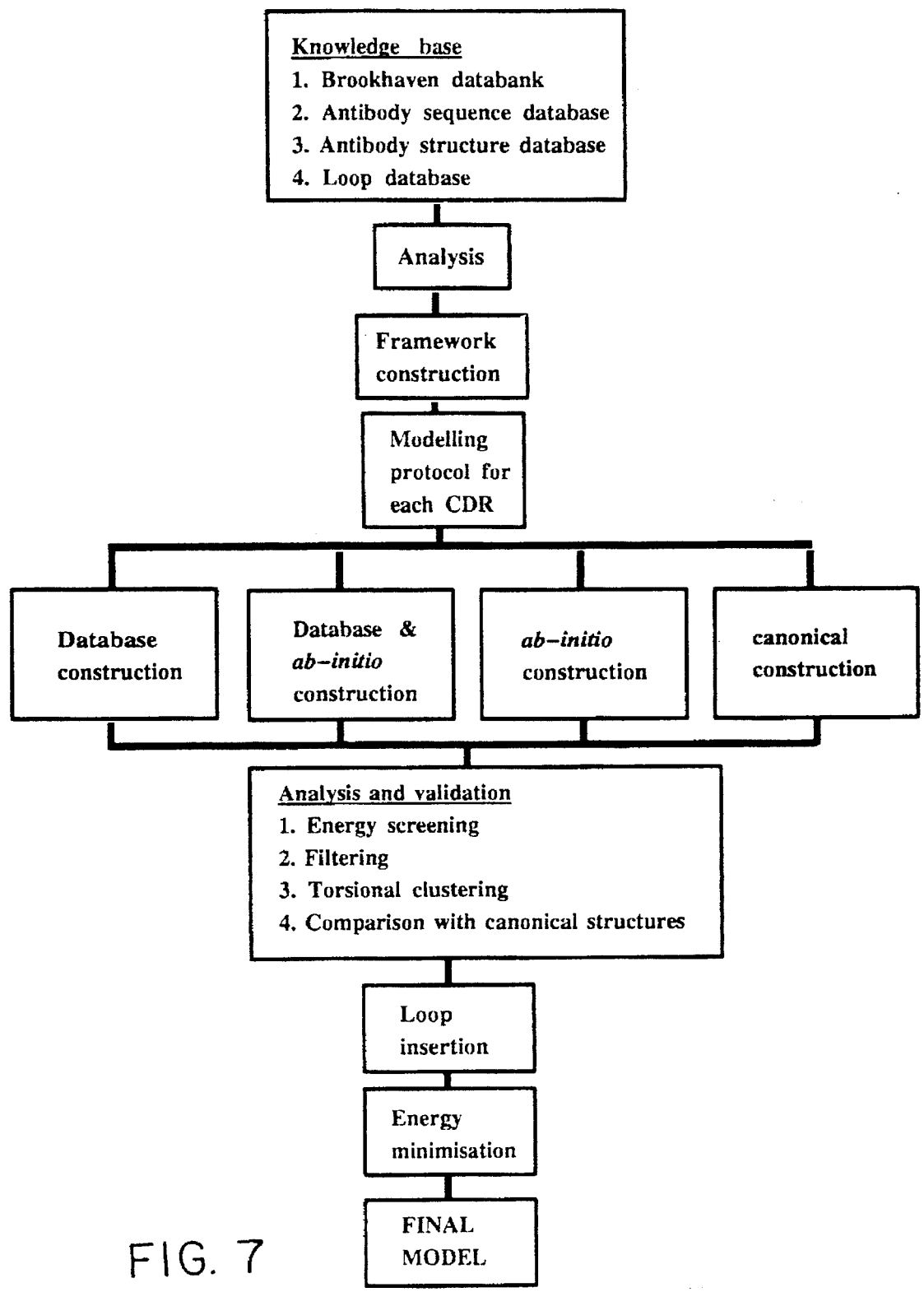
FIG. 7 is a flowchart of the overall modelling protocol known as CAMAL.

The procedure for predicting the structure of combining sites combines a database search with a conformational search procedure. The architecture of the program suite to perform this task is outlined in FIG. 7.

The database search utilizes distance constraints for each of the six CDR loops determined from known antibody structures. These constraints were determined by calculating Cα—Cα distances within known loops and using a search range of $\bar{x}+3.5\sigma$ (the mean ±3.5 standard deviation units). A database containing all the proteins in the Brookhaven Protein Databank (Bernstein et al., 1977) is then searched for fragments which satisfy the constraints for a loop of the required length. The middle section of the loop is then deleted and reconstructed using the conformational search program CONGEN (Bruccoleri and Karplus, 1987). For loops of six or seven residues, the structure database appears to saturate the conformational space available to the backbone adequately and only sidechains are built by conformational search. Loops shorter than six residues are built by conformational search alone since this is computationally feasible and the number of loops selected from the database becomes unacceptably large as loop length decreases.

When modelling a complete combining site, loops of 6 or more residues are modelled individually with the other loops absent. If the loops are built consecutively, small errors can accumulate leading to a poor result (Martin, 1990). All the loop conformations are then evaluated using a solvent modified potential, which excludes the attractive van der Waals and electrostatic terms of the non-bonded energy function contained within the GROMOS (Åqvist et al., 1985) potential. The lowest five energy conformations are selected and filtered using a "structurally determining residue" algorithm (FILTER), based on backbone torsion angles observed in the original database loops. Since the database search is not used for the shortest loops of 5 residues or fewer, the FILTER algorithm cannot be used. Energy is thus the only available selection criterion and the short loops are built last, in the presence of the longer loops.

Side Chains

The determination of sidechain positions was previously done using the iterative sidechain determination algorithm described by Bruccoleri et al. (Bruccoleri and Karplus, 1987). Unfortunately the CHARMM (Brooks et al., 1983) force field fails to select the correct conformations of exposed hydrophobic sidechains. There is no penalty for having an exposed uncharged atom, without solvent present. CONGEN is also unable to saturate the conformational space for a large number of sidechains (more than 6 residues).

Recently Lee et al. (Lee and Levitt, 1991; Lee and Subbiah, 1991) has proposed a method for searching conformational space for a large number of sidechains using MC simulated annealing. A simple energy function is used for the evaluation of conformations generated by a biased random walk:

$$E = \sum_{i=1}^{n} \epsilon_o \left( \left(\frac{r_o}{r}\right)^6 - 2\left(\frac{r_o}{r}\right)^{12} \right) + \kappa \cdot \cos(3\omega)$$

Where the first term is a simple Lennard-Jones potential which evaluates the non-bonded contacts between the atoms in a given molecule, the second term is a simple torsional term which only applies to C—C bonds. The torsional term biases the function towards 60° rotamers. $\epsilon_o$ and $\kappa_o$ are constants. The metropolis function:

$$P = C^{\frac{-\delta E}{T}}$$

is used to evaluate the energy function. Any move which results in a decrease in energy is accepted, and any move which results in a positive δE is only accepted with the probability P. This simple method can be used to search the large conformational space defined by a set of torsion angles in amino-acid sidechains, and find or define the global minimum which exist for a set of sidechains. T is the simulation temperature.

When searching sidechain conformations using this method the simulation system usually gets trapped in an energetic minima well before the global minimum is encountered, at a high temperature, without the solution space having been searched sufficiently. This problem can be solved by truncating the Lennard-Jones potential, thus allowing atoms to pass through each other. In reality this function would converge towards infinity when the distance r between the atoms approaches zero.

The evaluation of sidechain conformations generated is done solely on the basis of energy, for internal (core) residues, since good van der Waal's interactions are considered to be equal to a good packing of the sidechains. The situation becomes more complicated when trying to predict the conformation of surface residues. The lowest van der Waal's interaction is obtained by a combination of sidechain conformations which minimize the overlap of atoms, this means that the lowest energy is obtained with extended conformations of sidechains, without considering good packing of sidechains.

Using the fact that hydrophobic, bulky residues will be shielded by the hydrophilic sidechains, and will be buried in the surface, it is possible to generate a simple function which will evaluate these macroscopic observations. These functions can either be implemented in the objective evaluation function of the Monte Carlo simulation, or as is done here, added as a post processing step. Including an accessibility/hydrophobicity term in the evaluation function would slow down the calculation considerably, hence the term has been added as a post processing function. The function used is a sum of the product of relative exposed surface area multiplied by the residual hydrophobicities. The hydrophobicities used are taken from Cornette et al. (Cornette et al., 1987).

$$f_{conformation} = \sum_{i=1}^{n} -A_{irel} \cdot H_{irel}$$

n is the number of sidechains reconstructed. The surface area is calculated using the tesselated icosahedron approach (Chau and Dean, 1987), which is not very precise (0.1 percent), but is able to evaluate a large number of conformations. The function is evaluated for the final 2,000 conformations and the lowest value conformation selected as the best.

Using this simple approach it is possible to integrate over a large phase space with many degrees of freedom, and get a complete sampling of the space.

Predicted Structures of an Anti-hapten, Anti-peptide and Two Anti-protein Antibodies In the following section the predicted structures of four different antibody $F_V$ regions are presented and analyzed. The antibodies are:

Gloop-2 (Darsley and Rees, 1985), an anti-lysozyme antibody whose Fab structure was previously determined and which was used as a learning exercise during the development of CAMAL.

D1.3 (Amir et al., 1986), an anti-lysozyme antibody whose uncomplexed $F_V$ coordinates were supplied by R. Poljak et al. after the model coordinates had been deposited.

36–71 (Rose et al., 1990), an anti-phenylarsonate antibody whose Fab structure was carried out by D. R. Rose, et al., and whose coordinates were obtained after the model coordinates had been deposited.

3D6 (Grunow et al., 1988), an anti-protein (GP41 of HIV) antibody whose Fab structure was carried out by D. Carter et al. (Carter, 1991) and whose coordinates were obtained after the model coordinates had been deposited. For this antibody, the model was generated using the canonical loop method of Chothia & Lesk (Chothia et al., 1989; Chothia et al., 1986) for CDRs L1, L2, H1 and H2, while L3 and H3, which cannot be modelled using canonical structures, were constructed using CAMAL.

All four models were subjected to both restrained and unrestrained energy minimization using the DISCOVER (TM Biosym Technology) potential with 300 cycles of steepest descents, followed by conjugate gradient minimization until convergence to within 0.01 Kcal occurred.

The resolution and R-factors of the x-ray structures are given in Table 3 together with the parent frameworks selected in building the models. The structures and models were compared by global fits of the loops. The β-barrel strands 1 to 6, as described above, were least squares fitted and the RMS deviation was then calculated over the loops. The backbone (N,Cα,C) RMS values for fitting model and crystal structure frameworks were between 0.4 and 0.9 Å, illustrating the conservation of the core β-barrel. Using all eight strands RMS deviations between 0.6 and 1.2 Å were observed.

Global fits (Table 4) give a more realistic measure of the accuracy of the model than a local least-squares fit over the loops since they account for the overall positioning of the loops in the context of the $F_V$ structure. Local fits, which give lower RMS deviations, are also shown in Table 4. Differences between local and global RMS deviations arise from differences in $V_H/V_L$ domain packing and differences in loop 'take off' angles and positions.

Figure 8:
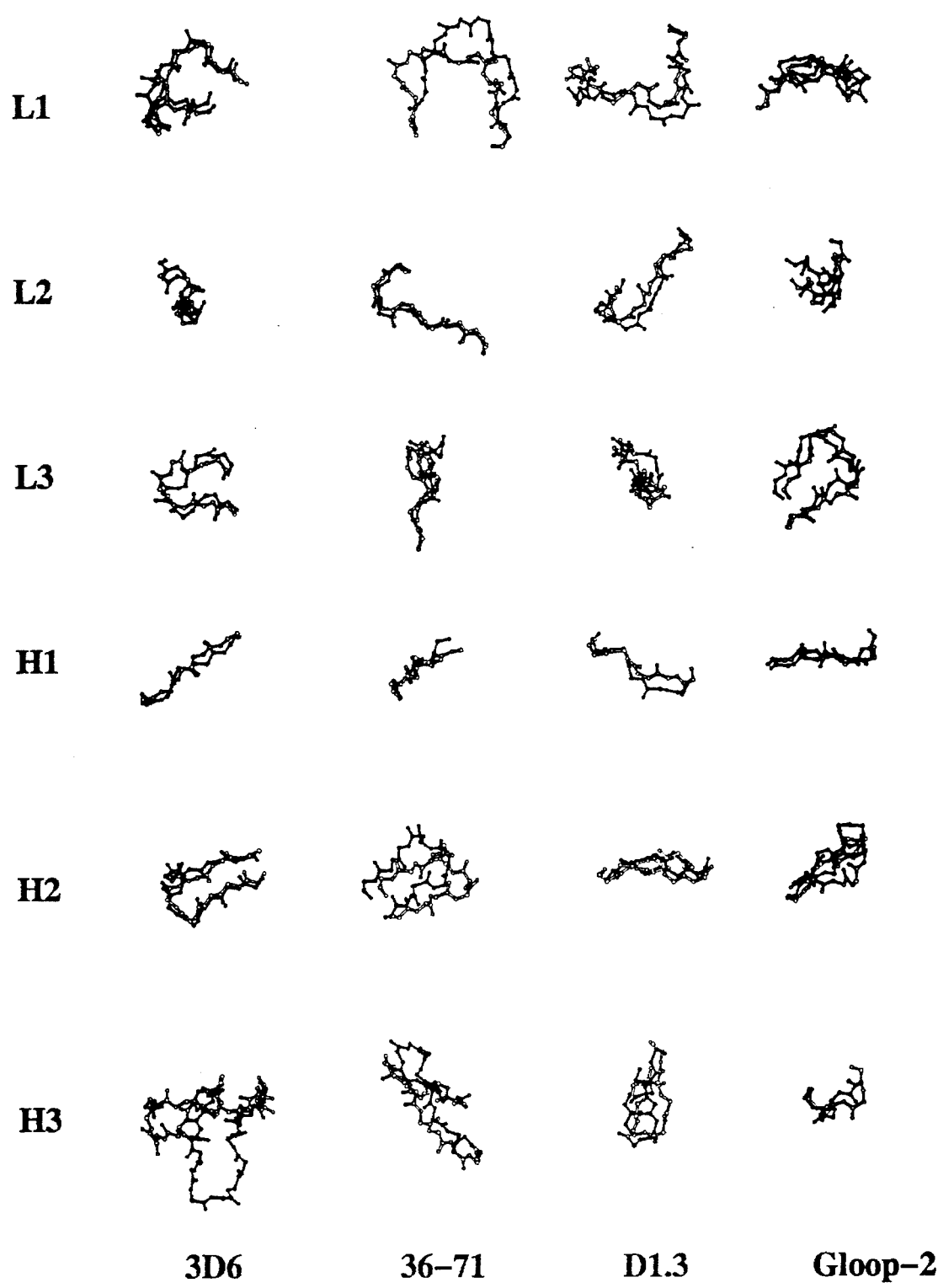
FIG. 8 is a plot of superimposed loop backbones for models and x-ray structures discussed in Example 2. The loops are positioned after global framework fit. This does not represent the best local least squares fit, but shows how the loops are positioned globally onto the framework.
Figure 9A:
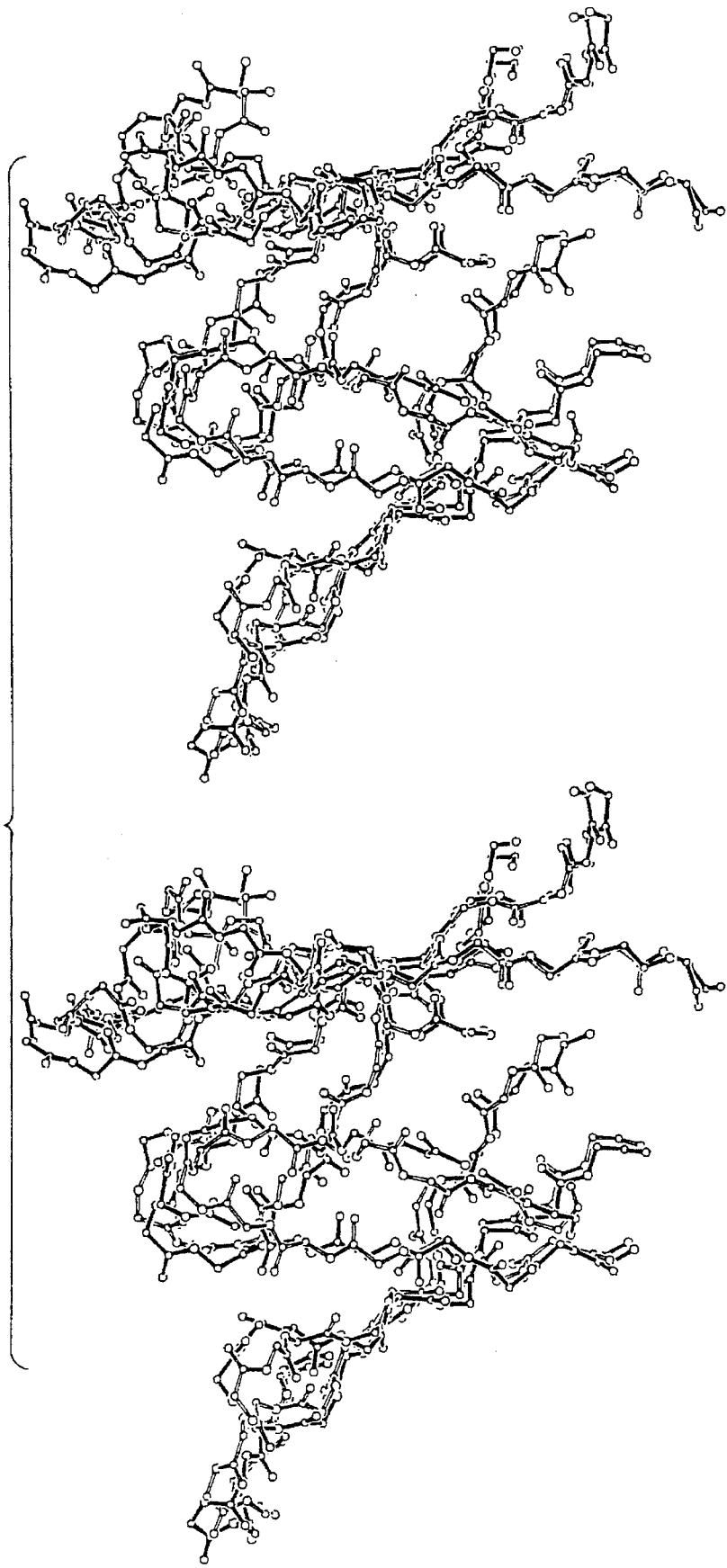
FIGS. 9A to 9D are stereo (N,C-α,C,O) representations of crystal structures and models of D1.3, 3671 and Gloop-2 variable domain and β-barrel strands described in Example 2. Crystal structures are shown with open bonds, model with solid bonds. The difference between the 3D6-H3 in the model and the crystal structure is due to a 5°-7° twist in the extended β-sheet conformation of this loop.
Figure 9B:
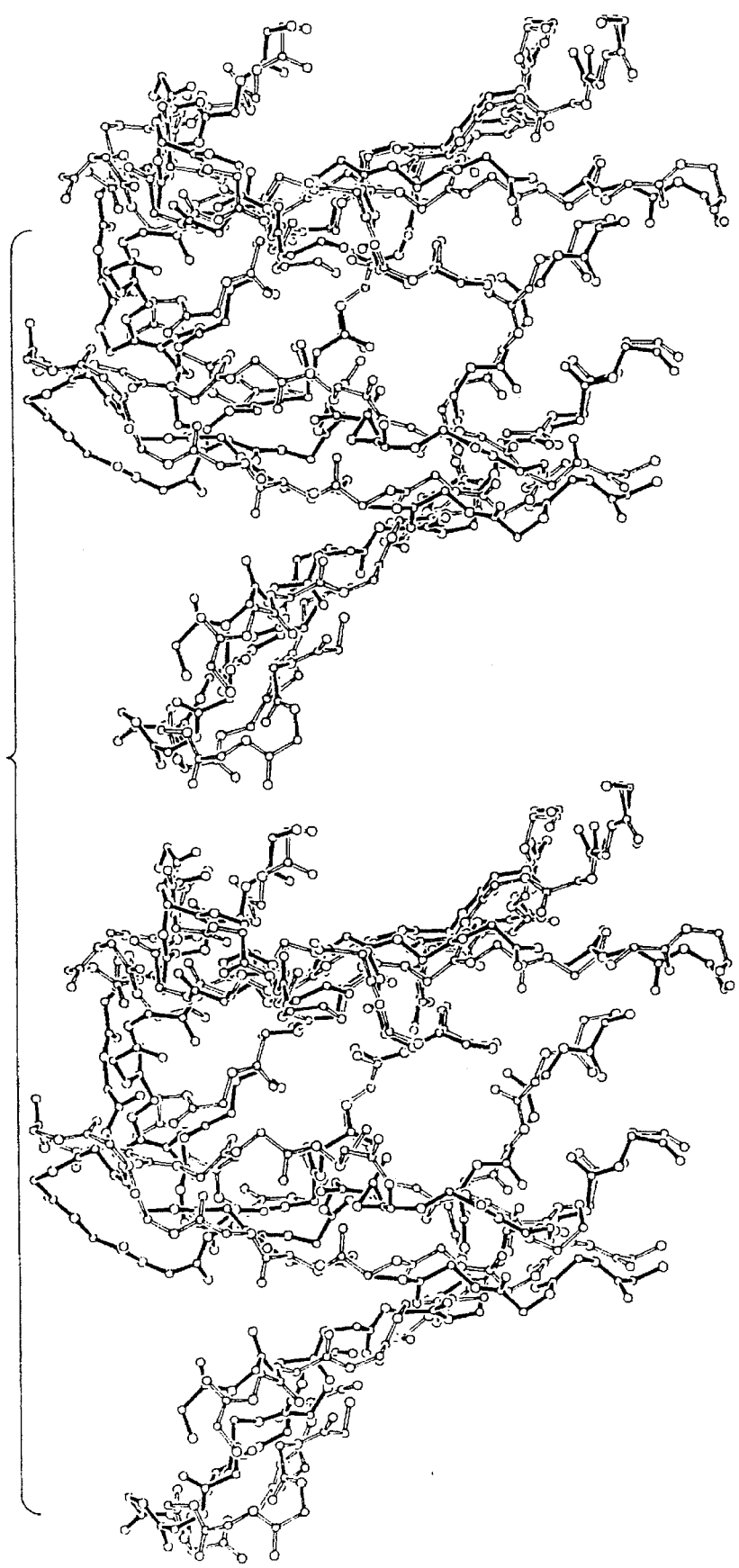
Figure 9C:
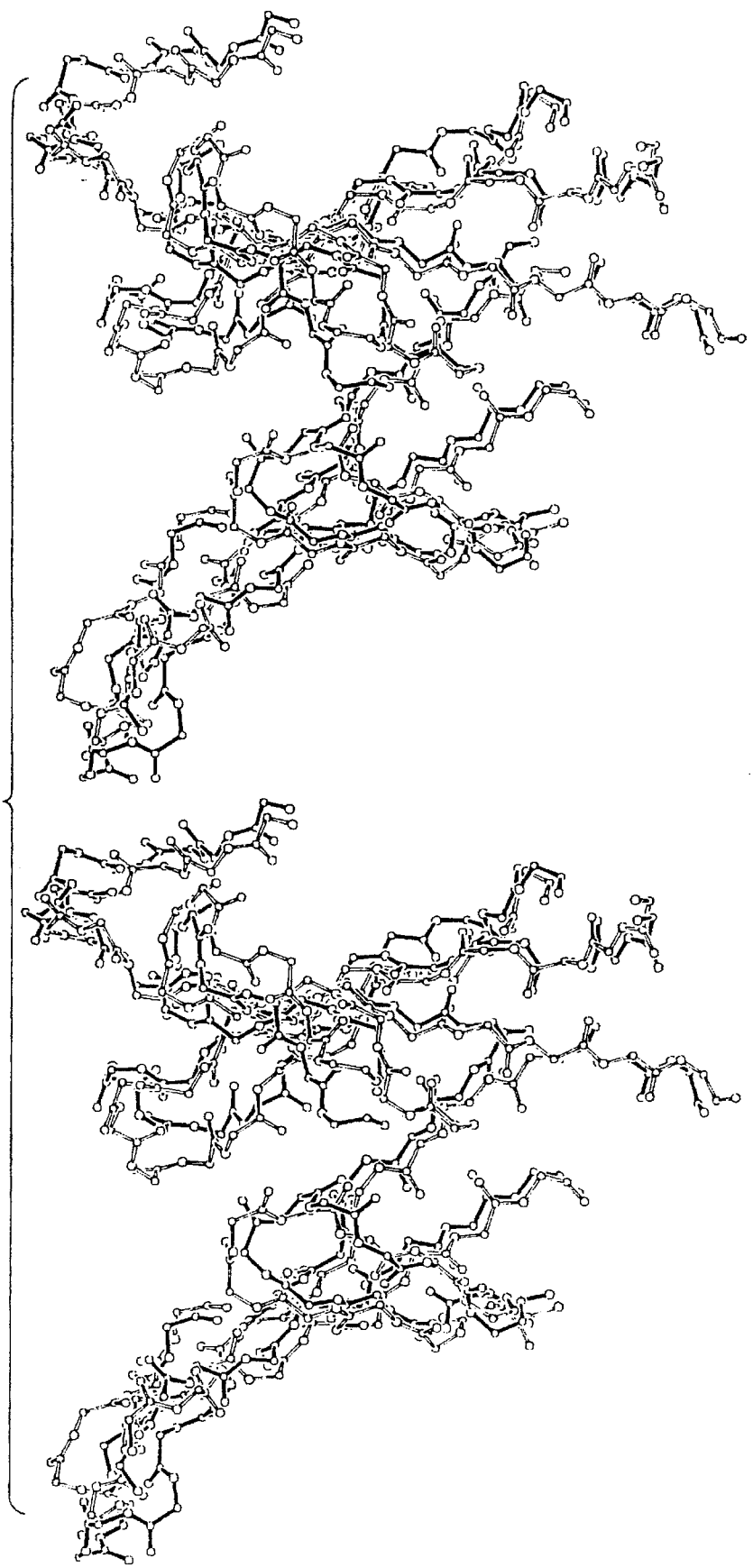
Figure 9D:
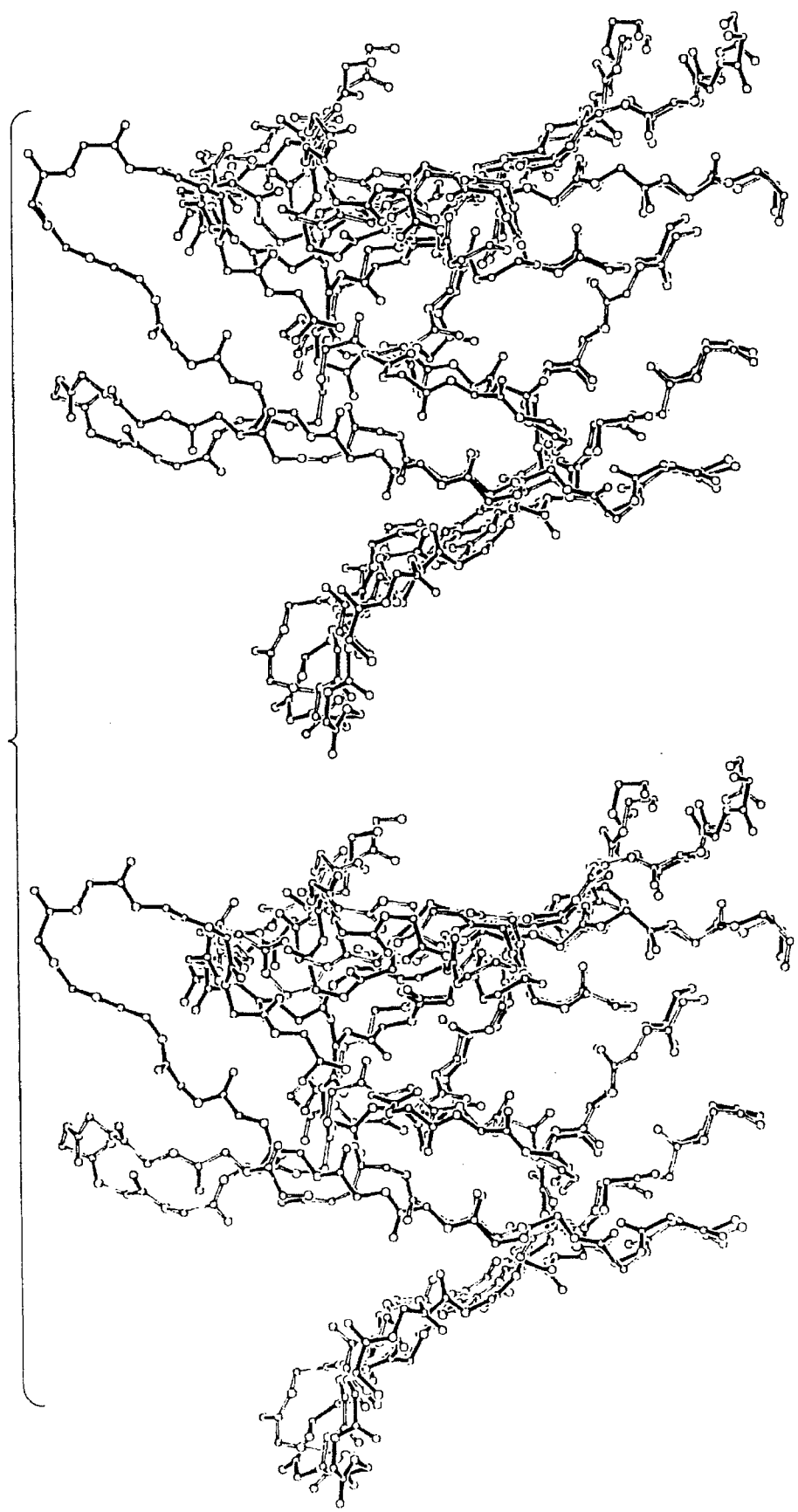

Table 5 shows the canonical loops selected from modelling 3D6. Backbone structures of the modelled CDRs, superimposed on the x-ray structures after global fitting are shown in FIG. 8. General features and points of interest for each of the six CDRs are discussed below.

Analysis of the CDR Regions

During the comparison of CDR conformations in the V-region models and the x-ray Fab structures it was observed that at certain positions in a CDR, the peptide backbone may adopt either of two conformations by undergoing a "peptide flip" (1,4 shift). This phenomenon is also seen in type 2 β-turns (Paul et al., 1990). Dynamics simulations of β-turns show that the transformation energy between $\phi1=-00$, $\psi1=-30$, $\phi2=-90$, $\psi2=0$ and $\phi1=-00$, $\psi1=120$, $\phi2=90$, $\psi2=0$ has a maximum value of 5 kcal (Paul et al., 1990). This is low enough to allow selection of either conformation. The peptide flip is observed within several canonical classes (as described by Chothia et al. (Chothia et al., 1989)) and the hydrogen bonding pattern used to determine the conformation of a canonical class does not disallow the peptide flip. Any modelling procedure should therefore take these, or any other multiple conformations, into consideration where the transformation energies are sufficiently low to permit population of the different conformational forms. Table 6 shows an example of the "peptide-flip" phenomenon from the crystallographic database of antibody structures. It should be noted that a single crystal structure will not show multiple conformations since the crystallization will 'freeze out' one of the conformations. During the modelling procedure the two populations of conformers are easily extracted from a set of ab initio generated loops, by using a torsional clustering algorithm.

CDR-L1

In Gloop-2 and D1.3, all five low energy conformations were very similar with RMS deviations differing by less than 0.25 Å (backbone) and 0.35 Å (all atoms). The FILTER algorithm was unable to distinguish between the conformations and the lowest energy structure was selected.

Although CDR-L1 of 3D6 was originally built using the canonical loop from HyHEL-10, the mid-section was rebuilt by conformational search, for the following reason. HyHEL-10 and REI CDR-L1 loops are placed in the same canonical ensemble (Chothia et al., 1989) although they contain a 1–4 shift (peptide flip) relative to one another between the fifth and eighth residues of the loop (residues 28–31) (see Table 6).

36–71 shows the same 1–4 shift between the model and crystal structure CDRs. Both crystal structure and model were compared with other loops of the same canonical class as defined by Chothia et al. (Chothia et al., 1989). It was found that the hydrogen bonding pattern which determines the conformation was conserved.

CDR-L2

CDR-L2 of D1.3 has two adjacent threonines (49, 50) which in the x-ray structure are packed against the tyrosine at the fourth position of CDR-H3, thus minimizing the exposed hydrophobic sidechains. In the unminimized model the threonine sidechains are exposed to the solvent, but after energy minimization, this packing is observed.

CDR-L3

In Gloop-2, D1.3 and 36–71 the proline at the seventh position in the loop is correctly predicted in the cis conformation. It has previously been suggested that the conformation of CDR-L3 is dictated by the presence of a proline in position 8 or 9 (Chothia et al., 1989) within the loop. 3D6 does not have a proline in either position. Only 7 out of 290 CDR-L3 sequences (Kabat et al., 1987) lack a proline at both positions and in all of the published x-ray structures this proline is present. This is an example of a situation where either a new canonical class may need to be defined or where the canonical rule breaks down altogether, and an alternative method must be employed.

The 3D6 L3 loop is 7 residues in length and was built using database loops alone where conformational space is saturated by means of fragments selected from the crystallographic database (Global RMS: 2.01 Å, N,Cα,C), and by using CAMAL (Construction: Q[Q(YNS)Y]S, Global RMS: 1.97 Å, N,Cα,C). The similarity of the structures generated by the two procedures illustrates the utility of the database search and suggests that, for shorter loops it is capable of saturating the available conformational space.

CDR-H1

Using the Kabat and Wu definition of CDR-H1 places this loop as an extension of the β-sheet. The extended nature of this stretch of peptide limits its conformational flexibility and CDR-H1 is generally modelled accurately (Martin et al., 1989; Chothia et al., 1989).

In Gloop-2 and D1.3, the Phe or Tyr sidechain at the second position in the loop is poorly placed and packs against Leu at the penultimate position in HFR1 (see Table 2). 36–71 has a well-placed Asn at this position, rather than the more common bulky hydrophobic sidechain.

CDR-H2

CDR-H2 of 36–71 is similar in sequence to F19.9 (Strong et al., 1991), (36–71: YNNPGNGYIA (SEQ ID NO:492); F19.9: YINPGKGYLS (SEQ ID NO:493)). While the structurally determining residues specified by Chothia and Lesk (Chothia et al., 1989) are conserved, the backbone conformations are different: F19.9 has a bulge at the —PGN— Gly, compared with 36–71, giving the loop a 'kink' in the middle. The model of 36–71 shows a 1–4 shift, though the sidechains are still well placed.

In Gloop-2, the all atom RMS deviation is poor (3.00 Å) when compared with the $P2_1$ crystal structure, owing to rotations of the Phe at position 3 in the loop and Tyr at position 10 by approximately 120° about the $\chi_2$ torsion angle. Gloop-2 has been solved in two different crystal forms, $P2_1$ and P1 Jeffrey, 1989). When compared with the P1 structure, the sidechains are placed almost perfectly and the all atom RMS (global fit) drops to 2.23 Å.

This concerted sidechain motion between crystal forms illustrates the effects of crystallization conditions on surface sidechain placement. Even though surface sidechains may show low temperature factors indicating low mobility in the crystal, their mobility in solution may be high. In the Gloop-2 P1 structure, the mean sidechain temperature factor for the $F_V$ domain is 13.46 ($\sigma$=8.20) while the sidechains of these two residues of H2 show mean temperature factors of 5.56 ($\sigma$=0.68) for the Phe at position 3 and 7.10 ($\sigma$=1.73) for the Tyr at position 10.

CDR-H3

CDR-H3 is the most variable of the six CDR's with all lengths up to 21 residues being represented in Kabat et al., (Kabat et al., 1987). This extreme variability results from V-D-J splicing (Schilling et al., 1980) and has always been a problem when attempting to model antibodies. Such loops may be divided into short (up to 7 residues), medium (up to 14 residues) and long (15 or more residues). Using the CAMAL procedure, short and medium CDR-H3's can be modelled as accurately as other CDR's of similar lengths. Although long CDR-H3's are more difficult and cannot, at present, be built to the same accuracy, the chain trace is still correct.

It is unlikely that the longer loops consist of 'pure' loops (i.e., all random coil or turn). In crystal structures of antibodies with medium to long CDR-H3 loops (McPC603 (Rudikoff et al., 1981): 11 amino acids (aa); KOL (Marquart et al., 1980): 17 aa; F19.9 (Lascombe et al., 1989): 15 aa) the loops consist of a disordered β-sheet extension from the β-barrel core and a 5–8 residue random coil/turn connecting these two strands.

To determine the nature of medium to long loops (>8 residues) which satisfy the CDR-H3 constraints, a complete search of the Protein Databank for loops of length 8–20 residues, was performed using the inter-Cα distance constraints determined from known antibody crystal structures for CDR-H3. The resulting loops were then analyzed using the DSSP (Kabsch and Sander, 1983) program, which is able to assign secondary structure to polypeptide structures. The amount of secondary structure for each length of loop was calculated, and it was observed that for loops longer than 12 residues the amount of secondary structure within each of the classes described in DSSP was constant. The number of loops selected is also constant (approximately 150 loops) for loops longer than 12 residues. A closer inspection of each of the length ensembles shows indeed that the loops are the same between the groups.

This analysis shows that, like the long CDR-H3 crystal structures, the selected fragments consist of β-strands connected by 5–8 residue loops. For loops above 12–13 residues in length, the same loops are selected, but with extensions to the β-strands. This is called the "sliding-ladder" effect. In addition, the maximum size of a random coil or turn fragment in any of the structures contained in the Protein Databank tends not to exceed 8 residues, as determined by DSSP. This implies that the conformational space of longer loops is not saturated by the database and, although it is unlikely that long loops in antibodies will differ significantly from long loops in other structures, confidence in the prediction must be correspondingly reduced.

By how much is the usefulness of the CAMAL algorithm reduced by this observation?

Figure 10:
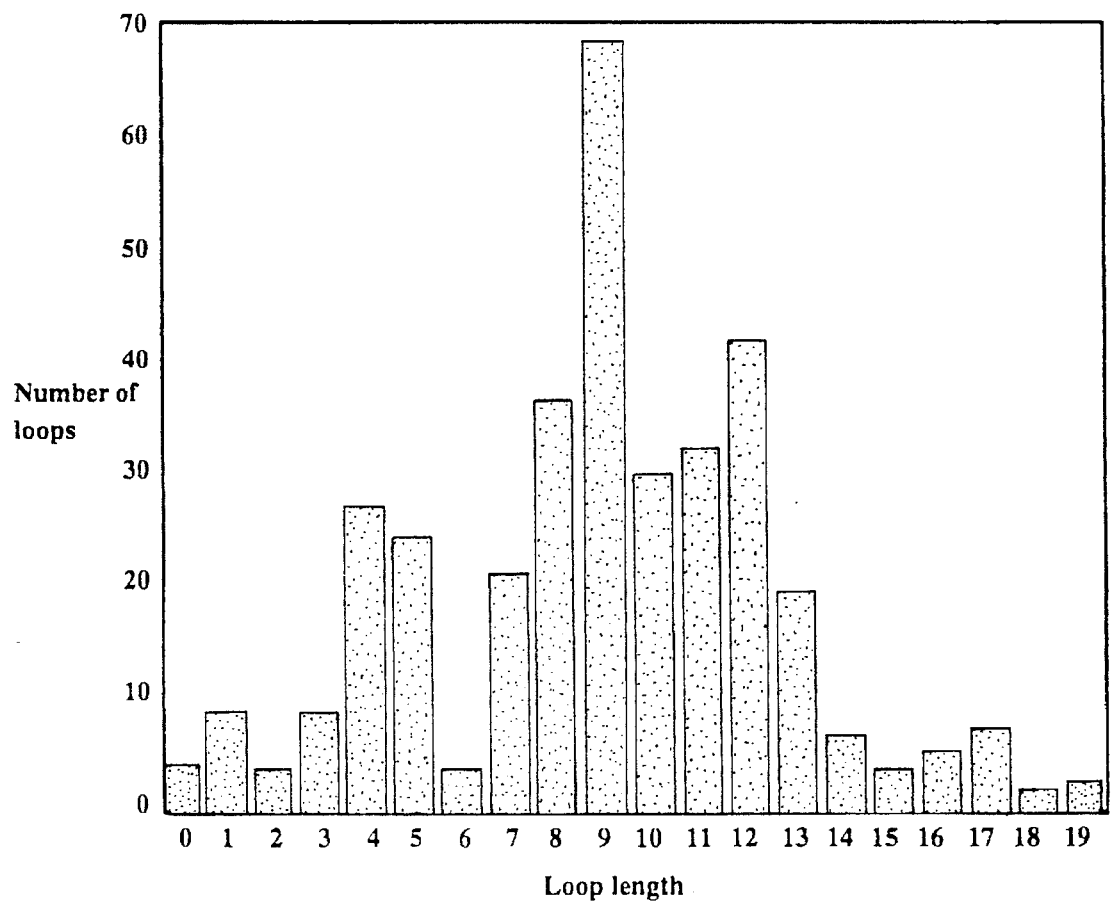
FIG. 10 is a histogram showing the distribution of loop length for CDR H3 loops, data from Kabat et al. (Kabat, E. A., Wu, T. T., Reid-Miller, M., Perry, H. M. and Gottesman, K. S. (1987), Sequences of Proteins of Immunological Interest. U.S. Department of Health and Human Services, Fourth Edition).

The frequency of occurrence of different CDR-H3 lengths in antibody sequences described by Kabat et al. (Kabat et al., 1987) was analyzed. FIG. 10 shows that more than 85% of H3 loops have lengths between 4 and 14 residues which can be modelled accurately by the CAMAL algorithm.

CDR-H3 of D1.3 is of average length (8 residues), though no loops of this length are seen in the available antibody structures. The crystal structure coordinate set showed an RMS of 1.9 Å compared with the model.

The 36–71 loop is 12 residues long. The conformation is correctly predicted as a short loop connecting an extension of the β-sheet.

The 3D6 H3 loop is 17 residues long. While KOL (Marquart et al., 1980) has the same length it has only one residue in common with 3D6 and only one conservative mutation. There is thus no reason to believe that the conformations would be similar. The final predicted conformation of 3D6 is an extended β-sheet, as in the crystal structure. The difference between the predicted and the crystal structure of 3D6-H3 is due to a twist of 5°–7° in the extended β-sheet loop (see FIGS. 9A–9D). Such a twist has also been observed for complexed and uncomplexed antibodies by Wilson et al. (Wilson and others). This suggests that long CDR-H3 loops may be flexible and actively involved in antigen binding.

The Complete Variable Region

Prediction of the strand positions and $V_L$-$V_H$ orientation in the framework β-barrel was exact for all of the four antibodies. The backbone (N,Cα,C) RMS deviations from the crystal structures were between 0.56 and 0.86 Å, despite the fact that, in all cases the $V_L$ and $V_H$ regions of a particular model were derived from different antibody structures. This suggests that this method will do well in procedures such as humanization (Gorman et al., 1991), where correct framework positioning is important. The backbones of all six CDRs in all four antibodies are essentially correctly predicted, as shown in FIG. 8. There are two important points to make about these predictions. First, the position of each CDR on its framework barrel is correct. Thus, CDR-framework interactions can be confidently monitored. The only deviation from the x-ray structure is CDR-H3 of antibody 3D6 which has been previously discussed. Second, the all atom RMS deviation between models and x-ray structures is dominated by sidechain positions. In most instances this deviation is due to a small number of incorrectly positioned, exposed sidechains (for example, in D1.3 the only sidechains which are incorrectly predicted are Tyr 9 of L1, Trp 4 of L3, Tyr 2 of H1 and Tyr 4 of H3). Since each CDR is constructed in the absence of other CDRs, the force field may choose a rotamer which is 120° away from that found in the crystal structure. This effect has also been observed by Lee et al. (Lee and Levitt, 1991).

Conclusion

For antibodies having CDR H3 regions of 14 residues or less the complete variable domain can be modelled to an accuracy approaching that of medium resolution x-ray structures. For antibodies with longer H3 loops the CAMAL algorithm is likely to need an additional procedure in which molecular dynamics simulations are also incorporated.

The canonical approach of Chothia et al. appears to work well (at least in modelling backbones) where it may be applied and may be used successfully in combination with the CAMAL procedure.

One important observation that has emerged from these studies is that a given loop can exist in several conformations. In particular, this seems likely for CDR-L1 and, to a lesser extent, CDR-L3 and longer CDR-H3's. A simple combinatorial calculation shows that, if each of these three loops can exist in three separate conformations, a given combining site can have $3^3=27$ different topographies. Clearly, this would explain the origins of cross reactivity and would allow for induced fit of antigens.

TABLE 2

Alignment of antibody sequences used in the modeling. '*' indicates CDR regions; '+' indicates β-strand regions used in the fitting for modelling frameworks. Nomenclature for β-barrel strands is (H or L - Chain) - FR(Framework region)-(Strand number), thus for example strand one of the heavy chain becomes HFR1.

| Antibody | SEQ. ID. No. | sequence L-chain |
|---|---|---|
| | | ********* ++++++ ***************** ++++++ ******* |
| gloop-2 | 1 | DIQMTQSPSSLSASLGERVSLTCRASQEISG----YLSWLQQKPDGTIKRLIYAASTL |
| d13 | 2 | DIQMTQSPASLSASVGETVTITCRASGNIHN----YLAWYQQKQGKSPQLLVYYTTTL |
| 3671 | 11 | DIQMTQIPSSLSASLGDRVSISCRASQDIN----NFLNWYQQKPDGSIKLLIYFTSRS |
| 3D6 | 12 | DIQMTQSPSTLSASVGDRVTITCRASQSISR----WLAWYQQKPGKVPKLLIYKASSL |
| | | ********** +++++ *************** |
| | | CDR L1                    CDR L2 |

| Antibody | Seq. ID. No. | sequence L-chain |
|---|---|---|
| | | ****** +++++++ ********** +++++ |
| gloop-2 | 1 | DSGVPKRFSGRRSGSDYSLTISSLESEDFADYYCLQYLS--YPLTFGAGTKLELKRA |
| d13 | 2 | ADGVPSRFSGSGSGTQYSLKINSLQPEDFGSYYCQHFWS--TPRTFGGGTKLEIKRR |
| 3671 | 11 | QSGVPSRFSGSGSGTDYSLTISNLEQEDIATYFCQQGNA--LPRTFGGGTKLEIKR- |
| 3D6 | 12 | ESGVPSRFSGSGSGTEFTLTISSLQPDDFATYYCQQYNS--YSFGPGTKVDIKE- |
| | | ** ++++++ *********** +++++ |
| | | CDR L3 |

| Antibody | Seq. ID. No. | sequence L-chain |
|---|---|---|
| | | ++++ **** ***************** +++++ |
| gloop-2 | 1 | QVQLQQSGTELARPGASVRLSCKASGYTFTTFGIT--WVKQRTGQGLEWIGEIFPGNS- |
| d13 | 2 | QVQLKESGPGLVAPSQSLSITCTVSGFSLTGYGVN--WVRQPPGKGLEWLGMIWGDG-- |
| 3671 | 11 | EVQLQQSGVEBLVRAGSSVKMSCKASGYTFTSNGIN--WVKQRPGQGLEWIGYNNPGNG-- |
| 3D6 | 12 | -VQLVESGGGLVQPGRSLRLSCAASGFTFNDYAMH--WVRQAPGKGLEWVSGISWDSS-- |

TABLE 2-continued

Alignment of antibody sequences used in the modeling. '*' indicates CDR regions; '+' indicates β-strand regions used in the fitting for modelling frameworks.
Nomenclature for β-barrel strands is (H or L - Chain) - FR(Framework region)-(Strand number), thus for example strand one of the heavy chain becomes HFR1.

```
                  ********  ++++++++********     ++++++++********
                  C D R  H 1                     C D R  H 2
            * * *
gloop-2  1  - - - - - - - - - K T Y Y A E R F K G K A T L T A D K S S T T A Y M Q L S S L T S E D S A V Y F C A R E I R - - - - - Y W G
d13      2  - - - - - - - - - N T D Y N S A L K S R L S I S K D N S K S Q V F L K M N S L H T D D T A R Y Y C A R E R D Y R L - - - - - D Y W G
3671    11  - - - - - - - - - Y I T Y N E K F K G K T T L T V D K S S N T A Y M Q L R S T L S E D S A V Y F C A R S E Y Y G G S Y K F - - - D Y W G
3D6     12  S I G Y A D S V K G R F T I S R D N A K N S L Y L Q M N S L R A E D M A L Y Y C V K G R D Y Y D S G G Y F T V A F D I W G
            * * *                                                     ++++++********                   C D R H s
```

TABLE 3

Details of the antibody crystal structures against which the models were compared and the parent frameworks used to build the models. Resolution data for D1.3 has not yet been published.

| | | | Framework Model | |
|---|---|---|---|---|
| Antibody | Resolution | R-factor | Light | Heavy |
| Gloop-2 | 2.80 | 21.2 | REI | HyHEL-5 |
| D1.3 | — | — | REI | NEW |
| 36–71 | 1.90 | 20.9 | Gloop2 | NEW |
| 3D6 | 2.70 | 17.7 | REI | KOL |

TABLE 4

Sequence and conformational search construction scheme for each of the 24 CRDs, [ ] = construction area, ( ) = Chain closure, all sidechains are constructed. RMS(Root Mean Square) difference between model and crystal loop coordinates. The RMS values are a global fit calculated by least-squares fitting the conserved core of the two structures upon each other and calculating the RMS over the loops. The total RMS of the frameworks (N,Ca,C) is 0.81, 0.60, 0.86 and 0.56 respectivly

| Antibody | CDR | sequence | SEQ. ID. No. | RMS local (Å) | | | | RMS global (Å) | | | |
|---|---|---|---|---|---|---|---|---|---|---|---|
| | | | | Cα | N,Cα,C | All CG | All MC | Cα | N,Cα,C | All CG | All MC |
| Gloop-2 | L1 | RAS[Q(EIS)G]YLS | 494 | 0.73 | 0.71 | 2.05 | 1.96 | 0.86 | 0.87 | 2.09 | 2.12 |
| D1.3 | | RAS[G(NIH)N]YLA | 495 | 2.29 | 1.93 | 4.34 | 3.94 | 2.72 | 2.43 | 4.59 | 4.32 |
| 36–71 | | RAS[Q(DIN)N]FLN | 496 | 2.71 | 2.43 | 4.80 | 4.59 | 3.51 | 3.31 | 5.19 | 5.67 |
| 3D6 | | RAS[Q(SIG)N]NLH | 497 | 0.51 | 0.54 | 2.48 | 1.82 | 0.61 | 0.78 | 2.68 | 1.96 |
| Gloop-2 | L2 | AASTLDS | 498 | 0.25 | 0.23 | 0.80 | 1.00 | 0.66 | 0.68 | 1.10 | 1.10 |
| D1.3 | | Y[T(TTL)A]D | 499 | 0.67 | 0.73 | 1.80 | 1.40 | 0.99 | 1.02 | 2.01 | 1.98 |
| 36–71 | | F[T(SRS)Q]S | 500 | 0.64 | 0.66 | 2.34 | 2.23 | 0.73 | 0.72 | 2.43 | 2.40 |
| 3D6 | | KASSLES | 501 | 0.41 | 0.42 | 1.37 | 1.20 | 0.83 | 0.86 | 1.73 | 1.80 |
| Gloop-2 | L3 | LQ[Y(LSY)P]LT | 502 | 0.56 | 0.52 | 1.73 | 1.60 | 0.75 | 0.74 | 2.00 | 1.90 |
| D1.3 | | QH[F(WST)P]RT | 503 | 1.41 | 1.35 | 2.69 | 2.98 | 1.76 | 1.79 | 3.46 | 3.20 |
| 36–71 | | QQ[G(NAL)P]RT | 504 | 1.09 | 1.00 | 2.26 | 2.10 | 1.46 | 1.36 | 2.36 | 2.28 |
| 3D6 | | Q[Q(YNS)Y]S | 505 | 1.46 | 1.68 | 3.64 | 3.90 | 2.31 | 1.97 | 3.96 | 3.90 |
| Gloop-2 | H1 | [T(FGI)T] | 506 | 0.60 | 0.70 | 2.00 | 1.60 | 1.03 | 1.01 | 2.04 | 2.00 |
| D1.3 | | [G(YGV)N] | 507 | 0.44 | 0.62 | 2.33 | 2.00 | 0.65 | 0.90 | 3.24 | 2.98 |
| 36–71 | | [S(NGI)N] | 508 | 0.90 | 0.63 | 2.22 | 1.96 | 1.04 | 0.97 | 2.51 | 2.23 |
| 3D6 | | DYAMH | 509 | 0.67 | 0.77 | 1.52 | 1.11 | 0.61 | 0.72 | 1.59 | 1.20 |
| Gloop-2 | H2 | EI[F(PGN)S]KYY | 510 | 0.63 | 0.64 | 1.63 | 1.70 | 1.20 | 0.94 | 2.23 | 2.10 |
| D1.3 | | MI[W(GDG)N]TD | 511 | 0.42 | 0.42 | 1.55 | 1.40 | 0.87 | 0.85 | 1.66 | 1.80 |
| 36–71 | | YNN[P(GNG)Y]IA | 512 | 0.64 | 0.78 | 2.01 | 2.20 | 1.47 | 1.41 | 1.79 | 1.98 |
| 3D6 | | ISWDSSSIG | 513 | 0.45 | 0.52 | 2.35 | 2.03 | 0.95 | 0.89 | 2.85 | 2.10 |
| Gloop-2 | H3 | [R(EIR)Y] | 514 | 0.66 | 0.89 | 3.44 | 3.90 | 0.87 | 1.07 | 3.66 | 4.15 |
| D1.3 | | ER[D(YRL)D]Y | 515 | 0.38 | 0.53 | 1.66 | 1.20 | 1.25 | 0.01 | 1.96 | 1.33 |
| 36–71 | | SEYY[G(GSY)K]FDY | 516 | 1.95 | 1.75 | 4.40 | 4.00 | 2.65 | 2.53 | 4.60 | 4.09 |
| 3D6 | | GRDYY[D(SGG)YF]TVAFDI | 517 | 3.66 | 3.42 | 5.93 | 4.01 | 4.30 | 3.95 | 6.30 | 6.20 |

TABLE 5

Canonical loops selected for the model of 3D6(taken from Chothia et al (1989)).

| Loop | Canonical | Sequence | Seq. ID. No. |
|---|---|---|---|
| L1 | HyHEL-10 | R A S Q S I S R W L A | 518 |
| | (3D6) | R A S Q S I G N N L H | 497 |
| L2 | REI | E A S N D L A | 519 |
| | (3D6) | K A S S L E S | 501 |
| H1 | McPC603 | D F Y M E | 520 |
| | (3D6) | D Y A M H | 509 |
| H2 | KOL | I I W D D G S D Q | 521 |
| | (3D6) | I S W D S S S I G | 513 |

TABLE 6

Backbone φ and ψ angles of residues in CDR-L1 from HyHEL-10 and REI classified in the same canonical group by Chothia et al (1989). The residues exhibiting a peptide flip are indicated by a *.

| | | Residue Number | | | | | |
|---|---|---|---|---|---|---|---|
| | | 24 | 25 | 26 | 27 | 28* | 29* |
| REI | Sequence | Q | A | S | Q | S | I |
| | φ/ψ | —/138 | −103/157 | −96/7 | −158/142 | −40/108 | −112/9 |
| HyHEL-10 | Sequence | R | A | S | Q | S | I |
| | φ/ψ | —/108 | −85/135 | −88/64 | 172/160 | −64/−38 | 9/63 |

| | | Residue Number | | | | | |
|---|---|---|---|---|---|---|---|
| | | 30* | 31* | 32 | 33 | 32 | |
| REI | Sequence | I | K | Y | L | N | Seq. ID. NO. 522 |
| | φ/ψ | 79/−77 | −146/21 | −104/89 | −143/133 | −144/— | |
| HyHEL-10 | Sequence | G | N | N | L | H | Seq. ID. NO: 518 |
| | φ/ψ | −63/107 | 85/−15 | −105/72 | −129/118 | −126/— | |

M. J. Darsley, P de al Paz, D. C. Phillips and A. R. Rees in Methodological Surveys in Biochemistry and Analysis, pages 63–68, Volume 15, 1985, Plenum Press (Eds. E. Reid, G. M. W. Cook and D. J. Morre), Presented at the Ninth International Subcellular Methodology Forum, Sep. 3–6, 1984, Guildford, UK.

Amit, A. G., Mariuzza, R. A., Phillips, S. E. V. and Poljak, R. J. (1986). The Three-dimensional Structures of an Antigen-antibody Complex at 2.8 Å Resolution. Science 233, pp. 747–753.

Åqvist, J., van Gunsieren, W., Leifonmark, M. and Tapia, O. (1985), J. Mol. Biol. 183, pp. 461–477.

Bernstein, F., Koetzle, T., Williams, G., Meyer, E., Brice, M., Rodgers, J., Kennard, O., Shimanouchi, T. and Tasumi, M. (1977), J. Mol. Biol. 112, pp. 535–542.

Brooks, B., Bruccoleri, R., Olaison, B., States, D., Swaminathan, S. and Karplus, M. (1983), J. Comp. Chem. 4, pp. 187–217.

Bruccoleri, R. E. and Karplus, M. (1987), Prediction of the Folding of Short Polypeptide Segments by Uniform Conformational Sampling. Biopolymers 26, pp. 137–168.

Carter, D. et al. (1991). Protein Engineering, p. 9999.

Chau, P. and Dean P. (1987). Molecular Recognition: 3d Surface Structure Comparison by Gnomonic Projection. J. Mol. Graph. 5, pp. 97–100.

Chothia, C., Lesk, A., Levitt, M., Amit, A., Mariuzza, R., Phillips, S. and Poljak, R. (1986). The Predicted Structure of Immunoglobulin D1.3 and its Comparison with the Crystal Structure. Science 233, pp. 755–758.

Chothia, C., Lesk, A. M., Tramontano, A., Levitt, M., Smith-Gill, S. J., Air, G., Sheriff, S., Padlan, E. A., Davies, D. R., Tulip, W. R., Colman, P. M., Alzri, P. M. and Poljak, R. J. (1989). Conformations of Immunoglobulin Hypervariable Regions. Nature (London) 342, pp. 877–883.

Cornette, J. L., Cease, K. B., Margalit, H., Spouge, J. L., Berzofsky, J. A. and Delisi, C. (1987). Hydrophobicity Scales and Computational Techniques for Detecting Amphipatic Structures in Proteins. Journal of Molecular Biology 195.3, pp. 659–685.

Darsley, M. and Rees, A. (1985), EMBO J. 4, pp. 383–392.

Davies, D., Sheriff, S. and Padlan, E. (1988). Antibody Antigen Complexes. J. Biol. Chem. 263, pp. 10541–10544.

de la Paz, P., Sutton, B., Darsly, M. and Rees, A. (1986). Modelling of the Combining Sites of Three Antilysozyme Monoclonal Antibodies and of the Complex Between One of the Antibodies and Its Epitope. EMBO J. 5, pp. 415–425.

Fine, R., Wang, H., Shenkin, P., Yarmush, D. and Levinthar, C. (1986). Predicting Antibody Hypervariable Loop Conformations ii: Minimization and Molecular Dynamics Studies of McPC603 from Many Randomly Generated Loop Conformations. Proteins: Struct., Funct., Genet. 1, pp. 342–362.

Go, N. and Sheraga, H. (1970). Ring Closure and Local Conformational Deformations of Chain Molecules. Macromolecules 3, pp. 178–187.

Gorman, S., Clark, M., Rutledge, E., Cobbold, S. and Waldman, H. (1991). Reshaping a Therapeutic CD4 Antibody. Proc. Natl. Acad. Sci. U.S.A. 88, pp. 4181–4185.

Grunow, R., Jahn, S., Porstman, T., Kiessig, T., Steinkeller, H., Steindl, F., Mattanovich, D., Gurtler, L., Deinhardt, F., Katinger, H. and von R., B. (1988). The High Efficiency, Human B Cell Immortalizing Heteromyeloma cb-f7. J. Immunol. Meth. 106, pp. 257–265.

Jeffrey, P. (1989). The Structure and Specificity of Immunoglobulins. D. Phil. Thesis, University of Oxford.

Lascombe, M., Alzari, P., Boulot, G., Salujian, P., Tougard, P., Berek, C., Haba, S., Rosen, E., Nisonof, A. and Poljak, R. (1989). Three-dimensional Structure of Fab r19.9, A Monoclonal Murine Antibody Specific for the pazobenzenearsonate Group. Proc. Natl. Acad. Sci. U.S.A. 86, p. 607.

Lee, C. and Levitt, M. (1991). Accurate Prediction of the Stability and Activity Effects of Site-directed Mutagenesis on a Protein Core. Nature 352.6334, pp. 448–451.

Lee, C. and Subbiah, S. (1991). Prediction of Protein Sidechain Conformation by Packing Optimization. Journal of Molecular Biology 217.2, pp. 373–388.

Marquart, M., Deisenhofer, J. and Huber, R. (1980), Crystallographic Refinement and Atomic Models of the Intact Immunoglobulin Molecule KOL and Its Antigen-binding Fragment at 3.0 Å and 1.9 Å Resolution. J. Mol. Biol. 141, pp. 369–391.

Martin, A. C. R. (1990). Molecular Modelling of Antibody Combining Sites. D. Phil. Thesis, University of Oxford.

Martin, A. C. R., Cheetham, J. C. and Rees, A. R. (1989). Modelling Antibody Hypervariable Loops: A Combined Algorithm. Proc. Natl. Acad. Sci. U.S.A. 86, pp. 9268–9272.

Martin, A. C. R., Cheetham, J. C. and Rees, A. R. (1991). Modelling Antibody Hypervariable Loops using a 'Combined Algorithm'. Meth. Enz. In press.

Moult, J. and James, N. (1986). Proteins: Struct., Funct., Genet. 1, p. 146.

Padlan, E., Davies, D., Pecht, I., Givol, D. and Wright, C. (1976). Model Building Studies of Antigen-binding Sites: The Hapten-Binding Site of MOPC-315. Cold Spring Harbor Quant. Symp. Biochem. 41, pp. 627–637.

Palmer, K. and Sheraga, J. (1991). Standard-geometry Chains Fitted to X-ray Deviated Structures: Validation of the Rigid-geometry Approximation. I. Chain Closure through a Limited Search of Loop Conformations. J. Comp. Chem. 12, pp. 505–526.

Paul, P., Burney, P., Campbell, M. and Odguthorpe, D. (1990). The Conformational Preferences of γ-lactam and Its Role in Constraining Peptide Structure. J. Comp.-aided. Mol. Des. 4, pp. 239–253.

Rose, D. R., Strong, R. K., Margolis, M. N., Gefter, M. L. and Petsko, G. A. (1990). Crystal Structure of the Antigen-binding Fragment of the Murine Anti-arsonate Monoclonal Antibody 36–71 at 2.9 Å Resolution. Proc. Natl. Acad. Sci. U.S.A. 87, pp. 338–342.

Rudikoff, S., Satow, Y., Padlan, E. A., Davies, D. R. and Potter, M. (1981). Kappa Chain Structure from a Crystallized Murine Fab': The Role of the Joining Segment in Hapten Binding. Mol. Immunol. 18, pp. 705–711.

Schilling, J., Clevinger, B., Davie, J. M. and Hood, L. (1980). Amino Acid Sequence of Homogeneous Antibodies to Dextran and DNA Rearrangements in Heavy Chain V-region Gene Segments. Nature (London) 283, pp. 35–40.

Strong, R., Campbell, R., Rose, D., Petsko, G., Sharon, J. and Margolies, M. (1991). Three-dimensional Structure of Murine Anti-pazophenylarsonate Fab 36–71.1, X-ray Crystallography, Site-directed Mutagenesis, and Modeling of the Complex with Hapten. Biochemistry 30, pp. 3739–3748.

Thornton, J., Sibanda, B., Edwards, M. and Barlow, D. (1988). Analysis, Design and Modification of Loop Regions in Proteins. BioEssays 8, pp. 63–69.

Tramontano, A. Chothia, C. and Lesk, A. (1989). Structural Determinants of the Conformations of Medium-sized Loops in Proteins. Proteins: Struct., Funct., Genet. 6, pp. 382–394.

Wilson, I. et al., Presented at Structure and Function Meeting in Honour of Sir David Phillips, 1–3 Jul., 1991, Oxford, UK.

---

---

What is claimed is:

1. A method for producing a humanized rodent antibody or fragment thereof by resurfacing, said method consisting essentially of:

(a) generating position alignments from relative accessibility distributions from x-ray crystallographic structures of a pool of rodent and human antibody heavy and light chain variable regions to give a set of heavy and light chain variable region framework surface exposed positions wherein the alignment positions for all rodent and human variable regions are at least about 98% identical;

(b) defining for a rodent antibody or fragment thereof a set of heavy and light chain variable region framework surface exposed amino acid residues using said set of heavy and light chain variable region framework surface exposed positions generated in said step (a);

(c) identifying from human antibody amino acid sequences a set of heavy and light chain variable region framework surface exposed amino acid residues that is most closely identical to said set of rodent surface exposed amino acid residues defined in said step (b);

(d) substituting, in the variable region framework amino acid sequence of said rodent antibody or fragment thereof, said set of heavy and light chain variable region framework surface exposed amino acid residues defined in said step (b) with said set of heavy and light chain variable region framework surface exposed amino acid residues identified in said step (c);

(e) constructing three-dimensional models of said variable region of said rodent antibody or fragment thereof and of said variable region of said rodent antibody or fragment thereof resulting from the substituting specified in said step (d);

(f) comparing said three-dimensional models constructed in said step (e), and identifying any amino acid residues from said sets identified in said steps (b) or (c), that are within 5 Ångstroms of any atom of any residue of the complementarity determining regions of said rodent antibody or fragment thereof;

(g) changing any residues identified in said step (f) from the human to the original rodent amino acid residue to thereby define a humanizing set of surface exposed amino acid residues;

(h) replacing the set of rodent antibody variable region framework surface exposed amino acid residues defined in said step (b) with the humanizing set of variable region framework surface exposed amino acid residues defined in said step (g); and (i) producing said humanized rodent antibody or fragment thereof having binding specificity.

2. The method of claim 1, wherein said rodent antibody is an antibody fragment.

3. The method of claim 2, wherein said rodent antibody fragment is a single chain antibody, a $F_V$ fragment, a Fab fragment, a $F(ab')_2$ fragment or a Fab' fragment.

4. The method of claim 1 or 2, wherein said step (c) identifies a set of naturally paired heavy and light chain surface exposed amino acid residues that is most closely identical to said set of surface exposed amino acid residues defined in said step (b).

5. The method of claim 1 or 2, wherein the set of heavy and light chain surface exposed positions in step (a) is identical in at least 98% of said sequence alignment positions.

6. The method of claim 1 or 2, wherein said surface exposed amino acid residues are those residues whose solvent accessibility is above 30%.

7. The method of claim 1 or 2, wherein the rodent antibody or fragment thereof is a murine antibody.

8. The method of claim 1 or 2, wherein the rodent antibody or fragment thereof is murine antibody anti-N901.

9. The method of claim 1 or 2, wherein said set of framework positions of surface exposed amino acid residues is defined by the set shown in Table 1 and the alignments set forth in FIGS. 3A and 3B:

TABLE 1

| Position | Human | Mouse |
|---|---|---|
| | Light chain | |
| 1 | D 51 E 34 A 5 S 5 | D 76 Q 9 E 6 |
| 3 | V 38 Q 24 S 24 Y 6 | V 63 Q 22 L 5 |
| 5 | T 61 L 37 | T 87 |
| 9 | 9 26 S 26 G 17 A 14 L 7 | S 36 A 29 L 17 P 5 |
| 15 | P 62 V 25 L 12 | L 47 P 30 V 8 A 7 |
| 18 | R 57 S 18 T 13 P 6 | R 38 K 22 S 13 Q 12 T 9 |
| 46 | P 94 | P 82 S 9 |
| 47 | G 89 | G 71 D 18 |
| 51 | K 43 R 31 | K 70 Q 13 R 8 T 5 |
| 63 | G 91 | G 98 |
| 66 | D 43 S 25 A 9 | D 38 A 26 S 26 |
| 73 | S 96 | S 90 I 5 |
| 86 | P 44 A 27 S 17 T 8 | A 50 P 11 T 8 E 7 Q 6 |
| 87 | E 71 D 11 G 7 | E 91 D 6 |
| 111 | K 74 R 12 N 6 | K 93 |
| 115 | K 54 L 40 | K 87 L 5 |
| 116 | R 60 G 33 S 5 | R 89 G 9 |
| 117 | Q 50 T 37 E 6 P 6 | A 74 Q 14 P 5 R 5 |

TABLE 1-continued

| Position | Human | Mouse |
|---|---|---|
| | Heavy chain | |
| 118 | E 47 Q 46 | E 59 Q 29 D 10 |
| 120 | Q 83 T 7 | Q 68 K 26 |
| 122 | V 59 L 15 Q 13 | Q 57 V 27 L 5 K 5 |
| 126 | G 54 A 23 P 18 | G 36 9 30 A 29 |
| 127 | G 53 E 22 A 14 D 7 | E 45 G 43 S 6 |
| 128 | L 61 V 31 F 7 | L 96 |
| 130 | K 46 Q 41 E 5 | K 52 Q 27 R 17 |
| 131 | P 95 | P 91 A 5 |
| 132 | G 74 S 16 T 7 | G 82 S 17 |
| 136 | R 53 K 23 S 17 T 7 | K 66 S 17 R 13 |
| 143 | G 96 | G 98 |
| 145 | T 46 S 32 N 9 I 7 | T 63 S 19 N 7 A 5 D 5 |
| 160 | P 84 S 10 | P 89 H 7 |
| 161 | G 93 | G 71 E 24 |
| 162 | K 76 Q 10 R 8 | K 50 Q 30 N 10 H 5 |
| 183 | D 26 P 25 A 17 Q 10 T 7 | E 31 P 22 D 17 A 12 Q 11 |
| 184 | S 70 K 9 P 8 | K 42 S 37 T 6 |
| 186 | K 53 Q 22 R 7 N 5 | K 83 Q 7 |
| 187 | G 66 S 21 T 5 | G 62 S 18 D 10 |
| 195 | T 30 D 26 N 19 K 7 | T 36 K 30 N 26 D 6 |
| 196 | S 91 | S 76 A 16 |
| 197 | K 65 I 8 T 8 R 5 | S 46 K 34 Q 11 |
| 208 | R 46 T 18 K 17 D 6 | T 55 R 26 K 8 |
| 209 | A 50 P 21 S 13 T 8 | S 67 A 14 T 11 |
| 210 | E 46 A 18 D 13 S 9 Z 8 V 5 | E 88 D 7 |
| 212 | T 91 | T 53 S 43 |
| 222 | G 17 D 11 P 10 Y 9 V N 8 | D 67 A 18. |

10. A resurfaced rodent antibody or fragment thereof made by the method of claim 1.

11. The resurfaced antibody or fragment thereof of claim 10, wherein said rodent antibody is an antibody fragment.

12. The resurfaced antibody or fragment thereof of claim 10, wherein said rodent antibody fragment is a single chain antibody, a $F_V$ fragment, a Fab fragment, a $F(ab')_2$ fragment or a Fab' fragment.

13. The resurfaced antibody or fragment thereof of claim 10 or 11, wherein said surface exposed amino acid residues are those residues whose solvent accessibility is above 30%.

14. The resurfaced antibody or fragment thereof of claim 10, or 11, wherein the rodent antibody or fragment thereof is a murine antibody.

15. The resurfaced antibody or fragment thereof of claim 10 or 11, wherein the rodent antibody or fragment thereof to be humanized is murine antibody anti-N901.

16. The resurfaced antibody or fragment thereof of claim 10 or 11, wherein said set of framework positions of surface exposed amino acid residues is defined by the set shown in Table 1 and the alignments set forth in FIGS. 3A and 3B:

TABLE 1

| Position | Human | Mouse |
|---|---|---|
| | Light chain | |
| 1 | D 51 E 34 A 5 S 5 | D 76 Q 9 E 6 |
| 3 | V 38 Q 24 S 24 Y 6 | V 63 Q 22 L 5 |
| 5 | T 61 L 37 | T 87 |
| 9 | 9 26 S 26 G 17 A 14 L 7 | S 36 A 29 L 17 P 5 |
| 15 | P 62 V 25 L 12 | L 47 P 30 V 8 A 7 |
| 18 | R 57 S 18 T 13 P 6 | R 38 K 22 S 13 Q 12 T 9 |
| 46 | P 94 | P 82 S 9 |
| 47 | G 89 | G 71 D 18 |
| 51 | K 43 R 31 | K 70 Q 13 R 8 T 5 |
| 63 | G 91 | G 98 |

TABLE 1-continued

| Position | Human | Mouse |
|---|---|---|
| 66 | D 43 S 25 A 9 | D 38 A 26 S 26 |
| 73 | S 96 | S 90 I 5 |
| 86 | P 44 A 27 S 17 T 8 | A 50 P 11 T 8 E 7 Q 6 |
| 87 | E 71 D 11 G 7 | E 91 D 6 |
| 111 | K 74 R 12 N 6 | K 93 |
| 115 | K 54 L 40 | K 87 L 5 |
| 116 | R 60 G 33 S 5 | R 89 G 9 |
| 117 | Q 50 T 37 E 6 P 6 | A 74 Q 14 P 5 R 5 |
| Heavy chain | | |
| 118 | E 47 Q 46 | E 59 Q 29 D 10 |
| 120 | Q 83 T 7 | Q 68 K 26 |
| 122 | V 59 L 15 Q 13 | Q 57 V 27 L 5 K 5 |
| 126 | G 54 A 23 P 18 | G 36 9 30 A 29 |
| 127 | G 53 E 22 A 14 D 7 | E 45 G 43 S 6 |
| 128 | L 61 V 31 F 7 | L 96 |
| 130 | K 46 Q 41 E 5 | K 52 Q 27 R 17 |
| 131 | P 95 | P 91 A 5 |
| 132 | G 74 S 16 T 7 | G 82 S 17 |
| 136 | R 53 K 23 S 17 T 7 | K 66 S 17 R 13 |
| 143 | G 96 | G 98 |

TABLE 1-continued

| Position | Human | Mouse |
|---|---|---|
| 145 | T 46 S 32 N 9 I 7 | T 63 S 19 N 7 A 5 D 5 |
| 160 | P 84 S 10 | P 89 H 7 |
| 161 | G 93 | G 71 E 24 |
| 162 | K 76 Q 10 R 8 | K 50 Q 30 N 10 H 5 |
| 183 | D 26 P 25 A 17 Q 10 T 7 | E 31 P 22 D 17 A 12 Q 11 |
| 184 | S 70 K 9 P 8 | K 42 S 37 T 6 |
| 186 | K 53 Q 22 R 7 N 5 | K 83 Q 7 |
| 187 | G 66 S 21 T 5 | G 62 S 18 D 10 |
| 195 | T 30 D 26 N 19 K 7 | T 36 K 30 N 26 D 6 |
| 196 | S 91 | S 76 A 16 |
| 197 | K 65 I 8 T 8 R 5 | S 46 K 34 Q 11 |
| 208 | R 46 T 18 K 17 D 6 | T 55 R 26 K 8 |
| 209 | A 50 P 21 S 13 T 8 | S 67 A 14 T 11 |
| 210 | E 46 A 18 D 13 S 9 Z 8 V 5 | E 88 D 7 |
| 212 | T 91 | T 53 S 43 |
| 222 | G 17 D 11 P 10 Y 9 V N 8 | D 67 A 18. |

\* \* \* \* \*

UNITED STATES PATENT AND TRADEMARK OFFICE
CERTIFICATE OF CORRECTION

| | | |
|---|---|---|
| PATENT NO. | : 5,639,641 | Page 1 of 1 |
| APPLICATION NO. | : 07/942245 | |
| DATED | : June 17, 1997 | |
| INVENTOR(S) | : Jan T. Pedersen et al. | |

It is certified that error appears in the above-identified patent and that said Letters Patent is hereby corrected as shown below:

Table 1:

Column 12, line 40, please move the alignment of the third column heading "Mouse" to the far right, so that it is aligned above the residues listed in row 3 on lines 42-67.

Column 12, line 46, for residue 9, under column "Human," please replace "9 26" with --P 26.--

Column 12, lines 52-53, please insert a new row between residues 73 and 86, corresponding to residue 76, as follows: under column "Position," please insert --76--; under column "Human," please insert --D 43 T 18 S 16 E 15--; and under column "Mouse," please insert --D 67 S 15 A 5 K 5.--

Column 12, line 62, for residue 126, under column "Mouse," please replace "9 30" with --P 30.--

Signed and Sealed this

Twenty-sixth Day of February, 2008

JON W. DUDAS
*Director of the United States Patent and Trademark Office*

SEQUENCE LISTING ( 1 ) GENERAL INFORMATION:

( i i i ) NUMBER OF SEQUENCES: 522

( 2 ) INFORMATION FOR SEQ ID NO:1:

( i ) SEQUENCE CHARACTERISTICS:
        ( A ) LENGTH: 109 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:1:

```
Asp Ile Gln Met Thr Gln Ser Pro Ser Ser Leu Ser Ala Ser Leu Gly
  1               5                  10                      15

Glu Arg Val Ser Leu Thr Cys Arg Ala Ser Gln Glu Ile Ser Gly Tyr
                 20                  25                  30

Leu Ser Trp Leu Gln Gln Lys Pro Asp Gly Thr Ile Lys Arg Leu Ile
             35                  40                  45

Tyr Ala Ala Ser Thr Leu Asp Ser Gly Val Pro Lys Arg Phe Ser Gly
         50                  55                  60

Arg Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Leu Ser Tyr Pro Leu
                 85                  90                  95

Thr Phe Gly Ala Gly Thr Lys Leu Glu Leu Lys Arg Ala
                100                 105
```

( 2 ) INFORMATION FOR SEQ ID NO:2:

( i ) SEQUENCE CHARACTERISTICS:
        ( A ) LENGTH: 109 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:2:

```
Asp  Ile  Gln  Met  Thr  Gln  Ser  Pro  Ala  Ser  Leu  Ser  Ala  Ser  Val  Gly
 1              5                        10                       15

Glu  Thr  Val  Thr  Ile  Thr  Cys  Arg  Ala  Ser  Gly  Asn  Ile  His  Asn  Tyr
               20                       25                  30

Leu  Ala  Trp  Tyr  Gln  Gln  Lys  Gln  Gly  Lys  Ser  Pro  Gln  Leu  Leu  Val
          35                       40                  45

Tyr  Tyr  Thr  Thr  Thr  Leu  Ala  Asp  Gly  Val  Pro  Ser  Arg  Phe  Ser  Gly
     50                       55                  60

Ser  Gly  Ser  Gly  Thr  Gln  Tyr  Ser  Leu  Lys  Ile  Asn  Ser  Leu  Gln  Pro
 65                      70                  75                            80

Glu  Asp  Phe  Gly  Ser  Tyr  Tyr  Cys  Gln  His  Phe  Trp  Ser  Thr  Pro  Arg
               85                       90                            95

Thr  Phe  Gly  Gly  Gly  Thr  Lys  Leu  Glu  Ile  Lys  Arg  Arg
              100                      105
```

(2) INFORMATION FOR SEQ ID NO:3:

(i) SEQUENCE CHARACTERISTICS:
        (A) LENGTH: 107 amino acids
        (B) TYPE: amino acid
        (C) TOPOLOGY: linear (ii) MOLECULE TYPE: peptide (xi) SEQUENCE DESCRIPTION: SEQ ID NO:3:

```
Asp  Ile  Val  Leu  Thr  Gln  Ser  Pro  Ala  Ile  Met  Ser  Ala  Ser  Pro  Gly
 1              5                        10                       15

Glu  Lys  Val  Thr  Met  Thr  Cys  Ser  Ala  Ser  Ser  Ser  Val  Asn  Tyr  Met
               20                       25                       30

Tyr  Trp  Tyr  Gln  Gln  Lys  Ser  Gly  Thr  Ser  Pro  Lys  Arg  Trp  Ile  Tyr
          35                       40                  45

Asp  Thr  Ser  Lys  Leu  Ala  Ser  Gly  Val  Pro  Val  Arg  Phe  Ser  Gly  Ser
     50                       55                  60

Gly  Ser  Gly  Thr  Ser  Tyr  Ser  Leu  Thr  Ile  Ser  Ser  Met  Glu  Thr  Glu
 65                      70                  75                            80

Asp  Ala  Ala  Glu  Tyr  Tyr  Cys  Gln  Gln  Trp  Gly  Arg  Asn  Pro  Thr  Phe
               85                       90                            95

Gly  Gly  Gly  Thr  Lys  Leu  Glu  Ile  Lys  Arg  Ala
              100                      105
```

(2) INFORMATION FOR SEQ ID NO:4:

(i) SEQUENCE CHARACTERISTICS:
        (A) LENGTH: 109 amino acids
        (B) TYPE: amino acid
        (C) TOPOLOGY: linear (ii) MOLECULE TYPE: peptide (xi) SEQUENCE DESCRIPTION: SEQ ID NO:4:

```
Asp  Ile  Val  Leu  Thr  Gln  Ser  Pro  Ala  Thr  Leu  Ser  Val  Thr  Pro  Gly
 1              5                        10                       15

Asn  Ser  Val  Ser  Leu  Ser  Cys  Arg  Ala  Ser  Gln  Ser  Ile  Gly  Asn  Asn
               20                       25                       30

Leu  His  Trp  Tyr  Gln  Gln  Lys  Ser  His  Glu  Ser  Pro  Arg  Leu  Leu  Ile
          35                       40                  45

Lys  Tyr  Ala  Ser  Gln  Ser  Ile  Ser  Gly  Ile  Pro  Ser  Arg  Phe  Ser  Gly
     50                       55                  60

Ser  Gly  Ser  Gly  Thr  Asp  Phe  Thr  Leu  Ser  Ile  Asn  Ser  Val  Glu  Thr
 65                      70                  75                            80
```

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys Arg Ala
            100                 105

( 2 ) INFORMATION FOR SEQ ID NO:5:

( i ) SEQUENCE CHARACTERISTICS:
        ( A ) LENGTH: 108 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:5:

Glu Ile Val Leu Thr Gln Ser Pro Ala Ile Thr Ala Ala Ser Leu Gly
 1               5                  10                  15

Gln Lys Val Thr Ile Thr Cys Ser Ala Ser Ser Ser Val Ser Ser Leu
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
 50                  55                  60

Gly Ser Gly Thr Ser Tyr Ser Leu Thr Ile Asn Thr Met Glu Ala Glu
65                  70                  75                  80

Asp Ala Ala Ile Tyr Tyr Cys Gln Gln Trp Thr Tyr Pro Leu Ile Thr
                85                  90                  95

Phe Gly Ala Gly Thr Lys Leu Glu Leu Lys Arg Ala
            100                 105

( 2 ) INFORMATION FOR SEQ ID NO:6:

( i ) SEQUENCE CHARACTERISTICS:
        ( A ) LENGTH: 112 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:6:

Glu Ser Val Leu Thr Gln Pro Pro Ser Ala Ser Gly Thr Pro Gly Gln
 1               5                  10                  15

Arg Val Thr Ile Ser Cys Thr Gly Thr Ser Ser Asn Ile Gly Ser Ile
            20                  25                  30

Thr Val Asn Trp Tyr Gln Gln Leu Pro Gly Met Ala Pro Lys Leu Leu
        35                  40                  45

Ile Tyr Arg Asp Ala Met Arg Pro Ser Gly Val Pro Thr Arg Phe Ser
 50                  55                  60

Gly Ser Lys Ser Gly Thr Ser Ala Ser Leu Ala Ile Ser Gly Leu Glu
65                  70                  75                  80

Ala Glu Asp Glu Ser Asp Tyr Tyr Cys Ala Ser Trp Asn Ser Ser Asp
                85                  90                  95

Asn Ser Tyr Val Phe Gly Thr Gly Thr Lys Val Thr Val Leu Gly Gln
            100                 105                         110

( 2 ) INFORMATION FOR SEQ ID NO:7:

( i ) SEQUENCE CHARACTERISTICS:
        ( A ) LENGTH: 115 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:7:

| Asp | Ile | Val | Met | Thr | Gln | Ser | Pro | Ser | Ser | Leu | Ser | Val | Ser | Ala | Gly |
| 1 | | | | 5 | | | | | 10 | | | | | 15 | |

| Glu | Arg | Val | Thr | Met | Ser | Cys | Lys | Ser | Ser | Gln | Ser | Leu | Leu | Asn | Ser |
| | | | 20 | | | | | 25 | | | | | 30 | | |

| Gly | Asn | Gln | Lys | Asn | Phe | Leu | Ala | Trp | Tyr | Gln | Gln | Lys | Pro | Gly | Gln |
| | | | 35 | | | | 40 | | | | | 45 | | | |

| Pro | Pro | Lys | Leu | Leu | Ile | Tyr | Gly | Ala | Ser | Thr | Arg | Glu | Ser | Gly | Val |
| | | 50 | | | | 55 | | | | | 60 | | | | |

| Pro | Asp | Arg | Phe | Thr | Gly | Ser | Gly | Ser | Gly | Thr | Asp | Phe | Thr | Leu | Thr |
| 65 | | | | 70 | | | | | 75 | | | | | 80 | |

| Ile | Ser | Ser | Val | Gln | Ala | Glu | Asp | Leu | Ala | Val | Tyr | Tyr | Cys | Gln | Asn |
| | | | | 85 | | | | 90 | | | | | 95 | | |

| Asp | His | Ser | Tyr | Pro | Leu | Thr | Phe | Gly | Ala | Gly | Thr | Lys | Leu | Glu | Ile |
| | | | 100 | | | | | 105 | | | | | 110 | | |

| Lys | Arg | Ala |
| | | 115 |

( 2 ) INFORMATION FOR SEQ ID NO:8:

( i ) SEQUENCE CHARACTERISTICS:
( A ) LENGTH: 103 amino acids
( B ) TYPE: amino acid
( C ) TOPOLOGY: linear ( i i ) MOLECULE TYPE: peptide ( x i ) SEQUENCE DESCRIPTION: SEQ ID NO:8:

| Ser | Val | Leu | Thr | Gln | Pro | Pro | Ser | Val | Ser | Gly | Ala | Pro | Gly | Gln | Arg |
| 1 | | | | 5 | | | | | 10 | | | | | 15 | |

| Val | Thr | Ile | Ser | Cys | Thr | Gly | Ser | Ser | Ser | Asn | Ile | Gly | Ala | Gly | Asn |
| | | | 20 | | | | | 25 | | | | | 30 | | |

| His | Val | Lys | Trp | Tyr | Gln | Gln | Leu | Pro | Gly | Thr | Ala | Pro | Lys | Leu | Leu |
| | | 35 | | | | | 40 | | | | | 45 | | | |

| Ile | Phe | His | Asn | Asn | Ala | Arg | Phe | Ser | Val | Ser | Lys | Ser | Gly | Ser | Ser |
| | 50 | | | | | 55 | | | | | 60 | | | | |

| Ala | Thr | Leu | Ala | Ile | Thr | Gly | Leu | Gln | Ala | Glu | Asp | Glu | Ala | Asp | Tyr |
| 65 | | | | | 70 | | | | | 75 | | | | | 80 |

| Tyr | Cys | Gln | Ser | Tyr | Asp | Arg | Ser | Leu | Arg | Val | Phe | Gly | Gly | Gly | Thr |
| | | | | 85 | | | | | 90 | | | | | 95 | |

| Lys | Leu | Thr | Val | Leu | Arg | Gln |
| | | | 100 | | | |

( 2 ) INFORMATION FOR SEQ ID NO:9:

( i ) SEQUENCE CHARACTERISTICS:
( A ) LENGTH: 114 amino acids
( B ) TYPE: amino acid
( C ) TOPOLOGY: linear ( i i ) MOLECULE TYPE: peptide ( x i ) SEQUENCE DESCRIPTION: SEQ ID NO:9:

| Asp | Val | Val | Met | Thr | Gln | Thr | Pro | Leu | Ser | Leu | Pro | Val | Ser | Leu | Gly |
| 1 | | | | 5 | | | | | 10 | | | | | 15 | |

| Asp | Gln | Ala | Ser | Ile | Ser | Cys | Arg | Ser | Ser | Gln | Ser | Leu | Val | His | Ser |
| | | | 20 | | | | | 25 | | | | | 30 | | |

5,639,641

Gln Gly Asn Thr Tyr Leu Arg Trp Tyr Leu Gln Lys Pro Gly Gln Ser
        35                      40                      45

Pro Lys Val Leu Ile Tyr Lys Val Ser Asn Arg Phe Ser Gly Val Pro
        50                      55                      60

Asn Arg Phe Ser Gly Ser Gly Ser Gly Thr Asp Phe Thr Leu Lys Ile
 65                      70                      75                 80

Ser Arg Val Glu Ala Glu Asp Leu Gly Val Tyr Phe Cys Ser Gln Ser
                    85                      90                      95

Thr His Val Pro Trp Thr Phe Gly Gly Gly Thr Lys Leu Glu Ile Lys
                100                     105                     110

Arg Ala (2) INFORMATION FOR SEQ ID NO:10:

(i) SEQUENCE CHARACTERISTICS:
       (A) LENGTH: 109 amino acids
       (B) TYPE: amino acid
       (C) TOPOLOGY: linear (ii) MOLECULE TYPE: peptide (xi) SEQUENCE DESCRIPTION: SEQ ID NO:10:

Asp Ile Gln Met Thr Gln Thr Thr Ser Ser Leu Ser Ala Ser Leu Gly
 1                       5                      10                      15

Asp Arg Val Thr Ile Ser Cys Arg Ala Ser Gln Asp Ile Ser Asn Tyr
                    20                      25                      30

Leu Asn Trp Tyr Gln Gln Lys Pro Asp Gly Thr Val Lys Leu Leu Val
            35                      40                      45

Tyr Tyr Thr Ser Arg Leu His Ser Gly Val Pro Ser Arg Phe Ser Gly
        50                      55                      60

Ser Gly Ser Gly Thr Asp Tyr Ser Leu Thr Ile Ser Asn Leu Glu His
 65                      70                      75                 80

Glu Asp Ile Ala Thr Tyr Phe Cys Gln Gln Gly Ser Thr Thr Pro Arg
                    85                      90                      95

Thr Phe Gly Gly Gly Thr Lys Leu Glu Ile Lys Arg Arg
                100                     105

(2) INFORMATION FOR SEQ ID NO:11:

(i) SEQUENCE CHARACTERISTICS:
       (A) LENGTH: 109 amino acids
       (B) TYPE: amino acid
       (C) TOPOLOGY: linear (ii) MOLECULE TYPE: peptide (xi) SEQUENCE DESCRIPTION: SEQ ID NO:11:

Asp Ile Gln Met Thr Gln Ile Pro Ser Ser Leu Ser Ala Ser Leu Gly
 1                       5                      10                      15

Asp Arg Val Ser Ile Ser Cys Arg Ala Ser Gln Asp Ile Asn Asn Phe
                    20                      25                      30

Leu Asn Trp Tyr Gln Gln Lys Pro Asp Gly Thr Ile Lys Leu Leu Ile
            35                      40                      45

Tyr Phe Thr Ser Arg Ser Gln Ser Gly Val Pro Ser Arg Phe Ser Gly
        50                      55                      60

Ser Gly Ser Gly Thr Asp Tyr Ser Leu Thr Ile Ser Asn Leu Glu Gln
 65                      70                      75                 80

Glu Asp Ile Ala Thr Tyr Phe Cys Gln Gln Gly Asn Ala Leu Pro Arg
                    85                      90                      95

Thr Phe Gly Gly Gly Thr Lys Leu Glu Ile Lys Arg Ala
                100                 105

( 2 ) INFORMATION FOR SEQ ID NO:12:

( i ) SEQUENCE CHARACTERISTICS:
　　　　( A ) LENGTH: 107 amino acids
　　　　( B ) TYPE: amino acid
　　　　( C ) TOPOLOGY: linear ( i i ) MOLECULE TYPE: peptide ( x i ) SEQUENCE DESCRIPTION: SEQ ID NO:12:

Asp Ile Gln Met Thr Gln Ser Pro Ser Thr Leu Ser Ala Ser Val Gly
 1               5                  10                 15

Asp Arg Val Thr Ile Thr Cys Arg Ala Ser Gln Ser Ile Ser Arg Trp
            20                  25                 30

Leu Ala Trp Tyr Gln Gln Lys Pro Gly Lys Val Pro Lys Leu Leu Ile
         35                  40                 45

Tyr Lys Ala Ser Ser Leu Glu Ser Gly Val Pro Ser Arg Phe Ser Gly
     50                  55                 60

Ser Gly Ser Gly Thr Glu Phe Thr Leu Thr Ile Ser Ser Leu Gln Pro
65                  70                  75                 80

Asp Asp Phe Ala Thr Tyr Tyr Cys Gln Gln Tyr Asn Ser Tyr Ser Phe
             85                  90                 95

Gly Pro Gly Thr Lys Val Asp Ile Lys Arg Thr
              100                 105

( 2 ) INFORMATION FOR SEQ ID NO:13:

( i ) SEQUENCE CHARACTERISTICS:
　　　　( A ) LENGTH: 104 amino acids
　　　　( B ) TYPE: amino acid
　　　　( C ) TOPOLOGY: linear ( i i ) MOLECULE TYPE: peptide ( x i ) SEQUENCE DESCRIPTION: SEQ ID NO:13:

Gln Val Gln Leu Gln Gln Ser Gly Thr Glu Leu Ala Arg Pro Gly Ala
 1               5                  10                 15

Ser Val Arg Leu Ser Cys Lys Ala Ser Gly Tyr Thr Phe Thr Thr Phe
            20                  25                 30

Gly Ile Thr Trp Val Lys Gln Arg Thr Gly Gln Gly Leu Glu Trp Ile
         35                  40                 45

Gly Glu Ile Phe Pro Gly Asn Ser Lys Thr Tyr Tyr Ala Glu Arg Phe
     50                  55                 60

Lys Gly Lys Ala Thr Leu Thr Ala Asp Lys Ser Ser Thr Thr Ala Tyr
65                  70                  75                 80

Met Gln Leu Ser Ser Leu Thr Ser Glu Asp Ser Ala Val Tyr Phe Cys
             85                  90                 95

Ala Arg Glu Ile Arg Tyr Trp Gly
              100

( 2 ) INFORMATION FOR SEQ ID NO:14:

( i ) SEQUENCE CHARACTERISTICS:
　　　　( A ) LENGTH: 107 amino acids
　　　　( B ) TYPE: amino acid
　　　　( C ) TOPOLOGY: linear ( i i ) MOLECULE TYPE: peptide ( x i ) SEQUENCE DESCRIPTION: SEQ ID NO:14:

| Gln | Val | Gln | Leu | Lys | Glu | Ser | Gly | Pro | Gly | Leu | Val | Ala | Pro | Ser | Gln |
|---|---|---|---|---|---|---|---|---|---|---|---|---|---|---|---|
| 1 | | | | 5 | | | | | 10 | | | | | 15 | |

| Ser | Leu | Ser | Ile | Thr | Cys | Thr | Val | Ser | Gly | Phe | Ser | Leu | Thr | Gly | Tyr |
|---|---|---|---|---|---|---|---|---|---|---|---|---|---|---|---|
| | | | 20 | | | | | 25 | | | | | 30 | | |

| Gly | Val | Asn | Trp | Val | Arg | Gln | Pro | Pro | Gly | Lys | Gly | Leu | Glu | Trp | Leu |
|---|---|---|---|---|---|---|---|---|---|---|---|---|---|---|---|
| | | 35 | | | | | | 40 | | | | | 45 | | |

| Gly | Met | Ile | Trp | Gly | Asp | Gly | Asn | Thr | Asp | Tyr | Asn | Ser | Ala | Leu | Lys |
|---|---|---|---|---|---|---|---|---|---|---|---|---|---|---|---|
| | 50 | | | | | 55 | | | | | 60 | | | | |

| Ser | Arg | Leu | Ser | Ile | Ser | Lys | Asp | Asn | Ser | Lys | Ser | Gln | Val | Phe | Leu |
|---|---|---|---|---|---|---|---|---|---|---|---|---|---|---|---|
| 65 | | | | | 70 | | | | | 75 | | | | | 80 |

| Lys | Met | Asn | Ser | Leu | His | Thr | Asp | Asp | Thr | Ala | Arg | Tyr | Tyr | Cys | Ala |
|---|---|---|---|---|---|---|---|---|---|---|---|---|---|---|---|
| | | | | 85 | | | | | 90 | | | | | 95 | |

| Arg | Glu | Arg | Asp | Tyr | Arg | Leu | Asp | Tyr | Trp | Gly |
|---|---|---|---|---|---|---|---|---|---|---|
| | | | 100 | | | | | 105 | | |

( 2 ) INFORMATION FOR SEQ ID NO:15:

( i ) SEQUENCE CHARACTERISTICS:
        ( A ) LENGTH: 106 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:15:

| Val | Gln | Leu | Gln | Gln | Ser | Gly | Ala | Glu | Leu | Met | Lys | Pro | Gly | Ala | Ser |
|---|---|---|---|---|---|---|---|---|---|---|---|---|---|---|---|
| 1 | | | | 5 | | | | | 10 | | | | | 15 | |

| Val | Lys | Ile | Ser | Cys | Lys | Ala | Ser | Gly | Tyr | Thr | Phe | Ser | Asp | Tyr | Trp |
|---|---|---|---|---|---|---|---|---|---|---|---|---|---|---|---|
| | | | 20 | | | | | 25 | | | | | 30 | | |

| Ile | Glu | Trp | Val | Lys | Gln | Arg | Pro | Gly | His | Gly | Leu | Glu | Trp | Ile | Gly |
|---|---|---|---|---|---|---|---|---|---|---|---|---|---|---|---|
| | | 35 | | | | | | 40 | | | | | 45 | | |

| Glu | Ile | Leu | Pro | Gly | Ser | Gly | Ser | Thr | Asn | Tyr | His | Glu | Arg | Phe | Lys |
|---|---|---|---|---|---|---|---|---|---|---|---|---|---|---|---|
| | | 50 | | | | | 55 | | | | | 60 | | | |

| Gly | Lys | Ala | Thr | Phe | Thr | Ala | Asp | Thr | Ser | Ser | Ser | Thr | Ala | Tyr | Met |
|---|---|---|---|---|---|---|---|---|---|---|---|---|---|---|---|
| 65 | | | | | 70 | | | | | 75 | | | | | 80 |

| Gln | Leu | Asn | Ser | Leu | Thr | Ser | Glu | Asp | Ser | Gly | Val | Tyr | Tyr | Cys | Leu |
|---|---|---|---|---|---|---|---|---|---|---|---|---|---|---|---|
| | | | | 85 | | | | | 90 | | | | | 95 | |

| His | Gly | Asn | Tyr | Asp | Phe | Asp | Gly | Trp | Gly |
|---|---|---|---|---|---|---|---|---|---|
| | | | 100 | | | | | 105 | |

( 2 ) INFORMATION FOR SEQ ID NO:16:

( i ) SEQUENCE CHARACTERISTICS:
        ( A ) LENGTH: 104 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:16:

| Asp | Val | Gln | Leu | Gln | Glu | Ser | Gly | Pro | Ser | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ser | Val | Thr | Gly | Asp | Ser | Ile | Thr | Ser | Asp |
|---|---|---|---|---|---|---|---|---|---|---|---|---|---|---|---|
| | | | 20 | | | | | 25 | | | | | 30 | | |

| Tyr | Trp | Ser | Trp | Ile | Arg | Lys | Phe | Pro | Gly | Asn | Arg | Leu | Glu | Tyr | Met |
|---|---|---|---|---|---|---|---|---|---|---|---|---|---|---|---|
| | | 35 | | | | | | 40 | | | | | 45 | | |

| Gly | Tyr | Val | Ser | Tyr | Ser | Gly | Ser | Thr | Tyr | Tyr | Asn | Pro | Ser | Leu | Lys |
|---|---|---|---|---|---|---|---|---|---|---|---|---|---|---|---|
| | 50 | | | | | 55 | | | | | 60 | | | | |

| Ser | Arg | Ile | Ser | Ile | Thr | Arg | Asp | Thr | Ser | Lys | Asn | Gln | Tyr | Tyr | Leu |
|---|---|---|---|---|---|---|---|---|---|---|---|---|---|---|---|

-continued

| | | | 65 | | | | 70 | | | | 75 | | | | 80 |
|---|---|---|---|---|---|---|---|---|---|---|---|---|---|---|---|
| Asp | Leu | Asn | Ser | Val | Thr | Thr | Glu | Asp | Thr | Ala | Thr | Tyr | Tyr | Cys | Ala |
| | | | | 85 | | | | 90 | | | | | | 95 | |
| Asn | Trp | Asp | Gly | Asp | Tyr | Trp | Gly | | | | | | | | |
| | | | 100 | | | | | | | | | | | | |

( 2 ) INFORMATION FOR SEQ ID NO:17:

( i ) SEQUENCE CHARACTERISTICS:
        ( A ) LENGTH: 109 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:17:

| Glu | Val | Lys | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |
| Ser | Leu | Lys | Leu | Ser | Cys | Ala | Ala | Ser | Gly | Phe | Asp | Phe | Ser | Lys | Tyr |
| | | | 20 | | | | | 25 | | | | | 30 | | |
| Trp | Met | Ser | Trp | Val | Arg | Gln | Ala | Pro | Gly | Lys | Gly | Leu | Glu | Trp | Ile |
| | | | 35 | | | | | 40 | | | | | 45 | | |
| Gly | Glu | Ile | His | Pro | Asp | Ser | Gly | Thr | Ile | Asn | Tyr | Thr | Pro | Ser | Leu |
| | | 50 | | | | | 55 | | | | | 60 | | | |
| Lys | Asp | Lys | Phe | Ile | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Ser | Lys | Val | Arg | Ser | Glu | Asp | Thr | Ala | Leu | Tyr | Tyr | Cys |
| | | | | 85 | | | | 90 | | | | | | 95 | |
| Ala | Arg | Leu | His | Tyr | Tyr | Gly | Tyr | Asn | Ala | Tyr | Trp | Gly | | | |
| | | | 100 | | | | | 105 | | | | | | | |

( 2 ) INFORMATION FOR SEQ ID NO:18:

( i ) SEQUENCE CHARACTERISTICS:
        ( A ) LENGTH: 117 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:18:

| Glu | Val | Gln | Leu | Val | Gln | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ser | Ser | Ser | Gly | Phe | Ile | Phe | Ser | Ser | Tyr |
| | | | 20 | | | | | 25 | | | | | 30 | | |
| Ala | Met | Tyr | Trp | Val | Arg | Gln | Ala | Pro | Gly | Lys | Gly | Leu | Glu | Trp | Val |
| | | | 35 | | | | | 40 | | | | | 45 | | |
| Ala | Ile | Ile | Trp | Asp | Asp | Gly | Ser | Asp | Gln | His | Tyr | Ala | Asp | Ser | Val |
| | | 50 | | | | | 55 | | | | | 60 | | | |
| Lys | Gly | Arg | Phe | Thr | Ile | Ser | Arg | Asn | Asp | Ser | Lys | Asn | Thr | Leu | Phe |
| 65 | | | | | 70 | | | | | 75 | | | | | 80 |
| Leu | Gln | Met | Asp | Ser | Leu | Arg | Pro | Glu | Asp | Thr | Gly | Val | Tyr | Phe | Cys |
| | | | | 85 | | | | 90 | | | | | | 95 | |
| Ala | Arg | Asp | Gly | Gly | His | Gly | Phe | Cys | Ser | Ser | Ala | Ser | Cys | Phe | Gly |
| | | | 100 | | | | | 105 | | | | | 110 | | |
| Pro | Asp | Tyr | Trp | Gly | | | | | | | | | | | |
| | | | 115 | | | | | | | | | | | | |

( 2 ) INFORMATION FOR SEQ ID NO:19:

( i ) SEQUENCE CHARACTERISTICS:
  ( A ) LENGTH: 113 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:19:

Glu Val Lys Leu Val Glu Ser Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Gly Asn Lys Tyr Thr Thr Glu Tyr Ser Ala
        50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asn Tyr Tyr Gly Ser Thr Trp Tyr Phe Asp Val Trp
            100                 105                 110

Gly ( 2 ) INFORMATION FOR SEQ ID NO:20:

( i ) SEQUENCE CHARACTERISTICS:
    ( A ) LENGTH: 107 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:20:

Val Gln Leu Glu Gln Ser Gly Pro Gly Leu Val Arg Pro Ser Gln Thr
1               5                   10                  15

Leu Ser Leu Thr Cys Thr Val Ser Gly Thr Ser Phe Asp Asp Tyr Tyr
            20                  25                  30

Ser Thr Trp Val Arg Gln Pro Pro Gly Arg Gly Leu Glu Trp Ile Gly
        35                  40                  45

Tyr Val Phe Tyr His Gly Thr Ser Asp Thr Asp Thr Pro Leu Arg Ser
    50                  55                  60

Arg Val Thr Met Leu Val Asn Thr Ser Lys Asn Gln Phe Ser Leu Arg
65                  70                  75                  80

Leu Ser Ser Val Thr Ala Ala Asp Thr Ala Val Tyr Tyr Cys Ala Arg
                85                  90                  95

Asn Leu Ile Ala Gly Cys Ile Asp Val Trp Gly
            100                 105

( 2 ) INFORMATION FOR SEQ ID NO:21:

( i ) SEQUENCE CHARACTERISTICS:
    ( A ) LENGTH: 109 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:21:

Glu Val Lys Leu Asp Glu Thr Gly Gly Gly Leu Val Gln Pro Gly Arg
1               5                   10                  15

```
Pro  Met  Lys  Leu  Ser  Cys  Val  Ala  Ser  Gly  Phe  Thr  Phe  Ser  Asp  Tyr
          20                       25                      30

Trp  Met  Asn  Trp  Val  Arg  Gln  Ser  Pro  Glu  Lys  Gly  Leu  Glu  Trp  Val
          35                       40                      45

Ala  Gln  Ile  Arg  Asn  Lys  Pro  Tyr  Asn  Tyr  Glu  Thr  Tyr  Tyr  Ser  Asp
     50                       55                      60

Ser  Val  Lys  Gly  Arg  Phe  Thr  Ile  Ser  Arg  Asp  Asp  Ser  Lys  Ser  Ser
65                       70                      75                       80

Val  Tyr  Leu  Gln  Met  Asn  Asn  Leu  Arg  Val  Glu  Asp  Met  Gly  Ile  Tyr
               85                       90                       95

Tyr  Cys  Thr  Gly  Ser  Tyr  Tyr  Gly  Met  Asp  Tyr  Trp  Gly
               100                      105
```

( 2 ) INFORMATION FOR SEQ ID NO:22:

( i ) SEQUENCE CHARACTERISTICS:
        ( A ) LENGTH: 115 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:22:

```
Gln  Val  Gln  Leu  Lys  Glu  Ser  Gly  Ala  Glu  Leu  Val  Ala  Ala  Ser  Ser
1                   5                        10                       15

Ser  Val  Lys  Met  Ser  Cys  Lys  Ala  Ser  Gly  Tyr  Thr  Phe  Thr  Ser  Tyr
               20                       25                      30

Gly  Val  Asn  Trp  Val  Lys  Gln  Arg  Pro  Gly  Gln  Gly  Leu  Glu  Trp  Ile
          35                       40                      45

Gly  Tyr  Ile  Asn  Pro  Gly  Lys  Gly  Tyr  Leu  Ser  Tyr  Asn  Glu  Lys  Phe
     50                       55                      60

Lys  Gly  Lys  Thr  Thr  Leu  Thr  Val  Asp  Arg  Ser  Ser  Ser  Thr  Ala  Tyr
65                       70                      75                       80

Met  Gln  Leu  Arg  Ser  Leu  Thr  Ser  Glu  Asp  Ser  Ala  Val  Tyr  Phe  Cys
               85                       90                       95

Ala  Arg  Ser  Phe  Tyr  Gly  Gly  Ser  Asp  Leu  Ala  Val  Tyr  Tyr  Phe  Asp
               100                      105                      110

Ser  Trp  Gly
          115
```

( 2 ) INFORMATION FOR SEQ ID NO:23:

( i ) SEQUENCE CHARACTERISTICS:
        ( A ) LENGTH: 112 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:23:

```
Glu  Val  Gln  Leu  Gln  Gln  Ser  Gly  Val  Glu  Leu  Val  Arg  Ala  Gly  Ser
1                   5                        10                       15

Ser  Val  Lys  Met  Ser  Cys  Lys  Ala  Ser  Gly  Tyr  Thr  Phe  Thr  Ser  Asn
               20                       25                      30

Gly  Ile  Asn  Trp  Val  Lys  Gln  Arg  Pro  Gly  Gln  Gly  Leu  Glu  Trp  Ile
          35                       40                      45

Gly  Tyr  Asn  Asn  Pro  Gly  Asn  Gly  Tyr  Ile  Ala  Tyr  Asn  Glu  Lys  Phe
     50                       55                      60

Lys  Gly  Lys  Thr  Thr  Leu  Thr  Val  Asp  Lys  Ser  Ser  Ser  Thr  Ala  Tyr
65                       70                      75                       80
```

```
Met Gln Leu Arg Ser Leu Thr Ser Glu Asp Ser Ala Val Tyr Phe Cys
                85                  90                  95
Ala Arg Ser Glu Tyr Tyr Gly Gly Ser Tyr Lys Phe Asp Tyr Trp Gly
            100                 105                 110
```

( 2 ) INFORMATION FOR SEQ ID NO:24:

( i ) SEQUENCE CHARACTERISTICS:
    ( A ) LENGTH: 117 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:24:

```
Glu Val Gln Leu Val Glu Ser Gly Gly Leu Val Gln Pro Gly Arg
 1               5                   10                  15
Ser Leu Arg Leu Ser Cys Ala Ala Ser Gly Phe Thr Phe Asn Asp Tyr
            20                  25                  30
Ala Met His Trp Val Arg Gln Ala Pro Gly Lys Gly Leu Glu Trp Val
            35                  40                  45
Ser Gly Ile Ser Trp Asp Ser Ser Ile Gly Tyr Ala Asp Ser Val
    50                  55                  60
Lys Gly Arg Phe Thr Ile Ser Arg Asp Asn Ala Lys Asn Ser Leu Tyr
 65                 70                  75                  80
Leu Gln Met Asn Ser Leu Arg Ala Glu Asp Met Ala Leu Tyr Tyr Cys
                85                  90                  95
Val Lys Gly Arg Asp Tyr Tyr Asp Ser Gly Gly Tyr Phe Thr Val Ala
            100                 105                 110
Phe Asp Ile Trp Gly
            115
```

( 2 ) INFORMATION FOR SEQ ID NO:25:

( i ) SEQUENCE CHARACTERISTICS:
    ( A ) LENGTH: 111 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:25:

```
Asp Val Leu Met Thr Gln Thr Pro Leu Ser Leu Pro Val Ser Leu Gly
 1               5                   10                  15
Asp Gln Ala Ser Ile Ser Cys Arg Ser Ser Gln Ile Ile Ile His Ser
            20                  25                  30
Asp Gly Asn Thr Tyr Leu Glu Trp Phe Leu Gln Lys Pro Gly Gln Ser
            35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Met Ile
 65                 70                  75                  80
Ser Arg Val Glu Ala Glu Asp Leu Gly Val Tyr Tyr Cys Phe Gln Gly
                85                  90                  95
Ser His Val Pro His Thr Phe Gly Gly Gly Thr Lys Leu Glu Ile
            100                 105                 110
```

( 2 ) INFORMATION FOR SEQ ID NO:26:

( i ) SEQUENCE CHARACTERISTICS:

(A) LENGTH: 110 amino acids
(B) TYPE: amino acid
(C) TOPOLOGY: linear (ii) MOLECULE TYPE: peptide (xi) SEQUENCE DESCRIPTION: SEQ ID NO:26:

| Gln | Ser | Val | Leu | Thr | Gln | Pro | Pro | Ser | Ala | Ser | Gly | Thr | Pro | Gly | Gln |
|---|---|---|---|---|---|---|---|---|---|---|---|---|---|---|---|
| 1 | | | | 5 | | | | | 10 | | | | | 15 | |
| Arg | Val | Thr | Ile | Ser | Cys | Ser | Gly | Thr | Ser | Ser | Asn | Ile | Gly | Ser | Ser |
| | | | 20 | | | | | 25 | | | | | 30 | | |
| Thr | Val | Asn | Trp | Tyr | Gln | Gln | Leu | Pro | Gly | Met | Ala | Pro | Lys | Leu | Leu |
| | | 35 | | | | | 40 | | | | | 45 | | | |
| Ile | Tyr | Arg | Asp | Ala | Met | Arg | Pro | Ser | Gly | Val | Pro | Asp | Arg | Phe | Ser |
| | 50 | | | | | 55 | | | | | 60 | | | | |
| Gly | Ser | Lys | Ser | Gly | Ala | Ser | Ala | Ser | Leu | Ala | Ile | Gly | Gly | Leu | Gln |
| 65 | | | | | 70 | | | | | 75 | | | | | 80 |
| Ser | Glu | Asp | Glu | Thr | Asp | Tyr | Tyr | Cys | Ala | Ala | Trp | Asp | Val | Ser | Leu |
| | | | | 85 | | | | | 90 | | | | | 95 | |
| Asn | Ala | Tyr | Val | Phe | Gly | Thr | Gly | Thr | Lys | Val | Thr | Val | Leu | | |
| | | | 100 | | | | | 105 | | | | | 110 | | |

(2) INFORMATION FOR SEQ ID NO:27:

(i) SEQUENCE CHARACTERISTICS:
(A) LENGTH: 111 amino acids
(B) TYPE: amino acid
(C) TOPOLOGY: linear (ii) MOLECULE TYPE: peptide (xi) SEQUENCE DESCRIPTION: SEQ ID NO:27:

| Gln | Val | Leu | Met | Thr | Gln | Thr | Pro | Ser | Ser | Leu | Pro | Val | Thr | Leu | Gly |
|---|---|---|---|---|---|---|---|---|---|---|---|---|---|---|---|
| 1 | | | | 5 | | | | | 10 | | | | | 15 | |
| Gln | Gln | Ala | Ser | Ile | Ser | Cys | Arg | Ser | Ser | Gln | Ile | Ile | Ile | His | Ser |
| | | | 20 | | | | | 25 | | | | | 30 | | |
| Asp | Gly | Asn | Thr | Tyr | Leu | Glu | Trp | Phe | Leu | Gln | Lys | Pro | Gly | Gln | Ser |
| | | | 35 | | | | | 40 | | | | | 45 | | |
| Pro | Lys | Leu | Leu | Ile | Tyr | Lys | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Ser | Phe | Thr | Leu | Ala | Ile |
| 65 | | | | | 70 | | | | | 75 | | | | | 80 |
| Ser | Arg | Val | Glu | Ala | Glu | Asp | Glu | Gly | Val | Tyr | Tyr | Cys | Phe | Gln | Gly |
| | | | | 85 | | | | | 90 | | | | | 95 | |
| Ser | His | Val | Pro | His | Thr | Phe | Gly | Gly | Gly | Thr | Lys | Leu | Glu | Ile | |
| | | | 100 | | | | | 105 | | | | | 110 | | |

(2) INFORMATION FOR SEQ ID NO:28:

(i) SEQUENCE CHARACTERISTICS:
(A) LENGTH: 112 amino acids
(B) TYPE: amino acid
(C) TOPOLOGY: linear (ii) MOLECULE TYPE: peptide (xi) SEQUENCE DESCRIPTION: SEQ ID NO:28:

| Asp | Val | Val | Met | Thr | Gln | Ser | Pro | Leu | Ser | Leu | Pro | Val | Thr | Leu | Gly |
|---|---|---|---|---|---|---|---|---|---|---|---|---|---|---|---|
| 1 | | | | 5 | | | | | 10 | | | | | 15 | |
| Gln | Pro | Ala | Ser | Ile | Ser | Cys | Arg | Ser | Ser | Gln | Ser | Leu | Val | Tyr | Ser |
| | | | 20 | | | | | 25 | | | | | 30 | | |

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Met Gln Gly
                85                  90                  95

Thr His Trp Ser Trp Thr Phe Gly Gln Gly Thr Lys Val Glu Ile Lys
            100                 105                 110

( 2 ) INFORMATION FOR SEQ ID NO:29:

( i ) SEQUENCE CHARACTERISTICS:
        ( A ) LENGTH: 111 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:29:

Asp Val Leu Met Thr Gln Ser Pro Leu Ser Leu Pro Val Thr Leu Gly
 1                   5                  10                  15

Gln Pro Ala Ser Ile Ser Cys Arg Ser Ser Gln Ile Ile Ile His Ser
            20                  25                  30

Asp Gly Asn Thr Tyr Leu Glu Trp Phe Gln Gln Arg Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Phe Gln Gly
                85                  90                  95

Ser His Val Pro His Thr Phe Gly Gly Gly Thr Lys Val Glu Ile
            100                 105                 110

( 2 ) INFORMATION FOR SEQ ID NO:30:

( i ) SEQUENCE CHARACTERISTICS:
        ( A ) LENGTH: 112 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:30:

Asp Ile Val Met Thr Gln Ser Pro Asp Ser Leu Ala Val Ser Leu Gly
 1                   5                  10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                      70                  75                  80

Ile Ser Ser Leu Gln Ala Glu Asp Val Ala Val Tyr Tyr Cys Gln Gln
                85                  90                  95

Tyr Asp Thr Ile Pro Thr Phe Gly Gly Gly Thr Lys Val Glu Ile Lys
            100                 105                 110

( 2 ) INFORMATION FOR SEQ ID NO:31:

( i ) SEQUENCE CHARACTERISTICS:
        ( A ) LENGTH: 111 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:31:

```
Asp Val Leu Met Thr Gln Thr Pro Asp Ser Leu Pro Val Ser Leu Gly
 1               5                  10                  15
Asp Arg Ala Ser Ile Ser Cys Arg Ser Ser Gln Ile Ile Ile His Ser
            20                  25                  30
Asp Gly Asn Thr Tyr Leu Glu Trp Phe Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Met Ile
65                  70                  75                  80
Ser Arg Val Glu Ala Glu Asp Leu Gly Val Tyr Tyr Cys Phe Gln Gly
                85                  90                  95
Ser His Val Pro His Thr Phe Gly Gly Gly Thr Lys Leu Glu Ile
            100                 105                 110
```

( 2 ) INFORMATION FOR SEQ ID NO:32:

( i ) SEQUENCE CHARACTERISTICS:
        ( A ) LENGTH: 117 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:32:

```
Asp Val Gln Leu Val Glu Ser Gly Gly Gly Leu Val Gln Pro Gly Gly
 1               5                  10                  15
Ser Arg Lys Leu Ser Cys Ala Ala Ser Gly Phe Thr Phe Ser Ser Phe
            20                  25                  30
Gly Met His Trp Val Arg Gln Ala Pro Glu Lys Gly Leu Glu Trp Val
        35                  40                  45
Ala Tyr Ile Ser Ser Gly Ser Phe Thr Ile Tyr His Ala Asp Thr Val
    50                  55                  60
Lys Gly Arg Phe Thr Ile Ser Arg Asp Asn Pro Lys Asn Thr Leu Phe
65                  70                  75                  80
Leu Gln Met Thr Ser Leu Arg Ser Glu Asp Thr Ala Met Tyr Tyr Cys
                85                  90                  95
Ala Arg Met Arg Lys Gly Tyr Ala Met Asp Tyr Trp Gly Gln Gly Thr
            100                 105                 110
Thr Val Thr Val Ser
            115
```

( 2 ) INFORMATION FOR SEQ ID NO:33:

( i ) SEQUENCE CHARACTERISTICS:
        ( A ) LENGTH: 125 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:33:

| Glu | Val | Gln | Leu | Val | Gln | Ser | Gly | Gly | Val | Val | Gln | Pro | Gly | Arg |
|---|---|---|---|---|---|---|---|---|---|---|---|---|---|---|
| 1 | | | | 5 | | | | | 10 | | | | | 15 |

| Ser | Leu | Arg | Leu | Ser | Cys | Ser | Ser | Ser | Gly | Phe | Ile | Phe | Ser | Ser | Tyr |
|---|---|---|---|---|---|---|---|---|---|---|---|---|---|---|---|
| | | | 20 | | | | | 25 | | | | | 30 | | |

| Ala | Met | Tyr | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ile | Ile | Trp | Asp | Asp | Gly | Ser | Asp | Gln | His | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asn | Asp | Ser | Lys | Asn | Thr | Leu | Phe |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Arg | Pro | Glu | Asp | Thr | Gly | Val | Tyr | Phe | Cys |
|---|---|---|---|---|---|---|---|---|---|---|---|---|---|---|---|
| | | | | 85 | | | | | 90 | | | | | 95 | |

| Ala | Arg | Asp | Gly | Gly | His | Gly | Phe | Cys | Ser | Ser | Ala | Ser | Cys | Phe | Gly |
|---|---|---|---|---|---|---|---|---|---|---|---|---|---|---|---|
| | | | 100 | | | | | 105 | | | | | 110 | | |

| Pro | Asp | Tyr | Trp | Gly | Gln | Gly | Thr | Pro | Val | Thr | Val | Ser |
|---|---|---|---|---|---|---|---|---|---|---|---|---|
| | | 115 | | | | | 120 | | | | | 125 |

( 2 ) INFORMATION FOR SEQ ID NO:34:

( i ) SEQUENCE CHARACTERISTICS:
        ( A ) LENGTH: 117 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:34:

| Glu | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ile | Phe | Ser | Ser | Phe |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Tyr | Ile | Ser | Ser | Asp | Gly | Phe | Thr | Ile | Tyr | His | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asp | Pro | Lys | Asn | Thr | Leu | Phe |
|---|---|---|---|---|---|---|---|---|---|---|---|---|---|---|---|
| 65 | | | | | 70 | | | | | 75 | | | | | 80 |

| Leu | Gln | Met | Thr | Ser | Leu | Arg | Ser | Glu | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Met | Arg | Lys | Gly | Tyr | Ala | Met | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Thr | Val | Thr | Val | Ser |
|---|---|---|---|---|
| | | 115 | | |

( 2 ) INFORMATION FOR SEQ ID NO:35:

( i ) SEQUENCE CHARACTERISTICS:
        ( A ) LENGTH: 120 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:35:

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

```
Ala Met His Trp Val Arg Gln Ala Pro Gly Lys Gly Leu Glu Trp Val
         35                  40                  45
Ala Val Ile Ser Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Arg Lys Asp Trp Gly Trp Ala Leu Phe Asp Tyr Trp Gly
             100                 105                 110
Gln Gly Thr Leu Val Thr Val Ser
         115                 120
```

( 2 ) INFORMATION FOR SEQ ID NO:36:

( i ) SEQUENCE CHARACTERISTICS:
        ( A ) LENGTH: 117 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:36:

```
Gln Val Gln Leu Val Glu Ser Gly Gly Val Val Gln Pro Gly Arg
  1                  5                  10                 15
Ser Leu Arg Leu Ser Cys Ala Ala Ser Gly Phe Thr Phe Ser Ser Phe
             20                  25                  30
Gly Met His Trp Val Arg Gln Ala Pro Gly Lys Gly Leu Glu Trp Val
         35                  40                  45
Ala Tyr Ile Ser Ser Gly Ser Phe Thr Ile Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Met Arg Lys Gly Tyr Ala Met Asp Tyr Trp Gly Gln Gly Thr
             100                 105                 110
Leu Val Thr Val Ser
         115
```

( 2 ) INFORMATION FOR SEQ ID NO:37:

( i ) SEQUENCE CHARACTERISTICS:
        ( A ) LENGTH: 98 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:37:

```
Glu Val Gln Leu Val Glu Ser Gly Gly Gly Leu Val Gln Pro Gly Gly
  1                  5                  10                 15
Ser Leu Arg Leu Ser Cys Ala Ala Ser Gly Phe Thr Phe Ser Ser Tyr
             20                  25                  30
Trp Met Ser Trp Val Arg Gln Ala Pro Gly Lys Gly Leu Glu Trp Val
         35                  40                  45
Ala Asn Ile Lys Gln Asp Gly Ser Glu Lys Tyr Tyr Val Asp Ser Val
     50                  55                  60
Lys Gly Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Cys
                85                  90                  95

Ala Arg ( 2 ) INFORMATION FOR SEQ ID NO:38:

( i ) SEQUENCE CHARACTERISTICS:
        ( A ) LENGTH: 117 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:38:

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Phe Thr Ile Tyr His Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ala Glu Asp Thr Ala Met Tyr Tyr Cys
                85                  90                  95

Ala Arg Met Arg Lys Gly Tyr Ala Met Asp Tyr Trp Gly Gln Gly Thr
            100                 105                 110

Thr Val Thr Val Ser
            115

( 2 ) INFORMATION FOR SEQ ID NO:39:

( i ) SEQUENCE CHARACTERISTICS:
        ( A ) LENGTH: 15 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:39:

Met Gly Trp Ser Cys Ile Ile Leu Phe Leu Val Ala Thr Ala Thr
 1               5                  10                  15

( 2 ) INFORMATION FOR SEQ ID NO:40:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:40:

Lys Thr Ser Leu Arg Pro Gly Lys Gly Ser Ser Asp Tyr Glu Lys Lys
 1               5                  10                  15

( 2 ) INFORMATION FOR SEQ ID NO:41:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:41:

Lys Thr Ser Leu Arg Pro Gly Lys Gly Ser Ser Glu Tyr Glu Lys Lys
1               5                   10                  15

( 2 ) INFORMATION FOR SEQ ID NO:42:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:42:

Gln Thr Ser Leu Arg Pro Asp Lys Gly Ser Ser Asp His Glu Lys Lys
1               5                   10                  15

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:43:

Gln Thr Ser Leu Arg Pro Asp Lys Gly Ser Ser Asp Gln Glu Lys Lys
1               5                   10                  15

( 2 ) INFORMATION FOR SEQ ID NO:44:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:44:

Gln Ser Ser Leu Arg Pro Asp Lys Gly Ser Ser Asp Gln Glu Lys Lys
1               5                   10                  15

( 2 ) INFORMATION FOR SEQ ID NO:45:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:45:

Gln Thr Ser Leu Arg Pro Asp Lys Gly Ser Ser Asp Pro Glu Lys Lys
1               5                   10                  15

( 2 ) INFORMATION FOR SEQ ID NO:46:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:46:

Gln Thr Ser Leu Arg Pro Asp Lys Gly Ser Ser Asp Pro Glx Lys Lys (2) INFORMATION FOR SEQ ID NO:47:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:47:

```
Gln Thr Ser Leu Arg Pro Asp Lys Gly Ser Ser Asp Pro Glu Lys Thr
 1               5                  10                  15
```

(2) INFORMATION FOR SEQ ID NO:48:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:48:

```
Gln Thr Ser Leu Arg Ala Asp Lys Gly Ser Ser Asp Gln Glu Lys Lys
 1               5                  10                  15
```

(2) INFORMATION FOR SEQ ID NO:49:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:49:

```
Gln Thr Ser Leu Arg Pro Asp Lys Gly Lys Ser Asp Ser Glu Lys Lys
 1               5                  10                  15
```

(2) INFORMATION FOR SEQ ID NO:50:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:50:

```
Gln Thr Ser Leu Arg Pro Ala Arg Gly Ser Ser Asp Gln Glu Lys Lys
 1               5                  10                  15
```

(2) INFORMATION FOR SEQ ID NO:51:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:51:

```
Gln Thr Ser Leu Lys Pro Gly Arg Gly Ser Ser Asp Pro Glu Lys Lys
 1               5                  10                  15
```

(2) INFORMATION FOR SEQ ID NO:52:

( i ) SEQUENCE CHARACTERISTICS:
  ( A ) LENGTH: 16 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:52:

Gln Thr Ser Leu Arg Pro Gly Arg Gly Ser Ser Asp Thr Glu Lys Lys
 1               5                  10                  15

( 2 ) INFORMATION FOR SEQ ID NO:53:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:53:

Gln Ile Ser Leu Arg Pro Gly Lys Gly Ser Ser Asp Ser Glu Lys Lys
 1               5                  10                  15

( 2 ) INFORMATION FOR SEQ ID NO:54:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:54:

Gln Thr Ser Leu Arg Pro Gly Lys Gly Asp Ser Asp Glu Asp Lys Lys
 1               5                  10                  15

( 2 ) INFORMATION FOR SEQ ID NO:55:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:55:

Glu Thr Ala Leu Arg Pro Gly Lys Gly Ala Ser Asp Ala Asp Lys Lys
 1               5                  10                  15

( 2 ) INFORMATION FOR SEQ ID NO:56:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:56:

Val Thr Ala Leu Arg Pro Gly Lys Gly Ala Ser Asp Glu Asp Lys Lys
 1               5                  10                  15

( 2 ) INFORMATION FOR SEQ ID NO:57:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:57:

```
Val Thr Ala Leu Arg Pro Gly Lys Gly Ala Ser Asp Glu Glu Lys Lys
 1               5                  10                  15
```

( 2 ) INFORMATION FOR SEQ ID NO:58:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:58:

```
Val Thr Ala Leu Arg Pro Gly Lys Gly Ala Ser Asx Ala Asx Lys Lys
 1               5                  10                  15
```

( 2 ) INFORMATION FOR SEQ ID NO:59:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:59:

```
Val Thr Ala Leu Arg Pro Gly Lys Gly Ala Ser Asp Glu Asp Asp Glu
 1               5                  10                  15
```

( 2 ) INFORMATION FOR SEQ ID NO:60:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:60:

```
Gln Thr Ser Leu Arg Pro Asp Lys Gly Ser Ser Asp Gln Glu Thr Thr
 1               5                  10                  15
```

( 2 ) INFORMATION FOR SEQ ID NO:61:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:61:

```
Gln Asn Ser Leu Thr Pro Gly Lys Gly Ser Ser Ser Pro Glu Lys Lys
 1               5                  10                  15
```

( 2 ) INFORMATION FOR SEQ ID NO:62:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:62:

```
Val Thr Lys Val Arg Pro Gly Lys Gly Asp Ser Asp Ser Asp Lys Lys
```

(2) INFORMATION FOR SEQ ID NO:63:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:63:

Val Thr Lys Val Arg Pro Gly Lys Gly Asp Ser Asp Ala Glu Lys Lys
1            5                   10                15

(2) INFORMATION FOR SEQ ID NO:64:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:64:

Val Thr Arg Val Arg Pro Gly Lys Gly Asp Ser Asp Ala Glu Lys Lys
1            5                   10                15

(2) INFORMATION FOR SEQ ID NO:65:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:65:

Leu Thr Lys Val Arg Pro Gly Lys Gly Asp Ser Asp Ser Glu Lys Lys
1            5                   10                15

(2) INFORMATION FOR SEQ ID NO:66:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:66:

Val Thr Lys Val Arg Pro Gly Lys Gly Asp Ser Asp Ser Glu Gln Lys
1            5                   10                15

(2) INFORMATION FOR SEQ ID NO:67:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:67:

Val Thr Lys Val Arg Pro Glu Lys Gly Asp Ser Asp Ala Glu Lys Lys
1            5                   10                15

(2) INFORMATION FOR SEQ ID NO:68:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:68:

```
Val Thr Lys Val Arg Pro Glu Lys Gly Asp Ser Asp Ser Glu Lys Lys
 1               5                  10                  15
```

( 2 ) INFORMATION FOR SEQ ID NO:69:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:69:

```
Val Thr Lys Val Ser Pro Gly Lys Gly Asp Ser Asp Ala Glu Lys Lys
 1               5                  10                  15
```

( 2 ) INFORMATION FOR SEQ ID NO:70:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:70:

```
Val Thr Lys Val Arg Ser Gly Lys Gly Glu Ser Asp Ala Glu Lys Lys
 1               5                  10                  15
```

( 2 ) INFORMATION FOR SEQ ID NO:71:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:71:

```
Val Thr Ser Val Lys Pro Gly Lys Gly Asp Ser Asp Ala Glu Lys Lys
 1               5                  10                  15
```

( 2 ) INFORMATION FOR SEQ ID NO:72:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:72:

```
Val Ser Ser Val Lys Pro Gly Lys Gly Asp Ser Asp Ala Glu Lys Lys
 1               5                  10                  15
```

( 2 ) INFORMATION FOR SEQ ID NO:73:

( i ) SEQUENCE CHARACTERISTICS:
( A ) LENGTH: 16 amino acids
( B ) TYPE: amino acid
( C ) TOPOLOGY: linear ( i i ) MOLECULE TYPE: peptide ( x i ) SEQUENCE DESCRIPTION: SEQ ID NO:73:

Val Thr Ser Ala Lys Pro Gly Lys Gly Asp Ser Asp Ala Glu Lys Lys
 1               5                   10                  15

( 2 ) INFORMATION FOR SEQ ID NO:74:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:74:

Val Ser Ser Ala Lys Pro Gly Lys Gly Asp Ser Asp Ala Glu Lys Lys
 1               5                   10                  15

( 2 ) INFORMATION FOR SEQ ID NO:75:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:75:

Val Thr Ser Ala Arg Pro Gly Lys Gly Asp Ser Asp Ala Glu Lys Lys
 1               5                   10                  15

( 2 ) INFORMATION FOR SEQ ID NO:76:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:76:

Val Ser Pro Ala Lys Pro Gly Lys Gly Asp Ser Asp Ala Glu Lys Lys
 1               5                   10                  15

( 2 ) INFORMATION FOR SEQ ID NO:77:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:77:

Val Thr Lys Ala Arg Pro Gly Lys Gly Asp Ser Asp Val Glu Lys Asn
 1               5                   10                  15

( 2 ) INFORMATION FOR SEQ ID NO:78:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:78:

Val Thr Leu Ile Pro Pro Gly Lys Gly Asp Ser Asp Ala Glu Lys Lys (2) INFORMATION FOR SEQ ID NO:79:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:79:

```
Val Thr Leu Leu Gln Pro Gly Lys Gly Asp Ser Asp Ala Glu Lys Lys
 1               5                  10                  15
```

(2) INFORMATION FOR SEQ ID NO:80:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:80:

```
Val Thr Leu Leu Gln Pro Gly Lys Gly Asp Ser Asp Ala Asp Lys Lys
 1               5                  10                  15
```

(2) INFORMATION FOR SEQ ID NO:81:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:81:

```
Val Thr Leu Leu Gln Pro Gly Lys Gly Asp Ser Asp Ala Glu Arg Lys
 1               5                  10                  15
```

(2) INFORMATION FOR SEQ ID NO:82:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:82:

```
Val Thr Leu Leu Gln Ala Gly Lys Gly Asp Ser Asp Ala Glu Lys Lys
 1               5                  10                  15
```

(2) INFORMATION FOR SEQ ID NO:83:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:83:

```
Val Thr Leu Leu Gln Pro Gly Glu Gly Asp Ser Asp Ala Glu Lys Lys
 1               5                  10                  15
```

(2) INFORMATION FOR SEQ ID NO:84:

( i ) SEQUENCE CHARACTERISTICS:
  ( A ) LENGTH: 16 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:84:

Leu Thr Leu Leu Gln Pro Gly Asn Gly Asp Ser Asp Ala Glu Lys Lys
 1           5                   10                  15

( 2 ) INFORMATION FOR SEQ ID NO:85:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:85:

Val Thr Leu Leu Gln Pro Gly Lys Gly Asp Ser Asp Ala Glu Lys Ile
 1           5                   10                  15

( 2 ) INFORMATION FOR SEQ ID NO:86:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:86:

Val Thr Leu Phe Gln Pro Gly Gln Gly Asp Ser Asp Pro Glu Lys Lys
 1           5                   10                  15

( 2 ) INFORMATION FOR SEQ ID NO:87:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:87:

Val Thr Leu Pro Gln Pro Gly Lys Gly Asp Ser Asp Ala Glu Lys Lys
 1           5                   10                  15

( 2 ) INFORMATION FOR SEQ ID NO:88:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:88:

Val Thr Leu Pro Gln Pro Gly Lys Gly Asp Trp Asp Ala Glu Lys Lys
 1           5                   10                  15

( 2 ) INFORMATION FOR SEQ ID NO:89:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:89:

Val Thr Phe Leu Ser Pro Gly Gln Gly Asp Ser Asp Ala Glu Lys Lys
 1               5                  10                  15

( 2 ) INFORMATION FOR SEQ ID NO:90:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:90:

Glu Ser Ser Ala Arg Pro Gly Lys Gly Asp Ser Asp Ala Glu Lys Lys
 1               5                  10                  15

( 2 ) INFORMATION FOR SEQ ID NO:91:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:91:

Val Thr Leu Ser Ser Pro Gly Gln Gly Asp Ser Asp Ala Glu Lys Lys
 1               5                  10                  15

( 2 ) INFORMATION FOR SEQ ID NO:92:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:92:

Val Thr Thr Ala Lys Pro Glu Lys Gly Asp Ser Asp Val Glu Lys Lys
 1               5                  10                  15

( 2 ) INFORMATION FOR SEQ ID NO:93:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:93:

Val Thr Thr Pro Lys Pro Asp Lys Gly Asp Ser Asp Val Glu Lys Lys
 1               5                  10                  15

( 2 ) INFORMATION FOR SEQ ID NO:94:

( i ) SEQUENCE CHARACTERISTICS:
      ( A ) LENGTH: 16 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:94:

Val Thr Ala Pro Arg Pro Gly Lys Gly Ala Ser Ser Ala Glu Lys Lys (2) INFORMATION FOR SEQ ID NO:95:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:95:

```
Val Thr Ala Pro Lys Pro Gly Lys Gly Thr Ser Ser Ala Glu Lys Lys
 1               5                  10                  15
```

(2) INFORMATION FOR SEQ ID NO:96:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:96:

```
Val Thr Thr Pro Lys Pro Gly Lys Gly Ala Ser Ser Ala Glu Lys Lys
 1               5                  10                  15
```

(2) INFORMATION FOR SEQ ID NO:97:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:97:

```
Val Ser Ala Pro Lys Pro Gly Lys Gly Ala Ser Ser Ala Glu Lys Lys
 1               5                  10                  15
```

(2) INFORMATION FOR SEQ ID NO:98:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:98:

```
Val Thr Ala Pro Arg Ser Gly Lys Gly Ala Ser Ser Ala Glu Lys Lys
 1               5                  10                  15
```

(2) INFORMATION FOR SEQ ID NO:99:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:99:

```
Val Thr Ala Pro Lys Ser Gly Lys Gly Ala Ser Ser Ala Glu Lys Lys
 1               5                  10                  15
```

(2) INFORMATION FOR SEQ ID NO:100:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:100:

```
Val Thr Ala Pro Lys Pro Asp Lys Gly Val Ser Ser Ala Glu Lys Lys
 1               5                  10                  15
```

( 2 ) INFORMATION FOR SEQ ID NO:101:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:101:

```
Val Thr Ala Pro Lys Ser Glu Lys Gly Val Ser Ser Ala Glu Lys Lys
 1               5                  10                  15
```

( 2 ) INFORMATION FOR SEQ ID NO:102:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:102:

```
Phe Thr Ala Pro Lys Pro Gly Lys Gly Ala Ser Ser Ala Glu Lys Lys
 1               5                  10                  15
```

( 2 ) INFORMATION FOR SEQ ID NO:103:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:103:

```
Leu Thr Ala Pro Lys Pro Gly Arg Gly Val Ser Ser Ala Glu Lys Lys
 1               5                  10                  15
```

( 2 ) INFORMATION FOR SEQ ID NO:104:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:104:

```
Val Thr Ala Pro Lys Ser Gly Lys Gly Ala Ser Ser Ala Glu Lys Arg
 1               5                  10                  15
```

( 2 ) INFORMATION FOR SEQ ID NO:105:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:105:

Val Ser Ala Pro Lys Pro Gly Lys Glu Gly Ser Ser Ala Glu Lys Lys
1               5                   10                  15

( 2 ) INFORMATION FOR SEQ ID NO:106:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:106:

Val Thr Ala Pro Lys Pro Arg Lys Gly Ala Ser Ser Ala Glu Lys Lys
1               5                   10                  15

( 2 ) INFORMATION FOR SEQ ID NO:107:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:107:

Val Thr Phe Leu Ser Pro Gly Gln Gly Asn Ser Asp Ala Glu Leu Pro
1               5                   10                  15

( 2 ) INFORMATION FOR SEQ ID NO:108:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:108:

Val Thr Phe Leu Ser Pro Gly Gln Gly Asn Ser Asp Glu Asp Leu Pro
1               5                   10                  15

( 2 ) INFORMATION FOR SEQ ID NO:109:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:109:

Val Thr Leu Ser Ser Pro Gln Arg Gly Asp Ser Asp Ala Glu Lys Lys
1               5                   10                  15

( 2 ) INFORMATION FOR SEQ ID NO:110:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:110:

Val Thr Ala Pro Lys Ser Ser Lys Gly Gly Ser Ser Ala Glu Lys Lys (2) INFORMATION FOR SEQ ID NO:111:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:111:

Gln Thr Ser Pro Thr Pro Gly Lys Gly Ser Ser Asp Pro Glu Lys Lys
 1               5                  10                  15

(2) INFORMATION FOR SEQ ID NO:112:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:112:

Gln Ile Ser Leu Ile Pro Gly Lys Gly Ser Tyr Asp Asp Glu Lys Lys
 1               5                  10                  15

(2) INFORMATION FOR SEQ ID NO:113:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:113:

Val Thr Ala Leu Lys Ser Gly Lys Gly Ala Ser Ser Ala Glu Lys Lys
 1               5                  10                  15

(2) INFORMATION FOR SEQ ID NO:114:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:114:

Val Thr Ala Leu Lys Ser Asp Lys Gly Ala Ser Ser Gly Glu Lys Lys
 1               5                  10                  15

(2) INFORMATION FOR SEQ ID NO:115:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:115:

Val Thr Pro Pro Ser Pro Gly Gln Gly Asp Ser Ala Ala Glu Lys Lys
 1               5                  10                  15

(2) INFORMATION FOR SEQ ID NO:116:

( i ) SEQUENCE CHARACTERISTICS:
  ( A ) LENGTH: 16 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:116:

Val Thr Pro Pro Ser Pro Gly Gln Gly Asp Ser Ala Arg Glu Lys Lys
 1               5                  10                  15

( 2 ) INFORMATION FOR SEQ ID NO:117:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:117:

Val Thr Val Arg Lys Pro Gly Lys Gly Asp Ser Ser Asp Glu Lys Lys
 1               5                  10                  15

( 2 ) INFORMATION FOR SEQ ID NO:118:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:118:

Gln Thr Ser Val Arg Leu Gly Gln Gly Ser Ser Asp Pro Glu Lys Lys
 1               5                  10                  15

( 2 ) INFORMATION FOR SEQ ID NO:119:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:119:

Lys Thr Ser Leu Arg Pro Trp Lys Gly Ser Ser Asp Ser Asp Lys Lys
 1               5                  10                  15

( 2 ) INFORMATION FOR SEQ ID NO:120:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:120:

Gln Thr Asp Val Thr Gln Gly Gln Gly Ser Ser Gln Pro Glu Lys Lys
 1               5                  10                  15

( 2 ) INFORMATION FOR SEQ ID NO:121:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:121:

Gln Thr Ala Val Ser Gln Gly Gln Gly Ser Ser Gln Ser Glu Lys Lys
1               5                   10                  15

( 2 ) INFORMATION FOR SEQ ID NO:122:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:122:

Leu Thr Ala Pro Arg Thr Asn Arg Gly Ser Ser Asp Ser Glu Lys Lys
1               5                   10                  15

( 2 ) INFORMATION FOR SEQ ID NO:123:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:123:

Val Thr Ala Pro Ser Ser His Arg Gly Ser Ser Asp Thr Glu Lys Lys
1               5                   10                  15

( 2 ) INFORMATION FOR SEQ ID NO:124:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:124:

Leu Leu Ser Leu Ser Pro Leu Lys Gly Asp Ser Asp Pro Glu Lys Val
1               5                   10                  15

( 2 ) INFORMATION FOR SEQ ID NO:125:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:125:

Val Thr Ala Pro Thr Pro Asp Thr Gly Ala Ile Lys Thr Glu Lys Leu
1               5                   10                  15

( 2 ) INFORMATION FOR SEQ ID NO:126:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:126:

Val Thr Ile Pro Thr Pro Asp Thr Gly Ala Ile Lys Thr Glu Lys Leu ( 2 ) INFORMATION FOR SEQ ID NO:127:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:127:

```
Ala Val Ser Pro Thr Pro Asp Thr Gly Ala Ile Lys Thr Glu Lys Leu
 1               5                  10                  15
```

( 2 ) INFORMATION FOR SEQ ID NO:128:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:128:

```
Ala Val Ser Pro Thr Pro Asp Thr Gly Ala Ile Lys Thr Glu Lys Leu
 1               5                  10                  15
```

( 2 ) INFORMATION FOR SEQ ID NO:129:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:129:

```
Ala Val Ser Pro Thr Pro Asp Thr Gly Val Ile Lys Thr Glu Lys Leu
 1               5                  10                  15
```

( 2 ) INFORMATION FOR SEQ ID NO:130:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:130:

```
Ala Val Ser Pro Thr Pro Asp Thr Gly Ala Ile Lys Thr Glu Pro Ser
 1               5                  10                  15
```

( 2 ) INFORMATION FOR SEQ ID NO:131:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:131:

```
Tyr Leu Pro Pro Thr Pro Gly Val Ile Arg Ser Thr Ala Met Lys Leu
 1               5                  10                  15
```

( 2 ) INFORMATION FOR SEQ ID NO:132:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:132:

Tyr Leu Pro Pro Thr Pro Gly Val Ile Arg Ser Thr Ala Met Arg Leu
1               5                   10                  15

( 2 ) INFORMATION FOR SEQ ID NO:133:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:133:

Tyr Leu Pro Pro Thr Pro Gly Leu Ile Arg Ser Thr Ser Met Lys Leu
1               5                   10                  15

( 2 ) INFORMATION FOR SEQ ID NO:134:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:134:

Tyr Leu Pro Pro Thr Pro Gly Leu Ile Arg Ser Thr Ser Val Lys Leu
1               5                   10                  15

( 2 ) INFORMATION FOR SEQ ID NO:135:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:135:

Tyr Leu Pro Pro Thr Pro Gly Val Ile Arg Ser Thr Ala Glu Lys Leu
1               5                   10                  15

( 2 ) INFORMATION FOR SEQ ID NO:136:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:136:

Tyr Leu Pro Pro Thr Pro Gly Val Ile Arg Ser Thr Ala Gly Lys Leu
1               5                   10                  15

( 2 ) INFORMATION FOR SEQ ID NO:137:

( i ) SEQUENCE CHARACTERISTICS:
        ( A ) LENGTH: 16 amino acids
        ( B ) TYPE: amino acid
        ( C ) TOPOLOGY: linear (ii) MOLECULE TYPE: peptide (xi) SEQUENCE DESCRIPTION: SEQ ID NO:137:

Tyr Leu Pro Ala Thr Pro Gly Val Val Arg Ser Ser Ala Gly Met Leu
 1               5                   10                  15

(2) INFORMATION FOR SEQ ID NO:138:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:138:

Ser Leu Pro Pro Ser Pro Gly Lys Val Arg Ser Thr Ala Glu Lys Leu
 1               5                   10                  15

(2) INFORMATION FOR SEQ ID NO:139:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:139:

Ser Leu Pro Pro Ser Pro Gly Lys Val Arg Ser Thr Ala Asn Lys Leu
 1               5                   10                  15

(2) INFORMATION FOR SEQ ID NO:140:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:140:

Ser Leu Pro Pro Arg Pro Gly Lys Val Arg Ser Ser Ser Glu Lys Leu
 1               5                   10                  15

(2) INFORMATION FOR SEQ ID NO:141:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:141:

Ser Leu Pro Pro Arg Pro Gly Lys Val Arg Ser Ser Ser Asp Lys Leu
 1               5                   10                  15

(2) INFORMATION FOR SEQ ID NO:142:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:142:

Ser Leu Pro Pro Arg Pro Gly Arg Val Arg Ser Ser Ser Glu Lys Leu (2) INFORMATION FOR SEQ ID NO:143:

(i) SEQUENCE CHARACTERISTICS:
       (A) LENGTH: 16 amino acids
       (B) TYPE: amino acid
       (C) TOPOLOGY: linear (ii) MOLECULE TYPE: peptide (xi) SEQUENCE DESCRIPTION: SEQ ID NO:143:

Ser Leu Pro Pro Arg Pro Gly Lys Val Arg Ser Ser Ser Glu Gln Leu
 1               5                  10                  15

(2) INFORMATION FOR SEQ ID NO:144:

(i) SEQUENCE CHARACTERISTICS:
       (A) LENGTH: 16 amino acids
       (B) TYPE: amino acid
       (C) TOPOLOGY: linear (ii) MOLECULE TYPE: peptide (xi) SEQUENCE DESCRIPTION: SEQ ID NO:144:

Ser Leu Pro Pro Arg Pro Gly Lys Val Arg Ser Ser Ser Glu Thr Leu
 1               5                  10                  15

(2) INFORMATION FOR SEQ ID NO:145:

(i) SEQUENCE CHARACTERISTICS:
       (A) LENGTH: 16 amino acids
       (B) TYPE: amino acid
       (C) TOPOLOGY: linear (ii) MOLECULE TYPE: peptide (xi) SEQUENCE DESCRIPTION: SEQ ID NO:145:

Ser Leu Pro Pro Lys Pro Gly Lys Ile Arg Ser Ser Thr Gly Lys Leu
 1               5                  10                  15

(2) INFORMATION FOR SEQ ID NO:146:

(i) SEQUENCE CHARACTERISTICS:
       (A) LENGTH: 16 amino acids
       (B) TYPE: amino acid
       (C) TOPOLOGY: linear (ii) MOLECULE TYPE: peptide (xi) SEQUENCE DESCRIPTION: SEQ ID NO:146:

Ser Leu Pro Pro Lys Pro Gly Arg Ile Arg Ser Ser Thr Gly Lys Leu
 1               5                  10                  15

(2) INFORMATION FOR SEQ ID NO:147:

(i) SEQUENCE CHARACTERISTICS:
       (A) LENGTH: 16 amino acids
       (B) TYPE: amino acid
       (C) TOPOLOGY: linear (ii) MOLECULE TYPE: peptide (xi) SEQUENCE DESCRIPTION: SEQ ID NO:147:

Ser Leu Pro Pro Lys Pro Gly Lys Ile Arg Ser Ser Thr Gly Gln Leu
 1               5                  10                  15

(2) INFORMATION FOR SEQ ID NO:148:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:148:

Ser Leu Pro Pro Glu Pro Gly Lys Ile Arg Ser Ser Thr Gly Arg Leu
 1           5                  10                  15

( 2 ) INFORMATION FOR SEQ ID NO:149:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:149:

Ser Leu Ala Pro Ser Pro Gly Lys Ile Arg Ser Thr Ala Glu Lys Leu
 1           5                  10                  15

( 2 ) INFORMATION FOR SEQ ID NO:150:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:150:

Ser Leu Pro Pro Arg Pro Gly Lys Ile Arg Ser Thr Gly Asn Val
 1           5                  10                  15

( 2 ) INFORMATION FOR SEQ ID NO:151:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:151:

Ser Leu Arg Pro Ser Pro Gly Lys Val Arg Ser Thr Ala Glu Lys Leu
 1           5                  10                  15

( 2 ) INFORMATION FOR SEQ ID NO:152:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:152:

Ser Leu Arg Pro Ser Pro Gly Lys Val Arg Ser Thr Ala Asp Lys Leu
 1           5                  10                  15

( 2 ) INFORMATION FOR SEQ ID NO:153:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:153:

Ser Leu Arg Pro Ser Pro Gly Lys Val Arg Ser Thr Ala Glu Asn Leu
 1               5                   10                  15

( 2 ) INFORMATION FOR SEQ ID NO:154:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:154:

Ser Leu Arg Pro Ser Pro Gly Lys Val Arg Ser Ala Val Glu Lys Leu
 1               5                   10                  15

( 2 ) INFORMATION FOR SEQ ID NO:155:

( i ) SEQUENCE CHARACTERISTICS:
        ( A ) LENGTH: 15 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:155:

Ser Leu Pro Pro Arg Pro Gly Lys Arg Ser Ser Ala Glu Lys Leu
 1               5                   10                  15

( 2 ) INFORMATION FOR SEQ ID NO:156:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:156:

Ser Leu Ala Pro Ser Pro Gly Lys Val Arg Ser Thr Val Glu Arg Leu
 1               5                   10                  15

( 2 ) INFORMATION FOR SEQ ID NO:157:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:157:

Ser Leu Ala Pro Ser Pro Asp Lys Ile Arg Ser Thr Pro Asp Lys Leu
 1               5                   10                  15

( 2 ) INFORMATION FOR SEQ ID NO:158:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:158:

Ser Leu Ala Leu Ser Pro Gly Lys Val Arg Ser Thr Ala Glu Lys Leu (2) INFORMATION FOR SEQ ID NO:159:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:159:

```
Ser  Leu  Pro  Leu  Ser  Ala  Gly  Lys  Val  Arg  Ser  Thr  Ala  Glu  Lys  Leu
 1              5                        10                       15
```

(2) INFORMATION FOR SEQ ID NO:160:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:160:

```
Ser  Leu  Ala  Pro  Ser  Pro  Gly  Lys  Val  Arg  Ser  Thr  Ala  Glu  Tyr  Leu
 1              5                        10                       15
```

(2) INFORMATION FOR SEQ ID NO:161:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:161:

```
Ser  Leu  Pro  Leu  Thr  Pro  Gly  Leu  Ile  Arg  Ser  Thr  Ala  Glu  Lys  Leu
 1-             5                        10                       15
```

(2) INFORMATION FOR SEQ ID NO:162:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:162:

```
Ser  Leu  Pro  Leu  Thr  Pro  Arg  Val  Ile  Arg  Ser  Thr  Ala  Glu  Lys  Leu
 1              5                        10                       15
```

(2) INFORMATION FOR SEQ ID NO:163:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:163:

```
Phe  Leu  His  Pro  Thr  Pro  Gly  Thr  Asp  Ser  Ser  Thr  Glu  Lys  Leu
 1              5                        10                       15
```

(2) INFORMATION FOR SEQ ID NO:164:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:164:

Phe Leu Leu Pro Thr Pro Gly Thr Asp Ser Ser Thr Glu Arg Leu
1               5                   10                  15

( 2 ) INFORMATION FOR SEQ ID NO:165:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:165:

Phe Leu His Pro Thr Arg Val Thr Asp Ser Ser Thr Glu Lys Leu
1               5                   10                  15

( 2 ) INFORMATION FOR SEQ ID NO:166:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:166:

Leu Leu Pro Pro Thr Pro Gly Thr Asn Ser Ser Ser Asn Asp Lys Leu
1               5                   10                  15

( 2 ) INFORMATION FOR SEQ ID NO:167:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:167:

Val Leu Pro Leu Ser Pro His Arg Ile Arg Ser Glu Ser Glu Asn Leu
1               5                   10                  15

( 2 ) INFORMATION FOR SEQ ID NO:168:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:168:

Ser Leu Ala Pro Ser Pro Ala Lys Phe Arg Ser Thr Ala Glu Arg Asp
1               5                   10                  15

( 2 ) INFORMATION FOR SEQ ID NO:169:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:169:

Val Thr Ala Pro Arg Pro Gly Arg Ile Arg Ser Asp Pro Glu Lys Lys
 1               5                   10                  15

( 2 ) INFORMATION FOR SEQ ID NO:170:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:170:

Val Thr Ala Pro Arg Pro Gly Arg Val Arg Ser Asp Pro Glu Lys Lys
 1               5                   10                  15

( 2 ) INFORMATION FOR SEQ ID NO:171:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:171:

Val Thr Gly Pro Arg Pro Gly Arg Ile Arg Ser Asp Pro Glu Lys Lys
 1               5                   10                  15

( 2 ) INFORMATION FOR SEQ ID NO:172:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:172:

Val Thr Gly Pro Arg Pro Gly Arg Ile Arg Ser Asp Pro Asp Lys Lys
 1               5                   10                  15

( 2 ) INFORMATION FOR SEQ ID NO:173:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:173:

Val Thr Gly Pro Arg Pro Gly Arg Val Arg Ser Asp Pro Glu Lys Lys
 1               5                   10                  15

( 2 ) INFORMATION FOR SEQ ID NO:174:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:174:

Val Thr Gly Pro Arg Pro Gly Arg Ile Arg Ser Asp Pro Xaa Lys Lys (2) INFORMATION FOR SEQ ID NO:175:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:175:

Val Thr Ala Pro Arg Pro Gly Arg Ile Arg Ser Glu Ser Glu Arg Lys
 1               5                   10                  15

(2) INFORMATION FOR SEQ ID NO:176:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:176:

Val Thr Gly Pro Ser Arg Gly Arg Ile Arg Ser Asp Pro Glu Lys Lys
 1               5                   10                  15

(2) INFORMATION FOR SEQ ID NO:177:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:177:

Val Thr Val Pro Arg Pro Ser Arg Ile Arg Ser Glu Ser Glu Arg Lys
 1               5                   10                  15

(2) INFORMATION FOR SEQ ID NO:178:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:178:

Val Thr Ala Pro Gly Pro Gly Arg Ile Arg Ser Glu Ser Glu Arg Lys
 1               5                   10                  15

(2) INFORMATION FOR SEQ ID NO:179:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:179:

Gln Thr Ser Val Arg Pro Gly Arg Val Arg Ser Asp Pro Glu Arg Lys
 1               5                   10                  15

(2) INFORMATION FOR SEQ ID NO:180:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:180:

Gln Thr Ser Val Arg Pro Gly Lys Val Arg Ser Asp Pro Glu Arg Lys
 1               5                  10                  15

(2) INFORMATION FOR SEQ ID NO:181:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:181:

Gln Thr Ser Val Arg Pro Gly Lys Val Arg Ser Asp Pro Glu Lys Lys
 1               5                  10                  15

(2) INFORMATION FOR SEQ ID NO:182:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:182:

Gln Thr Ser Val Arg Pro Gly Lys Val Arg Ser Glu Pro Glu Lys Lys
 1               5                  10                  15

(2) INFORMATION FOR SEQ ID NO:183:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:183:

Gln Thr Ser Val Arg Pro Gly Lys Val Arg Ser Glu Pro Asp Lys Lys
 1               5                  10                  15

(2) INFORMATION FOR SEQ ID NO:184:

(i) SEQUENCE CHARACTERISTICS:
    (A) LENGTH: 16 amino acids
    (B) TYPE: amino acid
    (C) TOPOLOGY: linear (ii) MOLECULE TYPE: peptide (xi) SEQUENCE DESCRIPTION: SEQ ID NO:184:

Gln Thr Ser Val Arg Pro Gly Lys Val Arg Ala Glu Pro Glu Lys Lys
 1               5                  10                  15

(2) INFORMATION FOR SEQ ID NO:185:

(i) SEQUENCE CHARACTERISTICS:
    (A) LENGTH: 16 amino acids
    (B) TYPE: amino acid
    (C) TOPOLOGY: linear ( i i ) MOLECULE TYPE: peptide ( x i ) SEQUENCE DESCRIPTION: SEQ ID NO:185:

Gln Thr Ser Val Arg Pro Gly Lys Val Arg Ser Asx Pro Glx Lys Lys
1               5                   10                  15

( 2 ) INFORMATION FOR SEQ ID NO:186:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:186:

Gln Thr Ser Val Arg Pro Gly Lys Val Arg Ser Asp Pro Asx Lys Lys
1               5                   10                  15

( 2 ) INFORMATION FOR SEQ ID NO:187:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:187:

Gln Thr Ser Val Arg Pro Gly Gln Val Arg Ser Asp Pro Glu Arg Lys
1               5                   10                  15

( 2 ) INFORMATION FOR SEQ ID NO:188:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:188:

Gln Thr Ser Val Arg Pro Gly Lys Val Arg Ser His Pro Glu Lys Lys
1               5                   10                  15

( 2 ) INFORMATION FOR SEQ ID NO:189:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:189:

Gln Thr Ser Val Arg Pro Gly Asn Val Arg Ser Asp Pro Asp Lys Lys
1               5                   10                  15

( 2 ) INFORMATION FOR SEQ ID NO:190:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:190:

Gln Thr Ser Val Arg Pro Gly Lys Val Arg Ser Asp Pro Glu Lys Thr ( 2 ) INFORMATION FOR SEQ ID NO:191:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:191:

```
Gln  Thr  Ser  Val  Arg  Pro  Gly  Thr  Val  Arg  Ser  Glu  Pro  Glu  Lys  Lys
 1                  5                       10                      15
```

( 2 ) INFORMATION FOR SEQ ID NO:192:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:192:

```
Gln  Thr  Ser  Val  Arg  Pro  Glu  Lys  Val  Arg  Ser  Glu  Pro  Asp  Lys  Lys
 1                  5                       10                      15
```

( 2 ) INFORMATION FOR SEQ ID NO:193:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:193:

```
Gln  Thr  Ser  Val  Arg  Pro  Gly  Lys  Val  Arg  Ser  Glu  Ser  Asp  Lys  Lys
 1                  5                       10                      15
```

( 2 ) INFORMATION FOR SEQ ID NO:194:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:194:

```
Gln  Thr  Ser  Val  Arg  Pro  Gly  Glu  Val  Arg  Ser  Glu  Pro  Asp  Lys  Lys
 1                  5                       10                      15
```

( 2 ) INFORMATION FOR SEQ ID NO:195:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:195:

```
Gln  Thr  Ser  Val  Arg  Pro  Gly  Asx  Val  Arg  Ser  Asx  Pro  Glx  Arg  Lys
 1                  5                       10                      15
```

( 2 ) INFORMATION FOR SEQ ID NO:196:

( i ) SEQUENCE CHARACTERISTICS:
   ( A ) LENGTH: 16 amino acids
   ( B ) TYPE: amino acid
   ( C ) TOPOLOGY: linear ( i i ) MOLECULE TYPE: peptide ( x i ) SEQUENCE DESCRIPTION: SEQ ID NO:196:

Gln Thr Ser Val Ser Pro Gly Lys Val Arg Ser Asp Pro Glu Lys Lys
 1               5                  10                  15

( 2 ) INFORMATION FOR SEQ ID NO:197:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:197:

Gln Thr Ser Val Arg Pro Gly Lys Val Asn Ser Asp Pro Glu Lys Lys
 1               5                  10                  15

( 2 ) INFORMATION FOR SEQ ID NO:198:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:198:

Gln Thr Ser Val Arg Pro Gly Lys Val Arg Ser Asp Pro Asp Thr Lys
 1               5                  10                  15

( 2 ) INFORMATION FOR SEQ ID NO:199:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:199:

Gln Thr Ser Val Arg Pro Lys Lys Val Arg Ser Asp Pro Glx Lys Lys
 1               5                  10                  15

( 2 ) INFORMATION FOR SEQ ID NO:200:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:200:

Gln Thr Ser Val Arg Pro Lys Lys Val Arg Phe Asp Pro Glu Lys Lys
 1               5                  10                  15

( 2 ) INFORMATION FOR SEQ ID NO:201:

( i ) SEQUENCE CHARACTERISTICS:
       ( A ) LENGTH: 16 amino acids
       ( B ) TYPE: amino acid
       ( C ) TOPOLOGY: linear (ii) MOLECULE TYPE: peptide (xi) SEQUENCE DESCRIPTION: SEQ ID NO:201:

| Gln | Thr | Ser | Val | Arg | Ser | Gly | Lys | Val | Arg | Ser | Glu | Pro | Glu | Thr | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:202:

(i) SEQUENCE CHARACTERISTICS:
(A) LENGTH: 16 amino acids
(B) TYPE: amino acid
(C) TOPOLOGY: linear (ii) MOLECULE TYPE: peptide (xi) SEQUENCE DESCRIPTION: SEQ ID NO:202:

| Val | Thr | Asn | Leu | Arg | Pro | Gly | Lys | Val | Arg | Ser | Asp | Ala | Glu | Lys | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:203:

(i) SEQUENCE CHARACTERISTICS:
(A) LENGTH: 16 amino acids
(B) TYPE: amino acid
(C) TOPOLOGY: linear (ii) MOLECULE TYPE: peptide (xi) SEQUENCE DESCRIPTION: SEQ ID NO:203:

| Val | Thr | Asp | Leu | Arg | Pro | Gly | Lys | Val | Arg | Ser | Asp | Ala | Glu | Lys | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:204:

(i) SEQUENCE CHARACTERISTICS:
(A) LENGTH: 16 amino acids
(B) TYPE: amino acid
(C) TOPOLOGY: linear (ii) MOLECULE TYPE: peptide (xi) SEQUENCE DESCRIPTION: SEQ ID NO:204:

| Gln | Thr | Ser | Val | Ser | Pro | Gly | Asn | Ile | Arg | Ser | Glu | Ser | Asp | Lys | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:205:

(i) SEQUENCE CHARACTERISTICS:
(A) LENGTH: 16 amino acids
(B) TYPE: amino acid
(C) TOPOLOGY: linear (ii) MOLECULE TYPE: peptide (xi) SEQUENCE DESCRIPTION: SEQ ID NO:205:

| Lys | Thr | Ser | Val | Thr | Pro | Gly | Lys | Phe | Arg | Ser | Glu | Pro | Glu | Lys | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:206:

(i) SEQUENCE CHARACTERISTICS:
(A) LENGTH: 16 amino acids
(B) TYPE: amino acid
(C) TOPOLOGY: linear (ii) MOLECULE TYPE: peptide (xi) SEQUENCE DESCRIPTION: SEQ ID NO:206:

| Val | Thr | Leu | Leu | Pro | Pro | Gly | Arg | Val | Arg | Ser | Asp | Ala | Glu | Lys | Lys |
|-----|-----|-----|-----|-----|-----|-----|-----|-----|-----|-----|-----|-----|-----|-----|-----|

( 2 ) INFORMATION FOR SEQ ID NO:207:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:207:

Val Thr Leu Leu Pro Pro Gly Glu Val Arg Ser Asp Ala Glu Lys Lys
 1               5                  10                  15

( 2 ) INFORMATION FOR SEQ ID NO:208:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:208:

Val Thr Leu Pro Pro Pro Gly Glx Val Arg Ser Asp Ala Glu Arg Lys
 1               5                  10                  15

( 2 ) INFORMATION FOR SEQ ID NO:209:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:209:

Val Thr Leu Pro Pro Pro Gly Glx Val Arg Ser Asx Ala Glx Asn Lys
 1               5                  10                  15

( 2 ) INFORMATION FOR SEQ ID NO:210:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:210:

Val Thr Leu Pro Pro Pro Gln Gln Val Arg Ser Asp Ala Glu Lys Lys
 1               5                  10                  15

( 2 ) INFORMATION FOR SEQ ID NO:211:

( i ) SEQUENCE CHARACTERISTICS:
       ( A ) LENGTH: 16 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:211:

Val Thr Leu Pro Pro Pro Gly Gln Val Thr Ser Asp Ala Glu Lys Lys
 1               5                  10                  15

( 2 ) INFORMATION FOR SEQ ID NO:212:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:212:

```
Val Thr Leu Pro Pro Ala Gly Gln Val Arg Ser Asp Ala Glu Lys Arg
 1               5                  10                  15
```

( 2 ) INFORMATION FOR SEQ ID NO:213:

( i ) SEQUENCE CHARACTERISTICS:
    ( A ) LENGTH: 16 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:213:

```
Ala Leu Ser Pro Ser Ser Gly Gln Ser Ser Ser Ala Ser Glu Arg Leu
 1               5                  10                  15
```

( 2 ) INFORMATION FOR SEQ ID NO:214:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:214:

```
Glu Lys Val Gly Gly Leu Gln Pro Gly Arg Gly Thr Pro Gly Lys Ala
 1               5                  10                  15
Ser Arg Gly Asp Ser Gln Arg Pro Glu Ser
                20                  25
```

( 2 ) INFORMATION FOR SEQ ID NO:215:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:215:

```
Glu Lys Val Gly Gly Leu Gln Pro Gly Arg Gly Thr Pro Gly Lys Val
 1               5                  10                  15
Ser Arg Gly Asp Ser Gln Arg Pro Glu Ser
                20                  25
```

( 2 ) INFORMATION FOR SEQ ID NO:216:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:216:

```
Glu Lys Val Gly Gly Leu Gln Pro Gly Thr Gly Ala Pro Gly Lys Ala
 1               5                  10                  15
Ser Arg Gly Asp Ser Gln Arg Pro Glu Ser
                20                  25
```

( 2 ) INFORMATION FOR SEQ ID NO:217:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:217:

```
Glu Lys Val Gly Gly Leu Gln Pro Gly Arg Gly Thr Pro Gly Lys Ala
 1               5                  10                  15
Ser Lys Gly Asn Ser Gln Arg Ala Glu Ser
            20                  25
```

( 2 ) INFORMATION FOR SEQ ID NO:218:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:218:

```
Glu Lys Met Gly Gly Leu Gln Pro Gly Arg Gly Thr Pro Gly Lys Ala
 1               5                  10                  15
Ser Lys Gly Asn Ser Gln Arg Ala Glu Ser
            20                  25
```

( 2 ) INFORMATION FOR SEQ ID NO:219:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:219:

```
Glu Lys Val Gly Gly Leu Gln Pro Gly Arg Gly Thr Pro Gly Lys Ala
 1               5                  10                  15
Ser Lys Gly Thr Ser Gln Arg Ala Glu Ser
            20                  25
```

( 2 ) INFORMATION FOR SEQ ID NO:220:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:220:

```
Glu Lys Val Gly Gly Leu Gln Pro Gly Arg Gly Thr Pro Gly Lys Ala
 1               5                  10                  15
Ser Lys Gly Thr Ser Gln Arg Ala Glu Thr
            20                  25
```

( 2 ) INFORMATION FOR SEQ ID NO:221:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:221:

```
Glu Lys Val Gly Gly Leu Lys Pro Gly Arg Gly Thr Pro Gly Lys Ala
 1               5                   10                  15
Ser Lys Gly Thr Ser Gln Arg Ala Glu Thr
             20                  25
```

( 2 ) INFORMATION FOR SEQ ID NO:222:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:222:

```
Glu Asn Val Gly Gly Leu Gln Pro Gly Arg Gly Thr Pro Gly Lys Ala
 1               5                   10                  15
Ser Lys Gly Thr Ser Gln Arg Ala Glu Thr
             20                  25
```

( 2 ) INFORMATION FOR SEQ ID NO:223:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:223:

```
Glu Lys Val Gly Gly Leu Gln Ser Gly Arg Gly Thr Pro Gly Lys Ala
 1               5                   10                  15
Ser Lys Gly Thr Ser Gln Arg Ala Glu Thr
             20                  25
```

( 2 ) INFORMATION FOR SEQ ID NO:224:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:224:

```
Glu Lys Val Gly Gly Leu Gln Ser Gly Arg Gly Thr Pro Gly Lys Ala
 1               5                   10                  15
Ser Lys Gly Thr Ser Gln Arg Ala Glu Ser
             20                  25
```

( 2 ) INFORMATION FOR SEQ ID NO:225:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:225:

```
Glu Lys Val Gly Gly Leu Gln Pro Gly Arg Gly Thr Pro Gly Lys Ala
 1               5                   10                  15
```

Ser Lys Gly Ile Ser Gln Arg Ala Glu Arg
         20                  25

(2) INFORMATION FOR SEQ ID NO:226:

(i) SEQUENCE CHARACTERISTICS:
       (A) LENGTH: 26 amino acids
       (B) TYPE: amino acid
       (C) TOPOLOGY: linear (ii) MOLECULE TYPE: peptide (xi) SEQUENCE DESCRIPTION: SEQ ID NO:226:

Glu Lys Val Gly Gly Leu Gln Pro Gly Arg Gly Thr Pro Gly Lys Ser
 1               5                  10                  15

Ala Lys Gly Asx Ser Glx Arg Ala Gln Ser
         20                  25

(2) INFORMATION FOR SEQ ID NO:227:

(i) SEQUENCE CHARACTERISTICS:
       (A) LENGTH: 26 amino acids
       (B) TYPE: amino acid
       (C) TOPOLOGY: linear (ii) MOLECULE TYPE: peptide (xi) SEQUENCE DESCRIPTION: SEQ ID NO:227:

Glu Lys Val Gly Gly Leu Gln Pro Gly Ser Gly Thr Pro Gly Lys Ala
 1               5                  10                  15

Ser Lys Gly Asn Ser Gln Arg Ala Glu Ser
         20                  25

(2) INFORMATION FOR SEQ ID NO:228:

(i) SEQUENCE CHARACTERISTICS:
       (A) LENGTH: 26 amino acids
       (B) TYPE: amino acid
       (C) TOPOLOGY: linear (ii) MOLECULE TYPE: peptide (xi) SEQUENCE DESCRIPTION: SEQ ID NO:228:

Glu Lys Val Gly Gly Leu Gln Pro Gly Ser Gly Thr Pro Gly Lys Ala
 1               5                  10                  15

Ser Lys Gly Ser Ser Gln Arg Ala Glu Ser
         20                  25

(2) INFORMATION FOR SEQ ID NO:229:

(i) SEQUENCE CHARACTERISTICS:
       (A) LENGTH: 26 amino acids
       (B) TYPE: amino acid
       (C) TOPOLOGY: linear (ii) MOLECULE TYPE: peptide (xi) SEQUENCE DESCRIPTION: SEQ ID NO:229:

Glu Lys Val Gly Gly Leu Gln Pro Gly Arg Gly Thr Pro Arg Lys Ala
 1               5                  10                  15

Ser Lys Gly Asn Ser Gln Arg Ala Glu Ser
         20                  25

(2) INFORMATION FOR SEQ ID NO:230:

(i) SEQUENCE CHARACTERISTICS:
       (A) LENGTH: 26 amino acids (B) TYPE: amino acid
(C) TOPOLOGY: linear (ii) MOLECULE TYPE: peptide (xi) SEQUENCE DESCRIPTION: SEQ ID NO:230:

```
Glu Lys Met Gly Asn Leu Gln Pro Gly Ser Gly Thr Pro Gly Lys Ala
 1               5                  10                  15
Ser Lys Gly Asn Ser Gln Arg Pro Asp Ser
                20                  25
```

(2) INFORMATION FOR SEQ ID NO:231:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:231:

```
Glu Lys Val Gly Gly Leu Lys Pro Gly Lys Gly Thr Pro Glu Lys Asp
 1               5                  10                  15
Ser Lys Gly Asn Ala Arg Arg Ser Glu Thr
                20                  25
```

(2) INFORMATION FOR SEQ ID NO:232:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:232:

```
Glu Lys Val Gly Gly Leu Lys Pro Gly Lys Gly Ala Pro Glu Lys Asp
 1               5                  10                  15
Ser Lys Gly Asn Ala Arg Arg Ser Glu Thr
                20                  25
```

(2) INFORMATION FOR SEQ ID NO:233:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:233:

```
Glu Lys Val Gly Gly Leu Lys Pro Gly Lys Gly Thr Pro Glu Arg Asp
 1               5                  10                  15
Ser Lys Gly Asn Ala Arg Arg Ser Glu Thr
                20                  25
```

(2) INFORMATION FOR SEQ ID NO:234:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:234:

```
Asp Lys Val Gly Gly Leu Lys Pro Gly Lys Gly Thr Pro Glu Lys Asp
```

```
                 1               5                   10                      15
Ser Lys Gly Asn Ala Lys Arg Ser Glu Thr
                20                  25
```

(2) INFORMATION FOR SEQ ID NO:235:

(i) SEQUENCE CHARACTERISTICS:
  (A) LENGTH: 26 amino acids
  (B) TYPE: amino acid
  (C) TOPOLOGY: linear (ii) MOLECULE TYPE: peptide (xi) SEQUENCE DESCRIPTION: SEQ ID NO:235:

```
Asp Lys Val Gly Gly Leu Lys Pro Gly Lys Gly Thr Pro Glu Lys Asp
 1               5                   10                      15
Ser Lys Gly Asn Ala Lys Lys Ser Glu Thr
                20                  25
```

(2) INFORMATION FOR SEQ ID NO:236:

(i) SEQUENCE CHARACTERISTICS:
  (A) LENGTH: 26 amino acids
  (B) TYPE: amino acid
  (C) TOPOLOGY: linear (ii) MOLECULE TYPE: peptide (xi) SEQUENCE DESCRIPTION: SEQ ID NO:236:

```
Asp Lys Val Gly Gly Leu Lys Pro Gly Lys Gly Thr Pro Asp Lys Asp
 1               5                   10                      15
Asn Lys Gly Asn Ala Lys Lys Ser Glu Thr
                20                  25
```

(2) INFORMATION FOR SEQ ID NO:237:

(i) SEQUENCE CHARACTERISTICS:
  (A) LENGTH: 26 amino acids
  (B) TYPE: amino acid
  (C) TOPOLOGY: linear (ii) MOLECULE TYPE: peptide (xi) SEQUENCE DESCRIPTION: SEQ ID NO:237:

```
Glu Lys Val Gly Gly Leu Thr Pro Gly Lys Gly Thr Pro Glu Lys Asp
 1               5                   10                      15
Ser Lys Gly Asn Gly Arg Arg Ser Glu Thr
                20                  25
```

(2) INFORMATION FOR SEQ ID NO:238:

(i) SEQUENCE CHARACTERISTICS:
  (A) LENGTH: 26 amino acids
  (B) TYPE: amino acid
  (C) TOPOLOGY: linear (ii) MOLECULE TYPE: peptide (xi) SEQUENCE DESCRIPTION: SEQ ID NO:238:

```
Glu Met Val Gly Gly Leu Lys Pro Gly Lys Gly Thr Pro Glu Lys Asp
 1               5                   10                      15
Ser Lys Gly Asn Asp Arg Arg Ser Glu Thr
                20                  25
```

(2) INFORMATION FOR SEQ ID NO:239:

( i ) SEQUENCE CHARACTERISTICS:
   ( A ) LENGTH: 26 amino acids
   ( B ) TYPE: amino acid
   ( C ) TOPOLOGY: linear ( i i ) MOLECULE TYPE: peptide ( x i ) SEQUENCE DESCRIPTION: SEQ ID NO:239:

```
Glu Met Val Gly Gly Leu Lys Pro Gly Lys Gly Thr Pro Glu Lys Asp
 1               5                  10                  15
Ser Lys Gly Asn Asp Lys Arg Ser Glu Thr
             20                  25
```

( 2 ) INFORMATION FOR SEQ ID NO:240:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:240:

```
Glu Met Val Gly Gly Leu Lys Pro Gly Lys Gly Thr Pro Glu Lys Asp
 1               5                  10                  15
Ser Lys Gly Asn Ala Lys Arg Ser Glu Thr
             20                  25
```

( 2 ) INFORMATION FOR SEQ ID NO:241:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:241:

```
Glu Gln Val Gly Gly Leu Lys Pro Gly Lys Gly Thr Pro Glu Lys Asp
 1               5                  10                  15
Ser Lys Gly Asn Ala Lys Lys Ser Glu Thr
             20                  25
```

( 2 ) INFORMATION FOR SEQ ID NO:242:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:242:

```
Glu Gln Val Gly Gly Leu Lys Pro Gly Lys Gly Thr Pro Glu Lys Asp
 1               5                  10                  15
Thr Lys Gly Asn Ala Lys Lys Ser Glu Thr
             20                  25
```

( 2 ) INFORMATION FOR SEQ ID NO:243:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:243:

```
Glu Gln Val Gly Gly Leu Lys Pro Gly Lys Gly Ala Pro Glu Lys Asp
 1               5                  10                  15
Thr Lys Gly Asn Ala Lys Lys Ser Glu Thr
               20                  25
```

(2) INFORMATION FOR SEQ ID NO:244:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:244:

```
Glu Lys Val Gly Gly Leu Gln Pro Gly Lys Gly Thr Pro Glu Lys Asp
 1               5                  10                  15
Ser Lys Gly Asn Ala Lys Lys Ser Glu Thr
               20                  25
```

(2) INFORMATION FOR SEQ ID NO:245:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:245:

```
Glu Lys Val Gly Gly Leu Gln Pro Gly Lys Gly Thr Pro Glu Lys Asp
 1               5                  10                  15
Thr Lys Gly Asn Ala Lys Lys Ser Glu Thr
               20                  25
```

(2) INFORMATION FOR SEQ ID NO:246:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:246:

```
Glu Lys Val Gly Gly Leu Gln Pro Gly Arg Gly Thr Pro Glu Lys Asp
 1               5                  10                  15
Thr Lys Gly Asn Ala Lys Lys Ser Glu Thr
               20                  25
```

(2) INFORMATION FOR SEQ ID NO:247:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:247:

```
Glu Lys Val Gly Gly Leu Gln Pro Gly Lys Gly Ser Pro Glu Lys Asp
 1               5                  10                  15
Ser Lys Gly Asn Ala Lys Lys Ser Glu Thr
               20                  25
```

( 2 ) INFORMATION FOR SEQ ID NO:248:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:248:

```
Asp  Lys  Met  Gly  Gly  Leu  Lys  Pro  Gly  Lys  Gly  Thr  Pro  Glu  Lys  Asp
 1                    5                          10                          15
Ser  Lys  Gly  Asn  Ala  Lys  Gln  Ser  Glu  Thr
                20                        25
```

( 2 ) INFORMATION FOR SEQ ID NO:249:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:249:

```
Glu  Gln  Val  Gly  Gly  Leu  Gln  Pro  Gly  Lys  Gly  Thr  Pro  Asp  Lys  Asp
 1                    5                          10                          15
Ser  Lys  Gly  Asn  Ala  Lys  Lys  Ser  Glu  Thr
                20                        25
```

( 2 ) INFORMATION FOR SEQ ID NO:250:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:250:

```
Glu  Lys  Val  Gly  Gly  Leu  Gln  Pro  Gly  Lys  Gly  Thr  Pro  Glu  Lys  Asp
 1                    5                          10                          15
Ser  Lys  Gly  Asn  Ala  Glu  Lys  Ser  Glu  Thr
                20                        25
```

( 2 ) INFORMATION FOR SEQ ID NO:251:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:251:

```
Glu  Gln  Val  Gly  Asp  Leu  Lys  Pro  Gly  Lys  Gly  Thr  Pro  Glu  Lys  Asp
 1                    5                          10                          15
Thr  Lys  Gly  Asn  Ala  Arg  Arg  Ser  Glu  Thr
                20                        25
```

( 2 ) INFORMATION FOR SEQ ID NO:252:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:252:

Glu Asn Val Gly Asp Leu Lys Pro Gly Lys Gly Ala Pro Glu Lys Asp
1               5                   10                  15

Ser Lys Gly Asn Ala Arg Arg Ser Glu Thr
            20                  25

( 2 ) INFORMATION FOR SEQ ID NO:253:

( i ) SEQUENCE CHARACTERISTICS:
       ( A ) LENGTH: 26 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:253:

Glu Gln Val Gly Gly Leu Gln Pro Gly Lys Gly Thr Ser Asp Lys Asp
1               5                   10                  15

Ser Lys Gly Asn Ala Lys Lys Ser Glu Thr
            20                  25

( 2 ) INFORMATION FOR SEQ ID NO:254:

( i ) SEQUENCE CHARACTERISTICS:
       ( A ) LENGTH: 26 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:254:

Glu Gln Val Gly Gly Leu Gln Pro Gly Lys Gly Thr Pro Glu Lys Asp
1               5                   10                  15

Ser Lys Gly Asn Ala Lys Lys Ser Gly Thr
            20                  25

( 2 ) INFORMATION FOR SEQ ID NO:255:

( i ) SEQUENCE CHARACTERISTICS:
       ( A ) LENGTH: 26 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:255:

Asp Gln Val Gly Gly Leu Gln Pro Gly Lys Gly Thr Pro Glu Lys Asp
1               5                   10                  15

Thr Lys Gly Asn Pro Lys Arg Ser Glu Thr
            20                  25

( 2 ) INFORMATION FOR SEQ ID NO:256:

( i ) SEQUENCE CHARACTERISTICS:
       ( A ) LENGTH: 26 amino acids
       ( B ) TYPE: amino acid
       ( C ) TOPOLOGY: linear ( i i ) MOLECULE TYPE: peptide ( x i ) SEQUENCE DESCRIPTION: SEQ ID NO:256:

Asp Gln Val Gly Gly Leu Gln Pro Gly Gln Gly Thr Pro Glu Lys Asn
1               5                   10                  15

Thr Lys Gly Asn Pro Lys Arg Ser Asp Thr
            20                  25

( 2 ) INFORMATION FOR SEQ ID NO:257:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:257:

```
Glu Lys Val Gly Gly Leu Gln Pro Gly Lys Gly Thr Ser Glu Lys Asp
 1               5                  10                  15
Ile Lys Gly Asn Ala Lys Lys Ser Glu Thr
            20                  25
```

( 2 ) INFORMATION FOR SEQ ID NO:258:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:258:

```
Asp Lys Val Gly Gly Leu Lys Pro Gly Lys Arg Thr Pro Glu Lys Asp
 1               5                  10                  15
Asn Lys Gly Asn Ala Lys Lys Ser Glu Thr
            20                  25
```

( 2 ) INFORMATION FOR SEQ ID NO:259:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:259:

```
Asp Lys Val Gly Gly Leu Lys Leu Gly Lys Gly Thr Pro Glu Lys Asp
 1               5                  10                  15
Thr Lys Gly Asn Ala Lys Lys Ser Glu Thr
            20                  25
```

( 2 ) INFORMATION FOR SEQ ID NO:260:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:260:

```
Glu Lys Val Gly Gly Leu Gln Pro Gly Lys Gly Thr Pro Glu Lys Asp
 1               5                  10                  15
Ser Lys Gly Asn Ala Asn Thr Ser Glu Thr
            20                  25
```

( 2 ) INFORMATION FOR SEQ ID NO:261:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:261:

Glu His Val Gly Gly Leu Lys Pro Gly Lys Gly Thr Pro Glu Lys Asp
1               5                   10                  15
Ser Lys Gly Asn Ala Gly Arg Ser Glu Thr
            20                  25

( 2 ) INFORMATION FOR SEQ ID NO:262:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:262:

Glu Gln Val Gly Gly Leu Gln Pro Gly Asn Gly Thr Pro Glu Lys Asp
1               5                   10                  15
Thr Thr Gly Asn Ala Lys Arg Ser Glu Thr
            20                  25

( 2 ) INFORMATION FOR SEQ ID NO:263:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:263:

Glu Lys Glu Gly Gly Leu Gln Pro Gly Lys Gly Thr Pro Glu Lys Glu
1               5                   10                  15
Ser Lys Gly Asp Ser Lys Arg Ala Glu Thr
            20                  25

( 2 ) INFORMATION FOR SEQ ID NO:264:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:264:

Glu Lys Glu Gly Gly Leu Gln Pro Gly Lys Gly Thr Pro Glu Lys Glu
1               5                   10                  15
Ser Lys Gly Asp Ser Lys Arg Pro Glu Thr
            20                  25

( 2 ) INFORMATION FOR SEQ ID NO:265:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:265:

Glu Lys Glu Gly Gly Leu Gln Pro Gly Lys Gly Ser Pro Glu Lys Glu
1               5                   10                  15

-continued

Ser Lys Gly Asp Ser Lys Arg Ala Glu Thr
            20                  25

( 2 ) INFORMATION FOR SEQ ID NO:266:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:266:

Glu Lys Asp Gly Gly Leu Gln Pro Gly Lys Gly Thr Pro Glu Lys Asp
 1               5                  10                  15

Ser Lys Gly Asp Ser Lys Arg Val Glu Met
            20                  25

( 2 ) INFORMATION FOR SEQ ID NO:267:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:267:

Glu Gln Val Gly Gly Leu Lys Pro Gly Arg Gly Thr Pro Glu Lys Asp
 1               5                  10                  15

Thr Thr Gly Asp Ala Gln Arg Ser Glu Thr
            20                  25

( 2 ) INFORMATION FOR SEQ ID NO:268:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:268:

Glu Gln Val Gly Gly Leu Lys Pro Gly Arg Gly Thr Pro Glu Lys Asp
 1               5                  10                  15

Thr Thr Gly Asn Ala Lys Gly Ser Glu Thr
            20                  25

( 2 ) INFORMATION FOR SEQ ID NO:269:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:269:

Glu Lys Val Gly Gly Ser Lys Pro Gly Lys Gly Thr Pro Glu Lys Asp
 1               5                  10                  15

Ser Lys Gly Asn Ala Lys Thr Ser Glu Thr
            20                  25

( 2 ) INFORMATION FOR SEQ ID NO:270:

( i ) SEQUENCE CHARACTERISTICS:
        ( A ) LENGTH: 26 amino acids (B) TYPE: amino acid
(C) TOPOLOGY: linear (ii) MOLECULE TYPE: peptide (xi) SEQUENCE DESCRIPTION: SEQ ID NO:270:

Ser Asp Gln Gly Gly Leu Lys Pro Gly Lys Gly Thr Pro Glu Lys Asp
1               5                   10                  15
Thr Lys Gly Asn Ala Arg Arg Ser Glu Ser
            20                  25

(2) INFORMATION FOR SEQ ID NO:271:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:271:

Glu Lys Ile Gly Gly Leu Gln Pro Gly Lys Gly Asp Pro Gly Lys Pro
1               5                   10                  15
Ser Lys Asp Asn Ala Lys Arg Ser Glu Thr
            20                  25

(2) INFORMATION FOR SEQ ID NO:272:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:272:

Glu Lys Leu Gly Gly Leu Gln Pro Gly Lys Gly Asp Pro Gly Lys Pro
1               5                   10                  15
Ser Lys Asp Asn Ala Lys Arg Ser Glu Thr
            20                  25

(2) INFORMATION FOR SEQ ID NO:273:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:273:

Glu Lys Leu Gly Gly Leu Gln Pro Gly Lys Gly Asp Pro Gly Lys Pro
1               5                   10                  15
Phe Lys Asp Asn Ala Lys Arg Ser Glu Thr
            20                  25

(2) INFORMATION FOR SEQ ID NO:274:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:274:

Glu Lys Leu Gly Gly Leu Gln Pro Gly Lys Gly Asp Pro Gly Lys Leu

```
                1               5                    10                    15
Met  Lys  Glu  Asn  Ala  Lys  Arg  Ser  Glu  Thr
                    20                   25
```

( 2 ) INFORMATION FOR SEQ ID NO:275:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:275:

```
Glu  Asn  Leu  Gly  Gly  Leu  Gln  Pro  Gly  Lys  Gly  Asp  Pro  Gly  Lys  Leu
 1                 5                         10                        15
Lys  Xaa  Glu  Asn  Ala  Lys  Arg  Pro  Glu  Thr
                    20                   25
```

( 2 ) INFORMATION FOR SEQ ID NO:276:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:276:

```
Glu  Lys  Leu  Gly  Gly  Leu  Gln  Pro  Gly  Asn  Gly  Asp  Leu  Gly  Lys  Pro
 1                 5                         10                        15
Ser  Lys  Asp  Asn  Ala  Lys  Arg  Ser  Glu  Thr
                    20                   25
```

( 2 ) INFORMATION FOR SEQ ID NO:277:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:277:

```
Glu  Lys  Leu  Gly  Pro  Leu  Gln  Leu  Gly  Lys  Gly  Asp  Pro  Gly  Lys  Pro
 1                 5                         10                        15
Ser  Lys  Asp  Asp  Ala  Lys  Arg  Ser  Glu  Thr
                    20                   25
```

( 2 ) INFORMATION FOR SEQ ID NO:278:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:278:

```
Glu  Gln  Leu  Gly  Gly  Leu  Gln  Pro  Gly  Gly  Gly  Thr  Pro  Gly  Lys  Pro
 1                 5                         10                        15
Ser  Lys  Asp  Asn  Asp  Lys  Arg  Ser  Glu  Thr
                    20                   25
```

( 2 ) INFORMATION FOR SEQ ID NO:279:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:279:

```
Glu Gln Leu Gly Gly Leu Gln Pro Gly Gly Thr Pro Gly Lys Ala
 1               5                  10                  15
Ser Lys Asp Asn Asp Lys Arg Ser Glu Thr
              20                  25
```

( 2 ) INFORMATION FOR SEQ ID NO:280:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:280:

```
Glu Gln Val Gly Gly Leu Lys Ala Arg Lys Gly Thr Pro Glu Lys Asp
 1               5                  10                  15
Thr Thr Gly Asn Ala Lys Arg Ser Glu Thr
              20                  25
```

( 2 ) INFORMATION FOR SEQ ID NO:281:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:281:

```
Glu Met Val Gly Val Leu Glu Pro Gly Lys Gly Thr Pro Glu Lys Arg
 1               5                  10                  15
Gln Glu Gly Asn Ala Lys Arg Ser Glu Thr
              20                  25
```

( 2 ) INFORMATION FOR SEQ ID NO:282:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:282:

```
Glu Gln Val Gly Gly Leu Gln Pro Lys Lys Gly Ser Pro Gly Lys Asp
 1               5                  10                  15
Ser Lys Asp Asp Ser Gln Lys Thr Glu Thr
              20                  25
```

( 2 ) INFORMATION FOR SEQ ID NO:283:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:283:

```
Glu Gln Val Gly Gly Leu Gln Pro Lys Lys Gly Ser Pro Gly Lys Asp
 1               5                   10                  15
Ser Lys Asp Asp Ser Gln Lys Thr Glu Arg
              20              25
```

(2) INFORMATION FOR SEQ ID NO:284:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:284:

```
Gln Gln Val Pro Glu Leu Lys Pro Gly Arg Gly Thr Pro Gly Lys Glu
 1               5                   10                  15
Asp Lys Gly Thr Ser Ala Arg Asn Asp Thr
              20              25
```

(2) INFORMATION FOR SEQ ID NO:285:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:285:

```
Gln Gln Val Pro Glu Leu Lys Pro Gly Lys Gly Thr Pro Gly Lys Asp
 1               5                   10                  15
Asp Lys Gly Thr Ser Ala Lys Asn Glu Thr
              20              25
```

(2) INFORMATION FOR SEQ ID NO:286:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:286:

```
Gln Gln Val Pro Glu Leu Lys Pro Gly Lys Gly Thr Pro Gly Lys Asp
 1               5                   10                  15
Asp Lys Gly Thr Ser Ala Lys Asn Glu Met
              20              25
```

(2) INFORMATION FOR SEQ ID NO:287:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:287:

```
Gln Gln Lys Pro Glu Leu Lys Pro Gly Lys Gly Ser Pro Gly Gln Glu
 1               5                   10                  15
Lys Lys Gly Thr Ser Ser Thr Ser Glu Thr
              20              25
```

( 2 ) INFORMATION FOR SEQ ID NO:288:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:288:

```
Glu Gln Gln Pro Glu Leu Lys Pro Gly Lys Gly Thr Pro Gly Gln Glu
 1               5                  10                  15
Lys Lys Gly Lys Ser Ser Thr Ser Glu Ser
            20                  25
```

( 2 ) INFORMATION FOR SEQ ID NO:289:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:289:

```
Glu Gln Gln Pro Glu Leu Arg Pro Gly Lys Gly Thr Pro Gly Gln Glu
 1               5                  10                  15
Lys Lys Gly Lys Ser Ser Thr Ser Glu Ser
            20                  25
```

( 2 ) INFORMATION FOR SEQ ID NO:290:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:290:

```
Glu Gln Gln Pro Glu Leu Lys Pro Gly Lys Gly Thr Pro Gly Gln Glu
 1               5                  10                  15
Lys Lys Gly Lys Ser Ser Ala Ser Glu Ser
            20                  25
```

( 2 ) INFORMATION FOR SEQ ID NO:291:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:291:

```
Glu Gln Gln Pro Glu Leu Lys Pro Gly Lys Gly Thr Pro Gly Lys Gln
 1               5                  10                  15
Lys Lys Gly Lys Ser Ser Thr Ser Glu Ser
            20                  25
```

( 2 ) INFORMATION FOR SEQ ID NO:292:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:292:

Glu Gln Gln Pro Glu Leu Lys Pro Gly Lys Gly Thr His Gly Lys Gln
1               5                   10                  15

Lys Lys Gly Lys Ser Ser Thr Ser Glu Ser
                20                  25

( 2 ) INFORMATION FOR SEQ ID NO:293:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:293:

Glu Gln Gln Pro Glu Leu Lys Pro Gly Lys Gly Ser His Gly Lys Gln
1               5                   10                  15

Lys Lys Gly Lys Ser Ser Thr Ser Glu Ser
                20                  25

( 2 ) INFORMATION FOR SEQ ID NO:294:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:294:

Glu Gln Gln Pro Glu Leu Lys Pro Gly Lys Gly Ser His Gly Lys Gln
1               5                   10                  15

Lys Lys Gly Lys Ser Ser Ala Ser Glu Ser
                20                  25

( 2 ) INFORMATION FOR SEQ ID NO:295:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:295:

Glu Gln Gln Pro Glu Leu Lys Pro Gly Lys Gly Thr His Gly Lys Gln
1               5                   10                  15

Lys Lys Gly Lys Ser Ser Thr Phe Glu Ser
                20                  25

( 2 ) INFORMATION FOR SEQ ID NO:296:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:296:

Glu Gln Gln Pro Glu Leu Lys Pro Gly Lys Gly Thr His Gly Lys Gln
1               5                   10                  15

Lys Gln Gly Lys Ser Ser Thr Phe Glu Ser
                20                  25

( 2 ) INFORMATION FOR SEQ ID NO:297:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:297:

```
Glu Gln Gln Pro Glu Leu Lys Pro Gly Lys Gly Thr His Gly Lys Glu
 1               5                  10                  15
Lys Lys Asp Lys Ser Ser Thr Ser Glu Ser
            20                  25
```

( 2 ) INFORMATION FOR SEQ ID NO:298:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:298:

```
Glu Gln Gln Ala Glu Leu Lys Pro Gly Lys Gly Ser His Gly Lys Gln
 1               5                  10                  15
Lys Lys Gly Lys Ser Ser Thr Ser Glu Ser
            20                  25
```

( 2 ) INFORMATION FOR SEQ ID NO:299:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:299:

```
Glu Gln Gln Pro Glu Leu Lys Pro Gly Lys Gly Thr His Gly Lys Gln
 1               5                  10                  15
Lys Lys Ser Asn Ser Ser Thr Ser Glu Ser
            20                  25
```

( 2 ) INFORMATION FOR SEQ ID NO:300:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:300:

```
Gln Gln Gln Ala Glu Leu Arg Pro Gly Lys Gly Ala Pro Gly Gln Glu
 1               5                  10                  15
Lys Lys Gly Lys Ser Ser Thr Ser Glu Ser
            20                  25
```

( 2 ) INFORMATION FOR SEQ ID NO:301:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:301:

Gln Gln Gln Ala Glu Leu Arg Pro Gly Lys Gly Ala Pro Gly Gln Glu
1               5                   10                  15
Lys Lys Gly Lys Ser Ser Thr Ser Asp Ser
            20                  25

( 2 ) INFORMATION FOR SEQ ID NO:302:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:302:

Gln Gln Gln Ala Glu Leu Arg Pro Gly Lys Gly Val Pro Gly Gln Glu
1               5                   10                  15
Lys Lys Gly Lys Ser Ser Thr Ser Asp Ser
            20                  25

( 2 ) INFORMATION FOR SEQ ID NO:303:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:303:

Gln Gln Gln Pro Glu Leu Lys Pro Gly Lys Gly Ala Pro Gly Lys Gly
1               5                   10                  15
Lys Lys Gly Lys Ser Ser Thr Ser Glu Ser
            20                  25

( 2 ) INFORMATION FOR SEQ ID NO:304:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:304:

Gln Gln Gln Pro Glu Leu Lys Pro Gly Lys Gly Ala Pro Gly Lys Gly
1               5                   10                  15
Lys Lys Asp Lys Ser Ser Thr Ser Glu Ser
            20                  25

( 2 ) INFORMATION FOR SEQ ID NO:305:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:305:

Glu Gln Gln Pro Glu Ala Lys Pro Gly Lys Gly Thr His Gly Lys Gln
1               5                   10                  15

```
Lys Lys Gly Lys Ser Ser Thr Ser Asp Ser
         20                  25
```

( 2 ) INFORMATION FOR SEQ ID NO:306:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:306:

```
Gln Gln Gln Ala Glu Leu Lys Pro Gly Lys Gly Thr His Gly Lys Glu
 1               5                  10                  15
Lys Lys Asp Lys Ser Ser Thr Ser Asp Ser
         20                  25
```

( 2 ) INFORMATION FOR SEQ ID NO:307:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:307:

```
Gln Gln Gln Ala Glu Leu Arg Pro Gly Lys Gly Ala Pro Gly Gln Gly
 1               5                  10                  15
Lys Lys Gly Lys Ser Ser Thr Ser Glu Ser
         20                  25
```

( 2 ) INFORMATION FOR SEQ ID NO:308:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:308:

```
Gln Gln Gln Ala Glu Leu Lys Pro Gly Arg Gly Thr Pro Gly Gln Glu
 1               5                  10                  15
Lys Lys Gly Lys Ser Ser Thr Ser Glu Ser
         20                  25
```

( 2 ) INFORMATION FOR SEQ ID NO:309:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:309:

```
Glu Gln Gln Ala Glu Leu Arg Ala Gly Lys Gly Thr Pro Gly Gln Glu
 1               5                  10                  15
Lys Lys Gly Lys Ser Ser Thr Ser Glu Ser
         20                  25
```

( 2 ) INFORMATION FOR SEQ ID NO:310:

( i ) SEQUENCE CHARACTERISTICS:
        ( A ) LENGTH: 26 amino acids ( B ) TYPE: amino acid
( C ) TOPOLOGY: linear ( i i ) MOLECULE TYPE: peptide ( x i ) SEQUENCE DESCRIPTION: SEQ ID NO:310:

Glu Gln Gln Ala Glu Leu Arg Pro Gly Lys Gly Thr Pro Gly Gln Glu
1               5                   10                  15

Lys Lys Gly Thr Ser Ser Thr Ser Glu Ser
            20                  25

( 2 ) INFORMATION FOR SEQ ID NO:311:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:311:

Gln Gln Gln Ala Glu Leu Arg Pro Gly Lys Gly Thr Pro Gly His Glu
1               5                   10                  15

Lys Lys Gly Thr Ser Ser Thr Ser Glu Ser
            20                  25

( 2 ) INFORMATION FOR SEQ ID NO:312:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:312:

Gln Gln Gln Ala Glu Leu Lys Pro Gly Lys Gly Thr Pro Gly His Glu
1               5                   10                  15

Lys Lys Gly Thr Ser Ser Thr Ser Glu Ser
            20                  25

( 2 ) INFORMATION FOR SEQ ID NO:313:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:313:

Gln Gln Gln Ala Glu Leu Arg Pro Gly Lys Gly Thr Pro Gly His Glu
1               5                   10                  15

Asn Lys Gly Thr Ser Ser Thr Ser Glu Ser
            20                  25

( 2 ) INFORMATION FOR SEQ ID NO:314:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:314:

Gln Gln Gln Ala Glu Val Arg Pro Gly Lys Gly Thr Pro Gly His Glu

```
              1               5               10              15
Lys Lys Gly Thr Ser Ser Thr Ser Glu Ser
              20              25
```

( 2 ) INFORMATION FOR SEQ ID NO:315:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:315:

```
Gln Gln Gln Ala Glu Leu Lys Pro Gly Lys Gly Thr Pro Gly His Glu
 1               5               10              15
Asn Lys Gly Thr Ser Ser Thr Ser Glu Ser
              20              25
```

( 2 ) INFORMATION FOR SEQ ID NO:316:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:316:

```
Gln Gln Gln Ala Glu Leu Arg Pro Gly Lys Gly Thr Pro Gly Gln Gln
 1               5               10              15
Lys Lys Gly Lys Ser Ser Ala Ser Glu Ser
              20              25
```

( 2 ) INFORMATION FOR SEQ ID NO:317:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:317:

```
His Gln Gln Ala Glu Leu Lys Pro Gly Lys Gly Thr Pro Gly Gln Gln
 1               5               10              15
Lys Lys Gly Lys Ser Ser Thr Ser Glu Ser
              20              25
```

( 2 ) INFORMATION FOR SEQ ID NO:318:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:318:

```
Glu Gln Gln Val Glu Leu Arg Ala Gly Lys Gly Thr Pro Gly Gln Glu
 1               5               10              15
Lys Lys Gly Lys Ser Ser Thr Ser Glu Ser
              20              25
```

( 2 ) INFORMATION FOR SEQ ID NO:319:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:319:

Glu Gln Gln Ala Glu Leu Arg Pro Gly Lys Gly Thr Pro Gly Gln Glu
 1               5                  10                  15

Lys Gln Gly Thr Ser Ser Thr Ser Glu Ser
            20                  25

( 2 ) INFORMATION FOR SEQ ID NO:320:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:320:

Glu Gln Gln Ala Glu Leu Arg Pro Gly Lys Gly Thr Pro Gly His Asp
 1               5                  10                  15

Asn Lys Gly Thr Ser Ser Thr Ser Glu Ser
            20                  25

( 2 ) INFORMATION FOR SEQ ID NO:321:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:321:

Gln Gln Gln Ala Glu Val Arg Pro Gly Lys Gly Thr Pro Gly His Glu
 1               5                  10                  15

Lys Lys Gly Arg Ser Ser Thr Ser Glu Ser
            20                  25

( 2 ) INFORMATION FOR SEQ ID NO:322:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:322:

Gln Gln Gln Ala Glu Leu Arg Pro Gly Lys Gly Thr Pro Gly Gln Gln
 1               5                  10                  15

Lys Lys Asp Lys Ser Ser Thr Ser Glu Ser
            20                  25

( 2 ) INFORMATION FOR SEQ ID NO:323:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:323:

```
Gln Gln Gln Ala Glu Leu Lys Pro Gly Lys Gly Thr Pro Gly Gln Gln
 1               5                  10                  15
Lys Lys Asp Lys Ser Ser Thr Ser Glu Ser
             20                  25
```

( 2 ) INFORMATION FOR SEQ ID NO:324:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:324:

```
Gln Gln Gln Ala Glu Leu Lys Pro Gly Lys Gly Thr Pro Gly Gln Gln
 1               5                  10                  15
Lys Lys Asp Lys Ser Ser Thr Ser Asp Ser
             20                  25
```

( 2 ) INFORMATION FOR SEQ ID NO:325:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:325:

```
Gln Gln Gln Ala Glu Leu Lys Pro Gly Lys Gly Ser Pro Gly Gln Gln
 1               5                  10                  15
Lys Lys Asp Lys Ser Ser Thr Ser Glu Ser
             20                  25
```

( 2 ) INFORMATION FOR SEQ ID NO:326:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:326:

```
Gln His Gln Ala Glu Leu Lys Pro Gly Lys Gly Thr Pro Gly Gln Gln
 1               5                  10                  15
Lys Lys Asn Lys Ser Ser Thr Ser Glu Ser
             20                  25
```

( 2 ) INFORMATION FOR SEQ ID NO:327:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:327:

```
Gln Gln Gln Ala Glu Leu Lys Pro Gly Lys Gly Thr Pro Gly Gln Gln
 1               5                  10                  15
Asn Lys Asp Lys Ser Ser Thr Ser Glu Ser
             20                  25
```

( 2 ) INFORMATION FOR SEQ ID NO:328:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:328:

```
Glu Gln Gln Ala Glu Leu Arg Ala Gly Lys Gly Ile Pro Gly Gln Glu
 1               5                  10                  15
Lys Lys Gly Lys Ser Ser Thr Ser Glu Ser
                20                  25
```

( 2 ) INFORMATION FOR SEQ ID NO:329:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:329:

```
Gln Gln Gln Ala Glu Leu Lys Pro Gly Lys Gly Thr Pro Gly Gln Glu
 1               5                  10                  15
Lys Lys Ser Lys Ser Ser Thr Ser Glu Ser
                20                  25
```

( 2 ) INFORMATION FOR SEQ ID NO:330:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:330:

```
Gln Gln Gln Ser Glu Leu Lys Pro Gly Lys Gly Thr Pro Gly Gln Glu
 1               5                  10                  15
Lys Lys Ser Lys Ser Ser Thr Ser Glu Ser
                20                  25
```

( 2 ) INFORMATION FOR SEQ ID NO:331:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:331:

```
Gln Gln Gln Thr Glu Leu Lys Pro Gly Lys Gly Thr Pro Gly Gln Glu
 1               5                  10                  15
Lys Lys Ser Lys Ser Ser Thr Ser Glu Ser
                20                  25
```

( 2 ) INFORMATION FOR SEQ ID NO:332:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:332:

Glu Gln Gln Ala Glu Leu Arg Thr Gly Lys Gly Thr Pro Gly Gln Glu
 1               5                  10                      15

Arg Lys Gly Lys Ser Ser Thr Ser Glu Ser
            20                  25

( 2 ) INFORMATION FOR SEQ ID NO:333:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:333:

Gln Gln Gln Ala Glu Leu Lys Pro Gly Lys Gly Thr Pro Gly Gln Gln
 1               5                  10                      15

Lys Lys Asp Lys Ser Ser Thr Phe Glu Ser
            20                  25

( 2 ) INFORMATION FOR SEQ ID NO:334:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:334:

Glu Gln Gln Ala Glu Leu Arg Pro Gly Thr Gly Ala Pro Gly Gln Glu
 1               5                  10                      15

Lys Lys Gly Lys Ser Ser Thr Ser Glu Ser
            20                  25

( 2 ) INFORMATION FOR SEQ ID NO:335:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:335:

Gln Gln Gln Pro Glu Val Arg Pro Gly Lys Gly Thr His Ala Lys Gln
 1               5                  10                      15

Lys Lys Gly Lys Ser Ser Thr Ser Glu Ser
            20                  25

( 2 ) INFORMATION FOR SEQ ID NO:336:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:336:

Gln Gln Gln Pro Glu Val Arg Pro Gly Lys Asp Thr His Ala Lys Gln
 1               5                  10                      15

Lys Lys Gly Lys Ser Ser Thr Ser Glu Ser
            20                  25

( 2 ) INFORMATION FOR SEQ ID NO:337:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:337:

```
Gln Gln Gln Ala Glu Leu Lys Pro Gly Lys Gly Thr Pro Glu Gln Glu
 1               5                  10                  15
Lys Lys Gly Lys Ser Ser Thr Ser Glu Ser
            20                  25
```

( 2 ) INFORMATION FOR SEQ ID NO:338:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:338:

```
Glu Gln Gln Thr Glu Leu Arg Ala Gly Lys Gly Thr Pro Gly Gln Glu
 1               5                  10                  15
Lys Lys Gly Arg Ser Ser Thr Ser Glu Ala
            20                  25
```

( 2 ) INFORMATION FOR SEQ ID NO:339:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:339:

```
Gln Gln Gln Ala Glu Leu Lys Pro Gly Lys Gly Thr Pro Gly Arg Glu
 1               5                  10                  15
Lys Lys Ser Lys Pro Ser Thr Ser Glu Ser
            20                  25
```

( 2 ) INFORMATION FOR SEQ ID NO:340:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:340:

```
Gln Gln Gln Ser Glu Leu Lys Pro Gly Lys Gly Thr Pro Gly Arg Glu
 1               5                  10                  15
Lys Lys Ser Lys Pro Ser Thr Ser Glu Ser
            20                  25
```

( 2 ) INFORMATION FOR SEQ ID NO:341:

( i ) SEQUENCE CHARACTERISTICS:
        ( A ) LENGTH: 26 amino acids
        ( B ) TYPE: amino acid
        ( C ) TOPOLOGY: linear (ii) MOLECULE TYPE: peptide (xi) SEQUENCE DESCRIPTION: SEQ ID NO:341:

```
Gln Gln Arg Ala Glu Leu Lys Pro Gly Lys Asp Thr Pro Gly Arg Glu
 1               5                  10                  15
Lys Lys Asn Lys Pro Ser Thr Ser Glu Ser
             20                  25
```

(2) INFORMATION FOR SEQ ID NO:342:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:342:

```
Gln Gln Gln Ala Glu Leu Lys Pro Gly Lys Gly Thr Pro Gly Arg Glu
 1               5                  10                  15
Lys Lys Ser Thr Ser Ser Thr Ser Glu Ser
             20                  25
```

(2) INFORMATION FOR SEQ ID NO:343:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:343:

```
Gln Gln Gln Ala Glu Leu Lys Pro Gly Lys Gly Thr Pro Gly Gln Glu
 1               5                  10                  15
Lys Lys Ser Thr Ser Ser Thr Ser Asp Ser
             20                  25
```

(2) INFORMATION FOR SEQ ID NO:344:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:344:

```
Gln Gln Gln Ala Glu Leu Arg Pro Gly Lys Gly Thr Pro Ile Gln Gln
 1               5                  10                  15
Lys Lys Asp Lys Ser Ser Thr Ser Glu Ser
             20                  25
```

(2) INFORMATION FOR SEQ ID NO:345:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:345:

```
Gln Gln Gln Ala Glu Phe Lys Pro Gly Lys Gly Thr Pro Gly Arg Glu
 1               5                  10                  15
```

His Arg Ser Lys Pro Ser Thr Ser Glu Ser
                20                  25

( 2 ) INFORMATION FOR SEQ ID NO:346:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:346:

Gln Gln Gln Ala Glu Leu Arg Pro Gly Lys Gly Ala Leu Gly Gln Glu
 1               5                  10                      15

Lys Lys Gly Lys Ser Ser Thr Ser Asp Ser
                20                  25

( 2 ) INFORMATION FOR SEQ ID NO:347:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:347:

Gln Gln Gln Pro Glu Val Lys Pro Gly Lys Gly Ala Pro Gly Lys Gly
 1               5                  10                      15

Asn Thr Asp Lys Ser Ser Thr Ser Glu Ser
                20                  25

( 2 ) INFORMATION FOR SEQ ID NO:348:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:348:

Glu Gln Gln Ala Glu Val Arg Ala Gly Lys Gly Ser Pro Gly Gln Glu
 1               5                  10                      15

Lys Lys Gly Lys Ser Ser Thr Ser Glu Ser
                20                  25

( 2 ) INFORMATION FOR SEQ ID NO:349:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:349:

Gln Gln Leu Ala Glu Leu Lys Pro Gly Lys Gly Thr Pro Gly His Glu
 1               5                  10                      15

Lys Lys Gly Ile Ser Ser Thr Ser Glu Ser
                20                  25

( 2 ) INFORMATION FOR SEQ ID NO:350:

( i ) SEQUENCE CHARACTERISTICS:
        ( A ) LENGTH: 26 amino acids (B) TYPE: amino acid
(C) TOPOLOGY: linear (ii) MOLECULE TYPE: peptide (xi) SEQUENCE DESCRIPTION: SEQ ID NO:350:

Gln Gln Gln Ala Glu Leu Lys Pro Gly Lys Gly Lys Pro Gln Glu
 1               5                  10                 15
Lys Lys Gly Thr Ser Ser Thr Ser Glu Ser
            20                  25

(2) INFORMATION FOR SEQ ID NO:351:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:351:

Gln Gln Gln Pro Glu Leu Lys Pro Gly Lys Gly Arg Asn Gly Lys Glu
 1               5                  10                  15
Asn Lys Gly Lys Ser Ser Thr Ser Glu Ser
            20                  25

(2) INFORMATION FOR SEQ ID NO:352:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:352:

Gln Gln Gln Thr Glu Leu Arg Pro Gly Arg Gly Thr Thr Gly Gln Glu
 1               5                  10                  15
Arg Lys Gly Lys Ser Ser Thr Ser Glu Ser
            20                  25

(2) INFORMATION FOR SEQ ID NO:353:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:353:

Gln His Gln Ala Glu Leu Lys Pro Gly Lys Gly Thr Pro Gly His Glu
 1               5                  10                  15
Asn Lys Val Thr Ser Ser Thr Ser Glu Ser
            20                  25

(2) INFORMATION FOR SEQ ID NO:354:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:354:

Glu Gln Gln Ala Glu Leu Arg Ala Gly Lys Gly Thr Pro Gly Gln Glu

```
                    1               5                    10                        15
Gln Lys Ala Lys Ser Ser Thr Ser Glu Ser
                   20                    25
```

( 2 ) INFORMATION FOR SEQ ID NO:355:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:355:

```
Gln Gln Gln Ala Glu Leu Lys Pro Gly Lys Gly Thr Pro Gly Gln Gln
 1               5                    10                        15
Lys Thr Gly Thr Ser Ser Thr Thr Glu Ser
                   20                    25
```

( 2 ) INFORMATION FOR SEQ ID NO:356:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:356:

```
Gln Gln Gln Ala Glu Leu Lys Pro Gly Lys Gly Asn Pro Gly Gln Glu
 1               5                    10                        15
Lys Lys Ser Thr Ser Ser Ala Ser Glu Ser
                   20                    25
```

( 2 ) INFORMATION FOR SEQ ID NO:357:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:357:

```
Glu Gln Gln Thr Val Leu Arg Pro Gly Lys Gly Thr Pro Gly Gln Gln
 1               5                    10                        15
Lys Lys Gly Thr Ser Ala Thr Asn Glu Ser
                   20                    25
```

( 2 ) INFORMATION FOR SEQ ID NO:358:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:358:

```
Gln Gln Leu Thr Glu Leu Lys Pro Gly Asn Gly Thr Pro Gly Gln Glu
 1               5                    10                        15
Lys Lys Ser Lys Ser Ser Thr Ser Glu Ser
                   20                    25
```

( 2 ) INFORMATION FOR SEQ ID NO:359:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:359:

| Gln | Gln | Gln | Ser | Val | Leu | Arg | Pro | Gly | Lys | Gly | Thr | Pro | Gly | Gln | Glu |
|---|---|---|---|---|---|---|---|---|---|---|---|---|---|---|---|
| 1 | | | | 5 | | | | | 10 | | | | | 15 | |

| Lys | Lys | Gly | Thr | Ser | Ser | Thr | Ser | Lys | Ser |
|---|---|---|---|---|---|---|---|---|---|
| | | | 20 | | | | | 25 | |

( 2 ) INFORMATION FOR SEQ ID NO:360:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:360:

| Leu | Gln | Gln | Pro | Val | Leu | Lys | Pro | Gly | Lys | Gly | Ser | His | Gly | Lys | Gln |
|---|---|---|---|---|---|---|---|---|---|---|---|---|---|---|---|
| 1 | | | | 5 | | | | | 10 | | | | | 15 | |

| Lys | Lys | Asp | Lys | Ser | Ser | Thr | Ser | Glu | Ser |
|---|---|---|---|---|---|---|---|---|---|
| | | | 20 | | | | | 25 | |

( 2 ) INFORMATION FOR SEQ ID NO:361:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:361:

| Glu | Gln | Gln | Pro | Glu | Thr | Lys | Pro | Gly | Lys | Gly | Thr | Leu | Gly | Lys | Gln |
|---|---|---|---|---|---|---|---|---|---|---|---|---|---|---|---|
| 1 | | | | 5 | | | | | 10 | | | | | 15 | |

| Lys | Lys | Ser | Lys | Ser | Ser | Thr | Ser | Glu | Ser |
|---|---|---|---|---|---|---|---|---|---|
| | | | 20 | | | | | 25 | |

( 2 ) INFORMATION FOR SEQ ID NO:362:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:362:

| Gln | Gln | Gln | Ala | Glu | Leu | Lys | Pro | Gly | Gln | Gly | Thr | Pro | Gly | Gln | Glu |
|---|---|---|---|---|---|---|---|---|---|---|---|---|---|---|---|
| 1 | | | | 5 | | | | | 10 | | | | | 15 | |

| Lys | Lys | Asn | Lys | Ser | Ser | Thr | Pro | Glu | Phe |
|---|---|---|---|---|---|---|---|---|---|
| | | | 20 | | | | | 25 | |

( 2 ) INFORMATION FOR SEQ ID NO:363:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:363:

```
Glu  Gln  Gln  Ala  Glu  Leu  Arg  Pro  Gly  Lys  Gly  Asn  Pro  Glu  Gln  Pro
 1                  5                        10                         15

Lys  Gln  Gly  Thr  Ser  Ser  Thr  Ser  Glu  Thr
               20                        25
```

(2) INFORMATION FOR SEQ ID NO:364:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:364:

```
Glu  Gln  Gln  Ala  Glu  Leu  Arg  Pro  Gly  Lys  Gly  Asn  Pro  Glu  Gln  Pro
 1                  5                        10                         15

Lys  Gln  Gly  Thr  Ser  Thr  Thr  Ser  Glu  Thr
               20                        25
```

(2) INFORMATION FOR SEQ ID NO:365:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:365:

```
Glu  Gln  Gln  Ala  Glu  Leu  Lys  Pro  Gly  Lys  Gly  Asn  Pro  Glu  Gln  Pro
 1                  5                        10                         15

Lys  Gln  Gly  Thr  Ser  Ser  Thr  Ser  Glu  Thr
               20                        25
```

(2) INFORMATION FOR SEQ ID NO:366:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:366:

```
Glu  Gln  Gln  Ala  Glu  Leu  Lys  Pro  Gly  Lys  Gly  Asn  Pro  Glu  Gln  Pro
 1                  5                        10                         15

Lys  Gln  Asp  Thr  Ser  Ser  Thr  Ser  Glu  Thr
               20                        25
```

(2) INFORMATION FOR SEQ ID NO:367:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:367:

```
Glu  Gln  Gln  Ala  Glu  Leu  Lys  Pro  Gly  Lys  Gly  Asn  Pro  Glu  Gln  Pro
 1                  5                        10                         15

Lys  Gln  Gly  Thr  Ser  Ser  Thr  Ser  Gly  Thr
               20                        25
```

( 2 ) INFORMATION FOR SEQ ID NO:368:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:368:

```
Glu Gln Gln Ala Glu Val Lys Pro Gly Lys Gly Asn Pro Glu Gln Pro
 1               5                  10                  15

Lys Gln Gly Thr Ser Ser Thr Ser Glu Thr
            20                  25
```

( 2 ) INFORMATION FOR SEQ ID NO:369:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:369:

```
Glu Gln Gln Ala Glu Leu Arg Pro Gly Lys Gly Asn Pro Glu Gln Pro
 1               5                  10                  15

Lys Gln Val Thr Ser Ser Thr Ser Glu Thr
            20                  25
```

( 2 ) INFORMATION FOR SEQ ID NO:370:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:370:

```
Glu Gln Gln Ala Glu Leu Arg Pro Gly Lys Gly Asn Pro Glu Gln Pro
 1               5                  10                  15

Lys Gln Ile Thr Ser Ser Thr Ser Glu Thr
            20                  25
```

( 2 ) INFORMATION FOR SEQ ID NO:371:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:371:

```
Glu Gln Gln Ala Glu Leu Arg Pro Gly Arg Gly Asn Pro Glu Gln Pro
 1               5                  10                  15

Lys Gln Val Thr Ser Ser Thr Ser Glu Thr
            20                  25
```

( 2 ) INFORMATION FOR SEQ ID NO:372:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide (x i) SEQUENCE DESCRIPTION: SEQ ID NO:372:

```
Glu Gln Gln Ala Glu Leu Arg Pro Gly Arg Gly Asn Pro Glu Gln Pro
 1               5                  10                  15
Lys His Val Thr Ser Ser Thr Ser Glu Thr
                20                  25
```

(2) INFORMATION FOR SEQ ID NO:373:

(i) SEQUENCE CHARACTERISTICS:
        (A) LENGTH: 26 amino acids
        (B) TYPE: amino acid
        (C) TOPOLOGY: linear (i i) MOLECULE TYPE: peptide (x i) SEQUENCE DESCRIPTION: SEQ ID NO:373:

```
Glu Gln Gln Ala Glu Leu Arg Pro Gly Lys Gly Asn Thr Glu Gln Pro
 1               5                  10                  15
Lys Gln Val Thr Ser Ser Thr Ser Glu Thr
                20                  25
```

(2) INFORMATION FOR SEQ ID NO:374:

(i) SEQUENCE CHARACTERISTICS:
        (A) LENGTH: 26 amino acids
        (B) TYPE: amino acid
        (C) TOPOLOGY: linear (i i) MOLECULE TYPE: peptide (x i) SEQUENCE DESCRIPTION: SEQ ID NO:374:

```
Glu Gln Gln Ala Glu Leu Lys Pro Gly Lys Gly Asn Thr Glu Gln Pro
 1               5                  10                  15
Lys Leu Ile Thr Ser Ser Thr Ser Glu Thr
                20                  25
```

(2) INFORMATION FOR SEQ ID NO:375:

(i) SEQUENCE CHARACTERISTICS:
        (A) LENGTH: 26 amino acids
        (B) TYPE: amino acid
        (C) TOPOLOGY: linear (i i) MOLECULE TYPE: peptide (x i) SEQUENCE DESCRIPTION: SEQ ID NO:375:

```
Thr Gly Gln Ala Glu Leu Arg Pro Gly Lys Gly Ala Pro Glu Gln Gly
 1               5                  10                  15
Lys Lys Gly Lys Ser Ser Thr Ser Asp Arg
                20                  25
```

(2) INFORMATION FOR SEQ ID NO:376:

(i) SEQUENCE CHARACTERISTICS:
        (A) LENGTH: 26 amino acids
        (B) TYPE: amino acid
        (C) TOPOLOGY: linear (i i) MOLECULE TYPE: peptide (x i) SEQUENCE DESCRIPTION: SEQ ID NO:376:

```
Gln Tyr Gln Ala Glu Leu Arg Pro Gly Lys Gly Thr Pro Arg Gln Gln
 1               5                  10                  15
Lys Lys Gly Lys Ser Ser Thr Ser Glu Ser
                20                  25
```

( 2 ) INFORMATION FOR SEQ ID NO:377:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:377:

```
Gln Gln Gln Ala Val Leu Arg His Gly Lys Gly Thr His Gly Gln Glu
 1               5                  10                  15
Lys Lys Gly Lys Ser Ser Thr Ser Glu Ser
             20                  25
```

( 2 ) INFORMATION FOR SEQ ID NO:378:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:378:

```
Gln Gln Gln Thr Lys Leu Gly Pro Gly Arg Gly Thr Pro Gly Gln Gly
 1               5                  10                  15
Arg Lys Gly Lys Ser Ser Thr Ser Gly Ser
             20                  25
```

( 2 ) INFORMATION FOR SEQ ID NO:379:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:379:

```
Glu Gln Gln Ala Glu Leu Arg Ala Gly Lys Gly Thr Pro Gly Gln Glu
 1               5                  10                  15
Lys Lys Gly Lys Ser Ser Val Tyr Phe Ala
             20                  25
```

( 2 ) INFORMATION FOR SEQ ID NO:380:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:380:

```
Glu Gln Gln Ala Glu Leu Lys Ala Gly Lys Gly Thr Pro Gly Gln Gln
 1               5                  10                  15
Lys Gln Gly Glu Ser Thr Arg Ser Glu Thr
             20                  25
```

( 2 ) INFORMATION FOR SEQ ID NO:381:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:381:

```
Gln Gln Lys Ala Glu Leu Ala Ala Ser Lys Gly Thr Pro Gly Gln Glu
  1               5                  10                  15
Lys Lys Gly Arg Ser Ser Thr Ser Glu Ser
             20                  25
```

( 2 ) INFORMATION FOR SEQ ID NO:382:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:382:

```
Gln Gln Gln Thr Glu Leu Arg Pro Gly Lys Gly Thr Pro Gly Gln Glu
  1               5                  10                  15
Lys Arg Gly Lys Ser Ser Asn Leu Arg Leu
             20                  25
```

( 2 ) INFORMATION FOR SEQ ID NO:383:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:383:

```
Glu Lys Val Gly Gly Leu Gln Gly Ser Ser Phe Asp Pro Gly Lys Ala
  1               5                  10                  15
Ser Lys Gly Thr Ser Gln Arg Ala Glu Thr
             20                  25
```

( 2 ) INFORMATION FOR SEQ ID NO:384:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:384:

```
Glu Gln Gln Ala Asp Leu Lys Leu Gly Lys Gly Asn Pro Glu Gln Pro
  1               5                  10                  15
Lys Leu Ala Thr Pro Ser Thr Ser Glu Thr
             20                  25
```

( 2 ) INFORMATION FOR SEQ ID NO:385:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:385:

```
Glu Gln Val Gly Gly Leu Lys Pro Gly Lys Gly Thr Pro Asp Lys Ser
  1               5                  10                  15
```

Asp Val Lys Asp Asn Ala Lys Ser Glu Thr
            20                  25

( 2 ) INFORMATION FOR SEQ ID NO:386:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:386:

Asp Gln Gln Pro Asp Leu Lys Pro Ser Ser Gly Ser Pro Gly His Pro
 1               5                  10                  15

Ser Lys Ser Thr Ser Lys Thr Thr Glu Thr
            20                  25

( 2 ) INFORMATION FOR SEQ ID NO:387:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:387:

Asp Gln Gln Pro Asp Leu Lys Pro Ser Ser Gly Ser Pro Gly Asn Pro
 1               5                  10                  15

Ser Lys Ser Thr Ser Lys Thr Thr Glu Thr
            20                  25

( 2 ) INFORMATION FOR SEQ ID NO:388:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:388:

Asp Gln Gln Pro Asp Leu Lys Pro Ser Ser Gly Ser Pro Gly Asn Pro
 1               5                  10                  15

Ser Lys Ser Thr Ser Lys Thr Ala Glu Thr
            20                  25

( 2 ) INFORMATION FOR SEQ ID NO:389:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:389:

Asp Gln Gln Pro Gly Leu Lys Pro Ser Ser Gly Ser Pro Gly Asn Pro
 1               5                  10                  15

Ser Lys Ser Thr Ser Lys Thr Thr Glu Thr
            20                  25

( 2 ) INFORMATION FOR SEQ ID NO:390:

( i ) SEQUENCE CHARACTERISTICS:
        ( A ) LENGTH: 26 amino acids (B) TYPE: amino acid
(C) TOPOLOGY: linear (ii) MOLECULE TYPE: peptide (xi) SEQUENCE DESCRIPTION: SEQ ID NO:390:

| Asp | Gln | Gln | Pro | Gly | Leu | Lys | Pro | Ser | Ser | Gly | Ser | Pro | Gly | Asn | Pro |
|---|---|---|---|---|---|---|---|---|---|---|---|---|---|---|---|
| 1 | | | | 5 | | | | | 10 | | | | | 15 | |

| Ser | Lys | Asn | Thr | Ser | Lys | Thr | Thr | Glu | Thr |
|---|---|---|---|---|---|---|---|---|---|
| | | | 20 | | | | | 25 | |

(2) INFORMATION FOR SEQ ID NO:391:

(i) SEQUENCE CHARACTERISTICS:
(A) LENGTH: 26 amino acids
(B) TYPE: amino acid
(C) TOPOLOGY: linear (ii) MOLECULE TYPE: peptide (xi) SEQUENCE DESCRIPTION: SEQ ID NO:391:

| Asp | Gln | Gln | Pro | Gly | Leu | Lys | Pro | Ser | Ser | Gly | Ser | Pro | Gly | Asp | Pro |
|---|---|---|---|---|---|---|---|---|---|---|---|---|---|---|---|
| 1 | | | | 5 | | | | | 10 | | | | | 15 | |

| Ser | Lys | Thr | Thr | Ser | Lys | Thr | Thr | Glu | Thr |
|---|---|---|---|---|---|---|---|---|---|
| | | | 20 | | | | | 25 | |

(2) INFORMATION FOR SEQ ID NO:392:

(i) SEQUENCE CHARACTERISTICS:
(A) LENGTH: 26 amino acids
(B) TYPE: amino acid
(C) TOPOLOGY: linear (ii) MOLECULE TYPE: peptide (xi) SEQUENCE DESCRIPTION: SEQ ID NO:392:

| Asp | Gln | Gln | Pro | Gly | Leu | Lys | Pro | Ser | Ser | Gly | Ser | Pro | Gly | Asn | Pro |
|---|---|---|---|---|---|---|---|---|---|---|---|---|---|---|---|
| 1 | | | | 5 | | | | | 10 | | | | | 15 | |

| Ser | Lys | Thr | Thr | Ser | Lys | Thr | Thr | Glu | Thr |
|---|---|---|---|---|---|---|---|---|---|
| | | | 20 | | | | | 25 | |

(2) INFORMATION FOR SEQ ID NO:393:

(i) SEQUENCE CHARACTERISTICS:
(A) LENGTH: 26 amino acids
(B) TYPE: amino acid
(C) TOPOLOGY: linear (ii) MOLECULE TYPE: peptide (xi) SEQUENCE DESCRIPTION: SEQ ID NO:393:

| Asp | His | Gln | Pro | Gly | Leu | Lys | Pro | Ser | Ser | Gly | Ser | Pro | Gly | Asn | Pro |
|---|---|---|---|---|---|---|---|---|---|---|---|---|---|---|---|
| 1 | | | | 5 | | | | | 10 | | | | | 15 | |

| Ser | Lys | Asn | Thr | Ser | Lys | Thr | Thr | Glu | Thr |
|---|---|---|---|---|---|---|---|---|---|
| | | | 20 | | | | | 25 | |

(2) INFORMATION FOR SEQ ID NO:394:

(i) SEQUENCE CHARACTERISTICS:
(A) LENGTH: 26 amino acids
(B) TYPE: amino acid
(C) TOPOLOGY: linear (ii) MOLECULE TYPE: peptide (xi) SEQUENCE DESCRIPTION: SEQ ID NO:394:

| Asp | Gln | Gln | Pro | Gly | Leu | Lys | Pro | Ser | Ser | Gly | Ser | Pro | Gly | Asn | Pro |
|---|---|---|---|---|---|---|---|---|---|---|---|---|---|---|---|

```
 1               5                    10                        15
Ser  Arg  Ser  Thr  Ser  Lys  Thr  Thr  Glu  Thr
                    20                    25
```

(2) INFORMATION FOR SEQ ID NO:395:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:395:

```
Asp  Gln  Gln  Pro  Gly  Leu  Lys  Pro  Ser  Ala  Gly  Ser  Pro  Gly  Asn  Pro
 1               5                    10                        15
Ser  Lys  Ser  Thr  Ser  Lys  Thr  Ala  Glu  Thr
                    20                    25
```

(2) INFORMATION FOR SEQ ID NO:396:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:396:

```
Glu  Gln  Gln  Pro  Gly  Leu  Lys  Pro  Ser  Ser  Gly  Ser  Pro  Gly  Asn  Pro
 1               5                    10                        15
Ser  Lys  Ser  Thr  Ser  Lys  Thr  Ser  Glu  Thr
                    20                    25
```

(2) INFORMATION FOR SEQ ID NO:397:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:397:

```
Asp  Gln  Gln  Pro  Gly  Leu  Lys  Pro  Ser  Ser  Gly  Ser  Pro  Gly  Asn  Pro
 1               5                    10                        15
Ser  Lys  Asn  Thr  Ser  Lys  Thr  Ile  Glu  Thr
                    20                    25
```

(2) INFORMATION FOR SEQ ID NO:398:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:398:

```
Asp  Gln  Gln  Pro  Gly  Leu  Lys  Pro  Ser  Ser  Gly  Ser  Pro  Gly  Asp  Pro
 1               5                    10                        15
Ser  Lys  Asn  Thr  Ser  Lys  Thr  Pro  Glu  Thr
                    20                    25
```

(2) INFORMATION FOR SEQ ID NO:399:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:399:

Glu Gln Gln Pro Ser Leu Lys Pro Ser Ser Gly Ser Pro Gly Asn Pro
 1               5                  10                  15
Ser Lys Ser Thr Ser Lys Thr Thr Glu Thr
             20                  25

( 2 ) INFORMATION FOR SEQ ID NO:400:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:400:

Asp Gln Gln Pro Gly Leu Lys Pro Ser Ser Gly Ser Pro Gly Asn Pro
 1               5                  10                  15
Ser Lys Asn Thr Ser Glu Thr Thr Glu Thr
             20                  25

( 2 ) INFORMATION FOR SEQ ID NO:401:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:401:

Asp Gln Gln Pro Gly Leu Lys Pro Ser Ser Gly Ser Pro Gly Asn Pro
 1               5                  10                  15
Ser Lys Asn Thr Ser Glu Thr Thr Glx Thr
             20                  25

( 2 ) INFORMATION FOR SEQ ID NO:402:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:402:

Glu Gln Gln Pro Ser Leu Lys Pro Ser Ser Gly Ser Pro Gly Asn Pro
 1               5                  10                  15
Ser Lys Ser Thr Ser Lys Thr Ser Glu Thr
             20                  25

( 2 ) INFORMATION FOR SEQ ID NO:403:

( i ) SEQUENCE CHARACTERISTICS:
    ( A ) LENGTH: 26 amino acids
    ( B ) TYPE: amino acid
    ( C ) TOPOLOGY: linear ( i i ) MOLECULE TYPE: peptide ( x i ) SEQUENCE DESCRIPTION: SEQ ID NO:403:

```
Glu  Gln  Gln  Pro  Ser  Leu  Lys  Pro  Ser  Ser  Gly  Ser  Pro  Gly  Asn  Pro
 1                    5                        10                         15

Ser  Lys  Ser  Thr  Ser  Arg  Thr  Thr  Glu  Thr
               20                        25
```

( 2 ) INFORMATION FOR SEQ ID NO:404:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:404:

```
Glu  Gln  Gln  Pro  Ser  Leu  Lys  Pro  Ser  Ser  Gly  Ser  Pro  Gly  Asn  Pro
 1                    5                        10                         15

Ser  Lys  Ser  Thr  Ser  Lys  Thr  Ala  Glu  Thr
               20                        25
```

( 2 ) INFORMATION FOR SEQ ID NO:405:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:405:

```
Asp  Gln  Gln  Pro  Asp  Leu  Lys  Pro  Ser  Ser  Gly  Phe  Pro  Gly  Asn  Pro
 1                    5                        10                         15

Ser  Lys  Ser  Thr  Ser  Lys  Thr  Thr  Glu  Thr
               20                        25
```

( 2 ) INFORMATION FOR SEQ ID NO:406:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:406:

```
Glu  Gln  Gln  Pro  Ser  Leu  Lys  Pro  Ser  Ser  Gly  Ser  Pro  Gly  Lys  Pro
 1                    5                        10                         15

Ser  Lys  Ser  Thr  Ser  Lys  Thr  Asn  Glu  Thr
               20                        25
```

( 2 ) INFORMATION FOR SEQ ID NO:407:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:407:

```
Glu  Gln  Gln  Pro  Ser  Leu  Lys  Pro  Ser  Ser  Gly  Ser  Pro  Gly  Asn  Pro
 1                    5                        10                         15

Ser  Lys  Ser  Thr  Phe  Lys  Thr  Ser  Glu  Thr
               20                        25
```

( 2 ) INFORMATION FOR SEQ ID NO:408:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:408:

```
Glu Gln Gln Pro Ser Leu Lys Pro Ser Ser Gly Ser Pro Gly Asn Pro
 1               5                  10                  15
Ser Lys Ser Thr Ser Thr Thr Ser Glu Thr
            20                  25
```

( 2 ) INFORMATION FOR SEQ ID NO:409:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:409:

```
Glu Gln Gln Leu Ser Leu Lys Pro Ser Ser Gly Ser Pro Gly Asn Pro
 1               5                  10                  15
Ser Lys Ser Thr Ser Lys Thr Thr Glu Thr
            20                  25
```

( 2 ) INFORMATION FOR SEQ ID NO:410:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:410:

```
Gln Gln Gln Pro Gly Leu Lys Pro Ser Phe Gly Pro Pro Gly Lys Pro
 1               5                  10                  15
Ser Gln Ser Thr Ser Lys Thr Thr Glu Thr
            20                  25
```

( 2 ) INFORMATION FOR SEQ ID NO:411:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:411:

```
Gln Gln Lys Pro Gly Leu Ala Pro Ser Ser Gly Ser Pro Gly Lys Ser
 1               5                  10                  15
Thr Lys Ser Asn Ser Lys Gln Thr Asp Thr
            20                  25
```

( 2 ) INFORMATION FOR SEQ ID NO:412:

( i ) SEQUENCE CHARACTERISTICS:
      ( A ) LENGTH: 26 amino acids
      ( B ) TYPE: amino acid
      ( C ) TOPOLOGY: linear ( i i ) MOLECULE TYPE: peptide ( x i ) SEQUENCE DESCRIPTION: SEQ ID NO:412:

Gln Gln Lys Pro Gly Leu Ala Pro Ser Ser Gly Ser Pro Gly Lys Ser
1               5                   10                  15

Ala Lys Ser Asn Ser Lys Gln Thr Asp Thr
            20                  25

( 2 ) INFORMATION FOR SEQ ID NO:413:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:413:

Gln Gln Lys Pro Gly Leu Ala Pro Ser Ser Gly Ser Pro Gly Lys Ser
1               5                   10                  15

Ala Met Ser Asn Ser Lys Gln Thr Asp Thr
            20                  25

( 2 ) INFORMATION FOR SEQ ID NO:414:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:414:

Gln Gln Lys Pro Gly Leu Ala Pro Ser Ser Gly Ser Pro Gly Lys Ser
1               5                   10                  15

Ala Ile Ser Asn Ser Lys Gln Thr Asp Thr
            20                  25

( 2 ) INFORMATION FOR SEQ ID NO:415:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:415:

Gln Gln Lys Pro Gly Leu Gln Pro Ser Ser Gly Ser Pro Gly Lys Ala
1               5                   10                  15

Ala Ile Ser Asn Ser Lys Gln Ser Asn Thr
            20                  25

( 2 ) INFORMATION FOR SEQ ID NO:416:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:416:

Gln Gln Lys Pro Gly Leu Gln Pro Ser Ser Gly Ser Pro Gly Lys Ala
1               5                   10                  15

Ala Ile Ser Asn Ser Lys Gln Ala Asn Thr
            20                  25

( 2 ) INFORMATION FOR SEQ ID NO:417:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:417:

```
Gln Gln Lys Pro Val Leu Ala Pro Ser Ser Gly Ser Pro Gly Lys Ser
 1               5                  10                  15
Ala Met Ser Asn Ser Lys Gln Ile Asp Thr
             20                  25
```

( 2 ) INFORMATION FOR SEQ ID NO:418:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:418:

```
Gln Gln Lys Pro Ser Leu Gln Pro Ser Ser Asp Ser Pro Gly Lys Ala
 1               5                  10                  15
Ala Met Ser Asn Ser Lys Gln Ala Asp Thr
             20                  25
```

( 2 ) INFORMATION FOR SEQ ID NO:419:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:419:

```
Glu Arg Val Gly Asp Leu Glu Pro Gly Arg Gly Ile Pro Gly Lys Ala
 1               5                  10                  15
Pro Lys Gly Asp Ser Lys Lys Ile Glu Thr
             20                  25
```

( 2 ) INFORMATION FOR SEQ ID NO:420:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:420:

```
Glu Arg Val Gly Asp Leu Glu Pro Glu Arg Gly Ile Pro Gly Lys Ala
 1               5                  10                  15
Pro Lys Gly Asp Ser Lys Lys Ile Glu Thr
             20                  25
```

( 2 ) INFORMATION FOR SEQ ID NO:421:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:421:

Glu Gln Val Gly Gly Leu Lys Pro Gly Arg Gly Thr Pro Gly Lys Ala
1               5                   10                  15

Pro Lys Gly Asp Ser Lys Lys Thr Glu Thr
            20                  25

( 2 ) INFORMATION FOR SEQ ID NO:422:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:422:

Glu Gln Val Gly Gly Leu Gln Pro Gly Lys Gly Thr Ser Gly Lys Ala
1               5                   10                  15

Ser Lys Gly Asp Ser Lys Lys Thr Glu Thr
            20                  25

( 2 ) INFORMATION FOR SEQ ID NO:423:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:423:

Glu Gln Leu Gly Gly Leu Gln Pro Gly Arg Gly Thr Pro Gly Lys Asx
1               5                   10                  15

Ser Lys Gly Asp Ser Lys Arg Ala Glu Thr
            20                  25

( 2 ) INFORMATION FOR SEQ ID NO:424:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:424:

Glu Gln Leu Gly Gly Leu Gln Pro Gly Arg Gly Thr Pro Gly Lys Asp
1               5                   10                  15

Ser Lys Gly Asn Ser Lys Arg Ala Glu Thr
            20                  25

( 2 ) INFORMATION FOR SEQ ID NO:425:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:425:

Glu Gln Leu Gly Gly Leu Gln Pro Gly Arg Gly Thr Pro Gly Lys Asp
1               5                   10                  15

Ser Arg Gly Asn Ser Lys Arg Ala Glu Thr
            20                  25

(2) INFORMATION FOR SEQ ID NO:426:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:426:

Glu Gln Val Gly Gly Leu Gln Pro Gly Arg Gly Thr Pro Gly Lys Asp
 1               5                  10                  15
Ser Lys Gly Asn Ser Lys Arg Ala Glu Thr
            20                  25

(2) INFORMATION FOR SEQ ID NO:427:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:427:

Glu Gln Val Gly Gly Leu Gln Pro Gly Arg Gly Thr Pro Gly Lys Asp
 1               5                  10                  15
Ser Lys Gly Asn Ala Lys Arg Ala Glu Thr
            20                  25

(2) INFORMATION FOR SEQ ID NO:428:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:428:

Glu Gln Val Gly Gly Leu Gln Pro Gly Arg Gly Thr Pro Gly Lys Asp
 1               5                  10                  15
Ser Lys Gly Asp Ser Arg Arg Ala Glu Thr
            20                  25

(2) INFORMATION FOR SEQ ID NO:429:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:429:

Glu Gln Val Gly Gly Leu Gln Pro Gly Arg Gly Thr Pro Gly Lys Asp
 1               5                  10                  15
Ser Lys Gly Asn Ser Arg Arg Ala Glu Thr
            20                  25

(2) INFORMATION FOR SEQ ID NO:430:

(i) SEQUENCE CHARACTERISTICS:
        (A) LENGTH: 26 amino acids ( B ) TYPE: amino acid
( C ) TOPOLOGY: linear ( i i ) MOLECULE TYPE: peptide ( x i ) SEQUENCE DESCRIPTION: SEQ ID NO:430:

```
Gln Gln Val Gly Gly Leu Glu Pro Gly Arg Gly Thr Pro Gly Lys Asp
 1               5                  10                  15
Ser Lys Gly Asx Ser Lys Arg Ala Glu Thr
             20                  25
```

( 2 ) INFORMATION FOR SEQ ID NO:431:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:431:

```
Glu Gln Leu Gly Asp Leu Gln Pro Gly Arg Gly Thr Pro Gly Lys Ala
 1               5                  10                  15
Ser Lys Gly Asn Ser Lys Arg Ala Glu Thr
             20                  25
```

( 2 ) INFORMATION FOR SEQ ID NO:432:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:432:

```
Glu Gln Val Gly Gly Leu Gln Pro Gly Arg Gly Thr Thr Gly Lys Asp
 1               5                  10                  15
Ser Lys Gly Asp Ser Lys Arg Ala Glu Thr
             20                  25
```

( 2 ) INFORMATION FOR SEQ ID NO:433:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:433:

```
Gln Gln Val Gly Gly Val Gln Pro Gly Arg Gly Thr Pro Gly Lys Asp
 1               5                  10                  15
Ser Lys Gly Asn Ser Lys Arg Ala Glu Thr
             20                  25
```

( 2 ) INFORMATION FOR SEQ ID NO:434:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:434:

```
Gln Gln Val Gly Gly Val Gln Pro Gly Arg Gly Ile Pro Gly Lys Asp
```

```
                    1               5                   10                      15
Ser  Lys  Gly  Asn  Ser  Lys  Arg  Pro  Glu  Thr
                    20                      25
```

( 2 ) INFORMATION FOR SEQ ID NO:435:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:435:

```
Glu  Gln  Val  Gly  Gly  Val  Gln  Pro  Gly  Arg  Gly  Ile  Pro  Gly  Lys  Asp
 1                   5                       10                         15
Ser  Lys  Gly  Asp  Ser  Lys  Arg  Pro  Glu  Thr
                    20                      25
```

( 2 ) INFORMATION FOR SEQ ID NO:436:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:436:

```
Gln  Gln  Val  Gly  Gly  Val  Gln  Pro  Gly  Arg  Gly  Thr  Pro  Gly  Lys  Asp
 1                   5                       10                         15
Ser  Asn  Gly  Asp  Ser  Lys  Arg  Pro  Glu  Thr
                    20                      25
```

( 2 ) INFORMATION FOR SEQ ID NO:437:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:437:

```
Gln  Lys  Val  Gly  Gly  Val  Gln  Pro  Gly  Arg  Gly  Thr  Pro  Gly  Lys  Asp
 1                   5                       10                         15
Ser  Lys  Gly  Asn  Ser  Lys  Arg  Thr  Glu  Thr
                    20                      25
```

( 2 ) INFORMATION FOR SEQ ID NO:438:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:438:

```
Gln  Glu  Val  Gly  Gly  Val  Glx  Pro  Gly  Arg  Gly  Thr  Pro  Gly  Lys  Asx
 1                   5                       10                         15
Ser  Lys  Gly  Asx  Ser  Lys  Arg  Ala  Glu  Thr
                    20                      25
```

( 2 ) INFORMATION FOR SEQ ID NO:439:

(i) SEQUENCE CHARACTERISTICS:
  (A) LENGTH: 26 amino acids
  (B) TYPE: amino acid
  (C) TOPOLOGY: linear (ii) MOLECULE TYPE: peptide (xi) SEQUENCE DESCRIPTION: SEQ ID NO:439:

```
Glu Gln Leu Gly Gly Leu Gln Pro Gly Arg Gly Thr Pro Gly Lys Asp
 1               5                   10                  15
Ser Asn Gly Asp Ser Lys Gln Ala Glx Thr
            20                  25
```

(2) INFORMATION FOR SEQ ID NO:440:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:440:

```
Glu Gln Leu Gly Gly Leu Gln Pro Gly Arg Gly Ser Pro Gly Lys Asp
 1               5                   10                  15
Thr Asn Gly Asp Ser Lys Glu Ala Glx Thr
            20                  25
```

(2) INFORMATION FOR SEQ ID NO:441:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:441:

```
Ala Gln Leu Gly Gly Leu Gln Pro Gly Arg Gly Thr Pro Gly Lys Asp
 1               5                   10                  15
Ser Asn Gly Asp Ser Lys Gln Ala Glx Ser
            20                  25
```

(2) INFORMATION FOR SEQ ID NO:442:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:442:

```
Glu Gln Leu Gly Gly Leu Gln Pro Gly Arg Gly Thr Pro Gly Lys Val
 1               5                   10                  15
Ser Gln Gly Asp Ser Lys Gln Ala Glx Thr
            20                  25
```

(2) INFORMATION FOR SEQ ID NO:443:

(i) SEQUENCE CHARACTERISTICS:
    (A) LENGTH: 26 amino acids
    (B) TYPE: amino acid
    (C) TOPOLOGY: linear (ii) MOLECULE TYPE: peptide (xi) SEQUENCE DESCRIPTION: SEQ ID NO:443:

Glu Gln Val Gly Gly Leu Gln Pro Gly Arg Gly Thr Pro Gly Lys Val
1               5                   10                  15

Ser Gln Gly Asp Ser Lys Glu Pro Glx Thr
            20                  25

( 2 ) INFORMATION FOR SEQ ID NO:444:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:444:

Glu Gln Leu Gly Gly Leu Gln Pro Glu Arg Gly Thr Pro Gly Lys Glu
1               5                   10                  15

Ser Lys Gly Asn Ser Met Arg Ala Glu Thr
            20                  25

( 2 ) INFORMATION FOR SEQ ID NO:445:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:445:

Glu Gln Val Gly Asp Leu Gln Pro Gly Arg Gly Asx Pro Gly Lys Asp
1               5                   10                  15

Ser Lys Gly Asn Ala Lys Arg Val Glu Thr
            20                  25

( 2 ) INFORMATION FOR SEQ ID NO:446:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:446:

Glu Gln Val Gly Asp Leu Gln Pro Gly Arg Gly Asn Pro Gly Lys Asp
1               5                   10                  15

Ser Lys Gly Asn Ala Gln Arg Pro Glu Thr
            20                  25

( 2 ) INFORMATION FOR SEQ ID NO:447:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:447:

Gln Gln Val Gly Gly Val Gln Pro Gly Arg Gly Thr Leu Gly Lys Asp
1               5                   10                  15

Ser Lys Gly Asn Ser Lys Arg Ala Glu Thr
            20                  25

( 2 ) INFORMATION FOR SEQ ID NO:448:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:448:

```
Gln  Glx  Val  Gly  Gly  Ala  Glx  Pro  Gly  Arg  Gly  Ser  Pro  Gly  Lys  Ala
 1                     5                         10                        15

Ser  Lys  Gly  Asx  Ser  Lys  Arg  Ala  Glu  Thr
                20                        25
```

( 2 ) INFORMATION FOR SEQ ID NO:449:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:449:

```
Gln  Gln  Val  Gly  Gly  Leu  Lys  Pro  Gly  Arg  Gly  Ser  Pro  Gly  Lys  Asp
 1                     5                         10                        15

Ser  Lys  Gly  Asn  Ala  Gln  Arg  Thr  Glx  Thr
                20                        25
```

( 2 ) INFORMATION FOR SEQ ID NO:450:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:450:

```
Asp  Gln  Val  Gly  Gly  Leu  Lys  Pro  Gly  Arg  Gly  Thr  Pro  Gly  Lys  Asn
 1                     5                         10                        15

Ser  Asn  Gly  Asp  Ser  Lys  Thr  Pro  Glx  Thr
                20                        25
```

( 2 ) INFORMATION FOR SEQ ID NO:451:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:451:

```
Glu  Gln  Leu  Gly  Gly  Leu  Gln  Pro  Gly  Arg  Gly  Thr  Ser  Arg  Glu  Asp
 1                     5                         10                        15

Ser  Lys  Gly  Asn  Ser  Lys  Arg  Ala  Glu  Thr
                20                        25
```

( 2 ) INFORMATION FOR SEQ ID NO:452:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:452:

Glu Gln Val Gly Ala Leu Gln Pro Gly Arg Gly Thr Pro Gly Lys Asp
1               5                   10                  15

Ser Gln Ala Asp Ser Lys Glu Ala Glx Thr
            20                  25

( 2 ) INFORMATION FOR SEQ ID NO:453:

( i ) SEQUENCE CHARACTERISTICS:
        ( A ) LENGTH: 22 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:453:

Glu Gln Leu Gly Gly Leu Gln Pro Gly Arg Gly Thr Pro Gly Lys Val
1               5                   10                  15

Glu Gly Ser Val Glu Thr
            20

( 2 ) INFORMATION FOR SEQ ID NO:454:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:454:

Glu Gln Val Gly Ala Phe Gln Pro Gly Arg Gly Asn Ser Gly Lys Ala
1               5                   10                  15

Ser Lys Gly Asp Ser Lys Arg Pro Asp Thr
            20                  25

( 2 ) INFORMATION FOR SEQ ID NO:455:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:455:

Glu Gln Val Gly Ala Phe Gln Pro Gly Lys Gly Asn Ser Gly Lys Ala
1               5                   10                  15

Ser Lys Gly Asp Ser Lys Arg Pro Asp Thr
            20                  25

( 2 ) INFORMATION FOR SEQ ID NO:456:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:456:

Glu Gln Val Gly Ala Phe Gln Pro Gly Lys Gly Asn Ser Gly Lys Ala
1               5                   10                  15

Ser Lys Gly Asp Ser Asn Arg Pro Asp Thr
            20                  25

( 2 ) INFORMATION FOR SEQ ID NO:457:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:457:

```
Gln Gln Val Gly Gly Val Gln Ala Gly Arg Ala Asn Pro Gly Lys Asp
 1               5                  10                  15
Ser Arg Gly Ile Ser Lys Arg Thr Glu Thr
            20                  25
```

( 2 ) INFORMATION FOR SEQ ID NO:458:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:458:

```
Gln Gln Val Ala Glu Val Lys Pro Gly Lys Gly Thr Pro Gly Gln Gln
 1               5                  10                  15
Lys Gln Gly Glu Ser Thr Arg Ser Glu Thr
            20                  25
```

( 2 ) INFORMATION FOR SEQ ID NO:459:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:459:

```
Gln Gln Val Ala Glu Val Lys Pro Gly Lys Gly Thr Pro Gly Gln Gln
 1               5                  10                  15
Lys Gln Gly Thr Ser Thr Arg Ser Glu Thr
            20                  25
```

( 2 ) INFORMATION FOR SEQ ID NO:460:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:460:

```
Gln Gln Val Ala Glu Val Lys Pro Gly Lys Gly Thr Pro Gly Gln Gln
 1               5                  10                  15
Lys Gln Gly Thr Ser Ala Arg Ser Glu Thr
            20                  25
```

( 2 ) INFORMATION FOR SEQ ID NO:461:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:461:

Gln Gln Val Ala Glu Val Lys Pro Gly Lys Gly Thr Pro Gly Gln Gln
1               5                   10                  15

Lys Gln Gly Thr Ser Ile Arg Ser Asp Thr
            20                  25

( 2 ) INFORMATION FOR SEQ ID NO:462:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:462:

Gln Gln Val Ala Glu Val Lys Pro Gly Lys Gly Thr Pro Gly Gln Glu
1               5                   10                  15

Lys Gln Gly Thr Ser Ile Arg Ser Asp Thr
            20                  25

( 2 ) INFORMATION FOR SEQ ID NO:463:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:463:

Gln Gln Val Ala Glu Val Lys Pro Gly Lys Gly Thr Pro Gly Gln Gln
1               5                   10                  15

Asn Gln Gly Thr Ser Thr Arg Ser Asp Thr
            20                  25

( 2 ) INFORMATION FOR SEQ ID NO:464:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:464:

Gln Gln Val Gly Glu Val Lys Pro Gly Arg Gly Thr Pro Gly Gln Gln
1               5                   10                  15

Lys Gln Asp Thr Ser Thr Arg Ser Asp Thr
            20                  25

( 2 ) INFORMATION FOR SEQ ID NO:465:

( i ) SEQUENCE CHARACTERISTICS:
  ( A ) LENGTH: 26 amino acids
  ( B ) TYPE: amino acid
  ( C ) TOPOLOGY: linear ( i i ) MOLECULE TYPE: peptide ( x i ) SEQUENCE DESCRIPTION: SEQ ID NO:465:

Gln Gln Val Ala Glu Val Lys Pro Gly Arg Gly Thr Pro Gly His Pro
1               5                   10                  15

Arg Gln Gly Ala Ser Phe Arg Ser Asp Ser
            20                  25

( 2 ) INFORMATION FOR SEQ ID NO:466:

( i ) SEQUENCE CHARACTERISTICS:
                ( A ) LENGTH: 26 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:466:

Gln Gln Val Ser Glu Leu Lys Pro Gly Lys Gly Thr Pro Gly Gln Gln
 1               5                  10                  15

Gly Thr Gly Thr Ser Val Lys Ala Glu Thr
            20                  25

( 2 ) INFORMATION FOR SEQ ID NO:467:

( i ) SEQUENCE CHARACTERISTICS:
                ( A ) LENGTH: 26 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:467:

Glu Gln Val Ala Glu Val Lys Pro Gly Lys Gly Ser Pro Gly Lys Pro
 1               5                  10                  15

Ser Gln Gly Lys Ser Ile Lys Ala Ser Thr
            20                  25

( 2 ) INFORMATION FOR SEQ ID NO:468:

( i ) SEQUENCE CHARACTERISTICS:
                ( A ) LENGTH: 26 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:468:

Glu Gln Val Ala Glu Val Lys Pro Gly Arg Gly Ser Pro Gly Lys Pro
 1               5                  10                  15

Ser Gln Gly Lys Ser Ile Lys Ala Ser Thr
            20                  25

( 2 ) INFORMATION FOR SEQ ID NO:469:

( i ) SEQUENCE CHARACTERISTICS:
                ( A ) LENGTH: 26 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:469:

Gln Gln Val Ala Glu Val Lys Pro Gly Arg Gly Asp Pro Gly Arg Pro
 1               5                  10                  15

Arg Gln Ala Ser Ser Thr Ile Ser Ala Thr
            20                  25

( 2 ) INFORMATION FOR SEQ ID NO:470:

( i ) SEQUENCE CHARACTERISTICS:
                ( A ) LENGTH: 26 amino acids ( B ) TYPE: amino acid
( C ) TOPOLOGY: linear ( i i ) MOLECULE TYPE: peptide ( x i ) SEQUENCE DESCRIPTION: SEQ ID NO:470:

Glu Gln Val Ala Glu Val Pro Gln Gly Lys Gly Arg Pro Gly Lys Ser
1               5                   10                  15
Leu Gln Gly Lys Ser Leu Lys Ala Ser Thr
            20                  25

( 2 ) INFORMATION FOR SEQ ID NO:471:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:471:

Gln Gln Met Ala Glu Val Lys Pro Gly Arg Gly Thr Pro Gly Lys Pro
1               5                   10                  15
Gly Val Val Pro Ser Phe Phe Ser Glu Thr
            20                  25

( 2 ) INFORMATION FOR SEQ ID NO:472:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:472:

Gln Gln Val Ala Glu Val Lys Pro Gly Arg Gly Thr Pro Gly Arg Tyr
1               5                   10                  15
Ile Trp Glu Pro Ser Phe Phe Asn Glu Gly
            20                  25

( 2 ) INFORMATION FOR SEQ ID NO:473:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:473:

Gln Gln Gln Ala Gly Leu Lys Pro Ser Ser Gly Ser Pro Gly Lys Pro
1               5                   10                  15
Ser Lys Ser Thr Ser Lys Thr Ala Ala Thr
            20                  25

( 2 ) INFORMATION FOR SEQ ID NO:474:

( i ) SEQUENCE CHARACTERISTICS:
( A ) LENGTH: 26 amino acids
( B ) TYPE: amino acid
( C ) TOPOLOGY: linear ( i i ) MOLECULE TYPE: peptide ( x i ) SEQUENCE DESCRIPTION: SEQ ID NO:474:

Gln Gln Gln Pro Gly Leu Lys Pro Ser Ser Gly Ser Pro Gly Lys Pro

```
                  1               5                    10                        15
Ser  Lys  Ser  Thr  Ser  Lys  Thr  Ala  Ala  Thr
                  20                       25
```

(2) INFORMATION FOR SEQ ID NO:475:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:475:

```
Gln  Gln  Gln  Pro  Gly  Leu  Lys  Pro  Ser  Ser  Gly  Ser  Pro  Gly  Lys  Pro
  1               5                    10                        15
Ser  Lys  Ser  Thr  Ser  Asn  Thr  Ala  Ala  Thr
                  20                       25
```

(2) INFORMATION FOR SEQ ID NO:476:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:476:

```
Gln  Gln  Gln  Pro  Gly  Leu  Lys  Pro  Ser  Ser  Gly  Ser  Ala  Gly  Lys  Pro
  1               5                    10                        15
Ser  Lys  Ser  Thr  Ser  Lys  Thr  Ala  Ala  Thr
                  20                       25
```

(2) INFORMATION FOR SEQ ID NO:477:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:477:

```
Arg  Gln  Gln  Pro  Gly  Leu  Lys  Pro  Ser  Ser  Gly  Pro  Pro  Gly  Lys  Pro
  1               5                    10                        15
Ser  Arg  Gly  Thr  Ser  Arg  Ser  Ala  Ala  Thr
                  20                       25
```

(2) INFORMATION FOR SEQ ID NO:478:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:478:

```
Gln  Gln  Gln  Ala  Gly  Leu  Lys  Pro  Ser  Ser  Gly  Ser  Pro  Gly  Arg  Thr
  1               5                    10                        15
Ser  Lys  Ser  Thr  Ser  Lys  Thr  Ala  Ala  Thr
                  20                       25
```

(2) INFORMATION FOR SEQ ID NO:479:

( i ) SEQUENCE CHARACTERISTICS:
(A) LENGTH: 26 amino acids
(B) TYPE: amino acid
(C) TOPOLOGY: linear ( i i ) MOLECULE TYPE: peptide ( x i ) SEQUENCE DESCRIPTION: SEQ ID NO:479:

Gln Gln Glu Pro Gly Leu Arg Pro Ser Ser Gly Thr Pro Gly Arg Thr
1               5                   10                  15

Pro Arg Ser Thr Ser Lys Thr Ala Ala Thr
            20                  25

( 2 ) INFORMATION FOR SEQ ID NO:480:

( i ) SEQUENCE CHARACTERISTICS:
(A) LENGTH: 26 amino acids
(B) TYPE: amino acid
(C) TOPOLOGY: linear ( i i ) MOLECULE TYPE: peptide ( x i ) SEQUENCE DESCRIPTION: SEQ ID NO:480:

Xaa Gln Glu Pro Gly Leu Arg Pro Ser Ser Gly Ser Pro Gly Arg Thr
1               5                   10                  15

Pro Arg Ser Thr Ser Lys Thr Ala Ala Thr
            20                  25

( 2 ) INFORMATION FOR SEQ ID NO:481:

( i ) SEQUENCE CHARACTERISTICS:
(A) LENGTH: 26 amino acids
(B) TYPE: amino acid
(C) TOPOLOGY: linear ( i i ) MOLECULE TYPE: peptide ( x i ) SEQUENCE DESCRIPTION: SEQ ID NO:481:

Gln Gln Gln Pro Gly Leu Lys Pro Ser Ser Gly Ser Pro Ser Arg Val
1               5                   10                  15

Ser Lys Ser Thr Ser Lys Thr Pro Glu Thr
            20                  25

( 2 ) INFORMATION FOR SEQ ID NO:482:

( i ) SEQUENCE CHARACTERISTICS:
(A) LENGTH: 26 amino acids
(B) TYPE: amino acid
(C) TOPOLOGY: linear ( i i ) MOLECULE TYPE: peptide ( x i ) SEQUENCE DESCRIPTION: SEQ ID NO:482:

Gln His Gln Ala Gly Leu Lys Arg Ser Ser Gly Pro Pro Gly Lys Pro
1               5                   10                  15

Ser Thr Ser Thr Ser Lys Thr Ala Ala Thr
            20                  25

( 2 ) INFORMATION FOR SEQ ID NO:483:

( i ) SEQUENCE CHARACTERISTICS:
(A) LENGTH: 26 amino acids
(B) TYPE: amino acid
(C) TOPOLOGY: linear ( i i ) MOLECULE TYPE: peptide ( x i ) SEQUENCE DESCRIPTION: SEQ ID NO:483:

```
Glx  Gln  Glu  Ser  Gly  Leu  Lys  Pro  Thr  Ser  Gly  Ser  Pro  Gly  Lys  Pro
 1                    5                        10                        15

Ser  Lys  Ser  Arg  Ser  Lys  Ala  Ala  Asp  Ala
                20                   25
```

(2) INFORMATION FOR SEQ ID NO:484:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:484:

```
Gln  Thr  Lys  Pro  Thr  Leu  Lys  Pro  Thr  Thr  Gly  Ser  Pro  Gly  Arg  Pro
 1                    5                        10                        15

Ser  Lys  Ser  Thr  Ser  Lys  Asp  Pro  Val  Thr
                20                   25
```

(2) INFORMATION FOR SEQ ID NO:485:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:485:

```
Gln  Thr  Lys  Pro  Thr  Leu  Lys  Pro  Thr  Thr  Gly  Ser  Pro  Gly  Lys  Pro
 1                    5                        10                        15

Ser  Arg  Ser  Thr  Ser  Arg  Asp  Pro  Val  Ser
                20                   25
```

(2) INFORMATION FOR SEQ ID NO:486:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:486:

```
Glu  Thr  Arg  Pro  Ala  Leu  Lys  Pro  Thr  Thr  Gly  Ser  Pro  Gly  Lys  Thr
 1                    5                        10                        15

Ser  Lys  Thr  Thr  Ser  Lys  Asp  Pro  Val  Thr
                20                   25
```

(2) INFORMATION FOR SEQ ID NO:487:

(i) SEQUENCE CHARACTERISTICS:
        (A) LENGTH: 26 amino acids
        (B) TYPE: amino acid
        (C) TOPOLOGY: linear (ii) MOLECULE TYPE: peptide (xi) SEQUENCE DESCRIPTION: SEQ ID NO:487:

```
Gln  Asn  Arg  Pro  Ala  Leu  Lys  Ala  Thr  Thr  Gly  Ser  Pro  Gly  Lys  Thr
 1                    5                        10                        15

Ser  Glu  Thr  Thr  Ser  Lys  Asp  Pro  Ala  Thr
                20                   25
```

( 2 ) INFORMATION FOR SEQ ID NO:488:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:488:

```
Gln  Thr  Thr  Pro  Ala  Leu  Lys  Pro  Lys  Thr  Gly  Ser  Pro  Gly  Lys  Thr
 1                    5                        10                        15
Ser  Arg  Thr  Asp  Ser  Lys  Asn  Pro  Val  Thr
                20                        25
```

( 2 ) INFORMATION FOR SEQ ID NO:489:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:489:

```
Gln  Thr  Arg  Pro  Ala  Leu  Arg  Pro  Thr  Thr  Gly  Ser  Pro  Gly  Glu  Ala
 1                    5                        10                        15
Ser  Glu  Thr  Thr  Ser  Lys  Gly  Pro  Gly  Thr
                20                        25
```

( 2 ) INFORMATION FOR SEQ ID NO:490:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:490:

```
Gln  Thr  Arg  Pro  Ala  Leu  Lys  Pro  Thr  Thr  Gly  Ser  Pro  Gly  Lys  Thr
 1                    5                        10                        15
Ser  Glu  Thr  Thr  Ser  Arg  Asp  Thr  Ala  Tyr
                20                        25
```

( 2 ) INFORMATION FOR SEQ ID NO:491:

( i ) SEQUENCE CHARACTERISTICS:
        ( A ) LENGTH: 26 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:491:

```
Leu  Glu  Gly  Val  Gln  Leu  Trp  Gly  Gly  Arg  Gly  Ile  Ser  Arg  Lys  Tyr
 1                    5                        10                        15
Ala  Lys  Gly  Asn  Gly  Lys  Arg  Glu  Asp  Ser
                20                        25
```

( 2 ) INFORMATION FOR SEQ ID NO:492:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:492:

Tyr Asn Asn Pro Gly Asn Gly Tyr Ile Ala
 1               5                   10

( 2 ) INFORMATION FOR SEQ ID NO:493:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:493:

Tyr Ile Asn Pro Gly Lys Gly Tyr Leu Ser
 1               5                   10

( 2 ) INFORMATION FOR SEQ ID NO:494:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:494:

Arg Ala Ser Gln Glu Ile Ser Gly Tyr Leu Ser
 1               5                   10

( 2 ) INFORMATION FOR SEQ ID NO:495:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:495:

Arg Ala Ser Gly Asn Ile His Asn Tyr Leu Ala
 1               5                   10

( 2 ) INFORMATION FOR SEQ ID NO:496:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:496:

Arg Ala Ser Gln Asp Ile Asn Asn Phe Leu Asn
 1               5                   10

( 2 ) INFORMATION FOR SEQ ID NO:497:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:497:

Arg Ala Ser Gln Ser Ile Gly Asn Asn Leu His
 1               5                   10

( 2 ) INFORMATION FOR SEQ ID NO:498:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:498:

Ala Ala Ser Thr Leu Asp Ser
1               5

( 2 ) INFORMATION FOR SEQ ID NO:499:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:499:

Tyr Thr Thr Thr Leu Ala Asp
1               5

( 2 ) INFORMATION FOR SEQ ID NO:500:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:500:

Phe Thr Ser Arg Ser Gln Ser
1               5

( 2 ) INFORMATION FOR SEQ ID NO:501:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:501:

Lys Ala Ser Ser Leu Glu Ser
1               5

( 2 ) INFORMATION FOR SEQ ID NO:502:

( i ) SEQUENCE CHARACTERISTICS:
        ( A ) LENGTH: 9 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:502:

Leu Gln Tyr Leu Ser Tyr Pro Leu Thr
1               5

( 2 ) INFORMATION FOR SEQ ID NO:503:

( i ) SEQUENCE CHARACTERISTICS:

( A ) LENGTH: 9 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:503:

Gln His Phe Trp Ser Thr Pro Arg Thr
 1               5

( 2 ) INFORMATION FOR SEQ ID NO:504:

( i ) SEQUENCE CHARACTERISTICS:
        ( A ) LENGTH: 9 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:504:

Gln Gln Gly Asn Ala Leu Pro Arg Thr
 1               5

( 2 ) INFORMATION FOR SEQ ID NO:505:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:505:

Gln Gln Tyr Asn Ser Tyr Ser
 1               5

( 2 ) INFORMATION FOR SEQ ID NO:506:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:506:

Thr Phe Gly Ile Thr
 1               5

( 2 ) INFORMATION FOR SEQ ID NO:507:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:507:

Gly Tyr Gly Val Asn
 1               5

( 2 ) INFORMATION FOR SEQ ID NO:508:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:508:

Ser Asn Gly Ile Asn
1               5

( 2 ) INFORMATION FOR SEQ ID NO:509:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:509:

Asp Tyr Ala Met His
1               5

( 2 ) INFORMATION FOR SEQ ID NO:510:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:510:

Glu Ile Phe Pro Gly Asn Ser Lys Thr Tyr
1               5                   10

( 2 ) INFORMATION FOR SEQ ID NO:511:

( i ) SEQUENCE CHARACTERISTICS:
        ( A ) LENGTH: 9 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:511:

Met Ile Trp Gly Asp Gly Asn Thr Asp
1               5

( 2 ) INFORMATION FOR SEQ ID NO:512:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:512:

Tyr Asn Asn Pro Gly Asn Gly Tyr Ile Ala
1               5                   10

( 2 ) INFORMATION FOR SEQ ID NO:513:

( i ) SEQUENCE CHARACTERISTICS:
        ( A ) LENGTH: 9 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:513:

Ile Ser Trp Asp Ser Ser Ser Ile Gly
1               5

( 2 ) INFORMATION FOR SEQ ID NO:514:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:514:

```
Arg  Glu  Ile  Arg  Tyr
 1                  5
```

( 2 ) INFORMATION FOR SEQ ID NO:515:

( i ) SEQUENCE CHARACTERISTICS:
        ( A ) LENGTH: 8 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:515:

```
Glu  Arg  Asp  Tyr  Arg  Leu  Asp  Tyr
 1                  5
```

( 2 ) INFORMATION FOR SEQ ID NO:516:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:516:

```
Ser  Glu  Tyr  Tyr  Gly  Gly  Ser  Tyr  Lys  Phe  Asp  Tyr
 1                  5                        10
```

( 2 ) INFORMATION FOR SEQ ID NO:517:

( i ) SEQUENCE CHARACTERISTICS:
        ( A ) LENGTH: 17 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:517:

```
Gly  Arg  Asp  Tyr  Tyr  Asp  Ser  Gly  Gly  Tyr  Phe  Thr  Val  Ala  Phe  Asp
 1                  5                        10                       15
Ile
```

( 2 ) INFORMATION FOR SEQ ID NO:518:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:518:

```
Arg  Ala  Ser  Gln  Ser  Ile  Ser  Arg  Trp  Leu  Ala
 1                  5                        10
```

( 2 ) INFORMATION FOR SEQ ID NO:519:

(i) SEQUENCE CHARACTERISTICS:
    (A) LENGTH: 7 amino acids
    (B) TYPE: amino acid
    (C) TOPOLOGY: linear (ii) MOLECULE TYPE: peptide (xi) SEQUENCE DESCRIPTION: SEQ ID NO:519:

Glu Ala Ser Asn Asp Leu Ala
1               5

(2) INFORMATION FOR SEQ ID NO:520:

(i) SEQUENCE CHARACTERISTICS:
    (A) LENGTH: 5 amino acids
    (B) TYPE: amino acid
    (C) TOPOLOGY: linear (ii) MOLECULE TYPE: peptide (xi) SEQUENCE DESCRIPTION: SEQ ID NO:520:

Asp Phe Tyr Met Glu
1               5

(2) INFORMATION FOR SEQ ID NO:521:

(i) SEQUENCE CHARACTERISTICS:
    (A) LENGTH: 9 amino acids
    (B) TYPE: amino acid
    (C) TOPOLOGY: linear (ii) MOLECULE TYPE: peptide (xi) SEQUENCE DESCRIPTION: SEQ ID NO:521:

Ile Ile Trp Asp Asp Gly Ser Asp Gln
1               5

(2) INFORMATION FOR SEQ ID NO:522:

(i) SEQUENCE CHARACTERISTICS:
    (A) LENGTH: 11 amino acids
    (B) TYPE: amino acid
    (C) TOPOLOGY: linear (ii) MOLECULE TYPE: peptide (xi) SEQUENCE DESCRIPTION: SEQ ID NO:522:

Gln Ala Ser Gln Ser Ile Ile Lys Tyr Leu Asn
1               5               10